(12) United States Patent
Asada et al.

(10) Patent No.: US 9,853,218 B2
(45) Date of Patent: Dec. 26, 2017

(54) HIGH-MOLECULAR COMPOUND AND LIGHT-EMITTING ELEMENT USING SAME

(71) Applicant: Sumitomo Chemical Company, Limited, Tokyo (JP)

(72) Inventors: Kohei Asada, Tsukuba (JP); Kazuei Ohuchi, Tsukuba (JP); Osamu Goto, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 412 days.

(21) Appl. No.: 14/408,462

(22) PCT Filed: Jun. 7, 2013

(86) PCT No.: PCT/JP2013/066407
§ 371 (c)(1),
(2) Date: Dec. 16, 2014

(87) PCT Pub. No.: WO2013/191086
PCT Pub. Date: Dec. 27, 2013

(65) Prior Publication Data
US 2015/0155495 A1    Jun. 4, 2015

(30) Foreign Application Priority Data

Jun. 19, 2012  (JP) .................... 2012-137538
Mar. 22, 2013  (JP) .................... 2013-059472

(51) Int. Cl.
| | | |
|---|---|---|
| B32B 9/00 | (2006.01) | |
| B32B 19/00 | (2006.01) | |
| H01L 51/00 | (2006.01) | |
| C09K 11/06 | (2006.01) | |
| C08G 61/12 | (2006.01) | |
| H05B 33/20 | (2006.01) | |
| C07F 5/04 | (2006.01) | |
| C08G 61/10 | (2006.01) | |
| C09K 11/02 | (2006.01) | |
| H01L 51/50 | (2006.01) | |

(52) U.S. Cl.
CPC ............ H01L 51/0043 (2013.01); C07F 5/04 (2013.01); C08G 61/10 (2013.01); C08G 61/122 (2013.01);
(Continued)

(58) Field of Classification Search
None
See application file for complete search history.

(56) References Cited

U.S. PATENT DOCUMENTS

2002/0146589 A1  10/2002  Akiyama et al.
2007/0205714 A1  9/2007  Busing et al.
(Continued)

FOREIGN PATENT DOCUMENTS

| JP | 2002-317033 A | 10/2002 |
| TW | 201211203 A | 3/2012 |
| WO | 2012008550 A1 | 1/2012 |

OTHER PUBLICATIONS

Bartual, et al, "Reductive dimerization of pulegone. V. Conversion of bicycle[4.3.0]nonane-7-spirocyclohexanes to phenanthrenes," Anales de Quimica, vol. 66, No. 7-8, pp. 693-699 (1970).
(Continued)

*Primary Examiner* — Jeffrey H Murray
(74) *Attorney, Agent, or Firm* — Panitch Schwarze Belisario & Nadel LLP

(57) ABSTRACT

A polymer compound has a repeating unit represented by general formula (1):

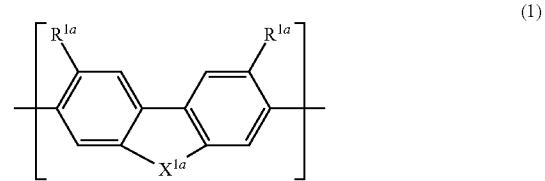

wherein $R^{1a}$ represents an alkyl group, an aryl group, a monovalent aromatic heterocyclic group or an aralkyl group, each possibly substituted and the same or different; and $X^{1a}$ represents a group selected from formulae (1a) to (1c).]

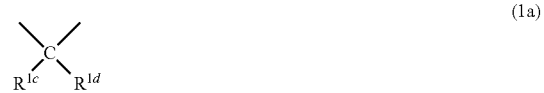

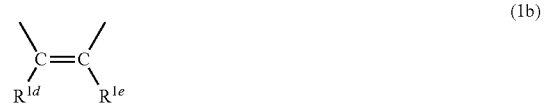

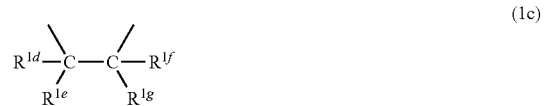

wherein $R^{1c}$ represents an aryl group or a monovalent aromatic heterocyclic group, possibly substituted; and $R^{1d}$ to $R^{1f}$ represent each independently an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom or a cyano group; and the pairs $R^{1d}$ and $R^{1e}$, $R^{1f}$ and $R^{1g}$, $R^{1d}$ and $R^{1f}$, and $R^{1e}$ and $R^{1g}$ may be mutually linked to form a ring together with a carbon atom to which they are linked.

15 Claims, No Drawings

(52) U.S. Cl.
CPC ............ *C09K 11/025* (2013.01); *C09K 11/06* (2013.01); *H01L 51/0035* (2013.01); *H01L 51/0039* (2013.01); *H01L 51/0085* (2013.01); *H01L 51/5012* (2013.01); *H05B 33/20* (2013.01); *C08G 2261/12* (2013.01); *C08G 2261/148* (2013.01); *C08G 2261/1412* (2013.01); *C08G 2261/18* (2013.01); *C08G 2261/312* (2013.01); *C08G 2261/3142* (2013.01); *C08G 2261/3221* (2013.01); *C08G 2261/95* (2013.01); *C09K 2211/1007* (2013.01); *C09K 2211/1059* (2013.01); *C09K 2211/1416* (2013.01); *C09K 2211/185* (2013.01); *H01L 51/0095* (2013.01); *H01L 51/5016* (2013.01)

(56) References Cited

U.S. PATENT DOCUMENTS

| | | |
|---|---|---|
| 2008/0200736 A1 | 8/2008 | Kosuge et al. |
| 2008/0254320 A1 | 10/2008 | Akino et al. |
| 2010/0227974 A1 | 9/2010 | Schulte et al. |
| 2011/0272686 A1 | 11/2011 | Ohuchi et al. |
| 2012/0199825 A1 | 8/2012 | Soga et al. |

OTHER PUBLICATIONS

Int'l Search Report dated Sep. 17, 2013 in Int'l Application No. PCT/JP2013/066407.

Office Action dated Sep. 22, 2016 in TW Application No. 102121316.

Office Action dated Sep. 29, 2016 in JP Application No. 2014-521414.

HIGH-MOLECULAR COMPOUND AND LIGHT-EMITTING ELEMENT USING SAME

CROSS-REFERENCE TO RELATED APPLICATION

This application is a Section 371 of International Application No. PCT/JP2013/066407, filed Jun. 7, 2013, which was published in the Japanese language on Dec. 27, 2013, under International Publication No. WO 2013/191086 A1, and the disclosure of which is incorporated herein by reference.

TECHNICAL FIELD

The present invention relates to a polymer compound and a raw material monomer of the polymer compound, and a composition, an organic film and a light emitting device each containing the polymer compound.

BACKGROUND ART

As a light emitting material used in a light emitting layer of a light emitting device, a composition prepared by doping a host material with a phosphorescent compound showing light emission from a triplet excited state is known.

It is important that the lowest triplet excited state (hereinafter, referred to also as "$T_1$") is at high energy level for realizing high light emission efficiency as the basic property of the above-described host material.

It is known that a polymer compound such as polyvinylcarbazole and the like can be suitably used as the above-described host material since an organic film can be formed with such a compound by a coating method (Patent document 1).

A polymer compound containing as a repeating unit a 1,4-phenylene group having specific substituents at 2-position and 5-position (Patent document 1) and a polymer compound containing as a repeating unit a fluorene-2,7-diyl group and a 1,4-phenylene group having specific substituents at 2-position and 5-position (Patent document 2) are known as the above-described host material.

PRIOR ART DOCUMENT

Patent Document

Patent document 1: JP-A No. 2002-50483
Patent document 2: WO 2007/032437

SUMMARY OF THE INVENTION

Problem to be Solved by the Invention

In a light emitting device produced by using the above-described polymer compound as the host material for a phosphorescent compound, however, the resultant luminance life is not necessarily sufficient.

Then, the present invention has an object of providing a polymer compound as the host material for a phosphorescent compound, which is useful for production of a light emitting device excellent in luminance life. Also, the present invention has an object of providing a composition, an organic film and a light emitting device each containing the polymer compound. Further, the present invention has an object of providing a raw material monomer useful for production of the polymer compound.

Means for Solving the Problem

In a first aspect, the present invention provides a polymer compound comprising as a repeating unit a group represented by the following general formula (1):

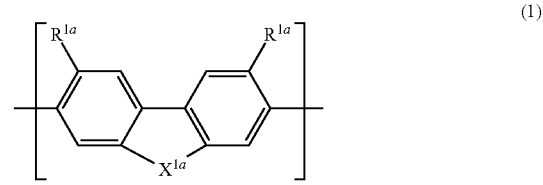

[in the formula (1),
$R^{1a}$ represents an alkyl group, an aryl group, a monovalent aromatic heterocyclic group or an aralkyl group, and these groups may have a substituent. A plurality of $R^{1a}$ may be the same or different.
$X^{1a}$ represents a group selected from the group consisting of the following formulae (1a) to (1c).]

[the formulae (1a) to (1c),
$R^{1c}$ represents an aryl group or a monovalent aromatic heterocyclic group, and these groups may have a substituent.
$R^{1d}$ to $R^{1f}$ represent each independently an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom or a cyano group. In the formula (1b), $R^{1d}$ and $R^{1e}$ may be mutually linked to form a ring together with a carbon atom to which they are linked. In the formula (1c), $R^{1d}$ and $R^{1e}$ may be mutually linked to form a ring together with a carbon atom to which they are linked, $R^{1f}$ and $R^{1g}$ may be mutually linked to form a ring together with a carbon atom to which they are linked, $R^{1d}$ and $R^{1f}$ may be mutually linked to form a ring together with a carbon atom to which they are linked, and $R^{1e}$ and $R^1$ g may be mutually linked to form a ring together with a carbon atom to which they are linked.].

In a second aspect, the present invention provides a composition comprising the above-described polymer compound and at least one material selected from the group consisting of a hole transporting material, an electron transporting material and a light emitting material.

In a third aspect, the present invention provides a composition comprising a polymer compound containing a group represented by the following general formula (1B) as a repeating unit, and a phosphorescent compound represented by the following general formula (Ir-1), (Ir-2) or (Ir-3):

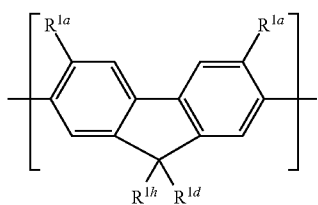

(1B)

[in the formula (1B), $R^{1a}$ represents an alkyl group, an aryl group, a monovalent aromatic heterocyclic group or an aralkyl group, and these groups may have a substituent. A plurality of $R^{1a}$ may be the same or different.

$R^{1h}$ and $R^{1d}$ represent each independently an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom or a cyano group. $R^{1h}$ and $R^{1d}$ may be mutually linked to form a ring together with a carbon atom to which they are linked.]

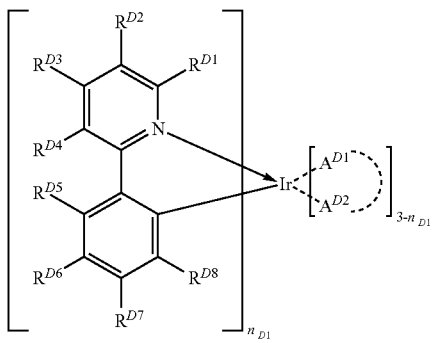

(Ir-1)

[in the formula (Ir-1), $R^{D1}$, $R^{D2}$, $R^{D3}$, $R^{D4}$, $R^{D5}$, $R^{D6}$, $R^{D7}$ and $R^{D8}$ represent each independently a hydrogen atom, an alkyl group, an alkoxy group, an aryl group, an aryloxy group, a monovalent aromatic heterocyclic group or a halogen atom, and these groups may have a substituent. Here, at least one of $R^{D1}$, $R^{D2}$, $R^{D3}$, $R^{D4}$, $R^{D5}$, $R^{D6}$, $R^{D7}$ and $R^{D8}$ is a group represented by the following formula (Dend-A) or (Dend-B).

-$A^{D1}$ - - - $A^{D2}$- represents an anionic bidentate ligand, and $A^{D1}$ and $A^{D2}$ represent each independently a carbon atom, an oxygen atom or a nitrogen atom linking to an iridium atom.

$n_{D1}'$ represents 1, 2 or 3.]

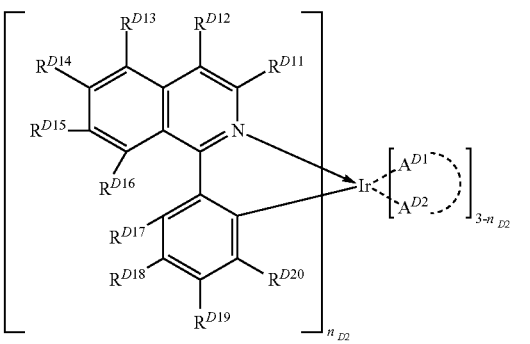

(Ir-2)

[in the formula (Ir-2), $R^{D11}$, $R^{D12}$, $R^{D13}$, $R^{D14}$, $R^{D15}$, $R^{D16}$, $R^{D17}$, $R^{D18}$, $R^{D19}$, and $R^{D20}$ represent each independently a hydrogen atom, an alkyl group, an alkoxy group, an aryl group, an aryloxy group, a monovalent aromatic heterocyclic group or a halogen atom, and these groups may have a substituent. Here, at least one of $R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ is a group represented by the following formula (Dend-A) or (Dend-B).

-$A^{D1}$ - - - $A^{D2}$- represents an anionic bidentate ligand, and $A^{D1}$ and $A^{D2}$ represent each independently a carbon atom, an oxygen atom or a nitrogen atom linking to an iridium atom.

$n_{D2}$ represents 1, 2 or 3.]

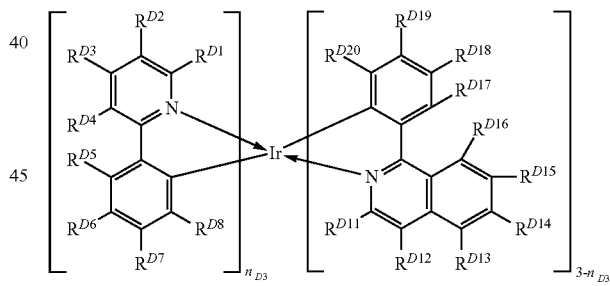

(Ir-3)

[in the formula (Ir-3), $R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ represent each independently a hydrogen atom, an alkyl group, an alkoxy group, an aryl group, an aryloxy group, a monovalent aromatic heterocyclic group or a halogen atom, and these groups may have a substituent. Here, at least one of $R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$, and $R^{D20}$ is a group represented by the following formula (Dend-A) or (Dend-B).

-$A^{D1}$ - - - $A^{D2}$- represents an anionic bidentate ligand, and $A^{D1}$ and $A^{D2}$ represent each independently a carbon atom, an oxygen atom or a nitrogen atom linking to an iridium atom.

$n_{D3}$ represents 1 or 2.]

(Dend-A)

[in the formula (Dend-A),
$G^{DA1}$ represents a nitrogen atom, a trivalent aromatic hydrocarbon group or a trivalent aromatic heterocyclic group.
$Ar^{DA1}$, $Ar^{DA2}$ and $Ar^{DA3}$ represent each independently an arylene group or a divalent aromatic heterocyclic group.
$T^{DA2}$ and $T^{DA3}$ represent each independently an aryl group or a monovalent aromatic heterocyclic group.
$m^{DA1}$, $m^{DA2}$ and $m^{DA3}$ represent each independently an integer of 0 or more.]

(Dend-B)

[in the formula (Dend-B),
$G^{DA1}$, $G^{DA2}$, and $G^{DA3}$ represent each independently a nitrogen atom, a trivalent aromatic hydrocarbon group or a trivalent aromatic heterocyclic group.
$Ar^{DA1}$, $Ar^{DA2}$, $Ar^{DA3}$, $Ar^{DA4}$, $Ar^{DA5}$, $Ar^{DA6}$ and $Ar^{DA7}$ represent each independently an arylene group or a divalent aromatic heterocyclic group.
$T^{DA4}$, $T^{DA5}$, $T^{DA6}$ and $T^{DA7}$ represent each independently an aryl group or a monovalent aromatic heterocyclic group.
$m^{DA1}$, $m^{DA2}$, $m^{DA3}$, $m^{DA4}$, $m^{DA5}$, $m^{DA6}$ and $m^{DA7}$ represent each independently an integer of 0 or more.].

In a fourth aspect, the present invention provides a liquid composition comprising the above-described polymer compound and a solvent.

In a fifth aspect, the present invention provides a light emitting device having an anode and a cathode and an organic layer disposed between the anode and the cathode, wherein the organic layer contains the above-described polymer compound.

In a sixth aspect, the present invention provides a compound represented by the following general formula (M1):

(M1)

[in the formula (M1),
$R^{1a}$ represents an alkyl group, an aryl group, a monovalent aromatic heterocyclic group or an aralkyl group, and these groups may have a substituent. A plurality of $R^{1a}$ may be the same or different.
$X^{1a}$ represents a group selected from the group consisting of the following formulae (1a) to (1c).
$X^1$ represents a group selected from the following substituent group (a) or a group selected from the following substituent group (b). A plurality of $X^2$ may be mutually the same or different.
(Substituent Group (a))
a chlorine atom, a bromine atom, an iodine atom and a group represented by $—O—S(=O)_2R^{20}$ ($R^{20}$ represents an alkyl group, or an aryl group which may have an alkyl group, an alkoxy group, a nitro group, a fluorine atom or a cyano group as a substituent.).
(Substituent Group (b))
a group represented by $—B(OR^{21})_2$ ($R^{21}$ represents a hydrogen atom or an alkyl group. A plurality of $R^{21}$ may be mutually the same or different and may be mutually linked to form a ring together with an oxygen atom to which they are linked.), a group represented by $—BF_4Q^1$ ($Q^1$ represents a monovalent cation of lithium, sodium, potassium, rubidium or cesium.), a group represented by $—Sn(R^{22})_3$ ($R^{22}$ represents a hydrogen atom or an alkyl group. A plurality of $R^{22}$ may be mutually the same or different and may be mutually linked to form a ring together with a tin atom to which they are linked), a group represented by $—MgY^1$ ($Y^1$ represents a chlorine atom, a bromine atom or an iodine atom.), and a group represented by $—ZnY^2$ ($Y^2$ represents a chlorine atom, a bromine atom or an iodine atom.).]

(1a)

(1b)

(1c)

[in the formulae (1a) to (1c),
$R^{1c}$ represents an aryl group or a monovalent aromatic heterocyclic group, and these groups may have a substituent.
$R^{1d}$ to $R^{1f}$ represent each independently an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom or a cyano group. In the formula (1b), $R^{1d}$ and $R^{1e}$ may be mutually linked to form a ring together with a carbon atom to which they are linked. In the formula (1c), $R^{1d}$ and $R^{1e}$ may be mutually linked to form a ring together with a carbon atom to which they are linked, $R^{1f}$ and $R^{1g}$ may be mutually linked to form a ring together with a carbon atom to which they are linked, $R^{1d}$ and $R^{1f}$ may be mutually linked to form a ring together with a carbon atom to which they are linked, and $R^{1e}$ and $R^{1g}$ may be mutually linked to form a ring together with a carbon atom to which they are linked.].

Effect of the Invention

The present invention can provide a polymer compound as a host material for a phosphorescent compound, which is useful for production of a light emitting device excellent in luminance life. Also, the present invention can provide a composition, an organic film and a light emitting device each containing the polymer compound. Further, the present invention can provide a raw material monomer useful for production of the polymer compound. The polymer compound of the present invention is particularly useful as a host material of a phosphorescent compound showing an emission color particularly in the blue range.

MODES FOR CARRYING OUT THE INVENTION

Suitable embodiments of the present invention will be illustrated in detail below.

[Explanation of Terms and Marks]

Terms and marks in the present specification will be illustrated below for further clarifying the present invention "Current efficiency" is a value obtained by dividing the luminance of a light emitting device by the input current per unit area, and [cd/A] is usually used as its unit.

"Luminance life" is driving time until luminance reaches a certain rate with respect to the initial value, and usually denotes a value obtained when driving at the constant current density. "Luminance life" is one of indices of the stability of a light emitting device.

In structural formulae in the present specification, the bond represented by an arrow represents a coordinate bond and the bond represented by a broken line represents a covalent bond or a coordinate bond.

"Residue" denotes "a k-valent group represented by an atomic group remaining after removing k hydrogen atoms from a compound", and the number represented by k and the positions of the hydrogen atoms to be removed will be illustrated in more detail in the present specification if necessary.

"Polymer compound" is a polymer having molecular weight distribution obtained by a polymerization reaction using monomers, and particularly denotes one having a polystyrene-equivalent number-average molecular weight of $1\times10^3$ to $1\times10^8$. "Low molecular weight compound" is a compound which does not have molecular weight distribution as shown by a polymer compound, and denotes one having a molecular weight of usually 5000 or less.

"Constitutional unit" denote a unit appearing once or more in a polymer compound, and it is preferable that this constitutional unit is present as "repeating unit" (unit appearing twice or more in a polymer compound) in the polymer compound. That is, the repeating unit is a constitutional unit or constitutional sequence formed by partial structures excluding a leaving group (polymerization active group) capable of forming a linkage in a polymerization reaction in producing a polymer compound. "Constitutional sequence" denotes a structure formed by linking two or more constitutional units via a single bond in a polymer compound.

"n-valent aromatic heterocyclic group" (n represents an integer of 1 or more) denotes an atomic group remaining after removing n hydrogen atoms among hydrogen atoms linking directly to carbon atoms constituting a ring from a monocyclic or condensed-cyclic heterocyclic compound showing aromaticity. "Heterocyclic compound" denotes an organic compound having a cyclic structure in which atoms constituting the ring include not only a carbon atom but also a hetero atom such as an oxygen atom, a sulfur atom, a nitrogen atom, a phosphorus atom, a boron atom, a silicon atom or the like.

"Aromatic heterocyclic compound" is a heterocyclic compound containing a hetero atom such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzosilole, dibenzophosphole and the like, and denotes a compound in which the heterocyclic ring itself shows aromaticity and a compound in which the hetero atom-containing heterocyclic ring itself does not show aromaticity but an aromatic ring is condensed to the heterocyclic ring such as phenoxazine, phenothiazine, dibenzoborole, dibenzosilole, benzopyran and the like.

In the present specification, Me represents a methyl group, Et represents an ethyl group, i-Pr and i-pro represent an isopropyl group, n-Bu represents a n-butyl group, and tBu, t-Bu and t-butyl group represent a tert-butyl group.

[Explanation of Substituent]

Various sorts of substituents shown in the present specification will be specifically explained. In the present specification, each group is as described below unless otherwise stated. Further, in the present specification, a hydrogen atom of a compound, a constitutional unit and a repeating unit may be optionally substituted with a deuterium atom, and also other atoms may be substituted with various isotopes occurring naturally in a similar fashion.

(Alkyl Group)

The alkyl group may be any of linear, branched or cyclic, and a linear alkyl group is preferable. The number of carbon atoms of the alkyl group, not including the number of carbon atoms of a substituent described later, is preferably 1 to 20 (in the case of a branched alkyl group and a cyclic alkyl group, 3 to 20), more preferably 1 to 15 (in the case of a branched alkyl group and a cyclic alkyl group, 3 to 15), further preferably 1 to 12 (in the case of a branched alkyl group and a cyclic alkyl group, 3 to 12). The substituent which the alkyl group may have includes, for example, an aryl group, a monovalent aromatic heterocyclic group, an alkoxy group, an aryloxy group, an arylalkoxy group, a substituted amino group, a substituted carbonyl group, a substituted oxycarbonyl group, a fluorine atom and a cyano group.

Examples of the alkyl group include a methyl group, an ethyl group, a propyl group, an isopropyl group, a butyl group, a sec-butyl group, an isobutyl group, a tert-butyl group, a pentyl group, an isoamyl group, a hexyl group, a cyclohexyl group, a heptyl group, an octyl group, a 2-ethylhexyl group, a nonyl group, a decyl group, a 3,7-dimethyloctyl group, a dodecyl group, a trifluoromethyl group, a pentafluoroethyl group, a perfluorobutyl group, a perfluorohexyl group and a perfluorooctyl group.

(Aryl Group)

The aryl group is an atomic group remaining after removing from a monocyclic or condensed-cyclic aromatic hydrocarbon one hydrogen atom linking directly to a carbon atom constituting its ring. The number of carbon atoms of the aryl group, not including the number of carbon atoms of a substituent described later, is preferably 6 to 60, more preferably 6 to 48, further preferably 6 to 20, particularly preferably 6 to 14. The substituent which the aryl group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the aryl group include a phenyl group and a naphthyl group.

(Monovalent Aromatic Heterocyclic Group)

The number of carbon atoms of the monovalent aromatic heterocyclic group, not including the number of carbon atoms of a substituent described later, is preferably 2 to 60, more preferably 3 to 20. The substituent which the monovalent aromatic heterocyclic group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the monovalent aromatic heterocyclic group include a 2-oxadiazolyl group, a 2-thiadiazolyl group, a 2-thiazolyl group, a 2-oxazolyl group, a 2-thienyl group, a 2-pyrrolyl group, a 2-furyl group, a 2-pyridyl group, a 3-pyridyl group, a 4-pyridyl group, a 2-pyrazyl group, a 2-pyrimidyl group, a 2-triazyl group, a 3-pyridazyl group, a 3-carbazolyl group, a 2-phenoxazinyl group, a 3-phenoxazinyl group, a 2-phenothiazinyl group and a 3-phenothiazinyl group.

(Alkoxy Group)

The alkoxy group may be any of linear, branched or cyclic, and a linear alkoxy group is preferable. The number of carbon atoms of the alkoxy group, not including the number of carbon atoms of a substituent described later, is preferably 1 to 20 (in the case of a branched alkoxy group and a cyclic alkoxy group, 3 to 20). The substituent which the alkoxy group may have includes, for example, an aryl group, a monovalent aromatic heterocyclic group, an alkoxy group, an aryloxy group, an arylalkoxy group, a substituted amino group, a substituted carbonyl group, a substituted oxycarbonyl group, a fluorine atom and a cyano group.

Examples of the alkoxy group include a methoxy group, an ethoxy group, a propyloxy group, an isopropyloxy group, a butoxy group, a sec-butoxy group, an isobutoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a dodecyloxy group, a trifluoromethoxy group, a pentafluoroethoxy group, a perfluorobutoxy group, a perfluorohexyloxy group, a perfluorooctyloxy group, a methoxymethyloxy group, a 2-methoxyethyloxy group and a 2-ethoxyethyloxy group.

(Aryloxy Group)

The number of carbon atoms of the aryloxy group, not including the number of carbon atoms of a substituent described later, is preferably 6 to 60. The substituent which the aryloxy group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the aryloxy group include a phenoxy group, a $C_1$ to $C_{12}$ alkoxyphenoxy group ("$C_1$ to $C_{12}$ alkoxy" means that the number of carbon atoms of the alkoxy portion is 1 to 12. The same shall apply hereinafter.), a $C_1$ to $C_{12}$ alkylphenoxy group, a 1-naphthyloxy group, a 2-naphthyloxy group and a pentafluorophenyloxy group.

(Aralkyl Group)

The number of carbon atoms of the aralkyl group, not including the number of carbon atoms of a substituent described later, is preferably 7 to 60.

The substituent which the aralkyl group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the aralkyl group include a phenyl-$C_1$ to $C_{12}$ alkyl group, a $C_1$ to $C_{12}$ alkoxyphenyl-$C_1$ to $C_{12}$ alkyl group and a $C_1$ to $C_{12}$ alkylphenyl-$C_1$ to $C_{12}$ alkyl group.

(Arylalkoxy Group)

The number of carbon atoms of the arylalkoxy group, not including the number of carbon atoms of a substituent described later, is preferably 7 to 60. The substituent which the arylalkoxy group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the arylalkoxy group include a phenyl-$C_1$ to $C_{12}$ alkoxy group, a $C_1$ to $C_{12}$ alkoxyphenyl-$C_1$ to $C_{12}$ alkoxy group and a $C_1$ to $C_{12}$ alkylphenyl-$C_1$ to $C_{12}$ alkoxy group.

(Substituted Amino Group)

The number of carbon atoms of the substituted amino group, including the number of carbon atoms of a substituent, is preferably 2 to 60. The substituent which the substituted amino group has includes, for example, an alkyl group, an aryl group, an aralkyl group and a monovalent aromatic heterocyclic group. The substituted amino group may also be a group in which substituents which the amino group has are mutually linked directly to form a ring structure together with a nitrogen atom to which they are linked and a group in which substituents which the amino group has are mutually linked via a carbon atom, an oxygen atom, a sulfur atom or the like to form a ring structure together with a nitrogen atom to which they are linked. The substituted amino group is preferably a dialkyl substituted amino group or a diaryl substituted amino group.

Examples of the substituted amino group include a dimethylamino group, a diethylamino group, a diphenylamino group, a di-4-tolylamino group, a di-4-tert-butylphenylamino group, a bis(3,5-di-tert-butylphenyl)amino group, a N-carbazolyl group, a N-phenoxazinyl group, a N-acridinyl group and a N-phenothiazinyl group.

(Substituted Carbonyl Group)

The number of carbon atoms of the substituted carbonyl group, including the number of carbon atoms of a substituent, is preferably 2 to 60.

The substituted carbonyl group includes a group represented by —$COR^{23}$ ($R^{23}$ represents a prescribed substituent) in which $R^{23}$ is an alkyl group, an aryl group, an aralkyl group or a monovalent aromatic heterocyclic group.

Examples of the substituted carbonyl group include an acetyl group, a butylyl group and a benzoyl group.

(Substituted Oxycarbonyl Group)

The number of carbon atoms of the substituted oxycarbonyl group, including the number of carbon atoms of a substituent, is preferably 2 to 60.

The substituted oxycarbonyl group includes a group represented by —$COOR^{24}$ ($R^{24}$ represents a substituent) in which $R^{24}$ is an alkyl group, an aryl group, an aralkyl group or a monovalent aromatic heterocyclic group.

Examples of the substituted oxycarbonyl group include a methoxycarbonyl group, an ethoxycarbonyl group, a butoxycarbonyl group, a phenoxycarbonyl group and a benzyloxycarbonyl group.

(Arylene Group)

The arylene group denotes an atomic group remaining after removing from a monocyclic or condensed-cyclic aromatic hydrocarbon two hydrogen atoms bonding directly to a carbon atom constituting the ring. The number of carbon atoms of the arylene group, not including the number of carbon atoms of a substituent described later, is preferably 6 to 60, more preferably 6 to 48, further preferably 6 to 30, particularly preferably 6 to 18. The substituent which the arylene group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the arylene group include phenylene groups such as a 1,4-phenylene group (the following formula 001), a 1,3-phenylene group (the following formula 002), a 1,2-phenylene group (the following formula 003) and the like; naphthalenediyl groups such as a naphthalene-1,4-diyl group (the following formula 004), a naphthalene-1,5-diyl group (the following formula 005), a naphthalene-2,6-diyl group (the following formula 006) and the like; dihydrophenanthrenediyl groups such as a 9,10-dihydrophenanthrene-2,7-diyl group (the following formula 007) and the like; fluorenediyl groups such as a fluorene-3,6-diyl group (the following formula 008), a fluorene-2,7-diyl group (the following formula 009) and the like.

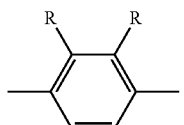

001

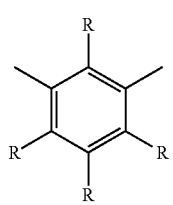

002

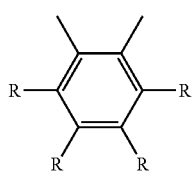

003

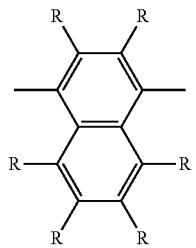

004

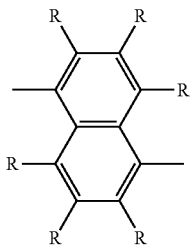

005

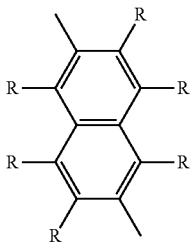

006

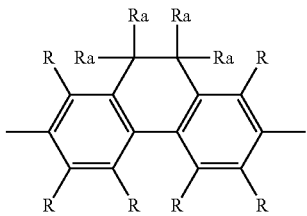

007

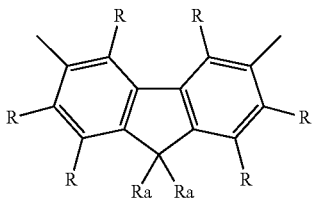

008

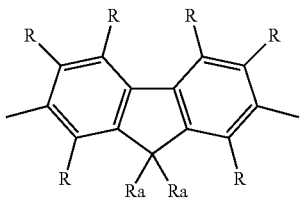

009

In the formulae 001 to 009, R represents a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom or a cyano group. Ra represents an alkyl group, an aryl group, a monovalent aromatic heterocyclic group or an aralkyl group. A plurality of R may be mutually the same or different and may be mutually linked to form a ring structure together with a carbon atom to which they are linked. A plurality of Ra may be mutually the same or different and may be mutually linked to form a ring structure together with a carbon atom to which they are linked.

In the formulae 001 to 009, R is preferably a hydrogen atom, an alkyl group, an aryl group, a monovalent aromatic heterocyclic group, an alkoxy group, an aryloxy group, an aralkyl group or a substituted amino group, more preferably a hydrogen atom, an alkyl group or an aryl group.

In the formulae 001 to 009, Ra is preferably an aryl group or an alkyl group, more preferably an aryl group which may have an alkyl group, an alkoxy group or an aryl group as a substituent, or an alkyl group, and it is further preferable that at least one Ra is an aryl group which may have an alkyl group, an alkoxy group or an aryl group as a substituent.

In the formulae 001 to 009, the ring structure formed by R and Ra is preferably a cyclopentyl ring which may have an alkyl group as a substituent, a cyclohexyl ring which may have an alkyl group as a substituent or a cycloheptyl ring which may have an alkyl group as a substituent. The ring structure may also be a condensed ring structure obtained by further condensing a benzene ring and the like.

(Divalent Aromatic Heterocyclic Group)

The number of carbon atoms of the divalent aromatic heterocyclic group, not including the number of carbon atoms of a substituent described later, is preferably 2 to 60, more preferably 3 to 20. The substituent which the divalent aromatic heterocyclic group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the divalent aromatic heterocyclic group include pyridinediyl groups such as a pyridine-2,5-diyl group (the following formula 101), a pyridine-2,6-diyl group (the following formula 102) and the like; pyrimidinediyl groups such as a pyrimidine-4,6-diyl group (the following formula 103) and the like; triazinediyl groups such as a triazine-2,4-diyl group (the following formula 104) and the like; pyrazinediyl groups such as a pyrazine-2,5-diyl group (the following formula 105) and the like; pyridazinediyl groups such as a pyridazine-3,6-diyl group (the following formula 106) and the like; quinolinediyl groups such as a quinoline-2,6-diyl group (the following formula 107) and the like; isoquinolinediyl groups such as a isoquinoline-1,4-diyl group (the following formula 108) and the like; quinoxalinediyl groups such as a quinoxaline-5,8-diyl group (the following formula 109) and the like; carbazolediyl groups such as a carbazole-3,6-diyl group (the following formula 110), a carbazole-2,7-diyl group (the following formula 111) and the like; dibenzofurandiyl groups such as a dibenzofuran-4,7-diyl group (the following formula 112), a dibenzofuran-3,8-diyl group (the following formula 113) and the like; dibenzothiophenediyl groups such as a dibenzothiophene-4,7-diyl group (the following formula 114), a dibenzothiophene-3,8-diyl group (the following formula 115) and the like; dibenzosilolediyl groups such as a dibenzosilole-4,7-diyl group (the following formula 116), a dibenzosilole-3,8-diyl group (the following formula 117) and the like; phenoxazinediyl groups such as a phenoxazine-3,7-diyl group (the following formula 118), a phenoxazine-2,8-diyl group (the following formula 119) and the like; phenothiazinediyl groups such as a phenothiazine-3,7-diyl group (the following formula 120), a phenothiazine-2,8-diyl group (the following formula 121) and the like; dihydroacridinediyl groups such as a dihydroacridine-2,7-diyl group (the following formula 122) and the like; a divalent group represented by the following formula 123; pyrrolediyl groups such as a pyrrole-2,5-diyl group (the following formula 124) and the like; furandiyl groups such as a furan-2,5-diyl group (the following formula 125) and the like; thiophenediyl groups such as a thiophene-2,5-diyl group (the following formula 126) and the like; diazolediyl groups such as a diazole-2,5-diyl group (the following formula 127) and the like; triazolediyl groups such as a triazole-2,5-diyl group (the following formula 128) and the like; oxazolediyl groups such as an oxazole-2,5-diyl group (the following formula 129) and the like; an oxadiazole-2,5-diyl group (the following formula 130); triazolediyl groups such as a triazole-2,5-diyl group (the following formulae 131) and the like; and a thiadiazole-2,5-diyl group (the following formula 132).

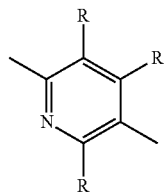

101

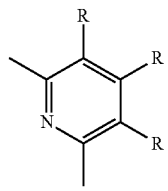

102

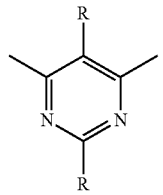

103

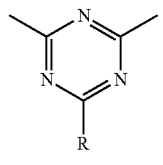

104

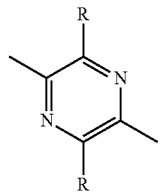

105

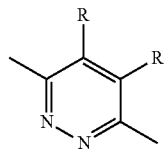

106

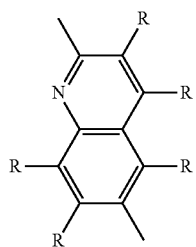

107

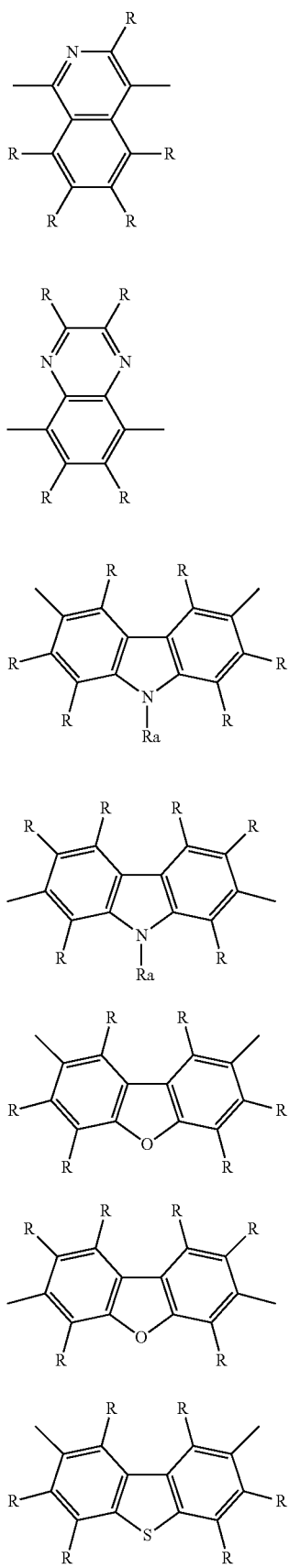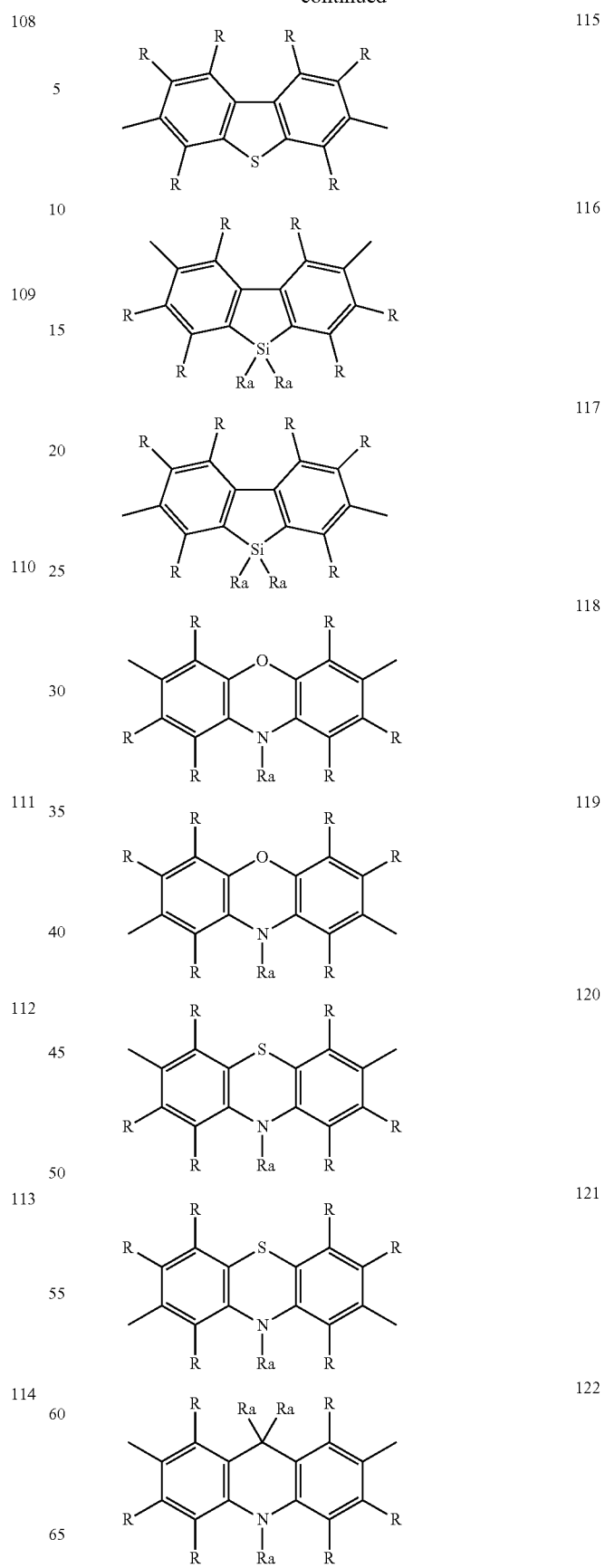

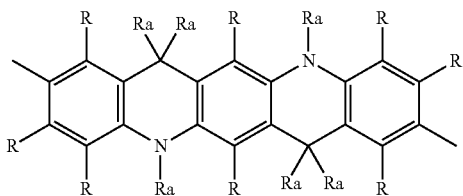

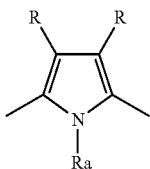

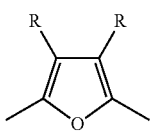

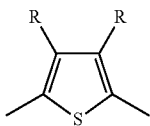

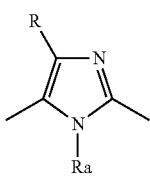

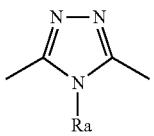

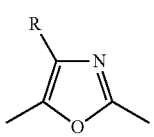

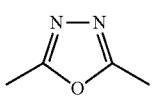

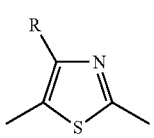

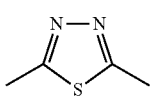

In the formulae 101 to 132, R and Ra represent the same meaning as described above.

(Divalent Aromatic Amine Residue)

The divalent aromatic amine residue is, for example, a group represented by the following general formula (4).

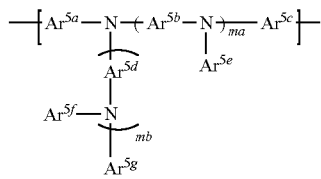

In the formula (4), $Ar^{5a}$, $Ar^{5b}$, $Ar^{5c}$ and $Ar^{5d}$ represent each independently an arylene group or a divalent aromatic heterocyclic group, and these groups may have a substituent.

$Ar^{5e}$, $Ar^{5f}$ and $Ar^{5g}$ represent each independently a hydrogen atom, an alkyl group, an aryl group or a monovalent aromatic heterocyclic group, and these groups may have a substituent.

The substituent which $Ar^{5a}$, $Ar^{5b}$, $Ar^{5c}$, $Ar^{5d}$, $Ar^{5e}$, $Ar^{5f}$ and $Ar^{5g}$ may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group, and an alkyl group, an aryl group and an aralkyl group are preferable.

The group represented by $Ar^{5d}$, $Ar^{5e}$, $Ar^{5f}$ and $Ar^{5g}$ may be bonded directly to or bonded via a group represented by —O—, —S—, —C(=O)—, —C(=O)—O—, —N($R^A$)—, —C(=O)—N($R^A$)— or C($R^A$)$_2$— to the other group than the group linked to a nitrogen atom to which the group is linked, and this ring structure is preferably a 5 to 7-membered ring. $R^A$ represents an alkyl group, an aryl group, a monovalent aromatic heterocyclic group or an aralkyl group, and these groups may have a substituent. When there are a plurality of $R^A$, these may be mutually the same or different and may be mutually linked to form a ring structure together with a carbon atom to which they are linked.

ma and mb represent each independently 0 or 1.

(Trivalent Aromatic Hydrocarbon Group)

Trivalent aromatic hydrocarbon group denotes an atomic group remaining after removing from a monocyclic or condensed-cyclic aromatic hydrocarbon three hydrogen atoms linking directly to carbon atoms constituting the ring. The number of carbon atoms of the trivalent aromatic hydrocarbon group, not including the number of carbon atoms of a substituent described later, is preferably 6 to 60, more preferably 6 to 48, further preferably 6 to 20, particularly preferably 6 to 14. The substituent which the trivalent aromatic hydrocarbon group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the trivalent aromatic hydrocarbon group include an atomic group remaining after removing from an aromatic hydrocarbon such as benzene, naphthalene, anthracene, phenanthrene, naphthacene, fluorene, pyrene, perylene and the like three hydrogen atoms linking directly to carbon atoms constituting the ring.

(Trivalent Aromatic Heterocyclic Group)

The trivalent aromatic heterocyclic group denotes an atomic group remaining after removing from a monocyclic or condensed-cyclic heterocyclic compound showing aromaticity three hydrogen atoms linking directly to carbon atoms or hetero atoms constituting the ring. The number of carbon atoms of the trivalent aromatic heterocyclic group, not including the number of carbon atoms of a substituent described later, is preferably 2 to 60, more preferably 3 to 20. The substituent which the trivalent aromatic heterocyclic group may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Examples of the trivalent aromatic heterocyclic group include an atomic group remaining after removing from an aromatic heterocyclic compound such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzosilole, dibenzophosphole, phenoxazine, phenothiazine, dibenzoborole, dibenzosilole, benzopyran and the like three hydrogen atoms linking directly to carbon atoms or hetero atoms constituting the ring.

[Polymer Compound]

Next, polymer compounds according to suitable embodiments will be explained. The polymer compound of the present invention contains a group represented by the formula (1) as a repeating unit. In a more suitable embodiment, a polymer compound represented by the formula (1) is contained as a repeating unit, and further, a group represented by the formula (2) and/or a group represented by the formula (3) is contained as a repeating unit. The polymer compound of the present embodiment may contain as a repeating unit the other group than the group represented by the formula (1), the group represented by the formula (2) and the group represented by the formula (3). The groups represented by the formula (1), the groups represented by the formula (2) and the groups represented by the formula (3) may each be contained singly or may each be contained in combination. These groups will be explained below.

(Group Represented by the Formula (1))

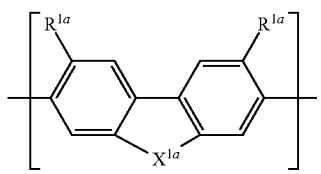

(1)

[in the formula (1), $R^{1a}$ represents an alkyl group, an aryl group, a monovalent aromatic heterocyclic group or an aralkyl group, and these groups may have a substituent. A plurality of $R^{1a}$ may be the same or different.

$X^{1a}$ represents a group selected from the group consisting of the following formulae (1a) to (1c).]

(1a)

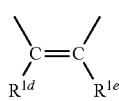

(1b)

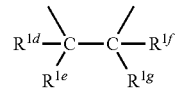

(1c)

[in the formulae (1a) to (1c), $R^{1c}$ represents an aryl group or a monovalent aromatic heterocyclic group, and these groups may have a substituent.

$R^{1d}$ to $R^{1f}$ represent each independently an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom or a cyano group. In the formula (1b), $R^{1d}$ and $R^{1e}$ may be mutually linked to form a ring together with a carbon atom to which they are linked. In the formula (1c), $R^{1d}$ and $R^{1e}$ may be mutually linked to form a ring together with a carbon atom to which they are linked, $R^{1f}$ and $R^{1g}$ may be mutually linked to form a ring together with a carbon atom to which they are linked, $R^{1d}$ and $R^{1f}$ may be mutually linked to form a ring together with a carbon atom to which they are linked, and $R^{1e}$ and $R^{1g}$ may be mutually linked to form a ring together with a carbon atom to which they are linked.]

As $R^{1c}$ in the formula (1), an aryl group is preferable, an aryl group having an alkyl group as a substituent is more preferable, a phenyl group having an alkyl group as a substituent is further preferable, since the luminance life of a light emitting device using the polymer compound of the present embodiment is more excellent.

As $R^{1d}$ to $R^{1f}$ in the formula (1), an alkyl group or an aryl group is preferable, since the luminance life of a light emitting device using the polymer compound of the present embodiment is more excellent.

Regarding the combination of $R^{1d}$ and $R^{1e}$ in the formula (1b), it is preferable that both are an alkyl group, both are an aryl group, or one is an alkyl group and the other is an aryl group, it is more preferable that both are an aryl group, or one is an alkyl group and the other is an aryl group, it is further preferable that one is an alkyl group and the other is an aryl group, since synthesis of the polymer compound of the present embodiment is easy.

$X^{1a}$ in the formula (1) is preferably a group represented by the formula (1a). That is, the group represented by the formula (1) is preferably a group represented by the formula (1A).

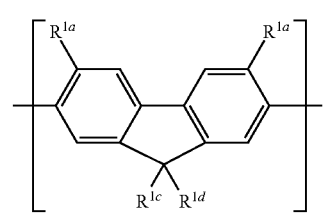

(1A)

[in the formula (1A), $R^{1a}$, $R^{1c}$ and $R^{1d}$ represent the same meaning as described above.]

The group represented by the formula (1) includes, for example, groups represented by the following formulae (1-1a) to (1-28a), (1-1b) to (1-8b) and (1-1c) to (1-10c), and groups represented by the formulae (1-1a) to (1-12a), (1-14a) to (1-28a), (1-2b) to (1-6b), (1-8b), and (1-2c) to (1-10c) are preferable since the luminance life of a light emitting device using the polymer compound of the present embodiment is more excellent.
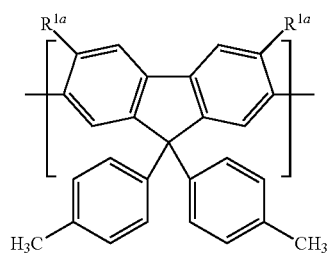
1-1a
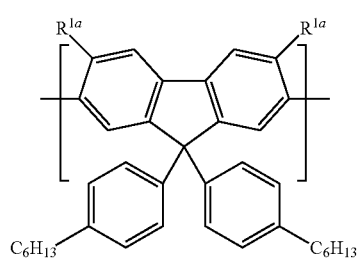
1-2a
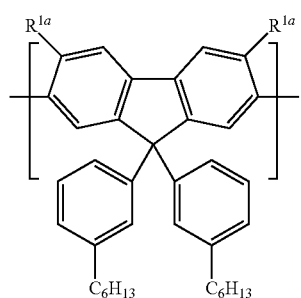
1-3a
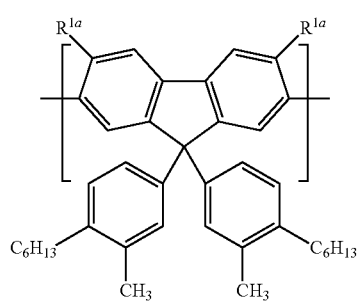
1-4a
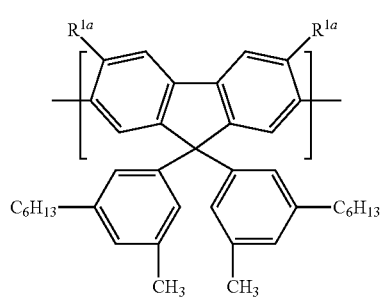
1-5a
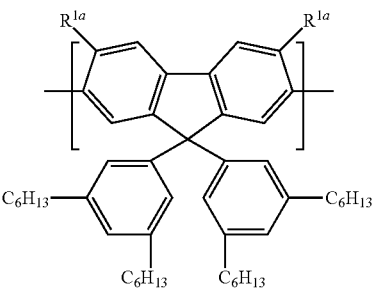
1-6a
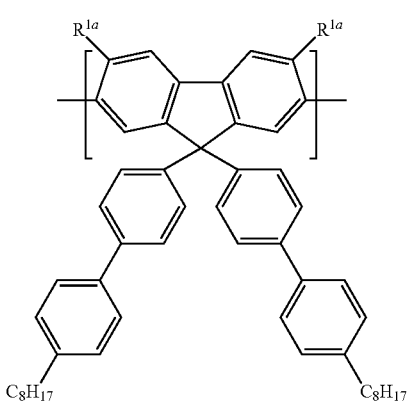
1-7a
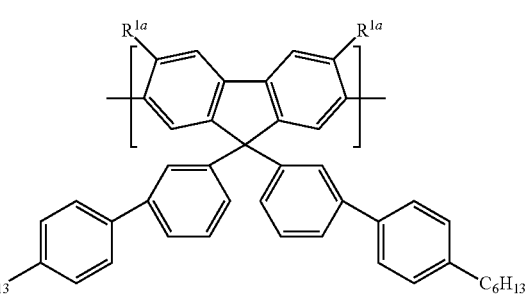
1-8a
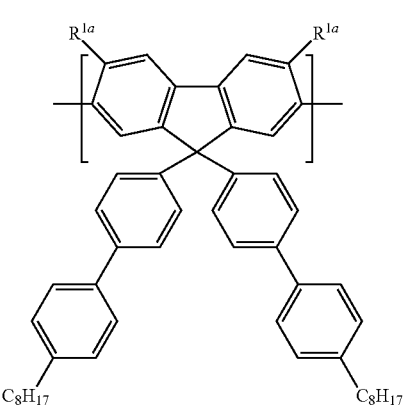
1-9a

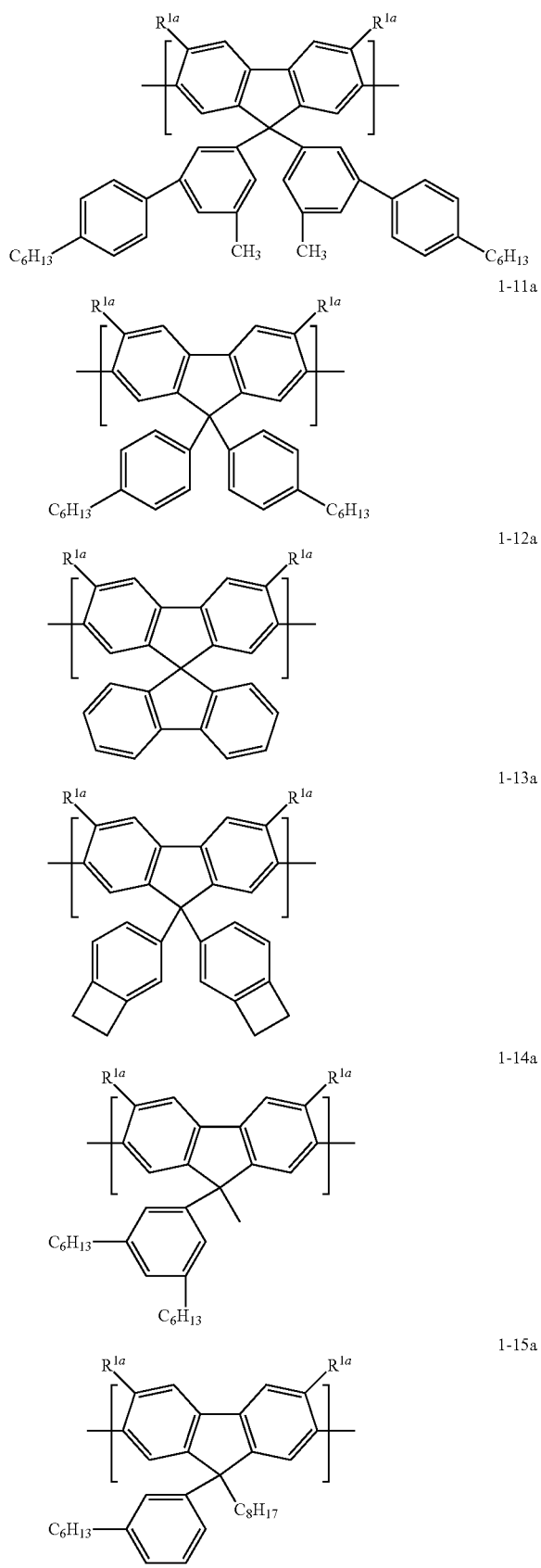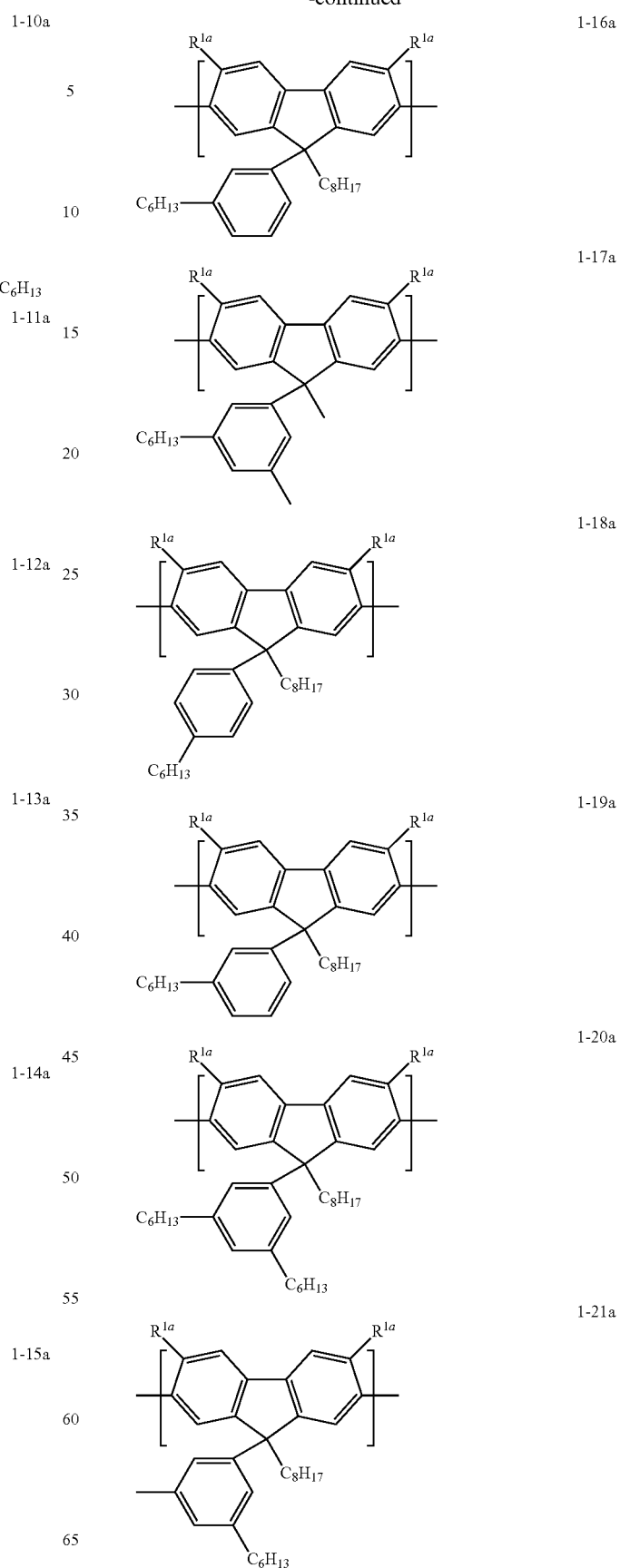

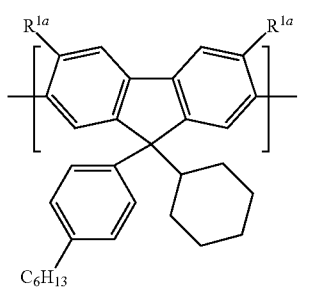
1-22a
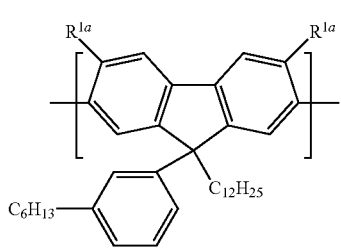
1-23a
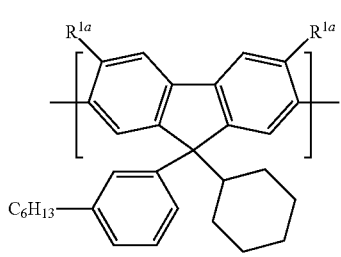
1-24a
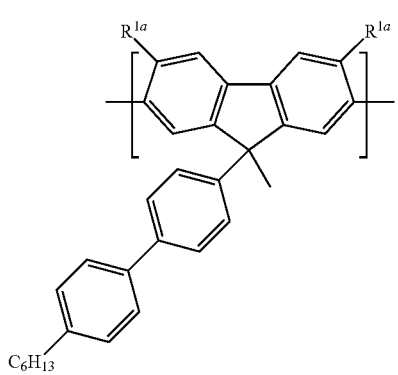
1-25a
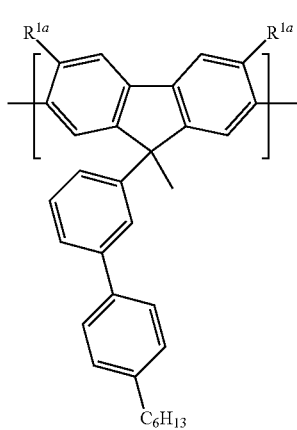
1-26a
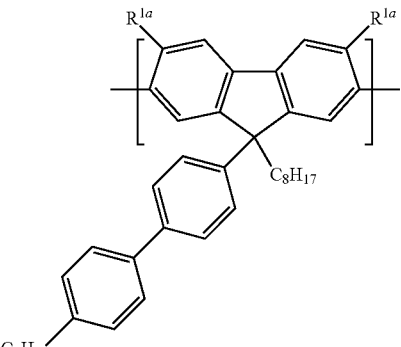
1-27a
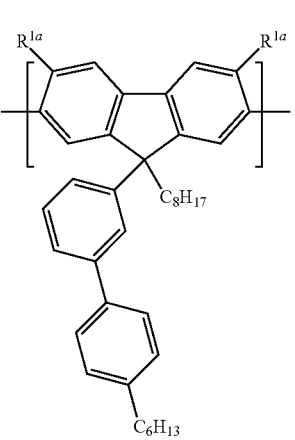
1-28a
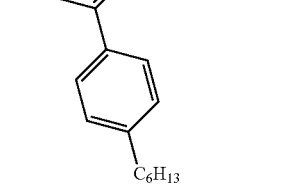
1-1b
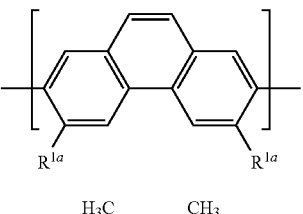
1-2b
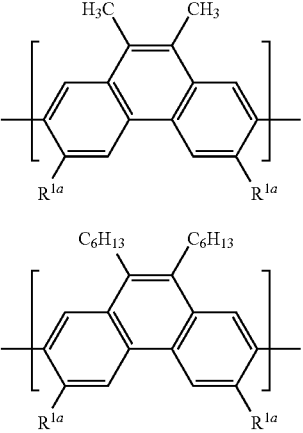
1-3b
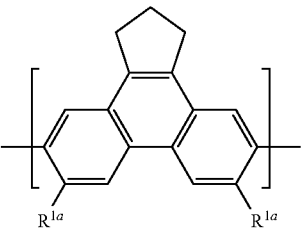
1-4b

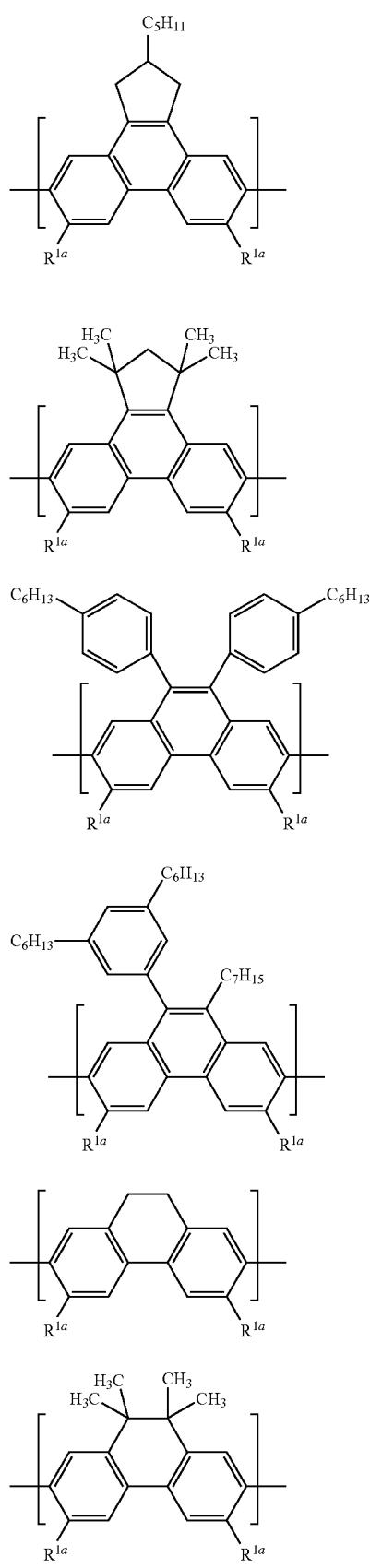
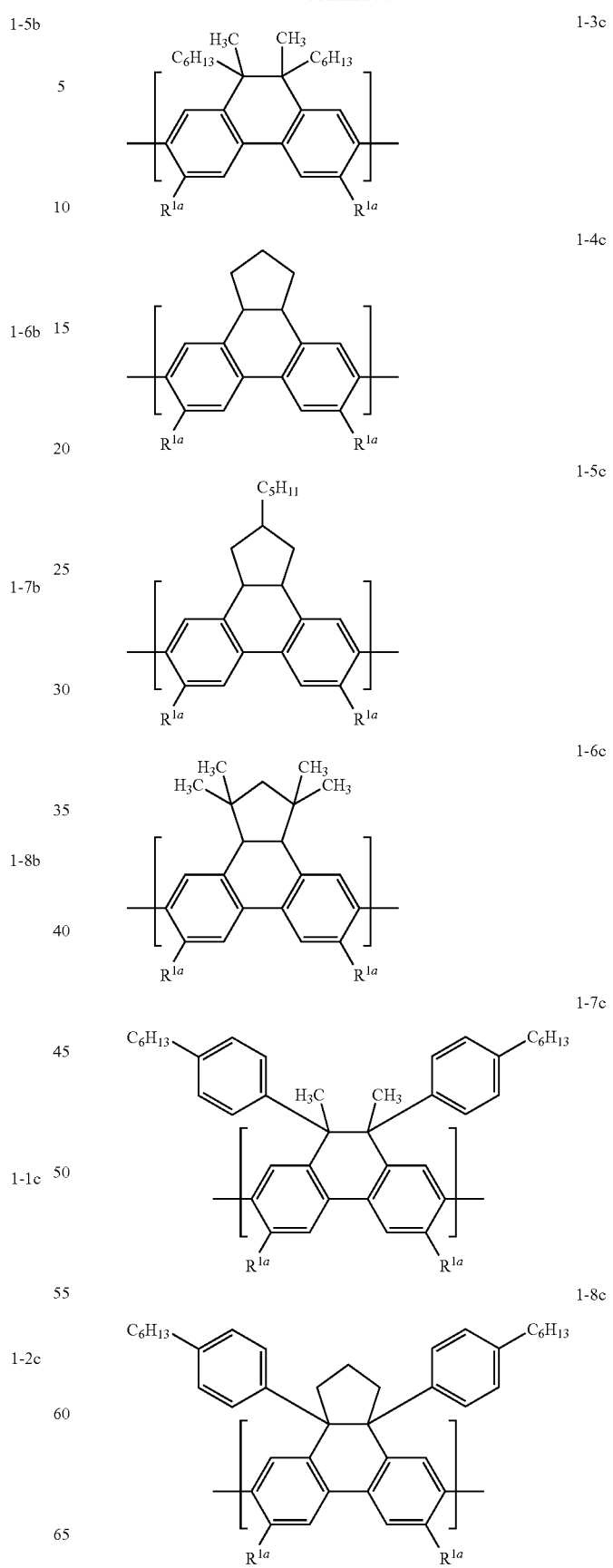

-continued

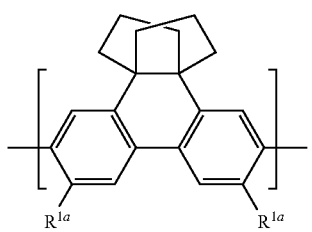
1-9c

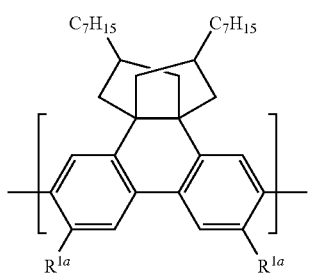
1-10c

The substituent which $R^{1a}$, $R^{1c}$ and $R^{1d}$ to $R^{1f}$ in the formula (1) may have includes, for example, an alkyl group, an aryl group, a monovalent aromatic heterocyclic group and an aralkyl group, and an alkyl group is preferable and a methyl group, an ethyl group, a propyl group and a hexyl group are more preferable since synthesis of a raw material monomer of the polymer compound of the present embodiment is simpler.

Regarding $R^{1a}$ in the formula (1), it is preferable that a plurality of $R^{1a}$ are the same, since synthesis of a raw material monomer of the polymer compound of the present embodiment is simpler. $R^{1a}$ represents further preferably a methyl group, an ethyl group or a propyl group, particularly preferably a methyl group.

(Group Represented by the Formula (2))

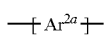
(2)

[in the formula (2), $Ar^{2a}$ represents an arylene group, a divalent aromatic heterocyclic group, or a divalent group obtained by mutually linking 2 to 10 groups selected from the group consisting of an arylene group and a divalent aromatic heterocyclic group, and these groups may have a substituent.

Here, in the group represented by the formula (2), at least one of carbon atoms adjacent to a carbon atom forming a bond to the other repeating unit has an alkyl group, an aryl group, a monovalent aromatic heterocyclic group or an aralkyl group as a substituent. The group represented by the formula (2) is different from the group represented by the formula (1).]

The group represented by the formula (2) is contained as a repeating unit in the polymer compound of the present embodiment, and when there are plural methods for recognizing the group represented by the formula (2) in a polymer chain, a group in which the number of $Ar^{2a}$ is least is recognized as the group represented by the formula (2).

In the group represented by the formula (2), at least one of carbon atoms adjacent to a carbon atom forming a bond to the other repeating unit has an alkyl group, an aryl group, a monovalent aromatic heterocyclic group or an aralkyl group as a substituent. By this, it becomes possible to enhance the $T_1$ energy level the polymer compound of the present embodiment. Of these substituents, an alkyl group is preferable since synthesis of a raw material monomer of the polymer compound of the present embodiment is simpler.

The group represented by the formula (2) is preferably a group represented by the formula (2A) since the $T_1$ energy level the polymer compound of the present embodiment is higher.

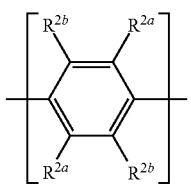
(2A)

[in the formula (2A), $R^{2a}$ represents an alkyl group, an aryl group, a monovalent aromatic heterocyclic group or an aralkyl group, and these groups may have a substituent. A plurality of $R^{2a}$ may be mutually the same or different.

$R^{2b}$ represents a hydrogen atom, an alkyl group, an aryl group, a monovalent aromatic heterocyclic group or an aralkyl group, and these groups may have a substituent. A plurality of $R^{2b}$ may be mutually the same or different.]

$R^{2a}$ in the formula (2A) is preferably an alkyl group or an aralkyl group, more preferably an alkyl group, particularly preferably a methyl group, an ethyl group, a propyl group, an isopropyl group, a butyl group, a sec-butyl group, an isobutyl group, a pentyl group, an isoamyl group, a hexyl group, a cyclohexyl group, a heptyl group, a cyclohexylmethyl group, an octyl group, a 2-ethylhexyl group, a 2-cyclohexylethyl group, a nonyl group, a decyl group, a 3,7-dimethyloctyl group or a dodecyl group, since the heat resistance of the polymer compound of the present embodiment and the solubility thereof in an organic solvent are obtained with good balance.

$R^{2b}$ in the formula (2A) is preferably a hydrogen atom, an alkyl group or an aralkyl group, more preferably a hydrogen atom or an alkyl group, further a hydrogen atom, since the heat resistance of the polymer compound of the present embodiment and the solubility thereof in an organic solvent are obtained with good balance and reactivity in polymerization of a raw material monomer of the polymer compound of the present embodiment is excellent.

The group represented by the formula (2A) includes, for example, groups represented by the following formulae 2A-001 to 2A-019 and 2A-101 to 2A-105, and groups represented by the formulae 2A-003 to 2A-015 and 2A-018 to 2A-019 are preferable and groups represented by the formulae 2A-005 to 2A-015 and 2A-019 are more preferable because of excellent solubility in a solvent.

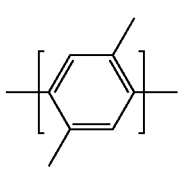
2A-001

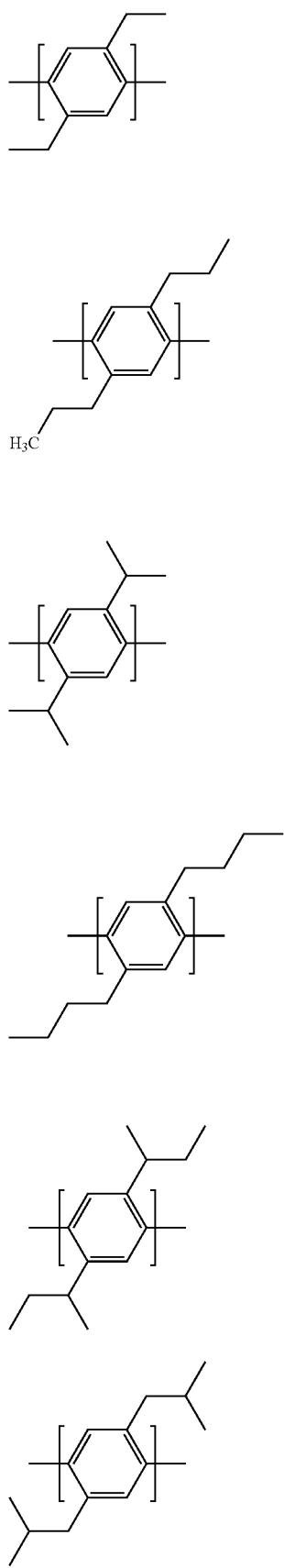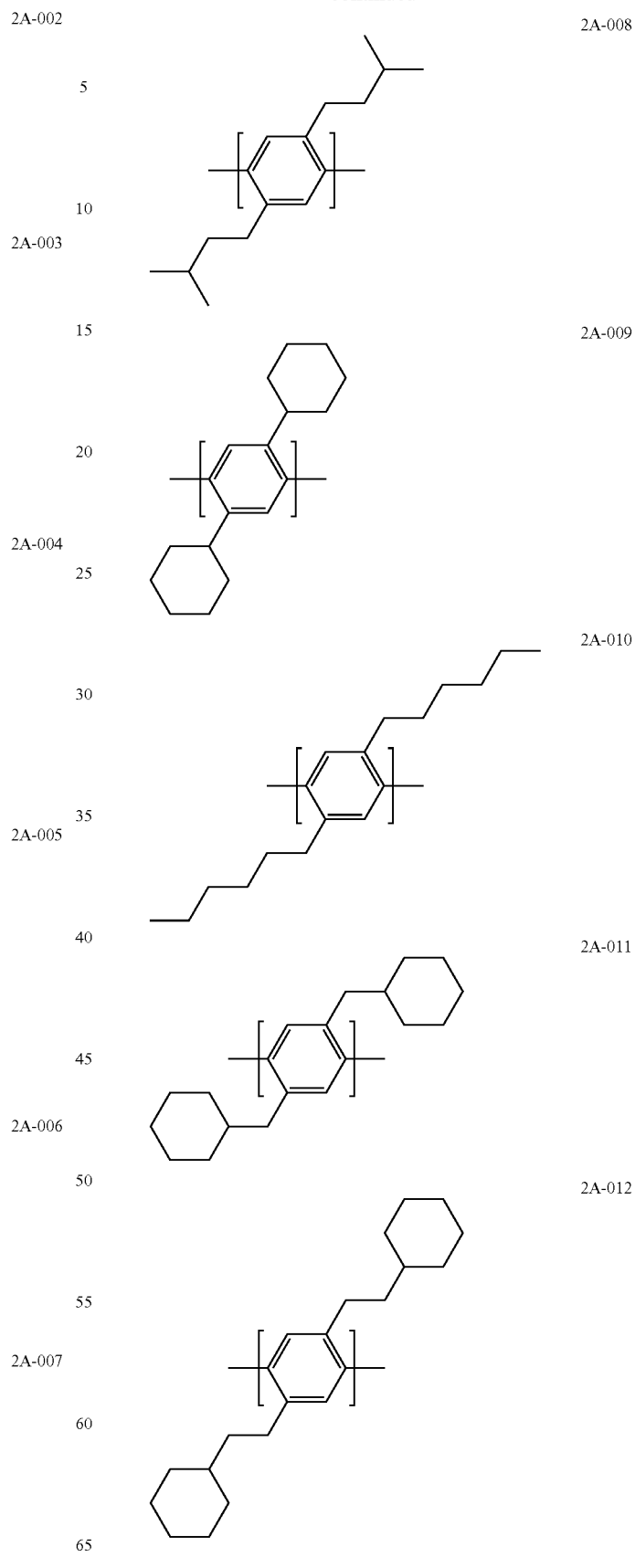

2A-013
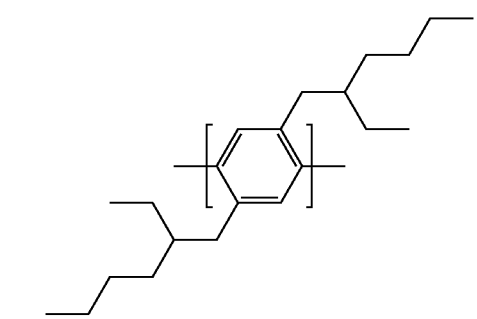
2A-014
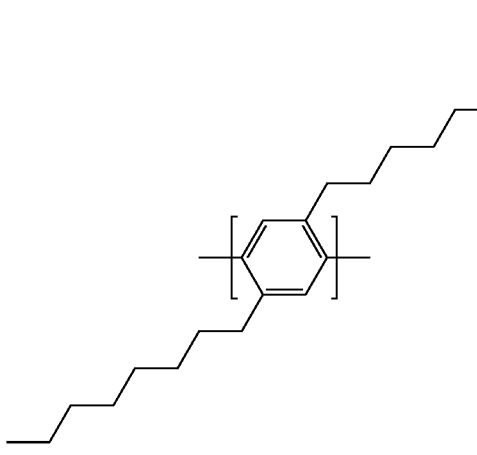
2A-015
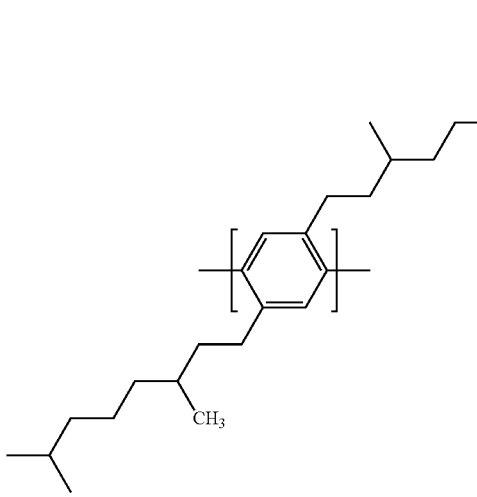
2A-016
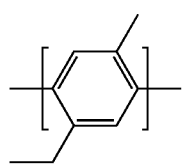
2A-017
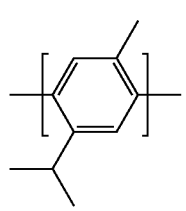
2A-018
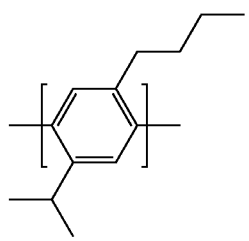
2A-019
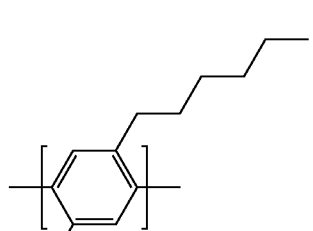
2A-101
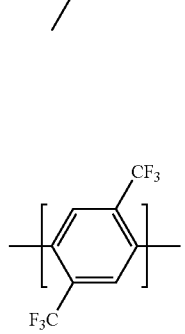
2A-102
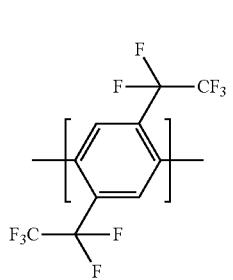
2A-103
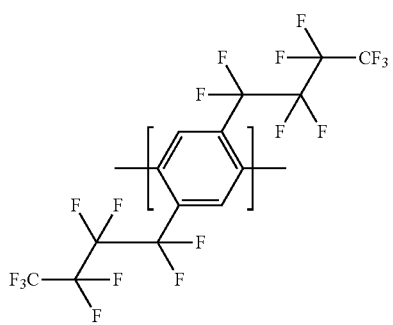

-continued

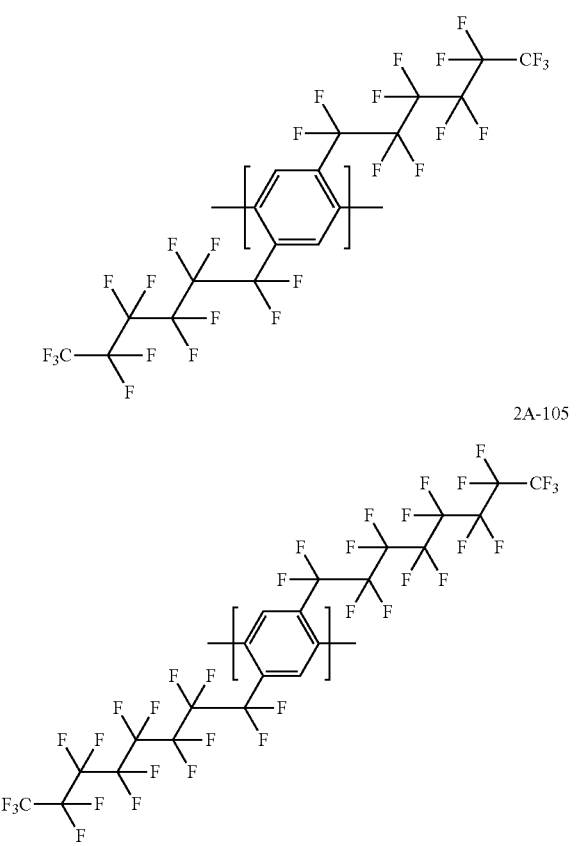

2A-104

2A-105

The group represented by the formula (2) is preferably a group represented by the formula (2B), since the $T_1$ energy level of the polymer compound of the present embodiment is higher and the driving voltage of a light emitting device using the polymer compound of the present embodiment is lower.

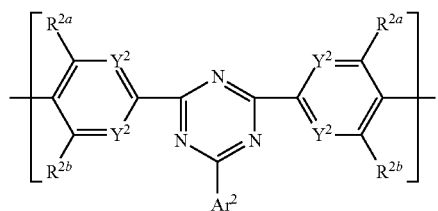

(2B)

[in the formula (2B),

Y$^2$ represents a carbon atom or a nitrogen atom, and the carbon atom may have an alkyl group, an aryl group, a monovalent aromatic heterocyclic group or an aralkyl group as a substituent. A plurality of Y$^2$ may be mutually the same or different.

R$^{2c}$ represents an alkyl group, an aryl group, a monovalent aromatic heterocyclic group or an aralkyl group, and these groups may have a substituent. A plurality of R$^{2c}$ may be mutually the same or different.

R$^{2d}$ represents a hydrogen atom, an alkyl group, an aryl group, a monovalent aromatic heterocyclic group or an aralkyl group, and these groups may have a substituent. A plurality of R$^{2d}$ may be mutually the same or different.

Ar$^2$ represents an aryl group or a monovalent aromatic heterocyclic group, and these groups may have a substituent.]

Y$^2$ in the formula (2B) is preferably a carbon atom or a nitrogen atom carrying an alkyl group as a substituent.

The substituent which Ar$^2$ in the formula (2B) may have includes, for example, an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

Ar$^2$ in the formula (2B) is preferably an aryl group or a monovalent aromatic heterocyclic group, more preferably an aryl group having an alkyl group as a substituent or a monovalent aromatic heterocyclic group having an alkyl group as a substituent, further preferably an aryl group having an alkyl group as a substituent, since the driving voltage of a light emitting device using the polymer compound of the present embodiment is lower.

R$^{2a}$ in the formula (2B) is preferably an alkyl group or an aralkyl group, more preferably an alkyl group, further preferably a methyl group, an ethyl group, a propyl group, an isopropyl group, a butyl group, a sec-butyl group, an isobutyl group, a pentyl group, an isoamyl group, a hexyl group, a cyclohexyl group, a heptyl group, a cyclohexylmethyl group, an octyl group, a 2-ethylhexyl group, a 2-cyclohexylethyl group, a nonyl group, a decyl group, a 3,7-dimethyloctyl group or an dodecyl group, since the heat resistance of the polymer compound of the present embodiment and the solubility thereof in an organic solvent are obtained with good balance.

R$^{2b}$ in the formula (2B) is preferably a hydrogen atom, an alkyl group or an aralkyl group, more preferably a hydrogen atom or an alkyl group, further preferably a hydrogen atom, since the heat resistance of the polymer compound of the present embodiment and the solubility thereof in an organic solvent are obtained with good balance and reactivity in polymerization of a raw material monomer of the polymer compound of the present embodiment is more excellent.

The group represented by the formula (2B) includes, for example, groups represented by the following formulae 2B-001 to 2B-012, 2B-101 to 2B-103, 2B-201 to 2B-203, 2B-301 to 2B-303 and 2B-401 to 2B-403, and groups represented by the formulae 2B-001 to 2B-012 are preferable since the driving voltage of a light emitting device using the polymer compound of the present embodiment is lower.

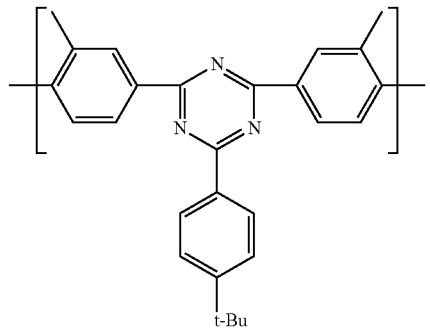

2B-001

-continued
2B-002
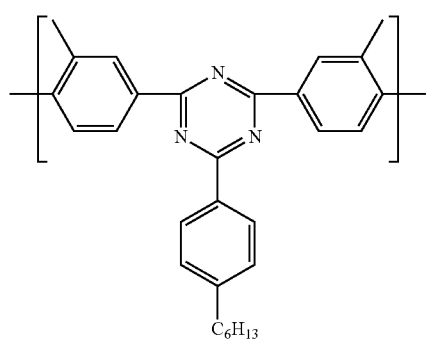
2B-003
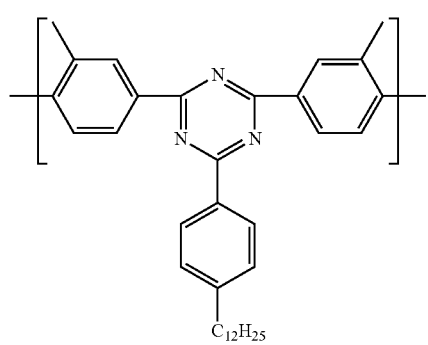
2B-004
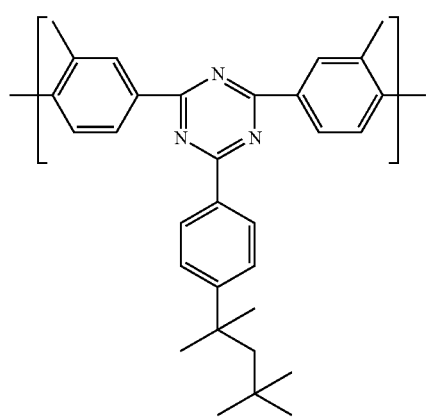
2B-005
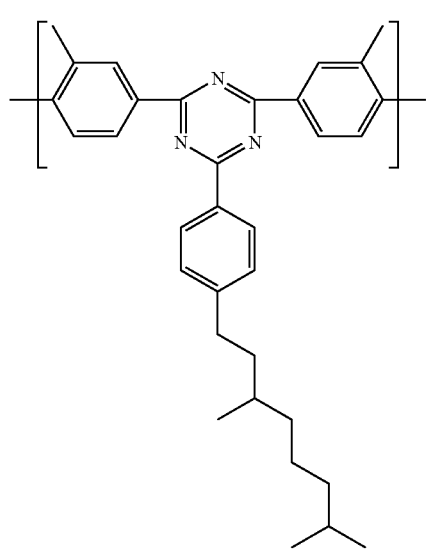
-continued
2B-006
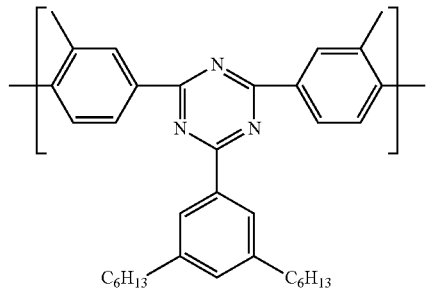
2B-007
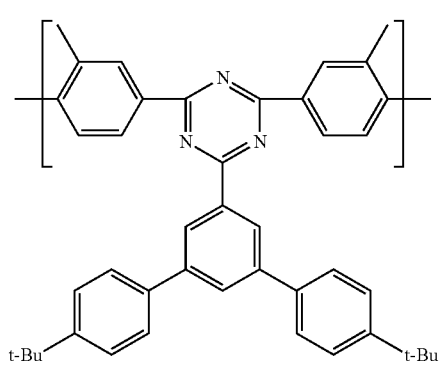
2B-008
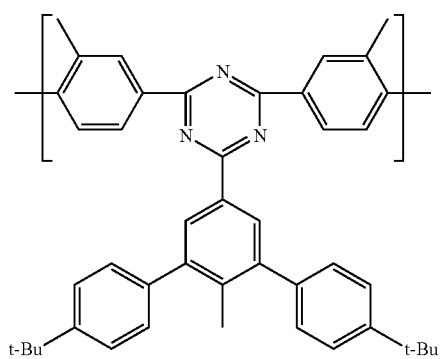
2B-009
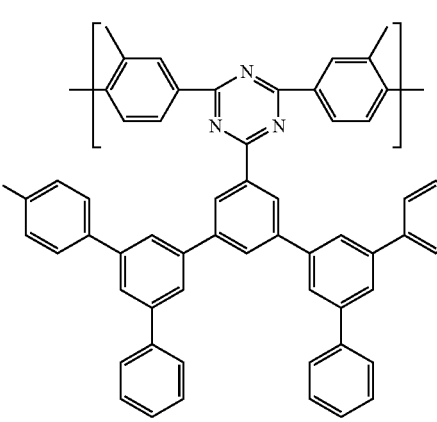

-continued
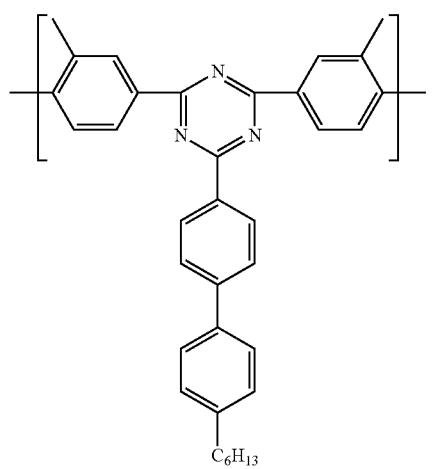
2B-010
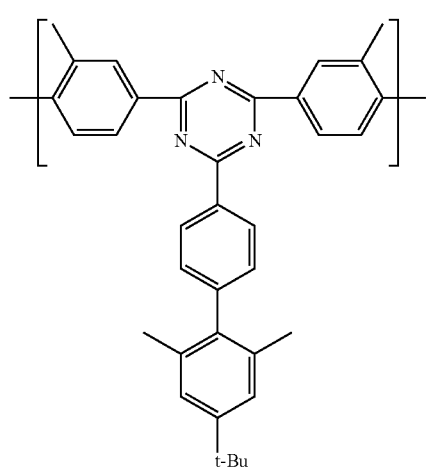
2B-011
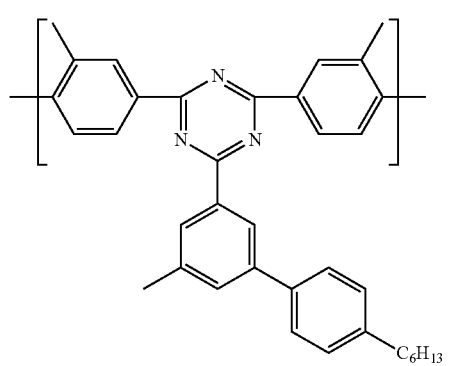
2B-012
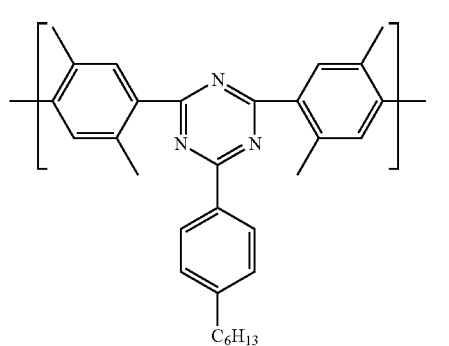
2B-101
-continued
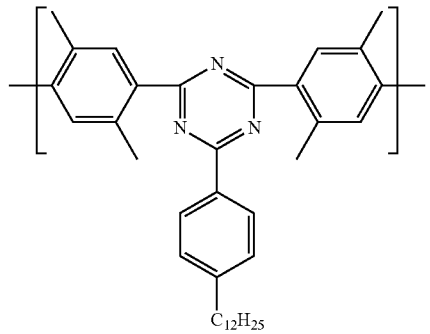
2B-102
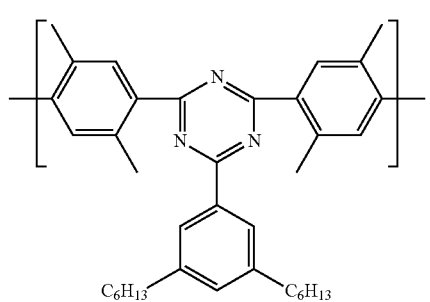
2B-103
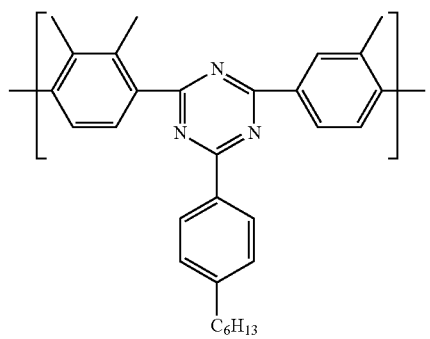
2B-201
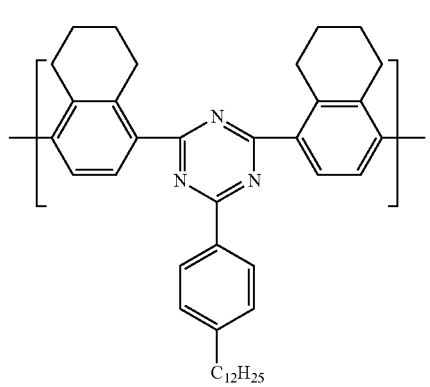
2B-202
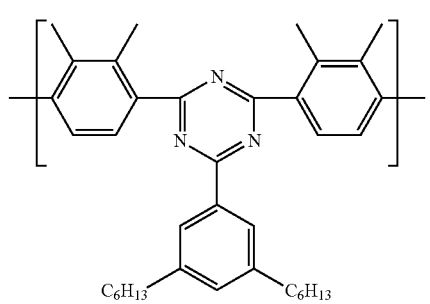
2B-203

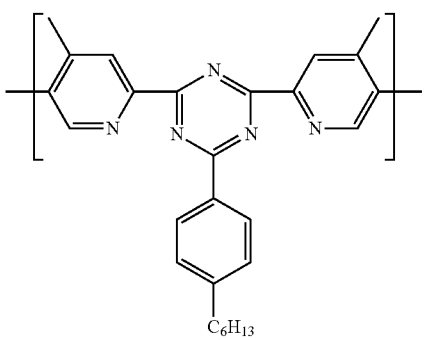

2B-301

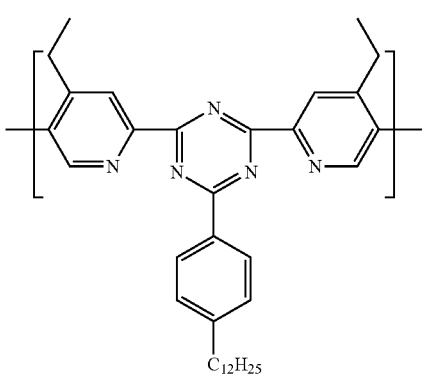

2B-302

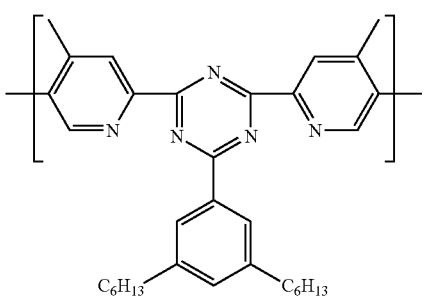

2B-303

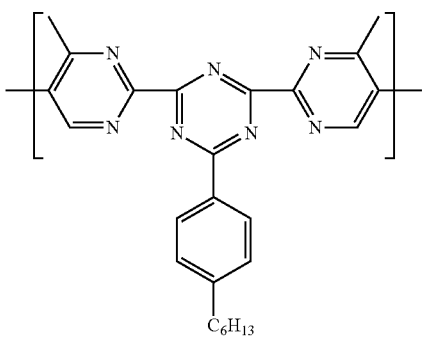

2B-401

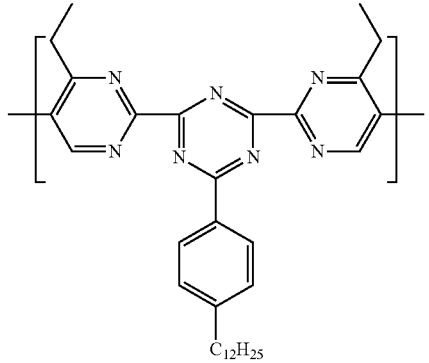

2B-402

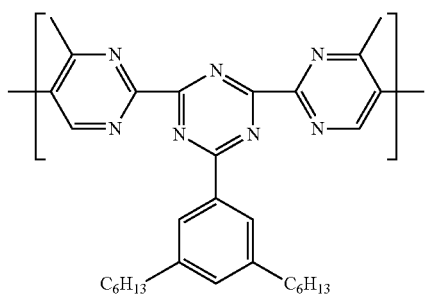

2B-403

(Group Represented by the Formula (3))

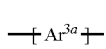

(3)

[in the formula (3),

Ar$^{3a}$ represents an arylene group, a divalent aromatic heterocyclic group, or a divalent group obtained by mutually linking 2 to 10 groups selected from the group consisting of an arylene group and a divalent aromatic heterocyclic group, and these groups may further have a substituent.

Here, the group represented by the formula (3) is different from the group represented by the above-described formula (1) and the group represented by the above-described formula (2).]

The group represented by the formula (3) is contained as a repeating unit in the polymer compound of the present embodiment, and when there are plural methods for recognizing the group represented by the formula (3) in a polymer chain, a group in which the number of Ar$^{3a}$ is least is recognized as the group represented by the formula (3).

The group represented by the formula (3) is a group different from the group represented by the formula (1) and the group represented by the formula (2) (here, at least one of carbon atoms adjacent to a carbon atom forming a bond to the other repeating unit is a group not having an alkyl group, an aryl group, a monovalent aromatic heterocyclic group or an aralkyl group as a substituent). By this, synthesis of the polymer compound of the present embodiment is simpler and the driving voltage of a light emitting device using the polymer compound of the present embodiment is lower.

The group represented by the formula (3) is preferably a group represented by the formula (3A), since the driving voltage of a light emitting device using the polymer compound of the present embodiment is lower.

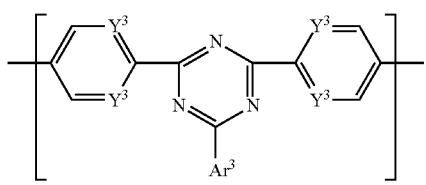

(3A)

[in the formula (3A), $Y^3$ represents a carbon atom or a nitrogen atom, and the carbon atom may have an alkyl group, an aryl group, a monovalent aromatic heterocyclic group or an aralkyl group as a substituent. A plurality of $Y^3$ may be the same or different.

$Ar^3$ represents an aryl group or a monovalent aromatic heterocyclic group, and these groups may have a substituent.]

$Y^3$ in the formula (3A) is preferably a carbon atom or a nitrogen atom carrying an alkyl group as a substituent.

The substituent which $Ar^3$ in the formula (3A) may have includes an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

$Ar^3$ in the formula (3A) is preferably an aryl group or a monovalent aromatic heterocyclic group, more preferably an aryl group having an alkyl group as a substituent or a monovalent aromatic heterocyclic group having an alkyl group as a substituent, further preferably an aryl group having an alkyl group as a substituent, since the luminance life of a light emitting device using the polymer compound of the present embodiment is more excellent.

The group represented by the formula (3A) includes, for example, groups represented by the following formulae 3A-001 to 3A-012, 3A-301 to 3A-303 and 3A-401 to 3A-403, and groups represented by the formulae 3A-001 to 3A-012 are preferable since the luminance life of a light emitting device using the polymer compound of the present embodiment is more excellent.

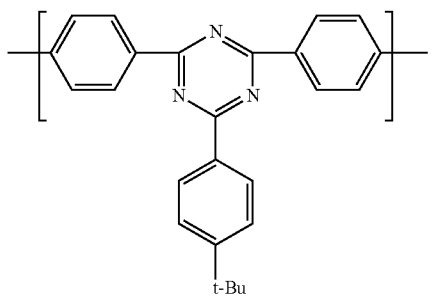

3A-001

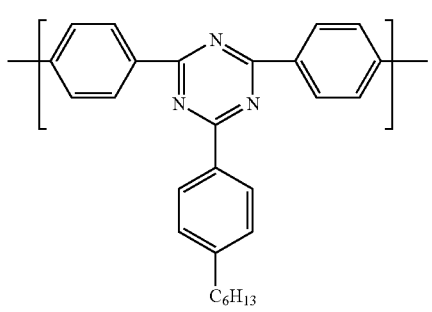

3A-002

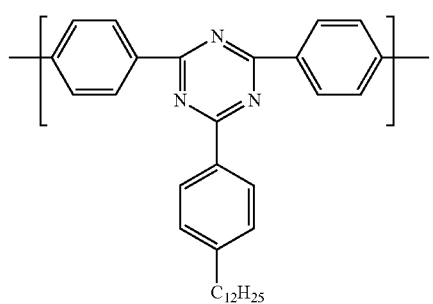

3A-003

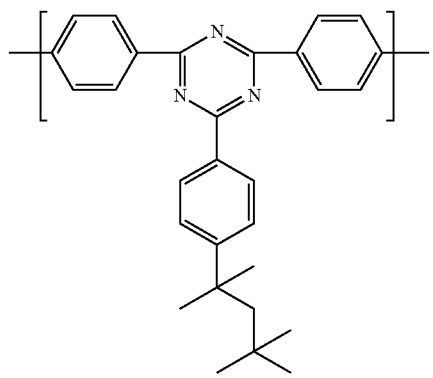

3A-004

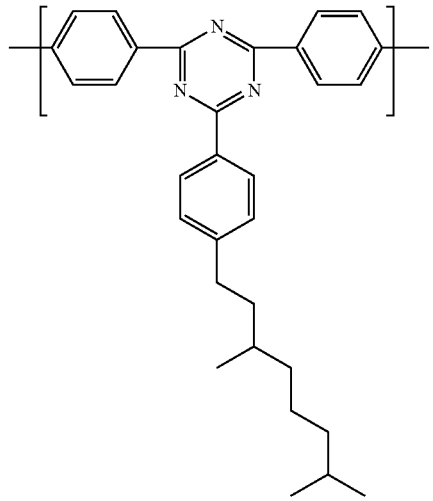

3A-005

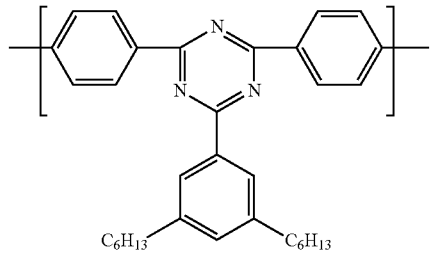

3A-006

3A-007
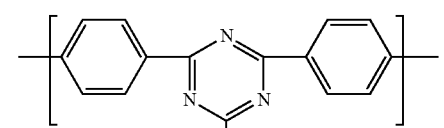
3A-008
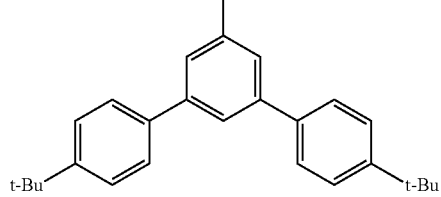
3A-009
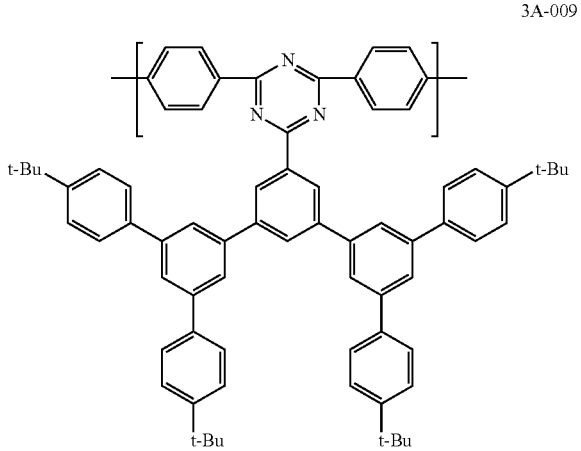
3A-010
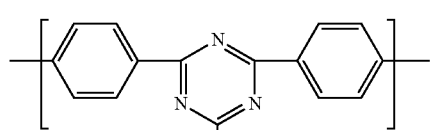
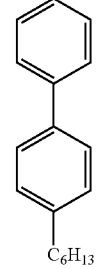
3A-011
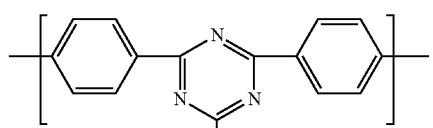
3A-012
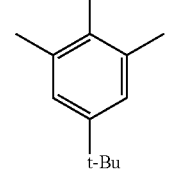
3A-301
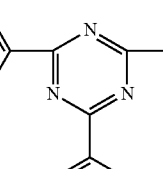
3A-302
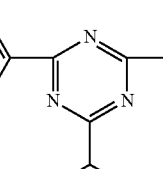
3A-303
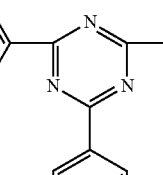

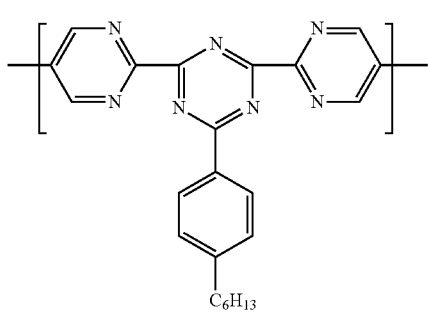

3A-401

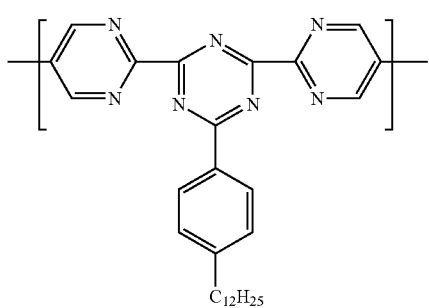

3A-402

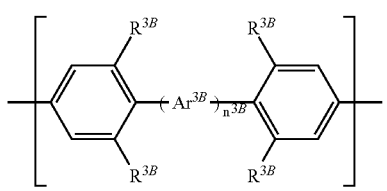

3A-403

The group represented by the formula (3) is preferably a group represented by the following formula (3B), since the current efficiency of a light emitting device using the polymer compound of the present embodiment is excellent.

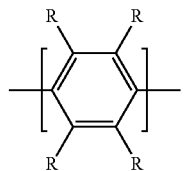

(3B)

[in the formula (3B), $n^{3B}$ represents an integer of 1 to 3.

$Ar^{3B}$ represents an arylene group or a divalent aromatic heterocyclic group, and these groups may have a substituent. When there are a plurality of $Ar^{3B}$, these may be mutually the same or different.

$R^{3B}$ represents an alkyl group, an aryl group, a monovalent aromatic heterocyclic group or an aralkyl group, and these groups may have a substituent. A plurality of $R^{3B}$ may be mutually the same or different.]

The group represented by the formula (3B) is contained as a repeating unit in the polymer compound of the present embodiment, and when there are plural methods for recognizing the group represented by the formula (3B) in a polymer chain, a group in which the value of $n^{3B}$ is lowest is recognized as the group represented by the formula (3B).

$R^{3B}$ in the formula (3B) is preferably an alkyl group, more preferably a methyl group, an ethyl group or a propyl group, further preferably a methyl group, since synthesis of a raw material monomer of the polymer compound of the present embodiment is simpler.

The substituent which $Ar^{3B}$ in the formula (3B) may have includes an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom and a cyano group.

$Ar^{3B}$ in the formula (3B) is preferably a 1,4-phenylene group (the formula 001), a 9,10-dihydrophenanthrene-2,7-diyl group (the formula 007), a fluorene-3,6-diyl group (the formula 008), a fluorene-2,7-diyl group (the formula 009), a 1,3,5-triazine-2,4-diyl group (the formula 104), a carbazole-3,6-diyl group (the formula 110), a carbazole-2,7-diyl group (the formula 111), a dibenzofuran-4,7-diyl group (the formula 112), a dibenzofuran-3,8-diyl group (the formula 113), a dibenzothiophene-4,7-diyl group (the formula 114) or a dibenzothiophene-3,8-diyl group (the formula 115).

When $Ar^{3B}$ in the formula (3B) is a 1,4-phenylene group (the formula 001), it is preferable that $n^{3B}$ is 1 or 2, and the group represented by $Ar^{3B}$ includes a group represented by the following formula 3B-001.

3B-001

(wherein, R represents the same meaning as described above.)

When $Ar^{3B}$ in the formula (3B) is a group selected from the group consisting of a 9,10-dihydrophenanthrene-2,7-diyl group (the formula 007), a fluorene-3,6-diyl group (the formula 008), a fluorene-2,7-diyl group (the formula 009), a carbazole-3,6-diyl group (the formula 110), a carbazole-2,7-diyl group (the formula 111), a dibenzofuran-4,7-diyl group (the formula 112), a dibenzofuran-3,8-diyl group (the formula 113), a dibenzothiophene-4,7-diyl group (the formula 114) and a dibenzothiophene-3,8-diyl group (the formula 115), it is preferable that $n^{3B}$ is 1.

When $Ar^{3B}$ in the formula (3B) includes a 1,3,5-triazine-2,4-diyl group (the formula 104), it is preferable that $n^{3B}$ is 3, and the group represented by $Ar^{3B}$ includes groups represented by the following formulae 3B-301 to 3B-321, and groups represented by the formulae 3B-301 to 3B-309 are preferable and groups represented by the formulae 3B-301, 3B-303, 3B-304, 3B-308 and 3B-309 are more preferable from the standpoint of easiness of synthesis of a monomer compound as a raw material.

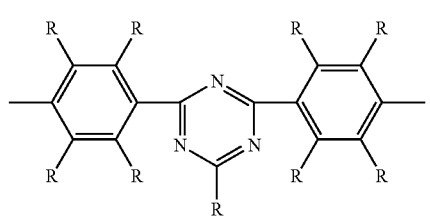

3B-301

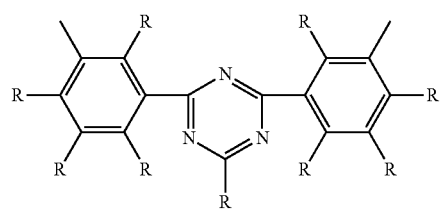
3B-302
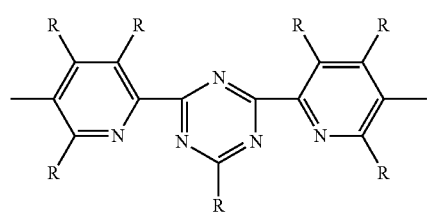
3B-303
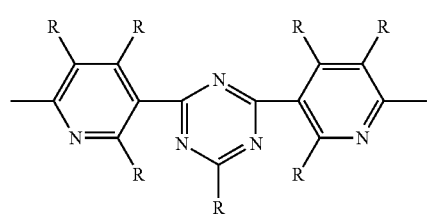
3B-304
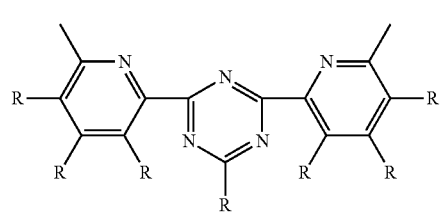
3B-305
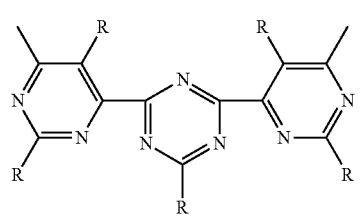
3B-306
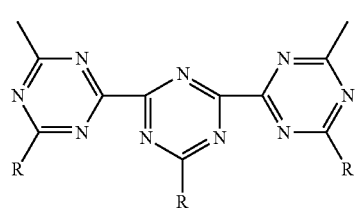
3B-307
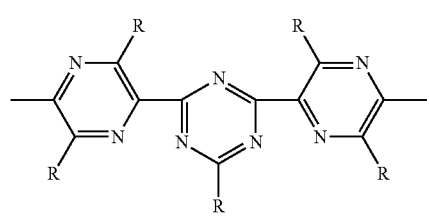
3B-308
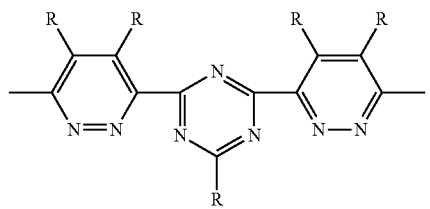
3B-309
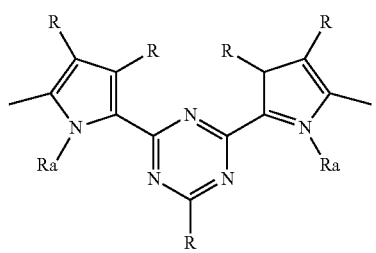
3B-310
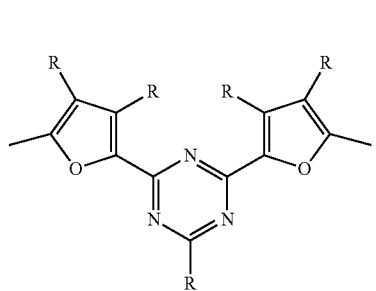
3B-311
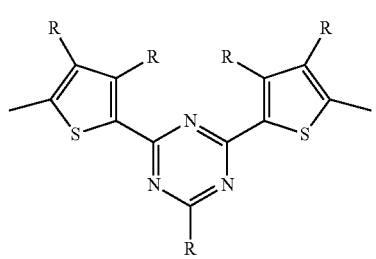
3B-312
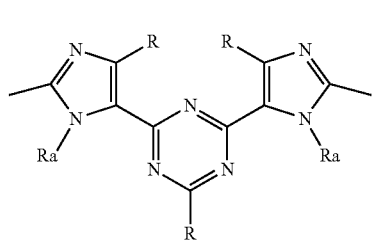
3B-313
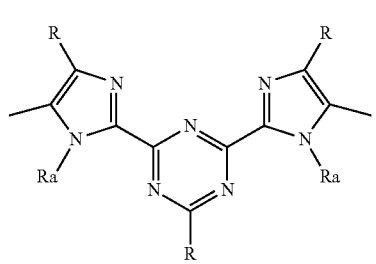
3B-314

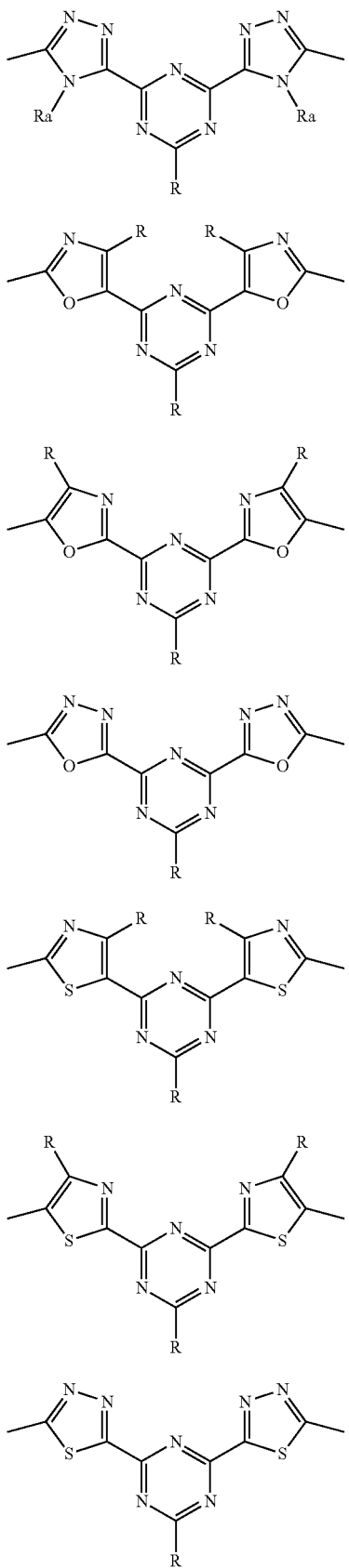

3B-315
3B-316
3B-317
3B-318
3B-319
3B-320
3B-321

(wherein, R and Ra represent the same meaning as described above.)

The group represented by the formula (3B) includes preferably those in which the group represented by $Ar^{3B}$ contains a 1,3,5-triazine-2,4-diyl group (the formula 104), and of them, groups represented by the following formulae 3B-401 to 3B-412, 3B-501 to 3B-503 and 3B-601 to 3B-603 are more preferable, since the luminance life of a light emitting device using the polymer compound of the present embodiment is more excellent.

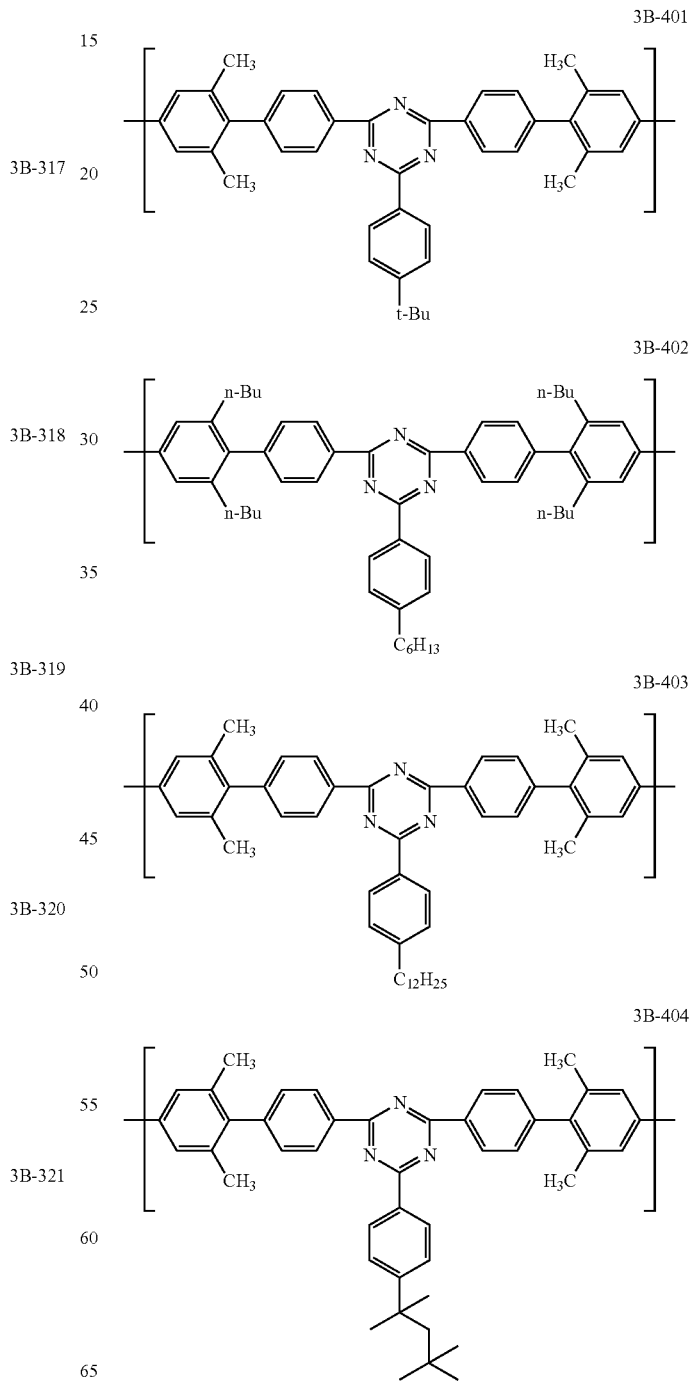

3B-401
3B-402
3B-403
3B-404

3B-405
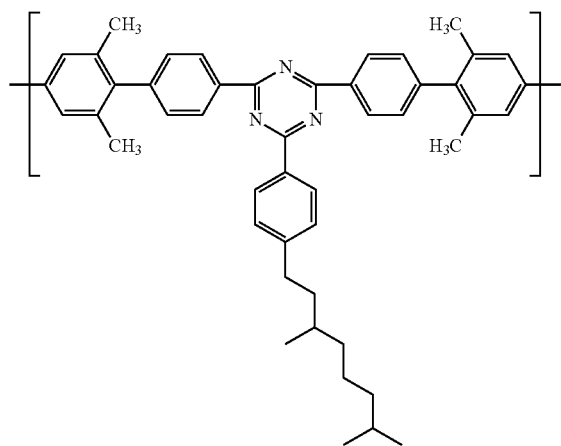
3B-406
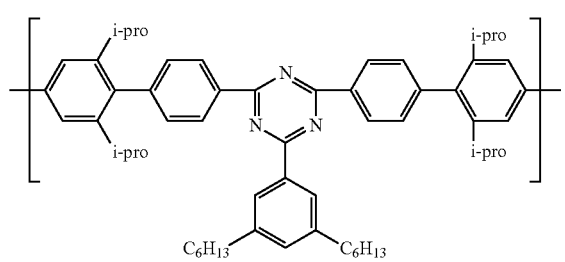
3B-407
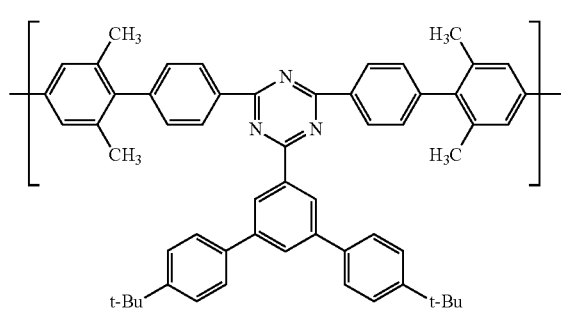
3B-408
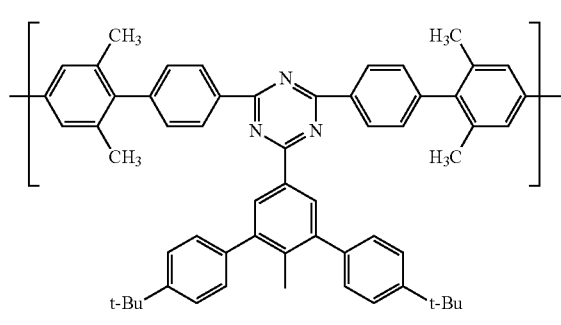
3B-409
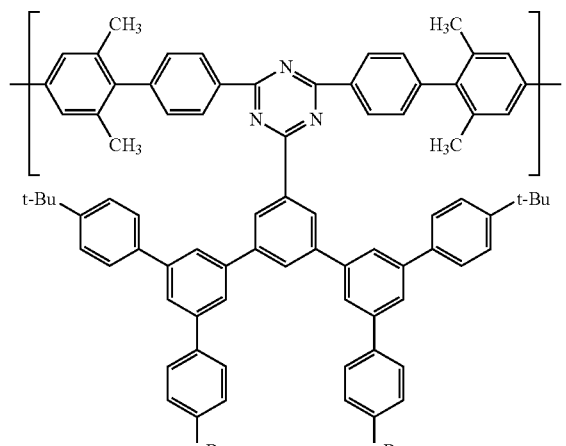
3B-410
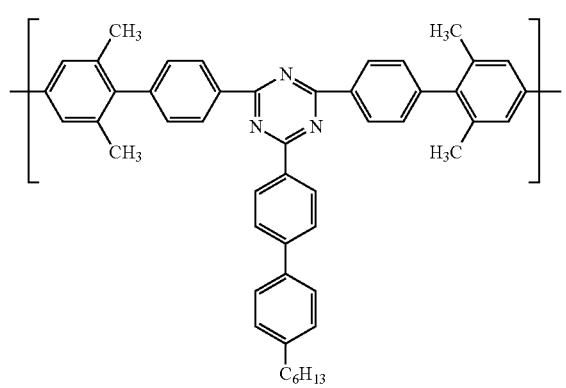
3B-411
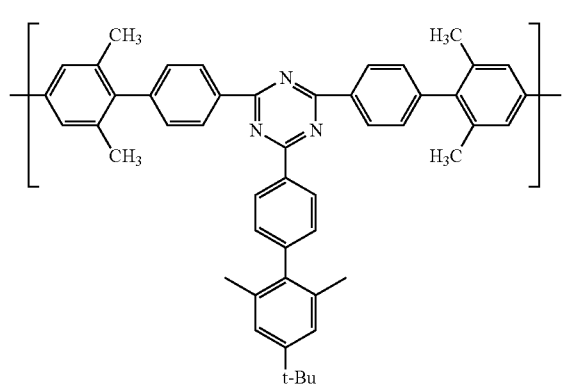
3B-412
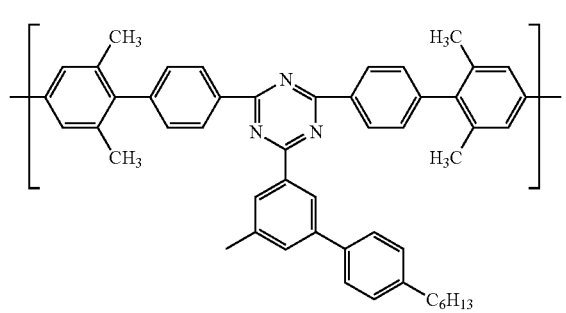

3B-501
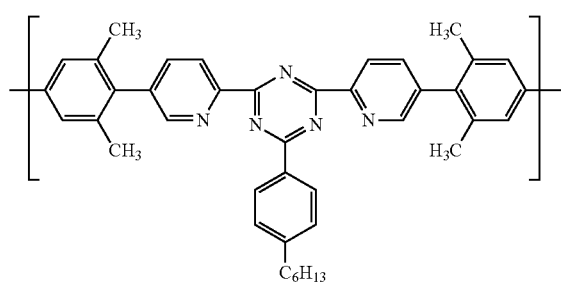

3B-502
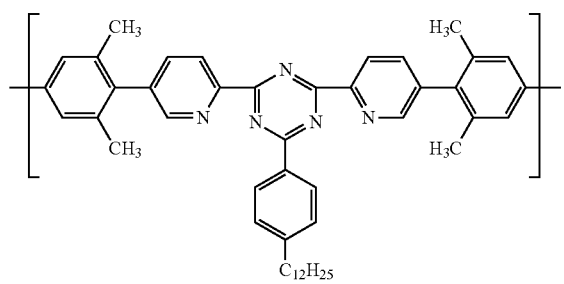

3B-503
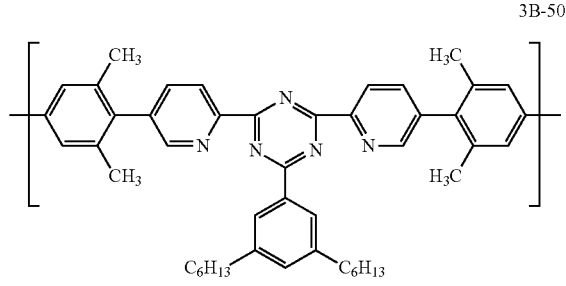

3B-601
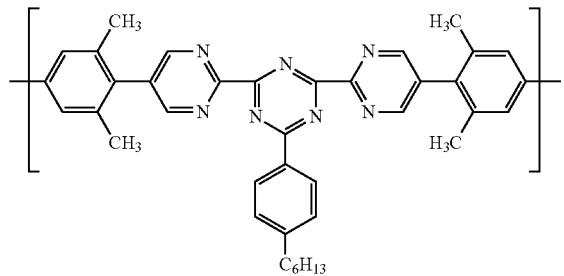

3B-602
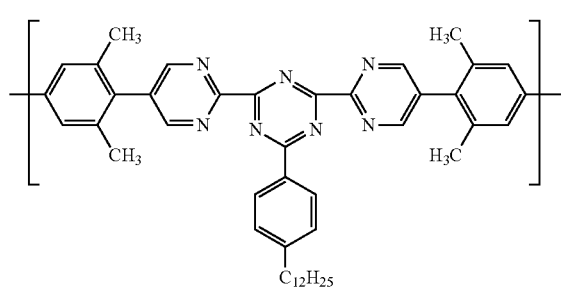

3B-603
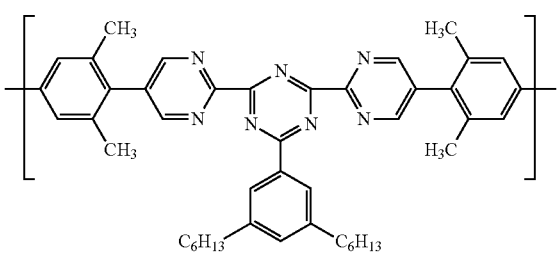

It is preferable that the polymer compound of the present invention further contains a divalent aromatic amine residue as a repeating unit, since the driving voltage of a light emitting device using the polymer compound of the present embodiment is lower.

The divalent aromatic amine residue is, for example, a group represented by the following general formula (4).

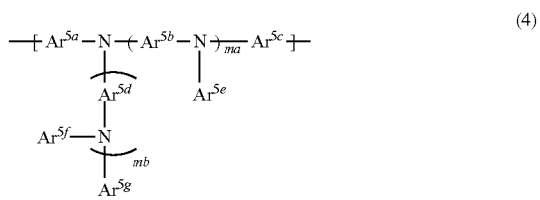

(4)

[in the formula (4), $Ar^{5a}$ to $Ar^{5g}$, ma and mb represent the same meaning as described above.]

It is preferable that ma and mb are 0 in the above-described general formula (4), since the current efficiency of a light emitting device using the polymer compound of the present embodiment is excellent.

Examples of the divalent aromatic amine residue include groups represented by the following formulae 4-001 to 4-006, and groups represented by the formulae 4-001 and 4-003 to 4-005 are preferable since the current efficiency of a light emitting device using the polymer compound of the present embodiment is excellent.

4-001
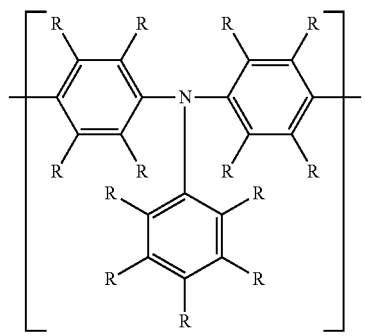

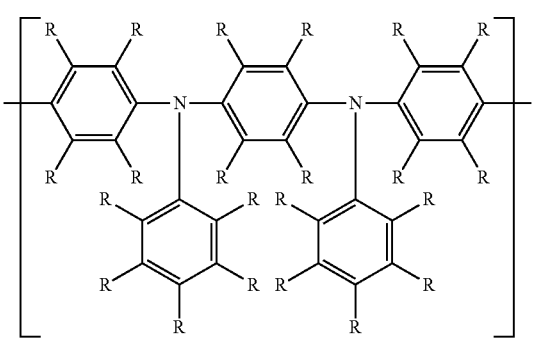

4-002

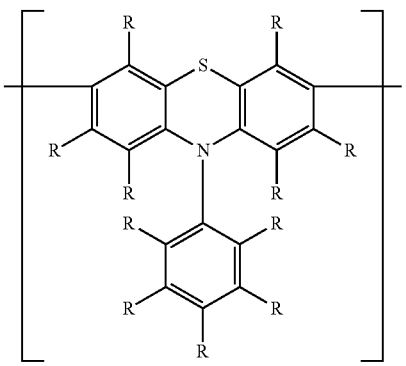

4-006

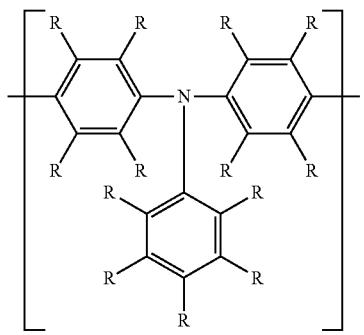

4-003

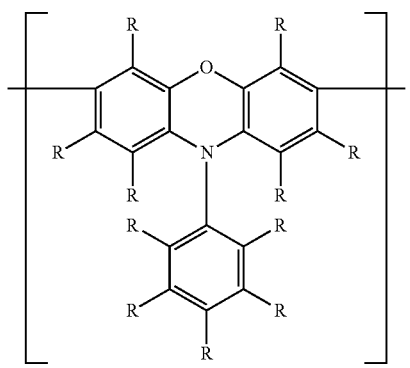

4-004

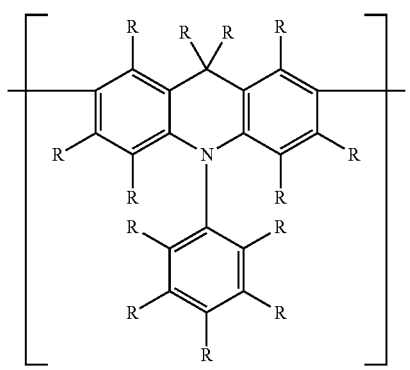

4-005

(Complex Polymer Compound)

The polymer compound of the present embodiment may be a polymer compound having as a constitutional unit a monovalent to trivalent group derived from the residue of a phosphorescent compound (hereinafter, referred to as "complex polymer compound").

The constitutional unit which is a monovalent to trivalent group derived from the residue of a phosphorescent compound contained in the complex polymer compound of the present embodiment includes a constitutional unit which is a monovalent group derived from the residue of a phosphorescent compound, present as a monovalent group at the end of a polymer chain, a constitutional unit which is a divalent group derived from the residue of a phosphorescent compound, present as a divalent group in the main chain of a polymer chain (preferably, a repeating unit), and a constitutional unit which is a trivalent group derived from the residue of a phosphorescent compound, present as a trivalent group in the main chain of a polymer chain (preferably, a repeating unit). In the constitutional unit which is a trivalent group derived from the residue of a phosphorescent compound, present as a trivalent group in the main chain of a polymer chain, the polymer chain branches at the constitutional unit.

The constitutional unit which is a monovalent group derived from the residue of a phosphorescent compound, present as a monovalent group at the end of a polymer chain includes a monovalent residue remaining after removing one hydrogen atom from a ligand represented by L in a phosphorescent compound represented by the formula (MM) described later.

The constitutional unit which is a divalent group derived from the residue of a phosphorescent compound, present as a divalent group in the main chain of a polymer chain includes an arylene group or a divalent aromatic heterocyclic group having as a substituent a monovalent residue obtained by removing one hydrogen atom from a ligand represented by L in a phosphorescent compound represented by the formula (MM) described later, a divalent residue obtained by removing two hydrogen atoms from one ligand represented by L in a phosphorescent compound represented by the formula (MM) described later, and a divalent residue obtained by removing each one hydrogen atom from two ligands represented by L in a phosphorescent compound represented by the formula (MM) described later.

The constitutional unit which is a trivalent group derived from the residue of a phosphorescent compound, present as a trivalent group in the main chain of a polymer chain includes a trivalent residue obtained by removing three hydrogen atoms from one ligand represented by L in a phosphorescent compound represented by the formula (MM) described later, a trivalent residue obtained by removing one hydrogen atom and two hydrogen atoms from two ligands represented by L in a phosphorescent compound represented by the formula (MM) described later, and a trivalent residue obtained by removing each one hydrogen atom from three ligands represented by L in a phosphorescent compound represented by the formula (MM) described later. (Tg and solubility of polymer compound)

The glass transition temperature (hereinafter, referred to as "Tg" in some cases) of the polymer compound of the present invention is preferably 60° C. or higher, more preferably 80° C. or higher, particularly preferably 100° C. or higher, since when the polymer compound of the present invention is used in production of a light emitting device, more stable shape of an organic film can be obtained, the preservation temperature range of the resultant light emitting device can be enlarged and the stability of the luminance life or the like of the resultant light emitting device can be improved. When the polymer compound of the present invention is used in the form of a composition with a phosphorescent compound described later, a metal complex as the phosphorescent compound has usually high glass transition temperature (Tg), thus, the glass transition temperature of the composition of the present embodiment is higher than the glass transition temperature of a single body of the polymer compound of the present invention.

For adjusting the glass transition temperature of the polymer compound of the present invention within the above-described preferable range, it is preferable to introduce a suitable substituent into a repeating unit contained in the polymer compound. The substituent is preferably an alkyl group.

Since a solution coating method is usually used when the polymer compound of the present invention is used for production of a light emitting device, if it is used together with a phosphorescent compound described later, it is preferable that the polymer compound manifests solubility in a solvent which is capable of dissolving the phosphorescent compound.

For allowing the polymer compound of the present invention to have suitable solubility, it is preferable to introduce a suitable substituent into a repeating unit contained in the polymer compound. The substituent is preferably an alkyl group.

(Structure of Polymer Compound)

The preferable structure of the polymer compound of the present invention will be illustrated below.

In the polymer compound of the present embodiment, the content of a group represented by the formula (1) is preferably 20 mol % or more, more preferably 25 mol % or more, further preferably 30 mol % or more with respect to the total content of repeating units contained in the polymer compound, since the luminance life of a light emitting device using a composition with a phosphorescent compound described later is more excellent.

When the polymer compound of the present embodiment is one containing as a repeating unit a group represented by the formula (2), its content is preferably 15 mol % or more and 90 mol % or less, more preferably 20 mol % or more and 70 mol % or less, further preferably 30 mol % or more and 50 mol % or less with respect to the total content of repeating units contained in the polymer compound, since the current efficiency of a light emitting device using a composition with a phosphorescent compound described later is more excellent.

When the polymer compound of the present embodiment contains as a repeating unit a group represented by the formula (3), the content of the group represented by the formula (3) is preferably 1 mol % or more and 50 mol % or less, more preferably 3 mol % or more and 30 mol % or less, further preferably 5 mol % or more and 20 mol % or less with respect to the total content of repeating units contained in the polymer compound, since the current efficiency of a light emitting device using a composition with a phosphorescent compound described later is more excellent.

When the polymer compound of the present embodiment contains the above-described divalent aromatic amine residue as a repeating unit, its content is preferably 1 mol % or more and 50 mol % or less, more preferably 3 mol % or more and 30 mol % or less, further preferably 5 mol % or more and 20 mol % or less with respect to the total content of repeating units contained in the polymer compound since the current efficiency of alight emitting device using a composition with a phosphorescent compound described later is more excellent.

When the polymer compound of the present embodiment contains groups represented by the formula (3) as a repeating unit, it is preferable that the content of groups represented by the formula (3) is 50 mol % or less with respect to the total content of repeating units contained in the polymer compound and the groups represented by the formula (3) are not mutually substantially adjacent since the current efficiency of a light emitting device using a composition with a phosphorescent compound described later is more excellent. The reason for this is that the $T_1$ energy level of the polymer compound of the present embodiment tends to lower by mutually linking groups represented by the formula (3).

The term "not substantially adjacent" described above means that the proportion of mutual linkage of groups represented by the formula (3) with respect to linkage of all repeating units contained in the polymer compound is 10 mol % or less, and the proportion is preferably 5 mol % or less, more preferably 1 mol % or less, further preferably 0 mol %.

When the polymer compound of the present embodiment contains a group represented by the formula (2) and a group represented by the formula (3) as a repeating unit, it is preferable that the content of a group represented by the formula (2) is 50 mol % or more with respect to the total content of repeating units contained in the polymer compound and groups represented by the formula (1), and a group represented by the formula (1) and a group represented by the formula (3) are not substantially adjacent, since the $T_1$ energy level of the polymer compound of the present embodiment is enhanced more and the driving voltage of a light emitting device using a composition with a phosphorescent compound described later is more excellent. The reason for this is that a constitutional unit obtained by mutual linkage of a group represented by the formula (1) and a group represented by the formula (2) provides a higher effect of reducing the driving voltage of a light emitting device using the polymer compound as compared with a constitutional unit obtained by mutual linkage of groups represented by the formula (1), and a constitutional unit obtained by mutual linkage of a group represented by the formula (1) and a group represented by the formula (2) provides a larger effect of enhancing the $T_1$ energy level of the polymer compound as compared with a constitutional unit obtained by mutual linkage of a group represented by the formula (1) and a group represented by the formula (3). Therefore, the polymer compound of the present embodiment is preferably one polymerized so as to contain a constitutional unit in which a group represented by the formula (2) is linked to both sides of a group represented by the formula (1).

This "not substantially adjacent" represents the same meaning as the above-described "no substantially adjacent".

The polymer compound of the present embodiment may be any of a block copolymer, a random copolymer, an alternate copolymer and a graft copolymer, or may also be another embodiment, and it is preferable, from the above-described standpoint, that the polymer compound of the present embodiment is a copolymer obtained by copolymerizing several kinds of raw material monomers.

[Production Method of Polymer Compound]

The polymer compound of the present invention can be produced by appropriately reacting raw material monomers for introducing repeating units constituting the polymer compound and other constitutional units. As the raw material monomer, use is made of a monomer having a structure in which two connecting bonds linking to a polymer chain of each repeating unit or each group are replaced by a leaving group (hereinafter, referred to also as "polymerization active group") capable of forming a linkage by a polymerization reaction. The polymerization reaction can be conducted, for example, by copolymerizing raw material monomers by applying known polymerization methods such as cross coupling and the like.

For introducing a repeating unit represented by the formula (1), it is preferable to use a compound represented by the following formula (M1).

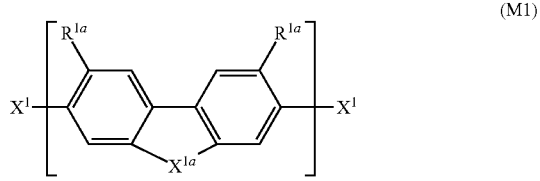

(M1)

[in the formula (M1), $R^{1a}$ represents an alkyl group, an aryl group, a monovalent aromatic heterocyclic group or an aralkyl group, and these groups may have a substituent. A plurality of $R^{1a}$ may be the same or different.

$X^{1a}$ represents a group selected from the group consisting of the following formulae (1a) to (1c).

$X^1$ represents a group selected from the following substituent group (a) or a group selected from the following substituent group (b). A plurality of $X^2$ may be mutually the same or different.

(Substituent Group (a))

a chlorine atom, a bromine atom, an iodine atom and a group represented by —O—S(=O)$_2$R$^{20}$ (R$^{20}$ represents an alkyl group, or an aryl group which may have an alkyl group, an alkoxy group, a nitro group, a fluorine atom or a cyano group as a substituent.).

(Substituent Group (b))

a group represented by —B(OR$^{21}$)$_2$ (R$^{21}$ represents a hydrogen atom or an alkyl group. A plurality of R$^{21}$ may be mutually the same or different and may be mutually linked to form a ring together with an oxygen atom to which they are linked.), a group represented by —BF$_4$Q$^1$ (Q$^1$ represents a monovalent cation of lithium, sodium, potassium, rubidium or cesium.), a group represented by —Sn(R$^{22}$)$_3$ (R$^{22}$ represents a hydrogen atom or an alkyl group. A plurality of R$^{22}$ may be mutually the same or different and may be mutually linked to form a ring together with a tin atom to which they are linked), a group represented by —MgY$^1$ (Y$^1$ represents a chlorine atom, a bromine atom or an iodine atom.), and a group represented by —ZnY$^2$ (Y$^2$ represents a chlorine atom, a bromine atom or an iodine atom.).]

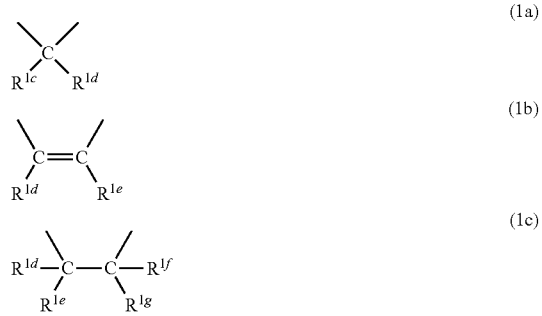

[in the formulae (1a) to (1c), $R^{1c}$ represents an aryl group or a monovalent aromatic heterocyclic group, and these groups may have a substituent.

$R^{1d}$ to $R^{1f}$ represent each independently an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom or a cyano group. In the formula (1b), $R^{1d}$ and $R^{1e}$ may be mutually linked to form a ring together with a carbon atom to which they are linked. In the formula (1c), $R^{1d}$ and $R^{1e}$ may be mutually linked to form a ring together with a carbon atom to which they are linked, $R^{1f}$ and $R^{1g}$ may be mutually linked to form a ring together with a carbon atom to which they are linked, $R^{1d}$ and $R^{1f}$ may be mutually linked to form a ring together with a carbon atom to which they are linked, and $R^{1e}$ and $R^{1g}$ may be mutually linked to form a ring together with a carbon atom to which they are linked.]

The method of producing a compound represented by the formula (M1) will be illustrated below. The compound represented by the formula (M1) can be produced by a method described, for example, in the following scheme 1.

Scheme 1

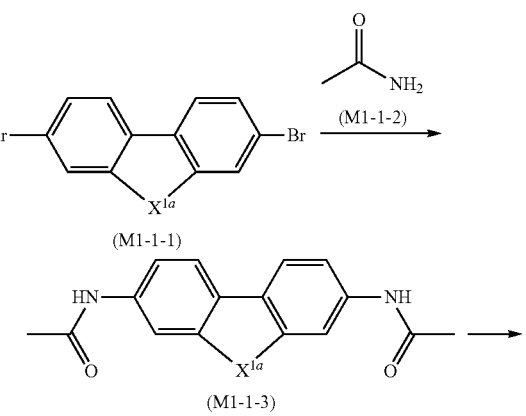

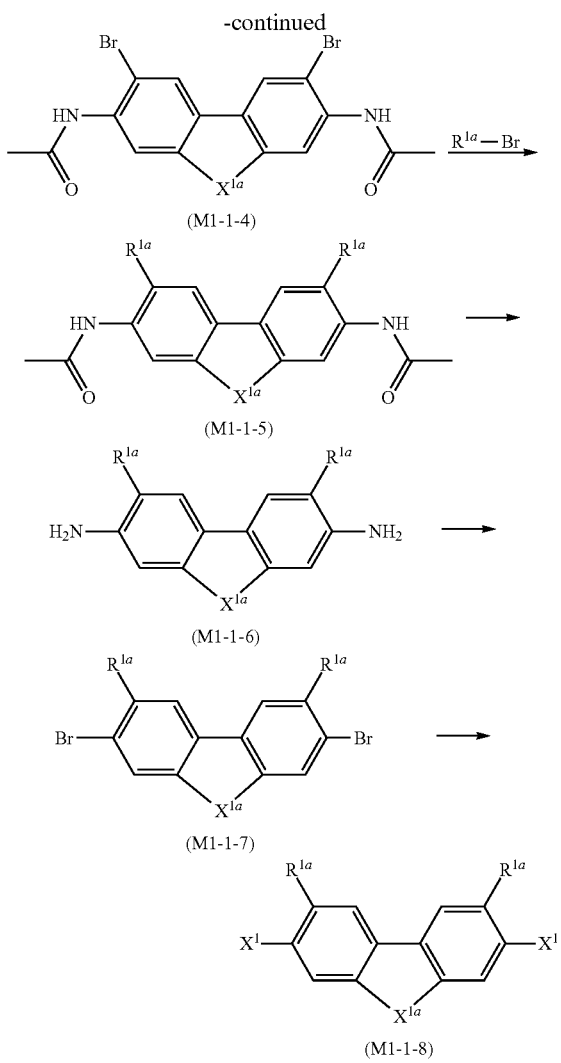

[in the scheme 1, $X^{1a}$, $X^1$ and $R^{1a}$ represent the same meaning as described above.]

In the scheme 1, first, a compound represented by the formula (M1-1-1) and an alkylamide such as acetamide and the like (in the scheme 1, described as acetamide (the formula 1-1-2) for simplification) are subjected to an amidation reaction using a phosphine ligand such as 4,5-bis-(diphenylphosphino)-9,9-dimethylxanthene and the like and a palladium catalyst such as tris(dibenzylideneacetone)dipalladium(0), palladium(II) acetate and the like, an inorganic base such as cesium carbonate, potassium carbonate, potassium hydroxide and the like or an organic base such as tetraalkylammonium hydroxide and the like, and, an organic solvent such as 1,4-dioxane, tetrahydrofuran and the like or a mixed solvent composed of the organic solvent and a water, thereby obtaining a compound represented by the formula (M1-1-3).

In the scheme 1, though a compound having a bromine atom as a substituent correlated with the reaction is described as the compound represented by the formula (M1-1-1), the compound may also be a group which can be subjected to the similar amidation reaction (for example, an iodine atom, a trifluoromethanesulfonyloxy group).

The compound represented by the formula (M1-1-3) can be usually derived to a compound represented by the formula (M1-1-4) by a halogenation reaction or the like using a halogenating agent such as N-bromosuccinimide and the like, an organic solvent such as chloroform, dichloromethane, N,N-dimethylformamide and the like, and, if necessary, an acid such as trifluoroacetic acid and the like, because of an influence of activation of a reaction at an ortho position of a benzene ring due to an amid group, and an influence of steric hindrance of a group represented by $X^{1a}$.

The halogenating agent is not limited to a brominating agent and, for example, a compound prepared by substituting a bromine atom contained in a compound represented by the formula (M1-1-4) with an iodine atom using an iodinating agent such as N-iodosuccinimide and the like may also be synthesized.

The compound represented by the formula (M1-1-4) can be derived into a compound represented by the formula (M-1-5), by subjecting to a coupling reaction such as the Suzuki coupling reaction, the Tamao coupling reaction, the Negishi coupling reaction, the Stille coupling reaction and the like using a known palladium catalyst, a base and an organic solvent or a mixed solvent composed of an organic solvent and water. Further, the compound represented by the formula (M1-1-4) can be derived into a compound represented by the formula (M1-1-5), by subjecting to alkylation and the like using an alkyllithium such as n-butyllithium and the like, an alkyl halide such as alkyl bromide, alkyl iodide and the like, and an organic solvent.

The compound represented by the formula (M1-1-5) can be derived into a compound represented by the formula (M1-1-6) by a treatment of converting an amide group into an amino group using an alcohol such as 2-propanol and the like or a mixed solvent composed of the alcohol and water, and an acid such as sulfuric acid and the like.

The compound represented by the formula (M1-1-6) can be derived into a compound represented by the formula (M1-1-7) by a known halogenation reaction such as the Sandmeyer halogenation and the like. After derivation of a compound prepared by substituting an amino group in the above-described formula (M1-1-6) with a hydrogen atom by the Sandmeyer reaction, the compound may further be derived into a compound represented by the formula (M1-1-7) using a halogenating agent such as, N-bromosuccinimide and the like.

The halogenating agent is not limited to a brominating agent and, for example, a compound prepared by substituting a bromine atom contained in a compound represented by the formula (M1-1-7) with an iodine atom using an iodinating agent such as N-iodosuccinimide and the like may also be synthesized.

Though the compound represented by the formula (M1-1-7) is in itself a compound represented by the formula (M1), it can be further derived, by a known method, into a compound represented by the formula (M1-1-8) prepared by substituting a bromine atom in the formula (M1-1-7) with the other substituent selected from the substituent group (a) or the other substituent selected from the substituent group (b). Also the compound represented by the formula (M1-1-8) is in itself a compound represented by the formula (M1).

When the group represented by $X^{1a}$ in a compound represented by the formula (M1) is a group represented by the above-described the formula (1a), namely, when the compound represented by the formula (M1) is a compound represented by the following formulae (M1a), it is preferable that production thereof is performed particularly by a method described in the subsequent scheme 2, since a compound represented by the formula (M1a) can be obtained more simply at higher purity.

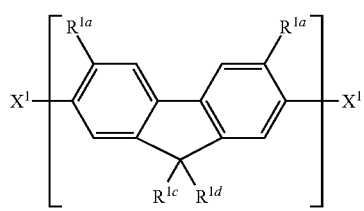

(M1a)

[in the formula (M1a), $X^1$, $R^{1a}$, $R^{1c}$ and $R^{1d}$ represent the same meaning as described above.]

Scheme 2

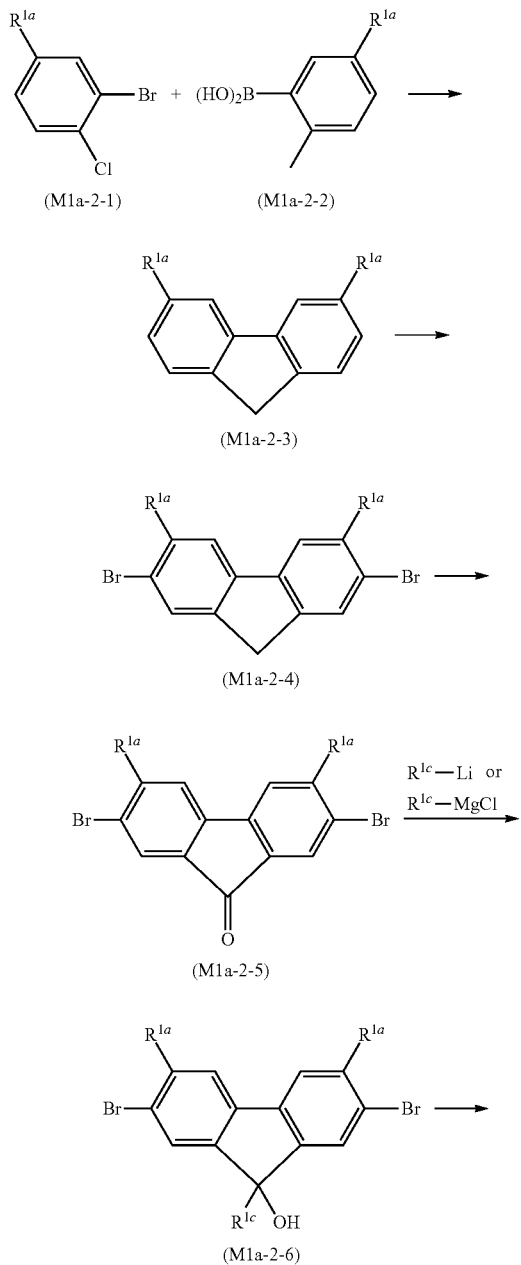

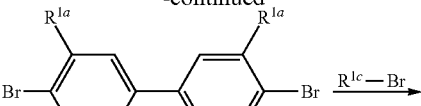

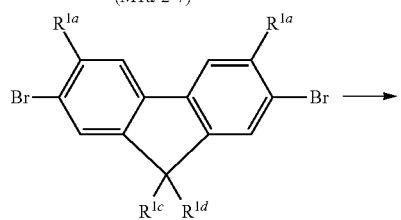

(M1a-2-8)

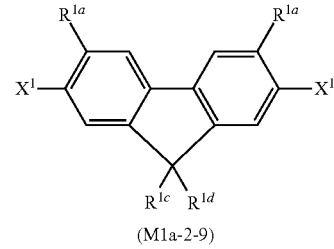

(M1a-2-9)

[in the scheme 2, $X^1$, $R^{1a}$, $R^{1c}$ and $R^{1d}$ represent the same meaning as described above.]

In the scheme 2, first, a compound represented by the formula (M1a-2-1) and a compound represented by the formula (M1a-2-2) are subjected to the Suzuki coupling reaction using a known palladium catalyst, a base and an organic solvent or a mixed solvent composed of an organic solvent and water, and a coupling reaction according to an intramolecular C—H activation reaction occurring subsequent to the above-described coupling reaction, to obtain a fluorene derivative represented by the formula (M1a-2-3).

As this reaction, reactions described in "Angewandte. Chemie. Int. Ed. 2010, 49, 2909-2912" and the like are preferable.

The compound represented by the formula (M1a-2-3) can be derived into a dibromofluorene derivative represented by the formula (M1a-2-4) usually by a halogenation reaction or the like using a halogenating agent such as N-bromosuccinimide and the like, an organic solvent such as chloroform, dichloromethane, N,N-dimethylformamide and the like, and, if necessary, an acid such as trifluoroacetic acid and the like.

The compound represented by the formula (M1a-2-4) can be derived into a fluorenone derivative represented by the formula (M1a-2-5), by subjecting to an oxygen oxidation reaction in which a base such as benzyltrimethyl ammonium hydroxide and the like is allowed to act in a pyridine solvent.

The compound represented by the formula (M1a-2-5) can be derived into a compound represented by the formula (M1a-2-6), by reacting with an aryllithium reagent, a Grignard reagent and the like in an organic solvent.

The compound represented by the formula (M1a-2-6) can be derived into a compound represented by the formula (M1a-2-7), by subjecting to a reduction reaction in which a reducing agent such as triethylsilane and the like is allowed to act in the presence of an acid such as trifluoroacetic acid and the like in an organic solvent.

The compound represented by the formula (M1a-2-7) can be derived into a compound represented by the formula (M1a-2-8), by a nucleophilic substitution reaction using an alkyl halide or the like and a base.

The compound represented by the formula (M1a-2-8) is in itself a compound represented by the formula (M1a), and can be further derived into a compound represented by the formula (M1a-2-9) prepared by substituting a bromine atom with the other substituent selected from the substituent group (a) or the other substituent selected from the substituent group (b) by a known method. When the group represented by $X^{1a}$ in a compound represented by the formula (M1) is a group represented by the above-described the formula (1b), namely, when the compound represented by the formula (M1) is a compound represented by the following formulae (M1b), it is preferable to perform production thereof particularly by a method described in the subsequent scheme 2b, since the compound represented by the formula (M1b) is obtained more simply at higher purity.

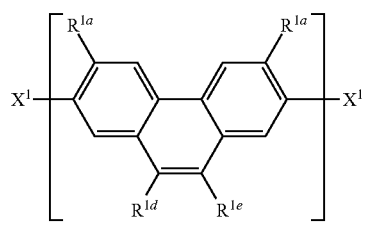

(M1b)

[in the formula (M1b), $X^1$, $R^{1a}$, $R^{1d}$ and $R^{1e}$ represent the same meaning as described above.]

Scheme 2b

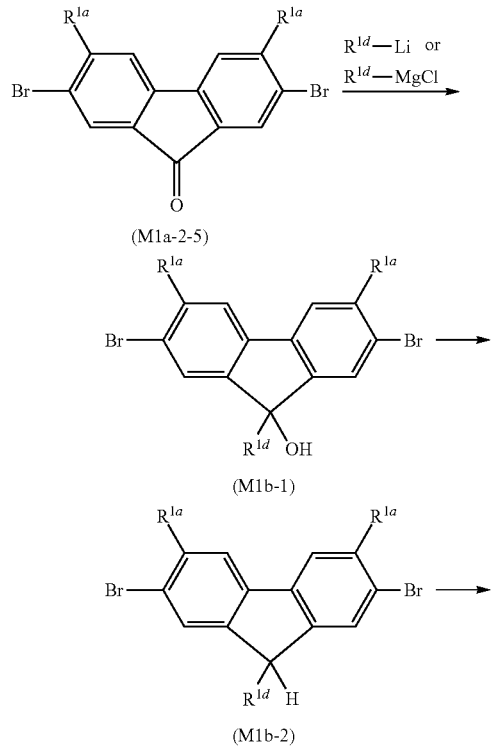

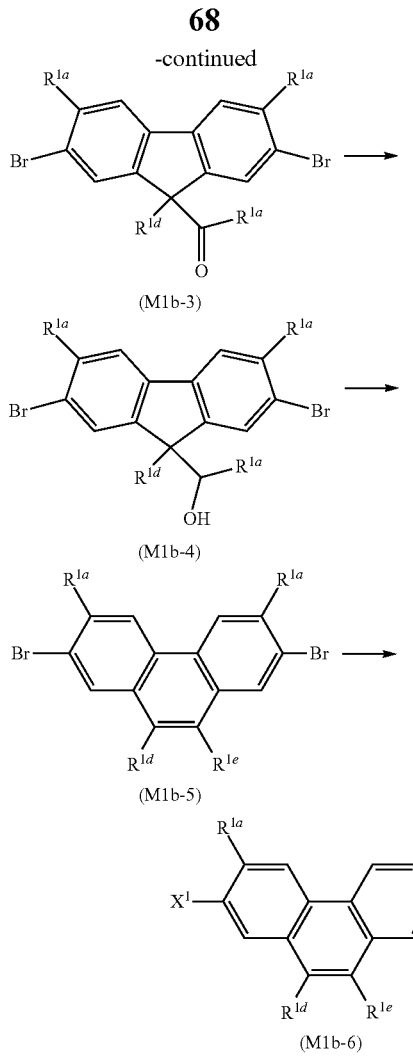

[in the scheme 2b, $X^1$, $R^{1a}$, $R^{1d}$ and $R^{1e}$ represent the same meaning as described above.]

In the scheme 2b, first, the compound represented by the formula (M1a-2-5) can be derived into a compound represented by the formula (M1b-1), by reacting with an alkyllithium reagent, an aryllithium reagent, a Grignard reagent and the like in an organic solvent.

The compound represented by the formula (M1b-1) can be derived into a compound represented by the formula (M1b-2), by subjecting to a reduction reaction in which a reducing agent such as triethylsilane and the like is allowed to act in the presence of an acid such as trifluoroacetic acid and the like in an organic solvent.

The compound represented by the formula (M1b-2) can be derived into a compound represented by the formula (M1b-3), by reacting with a base such as tert-butoxypotassium, sodium hydride and the like in an organic solvent, then, adding an acid chloride represented by the formula: $R^{1e}$ COCl ($R^{1e}$ represents the same meaning as described above.).

The compound represented by the formula (M1b-3) can be derived into a compound represented by the formula (M1b-4), by reducing using a reducing agent such as lithium aluminum hydride, sodium boron hydride and the like in an organic solvent.

The compound represented by the formula (M1b-4) can be derived into a compound represented by the formula (M1b-5), by reacting with diphosphorus pentaoxide and the like in an organic solvent, thereby causing a rearrangement reaction.

The compound represented by the formula (M1b-5) is in itself a compound represented by the formula (M1b), and can be further derived into a compound represented by the formula (M1b-6) prepared by substituting a bromine atom with the other substituent selected from the substituent group (a) or the other substituent selected from the substituent group (b) by a known method. The compound represented by the formula (M1b-6) is in itself a compound represented by the formula (M1b).

The case in which the group represented by $X^{1a}$ in a compound represented by the formula (M1) is a group represented by the above-described the formula (1c), namely, the compound represented by the formula (M1) is a compound represented by the following formulae (M1c), will be illustrated using a case in which the compound represented by the formula (M1c) is a compound represented by the following formulae (M1d), as an example.

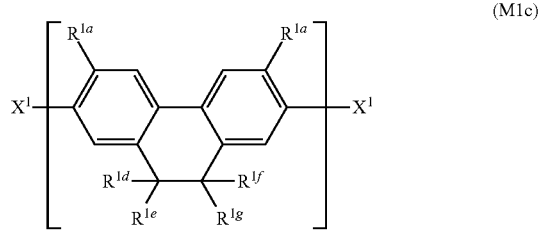

(M1c)

[in the formula (M1c), $X^1$, $R^{1a}$, $R^{1d}$, $R^{1e}$, $R^{1f}$ and $R^{1g}$ represent the same meaning as described above.]

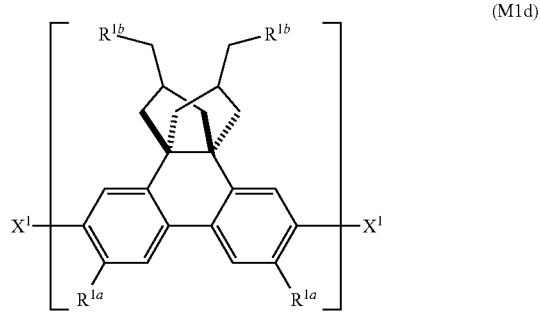

(M1d)

[in the formula (M1d), $X^1$ and $R^{1a}$ represent the same meaning as described above. $R^{1b}$ represents a hydrogen atom, an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom or a cyano group.]

It is preferable that a compound represented by the formula (M1d) is produced particularly by a method described in the subsequent scheme 2d, since a compound represented by the formula (M1d) is obtained more simply at higher purity.

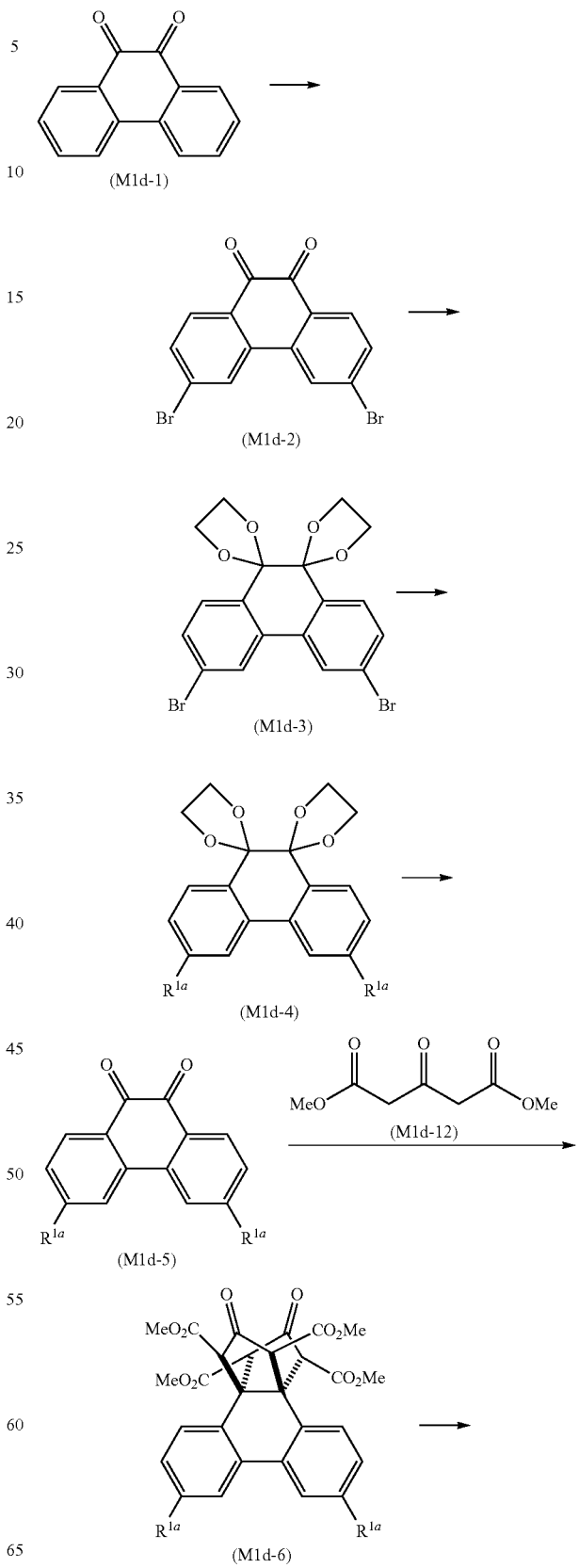

Scheme 2d

-continued

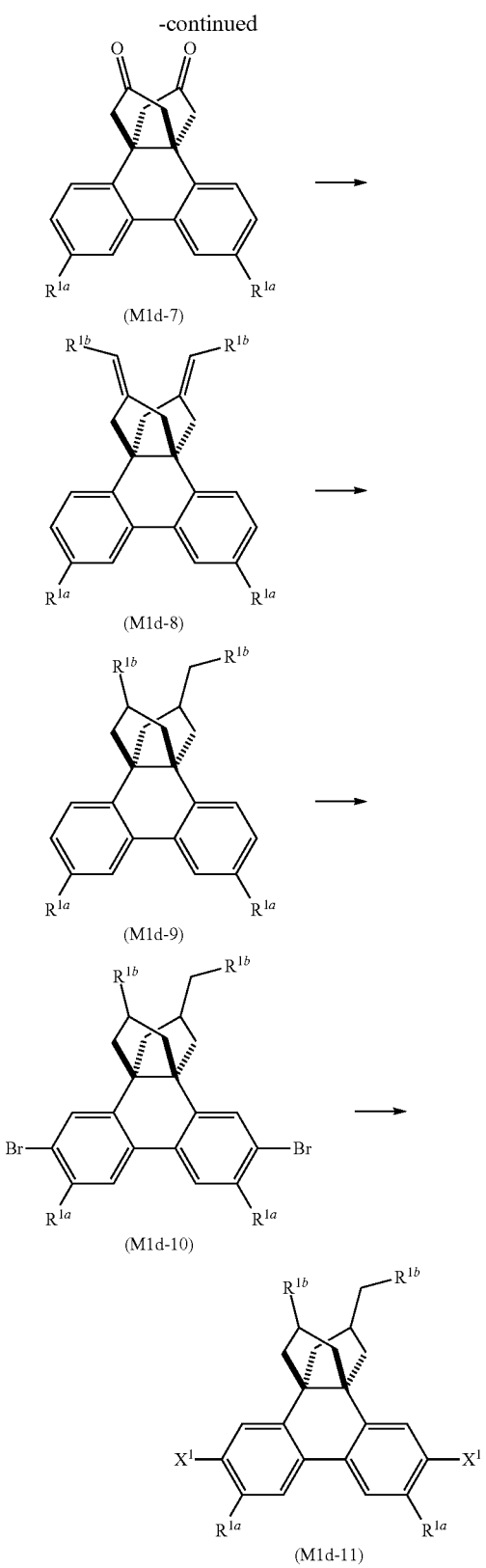

[in the scheme 2d, $X^1$, $R^{1a}$ and $R^{1b}$ represent the same meaning as described above. The wavy line means that a compound attached with this wavy line is a geometric isomer mixture.]

In the scheme 2d, first, a compound represented by the formula (M1d-1) is reacted in an organic solvent such as nitrobenzene and the like in the presence of bromine and a peroxide such as benzoyl peroxide and the like, to obtain a compound represented by the formula (M1d-2).

The compound represented by the formula (M1d-2) can be derived into a compound represented by the formula (M1d-3), by reacting with a diol such as ethylene glycol and the like in the presence of an acid such as para-toluenesulfonic acid and the like in an organic solvent such as 1,2-dichlorobenzene and the like.

The compound represented by the formula (M1d-3) can be derived into a compound represented by the formula (M1d-4), by subjecting to a coupling reaction such as the Suzuki coupling reaction, the Tamao coupling reaction, the Negishi coupling reaction, the Stille coupling reaction and the like using a known palladium catalyst, a base, and an organic solvent or a mixed solvent composed of an organic solvent and water. Further, the compound represented by the formula (M1d-3) can be derived into a compound represented by the formula (M1d-4), by subjecting to alkylation or the like using an alkyllithium such as n-butyllithium and the like, an alkyl halide such as alkyl bromide, alkyl iodide and the like, and an organic solvent. Furthermore, the compound represented by the formula (M1d-3) can be derived into a compound represented by the formula (M1d-4), by deriving into a compound having an alkyne side chain by the Hiyama coupling reaction with an acetylene derivative compound or the like, then, reducing by a hydrogenation reaction and the like.

The compound represented by the formula (M1d-4) can be derived into a compound represented by the formula (M1d-5), by reacting in an organic solvent or in a mixed solvent composed of an organic solvent and water in the presence of an acid such as para-toluenesulfonic acid and the like.

The compound represented by the formula (M1d-5) can be derived into a compound represented by the formula (M1d-6), by reacting with a compound represented by the formula (M1d-12). Here, the compound represented by the formula (M1d-12) may also be a compound obtained by converting a methoxy group in the compound into the other alkoxy group.

The compound represented by the formula (M1d-6) can be derived into a compound represented by the formula (M1d-7), by reacting in an organic solvent or in a mixed solvent composed of an organic solvent an water in the presence of an acid such as acetic acid and the like.

The compound represented by the formula (M1d-7) can be derived into a compound represented by the formula (M1d-8), by subjecting to the Wittig reaction using a compound represented by the formula: $R^{1b}$—$CH_2P^+Ph_3X^-$ ($R^{1b}$ represents the same meaning as described above. X represents a halogen atom such as a bromine atom, an iodine atom and the like), the Horner-Wadsworth-Emmons reaction using a compound represented by the formula: $R^{1b}$—$CH_2PO(OR')_2$ ($R^{1b}$ represents the same meaning as described above. R' represents an alkyl group, an aryl group or a monovalent aromatic heterocyclic group, and these groups may have a substituent.), and the like.

The compound represented by the formula (M1d-8) can be derived into a compound represented by the formula (M1d-9), by subjecting to a reducing reaction.

The compound represented by the formula (M1d-9) can be derived into a compound represented by the formula (M1d-10), by subjecting to a bromination reaction.

The compound represented by the formula (M1d-10) is in itself a compound represented by the formula (M1d), and can be further derived into a compound represented by the formula (M1d-11) obtained by converting a bromine atom in the formula (M1d-10) into the other substituent selected from the substituent group (a) or the other substituent selected from the substituent group (b) by a known method. The compound represented by the formula (M1d-11) is also in itself a compound represented by the formula (M1d).

In the above-described scheme 1, scheme 2, scheme 2b and scheme 2d, it is usually preferable that an operation of raising the purity of a compound obtained each step is carried out by a purification operation such as silica gel column chromatography, recrystallization and the like, before being used in the subsequent step.

Likewise, for introducing a repeating unit represented by the formula (2), it is preferable to use a compound represented by the following formula (M2), and for introducing a repeating unit represented by the formula (3), it is preferable to use a compound represented by the following formula (M3).

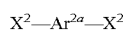  (M2)

(wherein, $X^2$ represents a group selected from the above-described substituent group (a) or a group selected from the above-described substituent group (b). A plurality of $X^2$ may be mutually the same or different.

$Ar^2$ represents the same meaning as described above.)

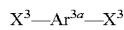  (M3)

(wherein, $X^3$ represents a group selected from the above-described substituent group (a) or a group selected from the following substituent group (b). A plurality of $X^3$ may be mutually the same or different.

$Ar^3$ represents the same meaning as described above.)

The compound represented by the formula (M2) includes a compound represented by the following formulae (M2B).

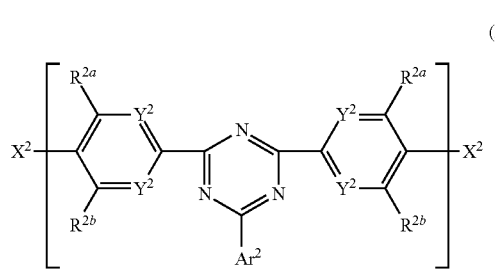

(M2B)

[in the formula (M2B), $Y^2$, $R^{2a}$, $R^{2b}$, $Ar^2$ and $X^2$ represent the same meaning as described above.]

The compound represented by the formula (M2B) can be produced, for example, by a method descried in the following scheme 3, scheme 4 or scheme 5.

Scheme 3

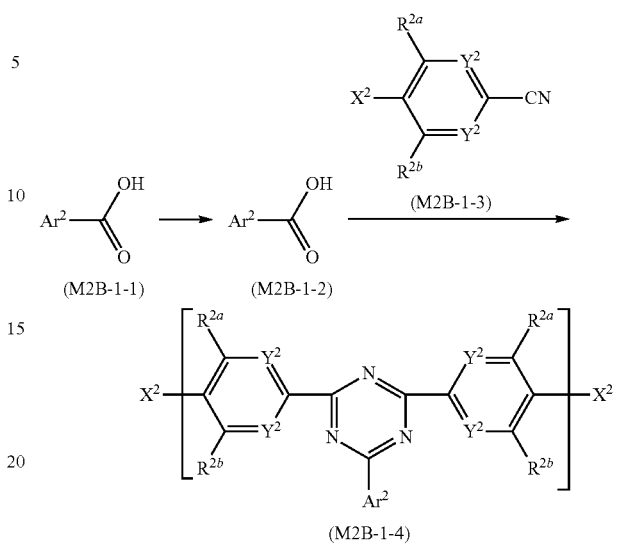

In the scheme 3, $Ar^2$, $X^2$, $R^{2a}$, $R^{2b}$ and $Y^2$ represent the same meaning as described above.

In the scheme 3, first, a compound represented by the formula (M2B-1-1) is converted to a compound represented by the formula (M2B-1-2) using a reagent such as thionyl chloride and the like, further, a compound represented by the formula (M2B-1-3) is reacted in the presence of a Lewis acid such as antimony chloride, aluminum chloride and the like, then, these are reacted with ammonia water, ammonia gas, ammonium chloride or the like, thus, a compound represented by the formula (M2B-1-4) can be obtained. The compound represented by the formula (M2B-1-4) is a compound represented by the formula (M2B).

For obtaining a compound represented by the formula (M2B-1-4) in good yield according to the above-described scheme, the molar ratio of a compound represented by the formula (M2B-1-2) to a compound represented by the formula (M2B-1-3) ([the mole number of a compound represented by the formula (M2B-1-3)]/[the mole number of a compound represented by the formula (M2B-1-2)]) is preferably 1.9 or more and 2.0 or less.

In the compound represented by the formula (M2B-1-4), the group represented by $X^2$ which is a group selected from the substituent group (a) or a group selected from the substituent group (b) can be converted to the other group selected from the substituent group (a) or the other group selected from the substituent group (b) by a known method.

Scheme 4

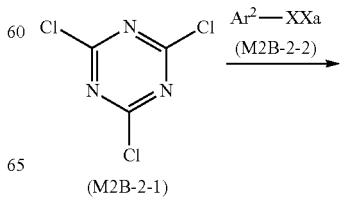

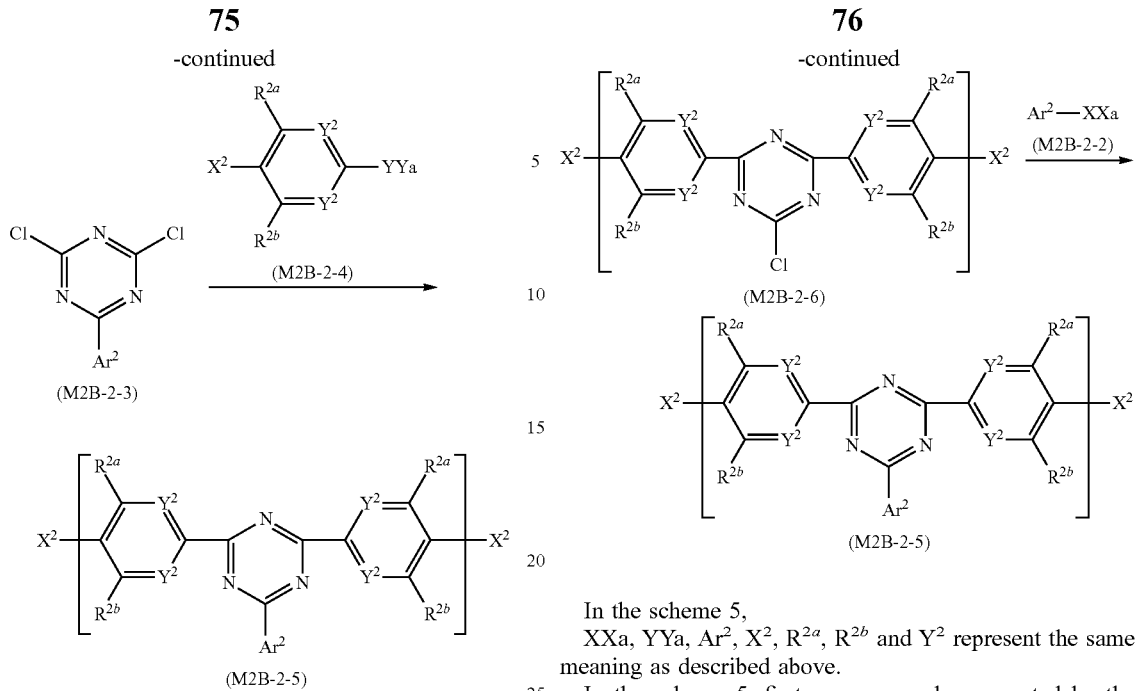

In the scheme 4,

XXa and YYa represent each independently a group selected from the above-described substituent group (b).

Ar², X², R²ᵃ, R²ᵇ and Y² represent the same meaning as described above.

In the scheme 4, first, a compound represented by the formula (M2B-2-1) and a compound represented by the formula (M2B-2-2) are subjected to a cross coupling reaction such as the Suzuki coupling reaction, the Grignard reaction, the Stille coupling reaction and the like, to obtain a compound represented by the formula (M2B-2-3).

Further, a compound represented by the formula (M2B-2-3) and a compound represented by the formula (M2B-2-4) are subjected to a cross coupling reaction such as the Suzuki coupling reaction, the Grignard reaction, the Stille coupling reaction and the like, to obtain a compound represented by the formula (M2B-2-5). The compound represented by the formula (M2B-2-5) is a compound represented by the formula (M2B).

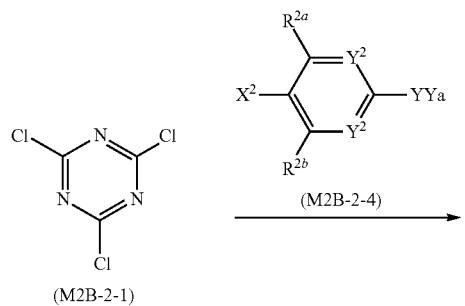

In the scheme 5,

XXa, YYa, Ar², X², R²ᵃ, R²ᵇ and Y² represent the same meaning as described above.

In the scheme 5, first, a compound represented by the formula (M2B-2-1) and a compound represented by the formula (M2B-2-4) are subjected to a cross coupling reaction such as the Suzuki coupling reaction, the Grignard reaction, the Stille coupling reaction and the like, to obtain a compound represented by the formula (M2B-2-6).

Further, a compound represented by the formula (M2B-2-6) and a compound represented by the formula (M2B-2-2) are subjected to a cross coupling reaction such as the Suzuki coupling reaction, the Grignard reaction, the Stille coupling reaction and the like, to obtain a compound represented by the formula (M2B-2-5). The compound represented by the formula (M2B-2-5) is a compound represented by the formula (M2B).

In the compound represented by the formula (M2B-2-5), the group represented by X² which is a group selected from the substituent group (a) or a group selected from the substituent group (b) can be converted to the other group selected from the substituent group (a) or the other group selected from the substituent group (b) by a known method.

Of the method represented by the scheme 3, the method represented by the scheme 4 and the method represented by the scheme 5 described above, preferable is the method represented by the scheme 3 since generation of impurities derived from a side reaction is generally small and it is easier to obtain a high purity compound represented by the formula (M2B).

The compound represented by the formula (M3) includes a compound represented by the following formulae (M3B).

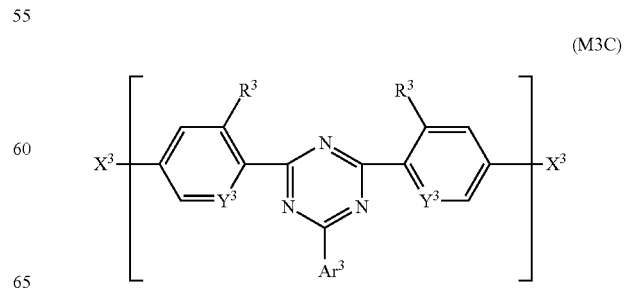

[in the formula (M3C),

Y³, Ar³ and R³ represent the same meaning as described above.

X³ represents a group selected from the above-described substituent group (a) or a group selected from the above-described substituent group (b). A plurality of X³ may be mutually the same or different.

The compound represented by the formula (M3C) can be produced, for example, by a method described in the following scheme 6, scheme 7 or scheme 8.

Scheme 6

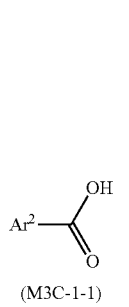

(M3C-1-1)    (M3C-1-2)    (M3C-1-3)

(M3C-1-4)

In the scheme 6, Ar³, X³, R³ and Y³ represent the same meaning as described above.

In the scheme 6, first, a compound represented by the formula (M3C-1-1) is converted to a compound represented by the formula (M3C-1-2) using a reagent such as thionyl chloride and the like, further, a compound represented by the formula (M3C-1-3) is reacted in the presence of a Lewis acid such as antimony chloride, aluminum chloride and the like, then, these are reacted with ammonia water, ammonia gas, ammonium chloride and the like, thus, a compound represented by the formula (M3C-1-4) can be obtained. The compound represented by the formula (M3C-1-4) is a compound represented by the formula (M3C).

For obtaining a compound represented by the formula (M3C-1-4) in good yield according to the above-described scheme, the molar ratio of a compound represented by the formula (M3C-1-2) and a compound represented by the formula (M3C-1-3) ([the mole number of a compound represented by the formula (M3C-1-3)]/ [the mole number of a compound represented by the formula (M3C-1-2)]) is preferably 1.9 or more and 2.0 or less.

In the compound represented by the formula (M3C-1-4), the group represented by X³ which is a group selected from the substituent group (a) or a group selected from the substituent group (b) can be converted to the other group selected from the substituent group (a) or the other group selected from the substituent group (b) by a known method.

Scheme 7

(M3C-2-1)

(M3C-2-2)

(M3C-2-3)

(M3C-2-4)

(M3C-2-5)

In the scheme 7, XXa, YYa, Ar³, X³, R³ and Y³ represent the same meaning as described above.

In the scheme 7, first, a compound represented by the formula (M3C-2-1) and a compound represented by the formula (M3C-2-2) are subjected to a cross coupling reaction such as the Suzuki coupling reaction, the Grignard reaction, the Stille coupling reaction and the like, to obtain a compound represented by the formula (M3C-2-3).

Further, a compound represented by the formula (M3C-2-3) and a compound represented by the formula (M3C-2-4) are subjected to a cross coupling reaction such as the Suzuki coupling reaction, the Grignard reaction, the Stille coupling reaction and the like, to obtain a compound represented by the formula (M3C-2-5). The compound represented by the formula (M3C-2-5) is a compound represented by the formula (M3C).

Scheme 8

(M3C-2-1)

(M3C-2-4)

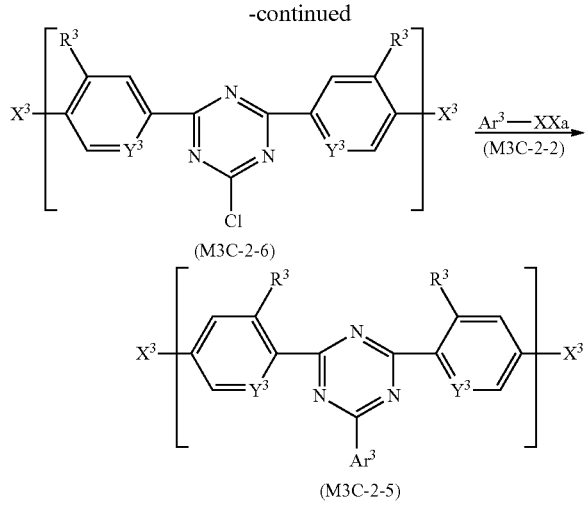

In the scheme 8, XXa, YYa, Ar$^3$, X$^3$, R$^3$ and Y$^3$ represent the same meaning as described above.

In the scheme 8, first, a compound represented by the formula (M3C-2-1) and a compound represented by the formula (M3C-2-4) are subjected to a cross coupling reaction such as the Suzuki coupling reaction, the Grignard reaction, the Stille coupling reaction and the like, to obtain a compound represented by the formula (M3C-2-6).

Further, a compound represented by the formula (M3C-2-6) and a compound represented by the formula (M3C-2-2) are subjected to a cross coupling reaction such as the Suzuki coupling reaction, the Grignard reaction, the Stille coupling reaction and the like, to obtain a compound represented by the formula (M3C-2-5). The compound represented by the formula (M3C-2-5) is a compound represented by the formula (M3C).

In the compound represented by the formula (M3C-2-5), the group represented by X$^3$ which is a group selected from the substituent group (a) or a group selected from the substituent group (b) can be converted to the other group selected from the substituent group (a) or the other group selected from the substituent group (b) by a known method.

Of the methods represented by the scheme 6, the scheme 7 and the scheme 8 described above, preferable is the method represented by the scheme 6 since generation of impurities derived from a side reaction is generally small and it is easier to obtain a high purity compound represented by the formula (M3C).

In the method of producing the polymer compound of the present invention, the raw material monomer mixture is mixed so that the total mole number of a raw material monomer represented by the formula (M1), a raw material monomer represented by the formula (M2) and a raw material monomer represented by the formula (M3) is preferably 60 to 100 mol %, more preferably 70 to 100 mol %, when the total mole number thereof is 100 mol %.

It is preferable that polymerization active groups X$^1$, X$^2$ and X$^3$ which the raw material monomer as described above has on its both ends are combined as described below, from the standpoint of producing a polymer compound in which the content of groups represented by the formula (3) is 50% or less with respect to the total content of repeating units contained in the polymer compound and groups represented by the formula (3) are not mutually substantially adjacent, which is the preferable embodiment of the polymer compound of the present invention described above. That is, it is preferable that X$^3$ is a group selected from the substituent group (a) and part or all of X$^1$ and X$^2$ are a group selected from the substituent group (b), or X$^3$ is a group selected from the substituent group (b) and part or all of X$^1$ and X$^2$ are a group selected from the substituent group (a). Of them, a combination in which X$^3$ is a group selected from the substituent group (a) and part or all of X$^1$ and X$^2$ are a group selected from the substituent group (b) is more preferable from the standpoint of easy progress of the polymerization reaction. According to the combination of them, polymerization using known various cross coupling reactions such as the Suzuki coupling reaction and the like is possible, and by this, it is made possible to produce a polymer compound which is the preferable embodiment of the polymer compound of the present invention described above.

Likewise, it is preferable that polymerization active groups X$^1$, X$^2$ and X$^3$ which the raw material monomer as described above has on its both ends are combined as described below, from the standpoint of producing a polymer compound in which the content of a group represented by the formula (2) is 50% or more with respect to the total content of repeating units contained in the polymer compound and groups represented by the formula (1), and a group represented by the formula (1) and a group represented by the formula (3) are not substantially adjacent, which is the preferable embodiment of the polymer compound of the present invention described above. That is, it is preferable that X$^1$ and X$^3$ are a group selected from the substituent group (a) and part or all of X$^2$ are a group selected from the substituent group (b), or X$^1$ and X$^3$ are a group selected from the substituent group (b) and part or all of X$^2$ are a group selected from the substituent group (a). Of them, a combination in which X$^1$ and X$^3$ are a group selected from the substituent group (a) and part or all of X$^2$ are a group selected from the substituent group (b) is more preferable from the standpoint of easy progress of the polymerization reaction. According to the combination of them, polymerization using known various cross coupling reactions such as the Suzuki coupling reaction and the like is possible, and by this, it is made possible to produce a polymer compound which is the preferable embodiment of the polymer compound of the present invention described above.

Here, the alkyl group as an example of R$^{20}$, R$^{21}$ and R$^{22}$ in a group represented by —O—S(=O)$_2$R$^{20}$ in the substituent group (a) and a group represented by —B(OR$^{21}$)$_2$ and a group represented by d Sn(R$^{22}$)$_3$ in the substituent group (b) has a number of carbon atoms of preferably 1 to 20, more preferably 1 to 15, further preferably 1 to 10.

The aryl group which may have an alkyl group, an alkoxy group, a nitro group, a fluorine atom or a cyano group as a substituent, which is one example of R$^{20}$, is preferably a phenyl group, a 4-tolyl group, a 4-methoxyphenyl group, a 4-nitrophenyl group, a 3-nitrophenyl group, a 2-nitrophenyl group or a 4-trifluoromethylphenyl group. When R$^{20}$, R$^{21}$ and R$^{22}$ are these groups, reactivity in polymerizing a raw material monomer is excellent and synthesis of a polymer compound tends to be easier.

The group represented by —O—S(=O)$_2$R$^{20}$ in the substituent group (a) includes, for example, a methanesulfonyloxy group, a trifluoromethanesulfonyloxy group, a phenylsulfonyloxy group, a 4-methylphenylsulfonyloxy group, a 4-trifluoromethylphenylsulfonyloxy group and the like.

The group represented by —B(OR$^{21}$)$_2$ in the substituent group (b) includes, for example, groups represented by the following formulae.

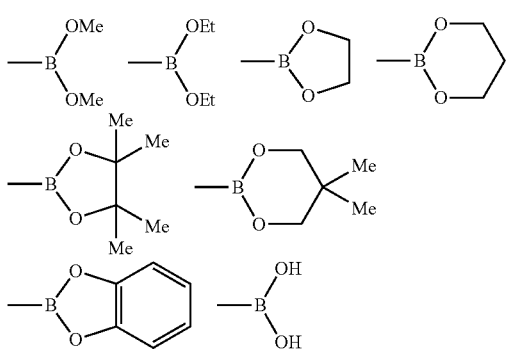

The group represented by —BF$_4$Q$^1$ in substituent group (b) includes a group represented by —BF$_4^-$K$^+$. Further, the group represented by —Sn (R$^{22}$)$_3$ in the substituent group (b) includes a trimethylstannanyl group, a triethylstannanyl group, a tributylstannanyl group and the like.

When compounds represented by the formulae (M1), (M2) and (M3) are used as raw material monomers and polymerized to produce a polymer compound, it is preferable to raise the purity of each raw material monomer before polymerization so at to obtain a polymer compound having higher purity. By producing a light emitting device using a high purity polymer compound, the resulting current efficiency, light emission efficiency and stability such as luminance life are more excellent.

The purity of a compound represented by the formula (M1), a compound represented by the formula (M2) and a compound represented by the formula (M3) can be raised by, for example, performing purification by distillation, sublimation purification, recrystallization and the like. Each compound having higher purity is more desirable. For example, in analysis according to high performance liquid chromatography (HPLC) using a UV detector (detection wavelength: 254 nm), the area percentage value shown by the peak of each compound is preferably 98.5% or more, more preferably 99.0% or more, further preferably 99.5% or more.

The polymerization reaction using a compound represented by the formula (M1), a compound represented by the formula (M2) and a compound represented by the formula (M3) includes, for example, a method of polymerization by the Suzuki coupling reaction as a method according to an aryl coupling reaction (Chem. Rev., vol. 95, pp. 2457-2483 (1995)), a method of polymerization by the Grignard reaction (Bull. Chem. Soc. Jpn., vol. 51, p. 2091 (1978)), a method of polymerization with a Ni (0) catalyst (Progress in Polymer Science), vol. 17, pp. 1153 to 1205, 1992) and a method using the Stille coupling reaction (European Polymer Journal, vol. 41, pp. 2923-2933 (2005)).

Of them, a method of polymerization by the Suzuki coupling reaction and a method of polymerization with a Ni (0) catalyst are preferable as the polymerization method from the standpoint of easiness of production of a polymer compound and simplicity of operation in a polymerization reaction. Further, methods of polymerization by a cross coupling reaction such as the Suzuki coupling reaction, the Grignard reaction, the Stille coupling reaction and the like are preferable and a method of polymerization by the Suzuki coupling reaction is particularly preferable from the standpoint of easiness of control of the structure of a polymer compound containing a specific chain constitution described above as one of preferable embodiments of the present invention.

As the groups represented by polymerization active groups X$^1$, X$^2$ and X$^3$ which a compound represented by the formula (M1), a compound represented by the formula (M2) and a compound represented by the formula (M3) have, a suitable group may be selected depending on the kind of a polymerization reaction. For example, in the case of polymerization by the Suzuki coupling reaction, a bromine atom, an iodine atom or a chlorine atom is preferable in the substituent group (a) and a group represented by —B(OR$^{21}$)$_2$ is preferable in the substituent group (b) as these groups, and it is more preferable to select a bromine atom and a group represented by —B(OR$^{21}$)$_2$ from the substituent group (a) and the substituent group (b), respectively. When these groups are contained as the polymerization active group, synthesis of a compound represented by the formula (M1), a compound represented by the formula (M2) and a compound represented by the formula (M3) is easy, and additionally, handling in polymerization is also excellent.

The polymerization method includes a method in which a compound represented by the formula (M1), a compound represented by the formula (M2) and a compound represented by the formula (M3) (raw material monomers) having the substituent group (a) and the substituent group (b) described above as the polymerization active group, and the like, are reacted if necessary together with a suitable catalyst and a suitable base. In the case of selection of a method of polymerization by a cross coupling reaction such as the Suzuki coupling reaction, the Grignard reaction, the Stille coupling reaction and the like, the ratio of the mole number of a group contained in the substituent group (b) to the mole number of a group contained in the substituent group (a) in the whole raw material monomer (ratio when the total mole number of a group contained in the substituent group (a) is the denominator and the total mole number of a group contained in the substituent group (b) is the numerator, hereinafter described as ratio (b/a) in some cases) may be adjusted so as to obtain a polymer compound having desired molecular weight. The ratio (b/a) is preferably 0.90 to 1.10, more preferably 0.95 to 1.05, further preferably 0.98 to 1.02 from the standpoint of the molecular weight of the polymer compound of the present embodiment. In contrast, when it is desired to control the existing proportion of a chain constitution by split addition or consecutive addition of a raw material monomer and the like, it is possible to control the molecular weight by conducting a polymerization reaction under condition wherein the above-described ratio (b/a) is set to a suitable value of less than 1, thereby generating a constitution in which both ends of a polymer compound is composed of a group contained in the substituent group (a) in the polymerization reaction, and it becomes possible to control the molecular weight further precisely by further adding a raw material monomer so that the ratio (b/a) approximates 1. Further, it is also possible to produce a block copolymer by later adding a raw material monomer as the different repeating unit from the raw material monomer added initially.

The polystyrene-equivalent number-average molecular weight (Mn) according to gel permeation chromatography (hereinafter, referred to as "GPC") of the polymer compound of the present invention is usually 1×10$^3$ to 1×10$^8$, preferably 1×10$^4$ to 1×10$^6$. The polystyrene-equivalent weight-average molecular weight (Mw) of the polymer compound of the present embodiment is usually 2×10$^3$ to 2×10$^8$, and, because of an improvement in film formability, preferably 2×10$^4$ to 2×10$^6$, more preferable 3×10$^4$ to 1×10$^6$, further preferably 5×10$^4$ to 5×10$^5$.

In the case of polymerization by the Suzuki coupling reaction, the catalyst includes, for example, transition metal complexes such as palladium complexes such as) [tetrakis (triphenylphosphine)]palladium(0) (Pd(PPh$_3$)$_4$), [tris(dibenzylideneacetone)]dipalladium (Pd$_2$(dba)$_3$), palladium(II) acetate (Pd(OAc)$_2$), dichlorobistriphenylphosphinepalladium(II) (PdCl$_2$(PPh$_3$)$_2$), dichlorobis[tris(2-methoxyphenyl)phosphine]palladium(II) (PdCl$_2$[P(2-MeOPh)$_3$]$_2$) and the like, and catalysts prepared by adding, if necessary, a ligand such as triphenylphosphine, tri(tert-butyl)phosphine, tris(2-methoxyphenyl)phosphine, tricyclohexylphosphine and the like to these transition metal complexes.

As these catalysts, those synthesized previously may be used, and those prepared in the reaction system may be used as they are. These catalysts may be used each singly or two or more of them may be used in combination. Further, these catalysts may be not only added in initiation of the polymerization, but also further added during the polymerization reaction.

When a catalyst is used, its use amount may be an effective amount as the catalyst. For example, the amount of a catalyst with respect to the sum of the mole numbers of raw material monomers to be used is preferably 0.00001 to 3 molar equivalent, more preferably 0.00005 to 0.5 molar equivalent, further preferably 0.0001 to 0.2 molar equivalent in terms of a transition metal.

In polymerization by the Suzuki coupling reaction, it is preferable to use a base as the catalyst. The base includes inorganic bases such as sodium carbonate, potassium carbonate, cesium carbonate, potassium fluoride, cesium fluoride, tripotassium phosphate and the like, and organic bases such as tetrabutylammonium fluoride, tetrabutylammonium chloride, tetrabutylammonium bromide, tetraethylammonium hydroxide, tetrabutylammonium hydroxide and the like. These bases may also be used in the form of an aqueous solution.

When a base is used, its amount is preferably set with respect to the sum of the mole numbers of raw material monomers to be used, and is preferably 0.5 to 20 molar equivalent, more preferably 1 to 10 molar equivalent.

The polymerization reaction may be conducted in the absence of a solvent or in the presence of a solvent, and it is more preferable to conduct the polymerization reaction in the presence of an organic solvent. The organic solvent includes toluene, xylene, mesitylene, tetrahydrofuran, 1,4-dioxane, dimethoxyethane, N,N-dimethylacetamide, N,N-dimethylformamide and the like. From the standpoint of suppression of side reactions, it is desired that the solvent is subjected to a deoxygenation treatment. The organic solvents may be used each singly or two or more of them may be used in combination.

The use amount of the organic solvent is adjusted so that the total concentration of raw material monomers in a solution is preferably 0.1 to 90 wt %, more preferably 1 to 50 wt %, further preferably 2 to 30 wt %.

The reaction temperature in the polymerization reaction is preferably 0 to 200° C., more preferably 20 to 150° C., further preferably 20 to 120° C. The reaction time is preferably 0.5 hours or more, more preferably 2 to 500 hours.

The polymerization reaction is preferably conducted under dehydrated condition when a group represented by —MgY' is used as the group contained in the substituent group (b). When the polymerization reaction is the Suzuki coupling reaction, the base to be used may be used in the form of an aqueous solution, and further, water may be added to an organic solvent and the resultant solution may be used as the solvent.

Further, it is preferable that the polymer compound of the present invention has a structure in which the polymerization active group in the polymerization reaction is removed by an operation such as an end treatment and the like or substituted with a stable group such as an unsubstituted phenyl group and the like from the standpoint of improvement of stability of the luminance life or the like of a light emitting device. In the polymerization reaction, it is preferable to further use a compound represented by the formula (19) as an end-capping agent for avoiding retention of polymerization active groups ($X^1$, $X^2$, $X^3$ and the like) at the end of the resultant polymer compound. By conducting the reaction with adding such a compound, a polymer compound in which the end of the polymer compound is substituted with an aryl group or a monovalent aromatic heterocyclic group can be obtained. The compounds represented by the formula (19) (functioning as an end-capping agent) may be used singly or two or more of them may be used in combination, in polymerization in producing a polymer compound.)

$$X^{19a}\text{—}Ar^{19a} \qquad (19)$$

[in the formula (19), $Ar^{19a}$ represents an aryl group or a monovalent aromatic heterocyclic group, and these groups may have a substituent.

$X^{19a}$ represents a group selected from the above-described substituent group (a) or the above-described substituent group (b).]

$Ar^{19a}$ in the formula (19) represents preferably an aryl group, more preferably an aryl group which may have an alkyl group, an aryl group, a monovalent aromatic heterocyclic group or a substituted amino group as a substituent, further preferably an aryl group which may have an alkyl group or an aryl group as a substituent, particularly preferably a phenyl group which may have an alkyl group or an aryl group as a substituent.

The post treatment of the polymerization reaction can be conducted by a known method. It can be conducted, for example, by a method in which a reaction liquid obtained in the polymerization reaction is added to a lower alcohol such as methanol and the like to cause deposition of a precipitate, which is then filtrated and dried.

When thus obtained polymer compound contains impurities such as a catalyst and abase used in the polymerization reaction and residues thereof and the like, it is possible to perform a purification treatment according to a known purification method. Particularly when the polymer compound is used in a light emitting device, its purity exerts an influence on performances of the device such as a light emission property and the like, therefore, it is preferable that, after condensation polymerization, impurities are removed and the polymer compound is purified by a purification treatment such as precipitation fractionation, extraction fractionation, silica gel column chromatography, adsorption, washing and the like.

Suitable embodiments of the polymer compound of the present invention are exemplified in the following Table 1.

TABLE 1

| Repeating unit | Formula (1):<br>(1-5a)~(1-18a)<br>(1-2b)~(1-6b)<br>(1-2c)~(1-10c)<br>v | Formulae (2):<br>(2A-005)~(2A-015)<br>(2A-019)<br>(2B-001)~(2B-012)<br>w | Formulae (3):<br>(3A-001)~(3A-012)<br>(3B-401)~(3B-412)<br>(3B-501)~(3B-503)<br>(3B-601)~(3B-603)<br>x | other<br>q |
|---|---|---|---|---|
| EP-1 | 70~100 | | | 0~30 |
| EP-2 | 0.1~49.9 | 50.1~99.9 | | 0~30 |
| EP-3 | 50.1~99.9 | 0.1~49.9 | | 0~30 |
| EP-4 | 50.1~99.9 | | 0.1~49.9 | 0~30 |
| EP-5 | 0.1~49.9 | 50 | 0.1~49.9 | 0~30 |

[in the table, v, w, x and q represent each independently the mole fraction.

Of them, the mole fraction of a repeating unit represented by the above-described the formulae (1-5a) to (1-18a), (1-2b) to (1-6b) and (1-2c) to (1-10c) is v, the mole fraction of a repeating unit represented by the above-described the formulae (2A-005) to (2A-015), (2A-019) and (2B-001) to (2B-012) is w, the mole fraction of a repeating unit represented by the above-described the formulae (3A-001) to (3A-012), (3B-401) to (3B-412), (3B-501) to (3B-503) and (3B-601) to (3B-603) is x, and the mole fraction of other raw material monomers is q.

Here, v, w, x and q satisfy v+w+x+q=100 and 100≥v+w+x≥70.]

[Composition]

The composition of the present invention comprises the polymer compound of the present invention and at least one material selected from the group consisting of a hole transporting material, an electron transporting material and a light emitting material. The composition of the present invention can be suitably used as a light emitting material, a hole transporting material or an electron transporting material. In the composition of the present embodiment, the polymer compounds of the present invention, hole transporting materials, electron transporting materials and light emitting materials may be used each singly or two or more of each of them may be used in combination.

Regarding the ratio of the composition of the present invention to "at least one material selected from the group consisting of a hole transporting material, an electron transporting material and a light emitting material" in the composition of the present embodiment, when the composition is used as a light emitting material, the proportion of "at least one material selected from the group consisting of a hole transporting material, an electron transporting material and a light emitting material" with respect to 100 parts by weight of the polymer compound of the present invention is preferably 0.01 to 400 parts by weight, more preferably 0.05 to 150 parts by weight, for every material. In the case of a composition containing a phosphorescent compound described later as a light emitting material, the proportion of the phosphorescent compound with respect to 100 parts by weight of the polymer compound of the present invention is preferably 0.01 to 80 parts by weight, more preferably 0.1 to 50 parts by weight, further preferably 1 to 40 parts by weight.

As the hole transporting material, compounds known as a hole transporting material of a light emitting device can be used. Examples thereof include polyvinylcarbazole and derivatives thereof, polysilane and derivatives thereof, polysiloxane derivatives having an aromatic amine structure in the side chain or main chain, pyrazoline derivatives, arylamine derivatives, stilbene derivatives, polyaniline and derivatives thereof, polythiophene and derivatives thereof, polyarylamine and derivatives thereof, polypyrrole and derivatives thereof, poly(p-phenylenevinylene) and derivatives thereof and poly(2,5-thienylenevinylene) and derivatives thereof. These derivatives may have an arylene group and a divalent aromatic heterocyclic group as a copolymerization component.

As the electron transporting material, compounds known as an electron transporting material of a light emitting device can be used. Examples thereof include oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, triaryltriazine and derivatives thereof, polyquinoline and derivatives thereof, polyquinoxaline and derivatives thereof, polyfluorene and derivatives thereof, and the like. These derivatives may have an arylene group and a divalent aromatic heterocyclic group as a copolymerization component.

As the light emitting material, compounds known as a light emitting material of a light emitting device can be used, and a phosphorescent compound described later is preferable from the standpoint of obtaining excellent light emission efficiency. As the light emitting material other than the phosphorescent compound, a fluorescent compound can be used. The fluorescent compound includes a low molecular weight fluorescent material and a high molecular weight fluorescent material. The low molecular weight fluorescent material has the spectrum peak of fluorescence usually in the wavelength range of 400 to 700 nm. The molecular weight of the low molecular weight fluorescent material is preferably less than 3000, more preferably 100 to 2000, further preferably 100 to 1000.

As the low molecular weight fluorescent material, compounds known as a light emitting material of a light emitting device can be used. Examples thereof include dye materials such as naphthalene derivatives, anthracene and derivatives thereof, perylene and derivatives thereof, quinacridone derivatives, xanthene dyes, coumarin dyes, cyanine dyes, triphenylamine derivatives, oxadiazole derivatives, pyrazoloquinoline derivatives, distyrylbenzene derivatives, distyrylarylene derivatives, pyrrole derivatives, thiophene ring compounds, pyridine ring compounds, oligothiophene derivatives and the like; metal complex type materials such as metal complexes having Al, Zn, Be and the like or a rare earth metal such as Tb, Eu, Dy and the like as the center metal and having oxadiazole, thiadiazole, phenylpyridine, phenylbenzoimidazole, quinolone structure or the like as a ligand, such as alumiquinolinol complexes, benzoquinolinolberyllium complexes, benzooxazolyl zinc complexes, benzothiazole zinc complexes, azomethyl zinc complexes, porphyrin zinc complexes, europium complexes and the like.

The high molecular weight fluorescent material includes materials obtained by increasing the molecular weight of the dyes and metal complex type light emitting materials exemplified as the above-described low molecular weight fluorescent material, such as polyparaphenylenevinylene derivatives, polythiophene derivatives, polyparaphenylene derivatives, polysilane derivatives, polyacetylene derivatives, polyfluorene derivatives, polyvinylcarbazole derivatives and the like.

[Phosphorescent Compound]

Next, the phosphorescent compound contained in a composition of a suitable embodiment will be explained.

As the phosphorescent compound to be used together with the polymer compound of the present invention, various phosphorescent compounds can be used since the polymer compound of the present invention usually has high $T_1$ energy level, and it is preferable to select a phosphorescent compound having the lowest excited triple state ($T_1$) of lower energy level than or equivalent to the lowest excited triple state ($T_1$) of the polymer compound of the present invention, for obtaining more excellent current efficiency.

More specifically, the energy level of the lowest excited triple state ($T_1$) of the polymer compound of the present invention (hereinafter, described as "TH") and the energy level of the lowest excited triple state ($T_1$) of the phosphorescent compound (hereinafter, described as "TM") satisfy preferably the relation of TH>TM−0.1(eV), more preferably the relation of

TH>TM, further preferably the relation of

TH>TM+0.1(eV).

TH of the polymer compound of the present invention can be determined by measuring the phosphorescent spectrum of the polymer compound at 77K. Specifically, if the intensity of the maximum peak wavelength (wavelength of the largest intensity) in the phosphorescent spectrum of the polymer compound measured is 1.0, the value obtained by converting the wavelength at the shortest side showing an intensity of 0.1 into energy is defined as TH. TM of a phosphorescent compound can be determined by measuring the phosphorescent spectrum of the phosphorescent compound at room temperature. Specifically, if the intensity of the maximum peak wavelength (wavelength of the largest intensity) in the phosphorescent spectrum of the phosphorescent compound is 1.0, the value obtained by converting the wavelength at the shortest side showing an intensity of 0.1 into energy is defined as TM.

Examples of the phosphorescent compound to be used together with the polymer compound of the present invention are shown below, but the phosphorescent compound to be used together is not limited to them, and a phosphorescent compound is useful if TH of the polymer compound of the present invention and TM of the phosphorescent compound satisfy the above-described relation.

As the phosphorescent compound, known compounds such as triplet emission complexes and the like can be used, and examples thereof include metal complexes described in Nature, (1998), 395, 151, Appl. Phys. Lett. (1999), 75(1), 4, Proc. SPIE-Int. Soc. Opt. Eng. (2001), 4105 (Organic Light-Emitting Materials and DevicesIV), 119, J. Am. Chem. Soc., (2001), 123, 4304, Appl. Phys. Lett., (1997), 71(18), 2596, Syn. Met., (1998), 94(1), 103, Syn. Met., (1999),99 (2), 1361, Adv. Mater., (1999), 11(10), 852, Inorg. Chem., (2003), 42, 8609, Inorg. Chem., (2004), 43, 6513, Journal of the SID 11/1, 161 (2003), WO 2002/066552, WO 2004/020504, WO 2004/020448 and the like.

As the metal complex which is a phosphorescent compound, one in which the proportion of the sum of squares of the orbital coefficients of the outermost d orbital of a central metal with respect to the sum of squares of all atomic orbital coefficients is ⅓ or more, in the highest occupied molecular orbital (HOMO) of a metal complex, is preferably applied from the standpoint of obtaining high emission quantum efficiency (namely, from the standpoint of obtaining excellent light emission efficiency in a light emitting device using the composition of the present embodiment). The metal complex as described above includes, for example, ortho metalated complexes in which the central metal is a transition metal belonging to the period V or the period VI.

The central metal of the metal complex which is a phosphorescent compound includes metals having an atomic number of 50 or more, showing spin-orbital interaction with the complex and which can cause intersystem crossing between the single state and the triplet state, and includes preferably ruthenium(II), rhodium(III), palladium(II), osmium(II), iridium(III) or platinum(II), more preferably platinum(II) or iridium(III), further preferably iridium(III).

As the phosphorescent compound, a phosphorescent compound represented by the following general formula (MM) is preferable.

$$M(L)_{ka}(Z)_{kb} \quad (MM)$$

In the formula (MM),

M represents a metal atom selected from the group consisting of ruthenium, rhodium, palladium, osmium, iridium and platinum.

L represents a neutral or 1 to 3-valent anionic ligand capable of making polydentate coordination by forming at least two bonds selected from the group consisting of a coordinate bond and a covalent bond between L and a metal atom represented by M. When there are a plurality of L, these may be mutually the same or different.

Z represents a counter anion. When there are a plurality of Z, these may be mutually the same or different.

ka represents an integer of 1 or more, kb represents an integer of 0 or more. Here, ka+kb are so present as to satisfy the valency of a metal atom M The phosphorescent compound represented by the formula (MM) has totally neutral valency.

M in the formula (MM) is preferably platinum (II) or iridium(III), more preferably iridium(III).

L in the formula (MM) includes a ligand bonding at a nitrogen atom and an oxygen atom to a metal atom by a coordinate bond or a covalent bond such as 8-quinolinol and derivatives thereof, benzoquinolinol and derivatives thereof and the like, a ligand bonding at a nitrogen atom and a carbon atom by a coordinate bond or a covalent bond such as 2-phenyl-pyridine and derivatives thereof and the like, a ligand bonding at an oxygen atom by a coordinate bond or a covalent bond such as acetylacetone and derivatives thereof and the like, a ligand bonding at a nitrogen atom by a coordinate bond such as 2,2'-bipyridyl and derivatives thereof and the like, a ligand bonding at a phosphorus atom and a carbon atom by a coordinate bond or a covalent bond, and the like, and preferable is a ligand bonding at a nitrogen atom and a carbon atom by a coordinate bond or a covalent bond or a ligand bonding at a nitrogen atom by a coordinate bond, more preferable is a monoanionic ortho metalated ligand bonding at a nitrogen atom and a carbon atom by a coordinate bond or a covalent bond or a 2-valent or 3-valent ortho metalated ligand formed by mutually bonding the monoanionic ortho metalated ligands, further preferable is a monoanionic ortho metalated ligand bonding at a nitrogen atom and a carbon atom by a coordinate bond or a covalent bond.

L in the formula (MM) may be used singly or two or more ligands L may be used in combination as described above, and when used singly, the phosphorescent compound represented by the formula (MM) is a homoleptic complex, and when two or more ligands are used in combination, the phosphorescent compound represented by the formula (MM) is a heteroleptic complex.

The monoanionic ortho metalated ligand bonding at a nitrogen atom and a carbon atom by a coordinate bond or a covalent bond, which is a preferable example of L in the formula (MM), is exemplified below.

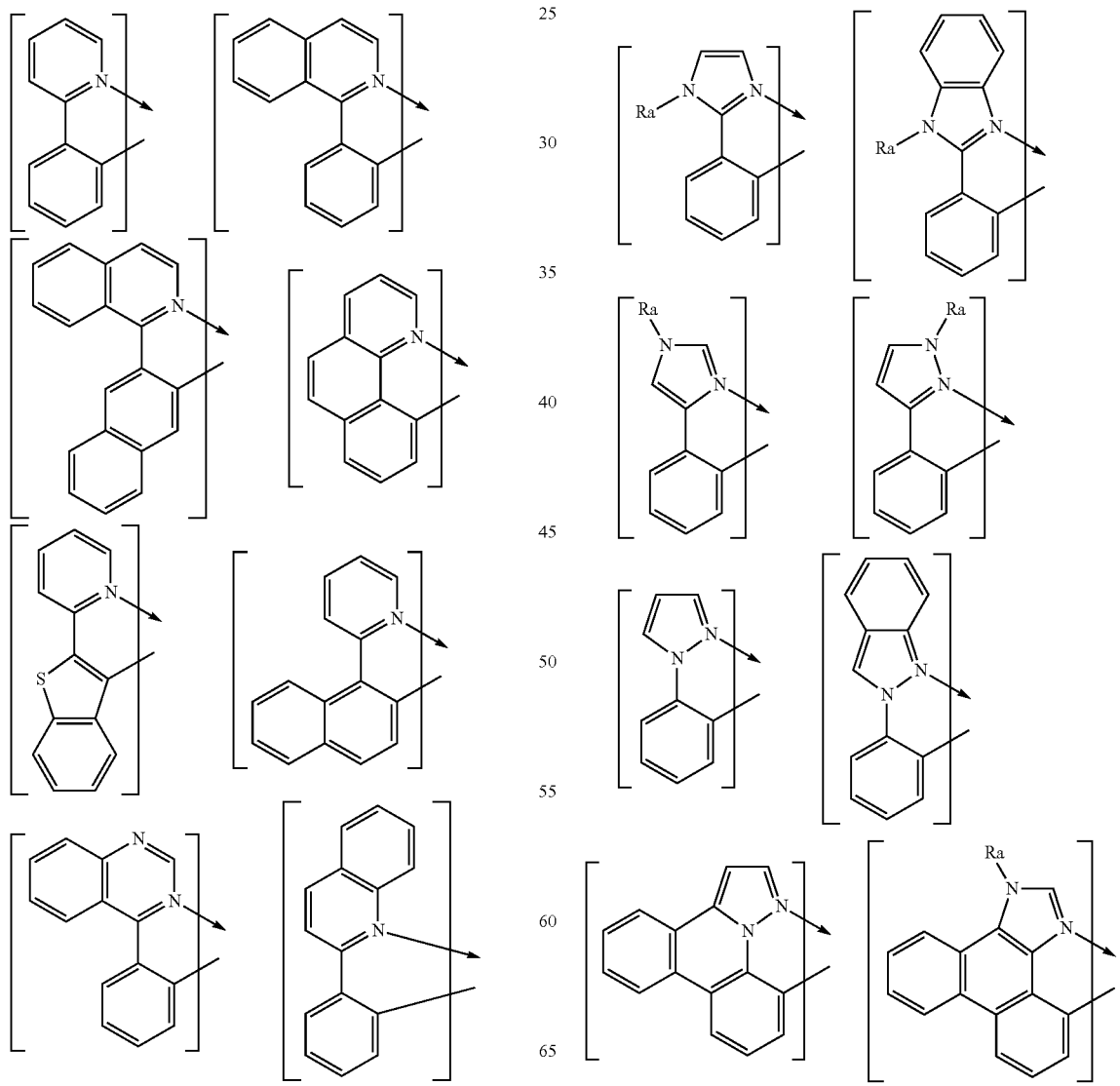

-continued

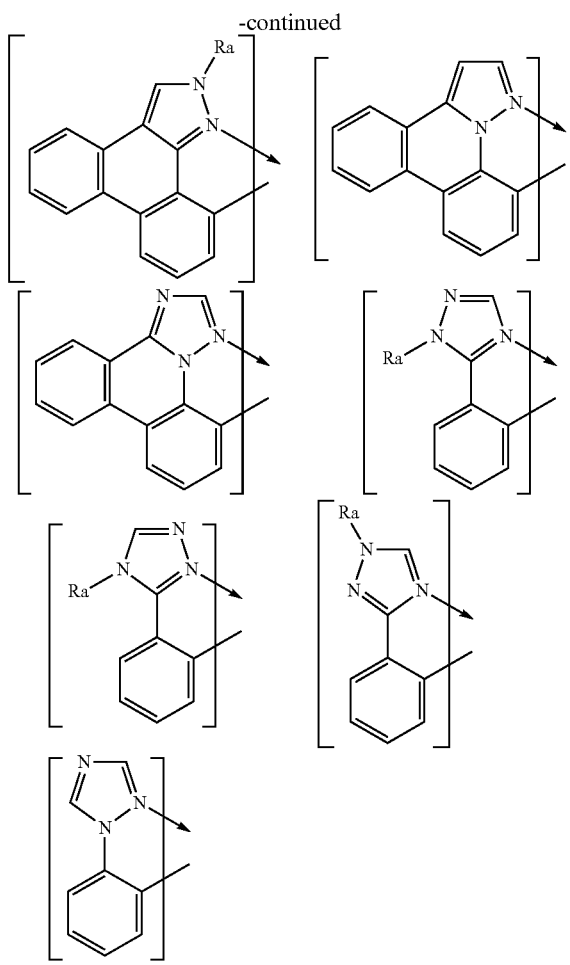

(wherein, Ra represents the same meaning as described above.)

Any hydrogen atom in the monoanionic ortho metalated ligand exemplified above may be substituted with an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom or a cyano group. When there are a plurality of the substituents, these may be the same or different and may be usually linked to form a ring structure together with an atom to which they are linked.

When a composition composed of the polymer compound of the present invention and a phosphorescent compound is used in production of a light emitting device, the composition is contained in an organic layer constituting the light emitting device, thus, it is preferable that the phosphorescent compound shows high compatibility with the polymer compound of the present invention (namely, phase separation scarcely occurs, and coating film formability is excellent).

In the phosphorescent compound to be used together with the polymer compound of the present invention, it is preferable to introduce a suitable substituent into a ligand held in the phosphorescent compound, from the above-described standpoint. As the substituent, an alkyl group, an alkoxy group, an aryl group, a monovalent aromatic heterocyclic group or an aralkyl group is preferable. The total number of atoms other than a hydrogen atom in the substituent is preferably 3 or more, more preferably 5 or more, further preferably 7 or more, particularly preferably 10 or more. It is preferable that the substituents are introduced into all ligands held in the phosphorescent compound. In this case, the substituents may be the same or different for every ligand.

As the above-described substituent, a dendron composed of an aryl group which may have a substituent or a monovalent aromatic heterocyclic group which may have a substituent is preferable. The dendron is a branching structure, and by introducing a dendron as a substituent into a ligand, the phosphorescent compound can be a phosphorescent compound having highly-condensed functionality endowed with, for example, functionality such as charge transportability and the like, and effects such as emission color adjustment and the like, in addition to the above-described improvement in coating film formability. A highly branched macro molecule having a dendron as a substituent is called a dendrimer in some cases, and described, for example, in WO 02/066575, WO 02/066552, WO 02/067343 and the like and designed and synthesized intending various functions.

Typical dendrons are exemplified below.

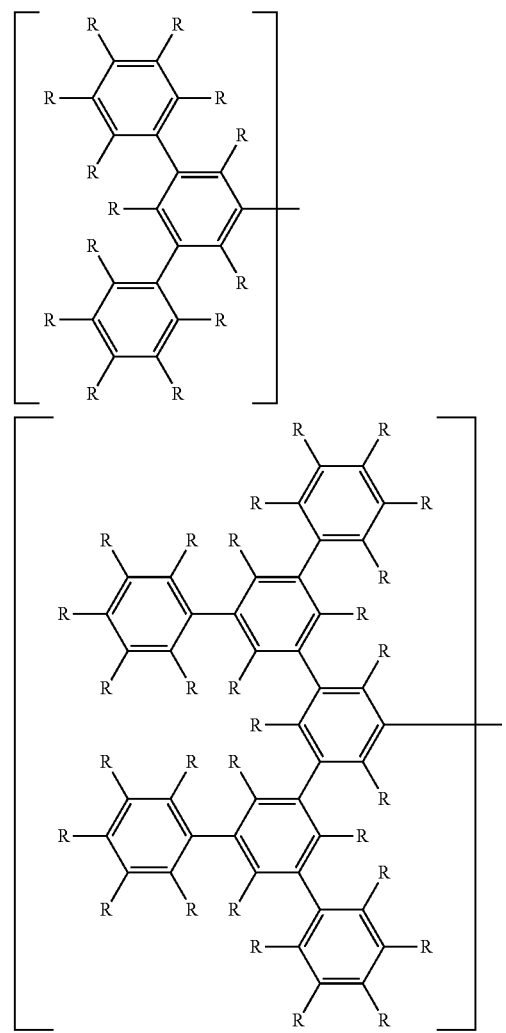

93
-continued
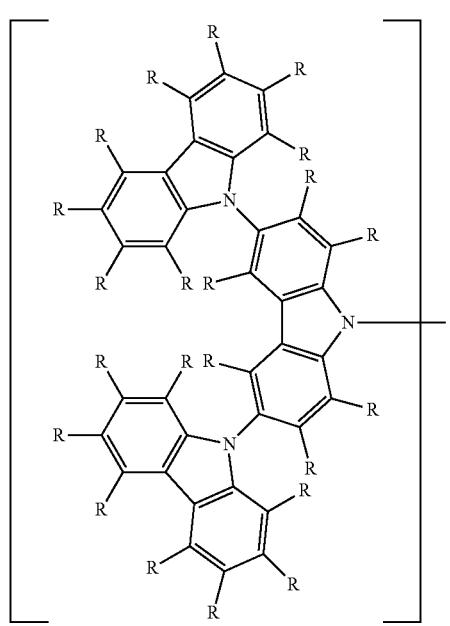
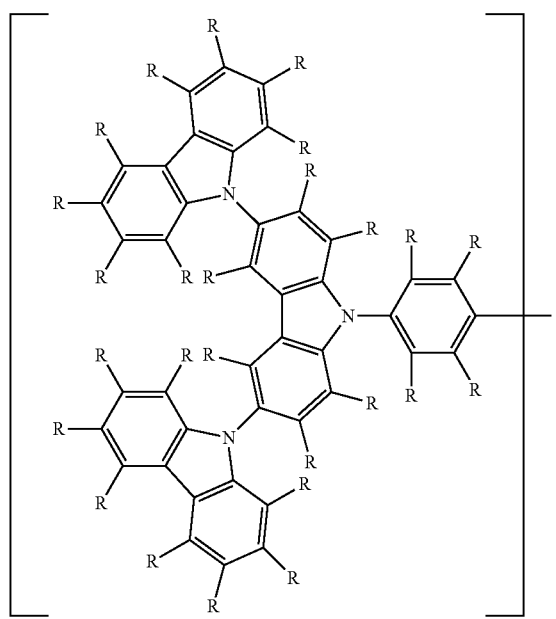
94
-continued
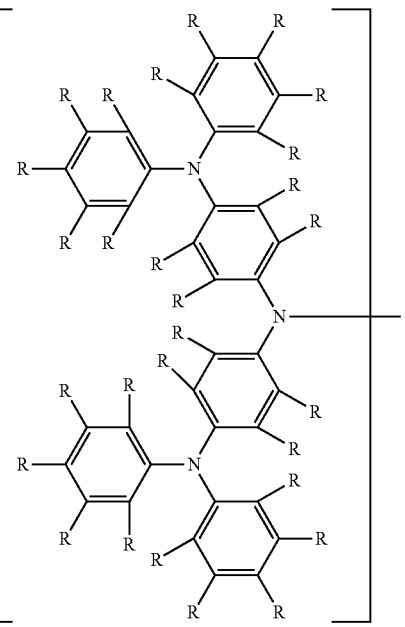
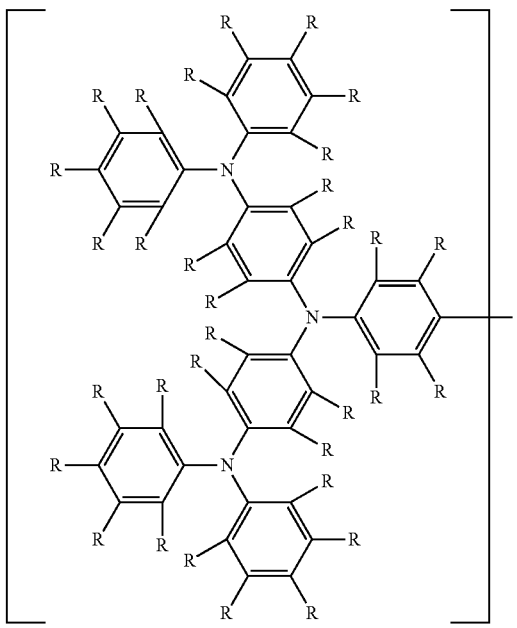

95
-continued
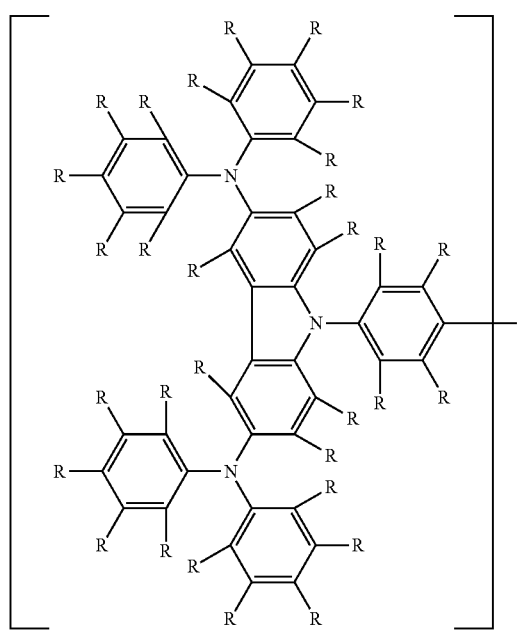
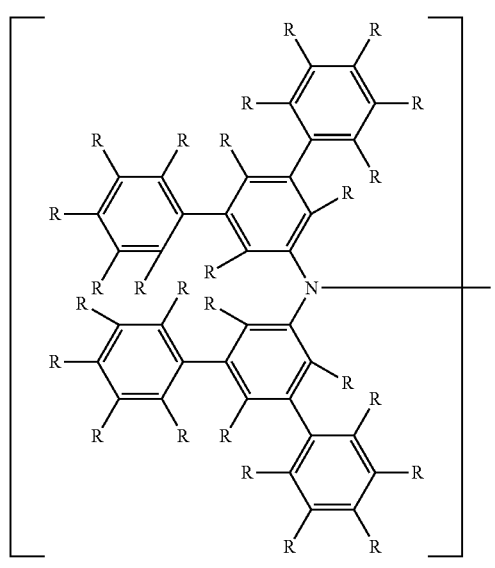
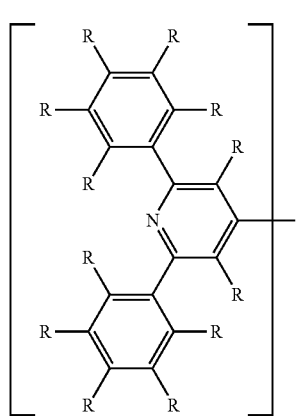
96
-continued
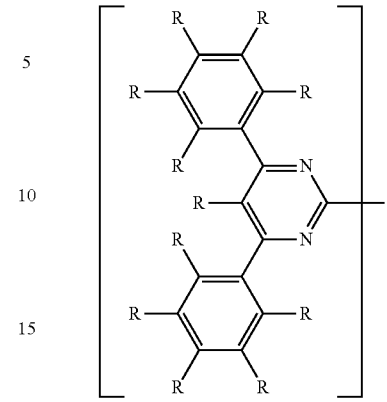
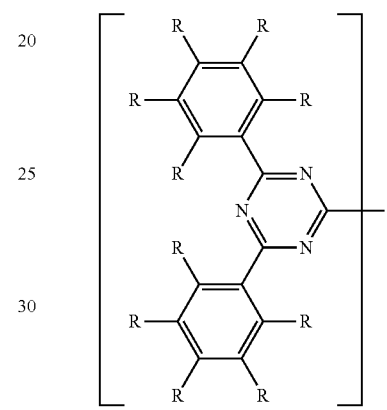
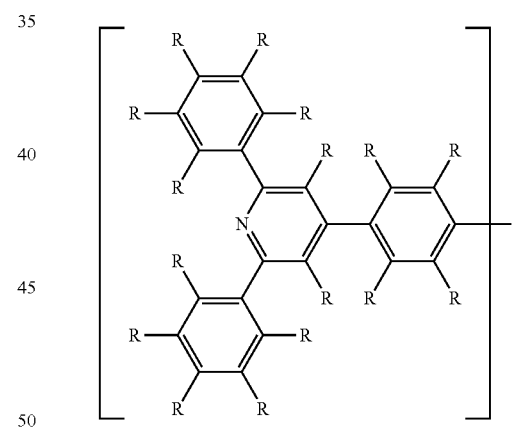
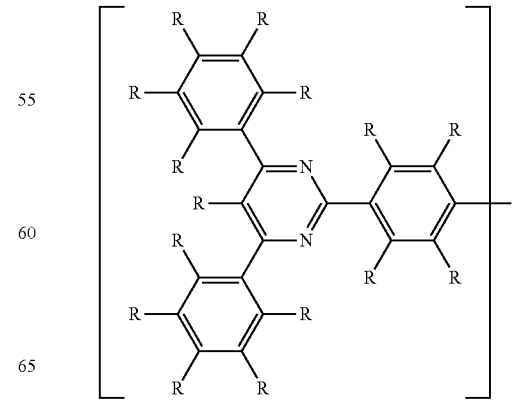

-continued

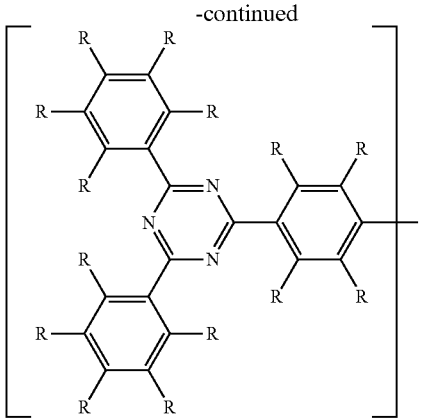

(wherein, R represents the same meaning as described above.)

Z in the formula (MM) includes, for example, conjugated bases of Broensted acids. Examples of the conjugated bases of Broensted acids include a fluoride ion, a chloride ion, a bromide ion, an iodide ion, a sulfate ion, a nitrate ion, a carbonate ion, a perchlorate ion, a tetrafluoroborate ion, a tetrakis(pentafluorophenyl)borate ion, a hexafluorophosphate ion, a methanesulfonate ion and a trifluoroacetate ion.

As the phosphorescent compound represented by the formula (MM), phosphorescent compounds in which M is iridium(III), L is a monoanionic ortho metalated ligand bonding at a nitrogen atom and a carbon atom to M by a coordinate bond or a covalent bond, ka is 3 and kb is 0 are preferable.

The phosphorescent compound represented by the formula (MM) includes preferably phosphorescent compounds represented by the following general formulae (Ir-1) to (Ir-3).

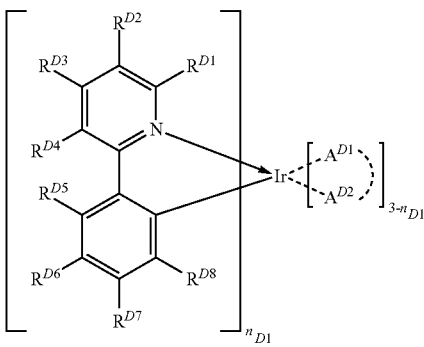

(Ir-1)

[in the formula (Ir-1)

$R^{D1}$, $R^{D2}$, $R^{D3}$, $R^{D4}$, $R^{D5}$, $R^{D6}$, $R^{D7}$ and $R^{D8}$ represent each independently a hydrogen atom, an alkyl group, an alkoxy group, an aryl group, an aryloxy group, a monovalent aromatic heterocyclic group or a halogen atom, and these groups may have a substituent. Here, at least one of $R^{D1}$, $R^{D2}$, $R^{D3}$, $R^{D4}$, $R^{D5}$, $R^{D6}$, $R^{D7}$ and $R^{D8}$ is a group represented by the following general formula (Dend-A) or (Dend-B).

-$A^{D1}$---$A^{D2}$- represents an anionic bidentate ligand, and $A^{D1}$ and $A^{D2}$ represent each independently a carbon atom, an oxygen atom or a nitrogen atom bonding to an iridium atom.

$n_{D1}$ represents 1, 2 or 3.]

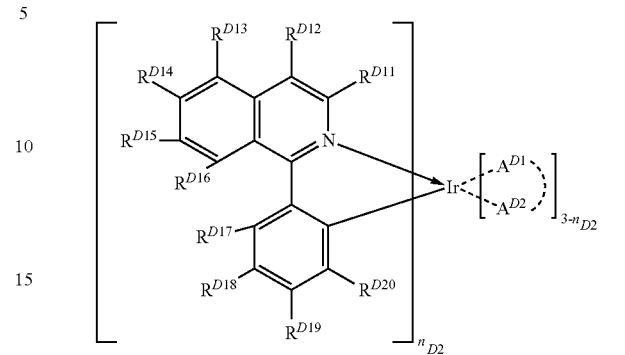

(Ir-2)

[in the formula (Ir-2), $R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ represent each independently a hydrogen atom, an alkyl group, an alkoxy group, an aryl group, an aryloxy group, a monovalent aromatic heterocyclic group or a halogen atom, and these groups may have a substituent. Here, at least one of $R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ is a group represented by the following general formula (Dend-A) or (Dend-B).

-$A^{D1}$---$A^{D2}$- represents an anionic bidentate ligand, and $A^{D1}$ and $A^{D2}$ represent each independently a carbon atom, an oxygen atom or a nitrogen atom bonding to an iridium atom.

$n_{D2}$ represents 1, 2 or 3.]

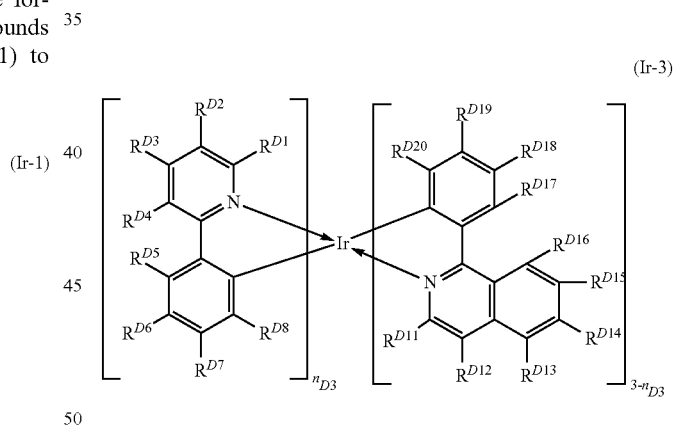

(Ir-3)

[in the formula (Ir-3)

$R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ represent each independently a hydrogen atom, an alkyl group, an alkoxy group, an aryl group, an aryloxy group, a monovalent aromatic heterocyclic group or a halogen atom, and these groups may have a substituent. Here, at least one of $R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ is a group represented by the following general formula (Dend-A) or (Dend-B).

-$A^{D1}$---$A^{D2}$- represents an anionic bidentate ligand, and $A^{D1}$ and $A^{D2}$ represent each independently a carbon atom, an oxygen atom or a nitrogen atom bonding to an iridium atom.

$n_{D3}$ represents 1 or 2.]

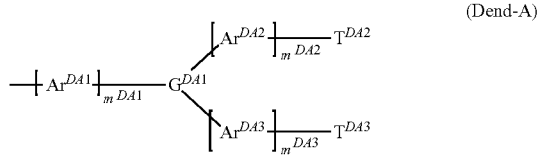
(Dend-A)

[in the formula (Dend-A), $G^{DA1}$ represents a nitrogen atom, a trivalent aromatic hydrocarbon group or a trivalent aromatic heterocyclic group.

$Ar^{DA1}$, $Ar^{DA2}$ and $Ar^{DA3}$ represent each independently an arylene group or a divalent aromatic heterocyclic group.

$T^{DA2}$ and $T^{DA3}$ represent each independently an aryl group or a monovalent aromatic heterocyclic group.

$m^{DA1}$, $m^{DA2}$ and $m^{DA3}$ represent each independently an integer of 0 or more.]

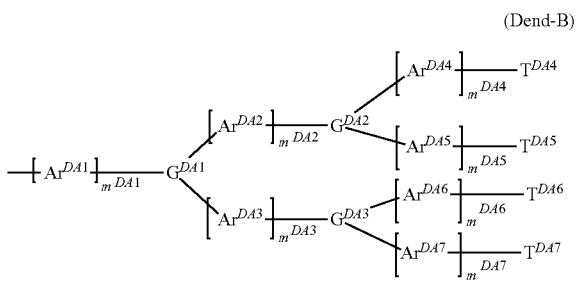
(Dend-B)

[in the formula (Dend-B), $G^{DA1}$, $G^{DA2}$ and $G^{DA3}$ represent each independently a nitrogen atom, a trivalent aromatic hydrocarbon group or a trivalent aromatic heterocyclic group.

$Ar^{DA1}$, $Ar^{DA2}$, $Ar^{DA3}$, $Ar^{DA4}$, $Ar^{DA5}$, $Ar^{DA6}$ and $Ar^{DA7}$ represent each independently an arylene group or a divalent aromatic heterocyclic group.

$T^{DA4}$, $T^{DA5}$, $T^{DA6}$ and $T^{DA7}$ represent each independently an aryl group or a monovalent aromatic heterocyclic group.

$m^{DA1}$, $m^{DA2}$, $m^{DA3}$, $m^{DA4}$, $m^{DA5}$, $m^{DA6}$ and $m^{DA7}$ represent each independently an integer of 0 or more.]

$G^{DA1}$ is preferably a group represented by the following formulae (GDA-11) to (GDA-15). $G^{DA2}$ is preferably a group represented by the following formulae (GDA-21) to (GDA-25). $G^{DA3}$ is preferably a group represented by the following formulae (GDA-31) to (GDA-35).

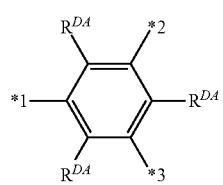
(GDA-11)

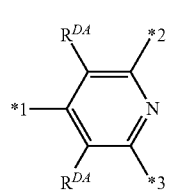
(GDA-12)

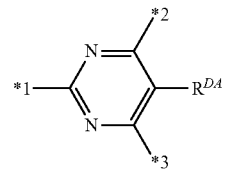
(GDA-13)

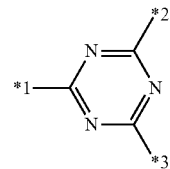
(GDA-14)

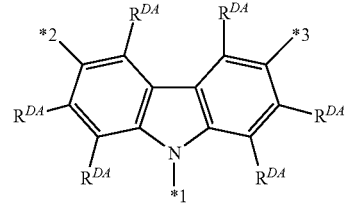
(GDA-15)

[in the formulae,

*1, *2 and *3 represent a linkage to $Ar^{DA1}$, $Ar^{DA2}$ and $Ar^{DA3}$, respectively $R^{DA}$ represents a hydrogen atom, an alkyl group, an alkoxy group, an aryl group or a monovalent aromatic heterocyclic group, and these groups may have a substituent. When there are a plurality of $R^{DA}$, these may be mutually the same or different.]

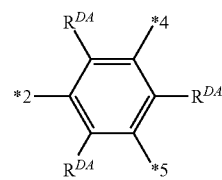
(GDA-21)

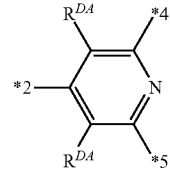
(GDA-22)

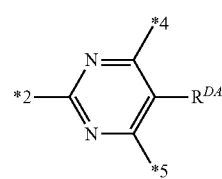
(GDA-23)

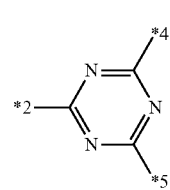
(GDA-24)

-continued

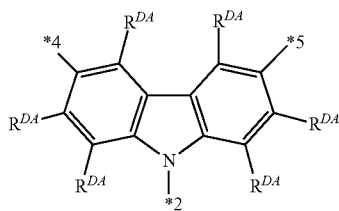
(GDA-25)

[in the formulae,

*2, *4 and *5 represent a linkage to $Ar^{DA2}$, $Ar^{DA4}$ and $Ar^{DA5}$, respectively $R^{DA}$ represents a hydrogen atom, an alkyl group, an alkoxy group, an aryl group or a monovalent aromatic heterocyclic group, and these groups may have a substituent. When there are a plurality of $R^{DA}$, these may be mutually the same or different.]

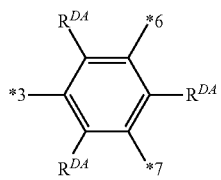
(GDA-31)

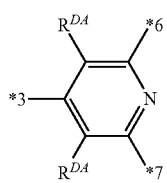
(GDA-32)

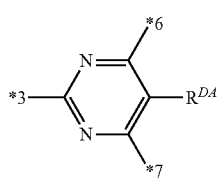
(GDA-33)

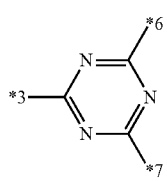
(GDA-34)

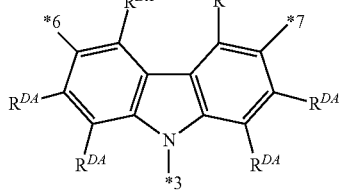
(GDA-35)

[in the formulae,

*3, *6 and *7 represent a linkage to $Ar^{DA3}$, $Ar^{DA6}$ and $Ar^{DA7}$, respectively.

$R^{DA}$ represents a hydrogen atom, an alkyl group, an alkoxy group, an aryl group or a monovalent aromatic heterocyclic group, and these groups may have a substituent. When there are a plurality of $R^{DA}$, these may be mutually the same or different.]

$R^{DA}$ represents preferably a hydrogen atom, an alkyl group or an alkoxy group, more preferably a hydrogen atom or an alkyl group, further preferably a hydrogen atom.

$Ar^{DA1}$, $Ar^{DA2}$, $Ar^{DA3}$, $Ar^{DA4}$, $Ar^{DA5}$, $Ar^{DA6}$ and $Ar^{DA7}$ are preferably a group represented by the following formulae (ArDA-1) to (ArDA-3). When there are a plurality of each of $Ar^{DA1}$, $Ar^{DA2}$, $Ar^{DA3}$, $Ar^{DA4}$, $Ar^{DA5}$, $Ar^{DA6}$ and $Ar^{DA7}$, these may each be mutually the same or different.

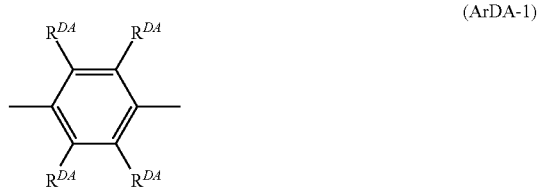
(ArDA-1)

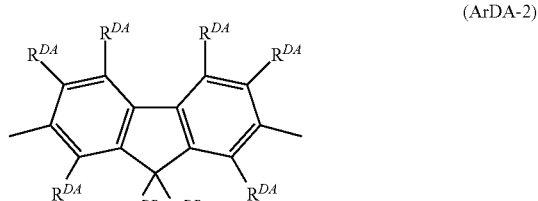
(ArDA-2)

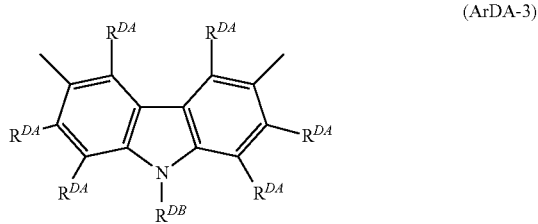
(ArDA-3)

[in the formulae, $R^{DA}$ represents the same meaning as described above.

$R^{DB}$ represents a hydrogen atom, an alkyl group, an alkoxy group, an aryl group or a monovalent aromatic heterocyclic group. When there are a plurality of $R^{DB}$, these may be mutually the same or different.]

$R^{DB}$ represents preferably an alkyl group, an aryl group or a monovalent aromatic heterocyclic group, more preferably an aryl group or a monovalent aromatic heterocyclic group, further preferably an aryl group.

$T^{DA2}$, $T^{DA3}$, $T^{DA4}$, $T^{DA5}$, $T^{DA6}$ and $T^{DA7}$ are preferably a group represented by the following formulae (TD-1) to (TD-3).

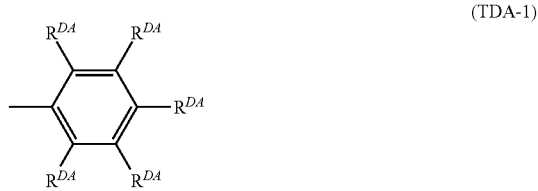
(TDA-1)

(TDA-2)

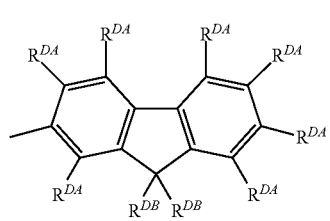

(TDA-3)

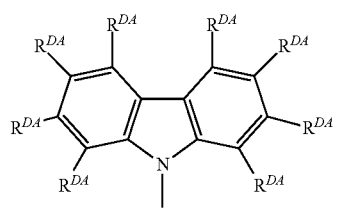

[in the formulae, $R^{DA}$ and $R^{DB}$ represent the same meaning as described above.].

$m^{DA1}$, $m^{DA2}$, $m^{DA3}$, $m^{DA4}$, $m^{DA5}$, $m^{DA6}$ and $m^{DA7}$ represent usually an integer of 10 or less, preferably an integer of 5 or less, more preferably 0 or 1, further preferably 0.

The group represented by the formula (Dend-A) is preferably a group represented by the following formula (Dend-A1), (Dend-A2) or (Dend-A3), more preferably a group represented by the formula (Dend-A1) or (Dend-A3), further preferably a group represented by the formula (Dend-A1).

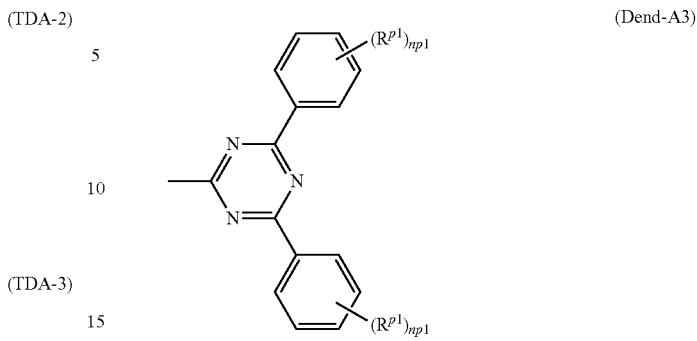

[in the formulae (Dend-A1) to (Dend-A3), $R^{p1}$, $R^{p2}$ and $R^{p3}$ represent each independently an alkyl group, an alkoxy group, an aryl group, an aryloxy group, a monovalent aromatic heterocyclic group or a halogen atom. When there are a plurality of each of $R^{p1}$ and $R^{p2}$, these may each be mutually the same or different.

np1 represents an integer of 0 to 5, np2 represents an integer of 0 to 3, and np3 represents 0 or 1. When there are a plurality of np1, these may be mutually the same or different.]

The group represented by the formula (Dend-B) is preferably a group represented by the following formula (Dend-B1), (Dend-B2) or (Dend-B3), more preferably a group represented by the formula (Dend-B1) or (Dend-B3), further preferably a group represented by the formula (Dend-B1).

(Dend-A1)

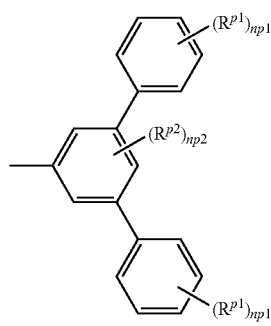

(Dend-A2)

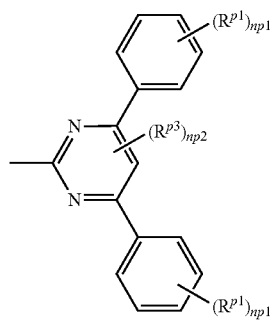

(Dend-B1)

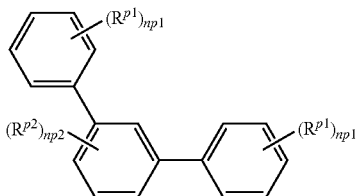

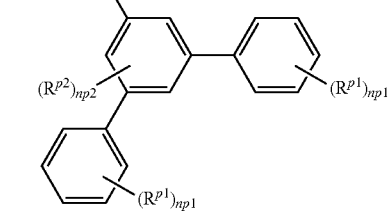

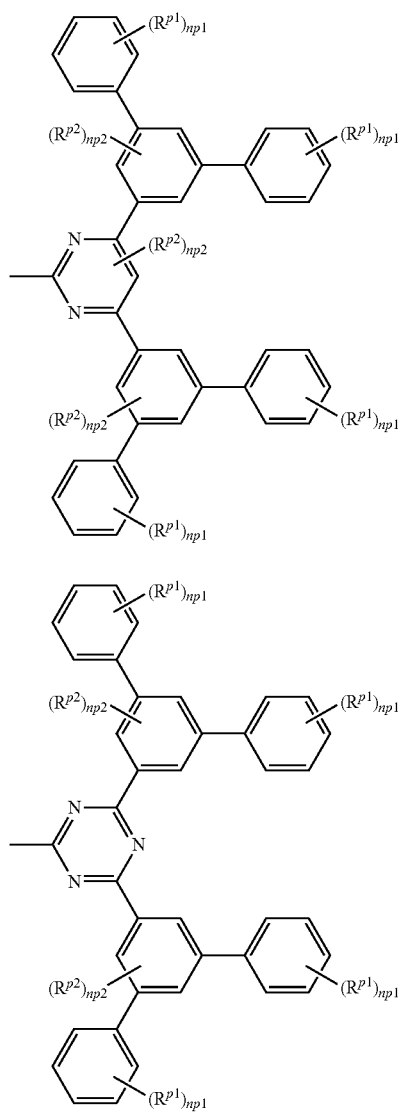

(Dend-B2)

(Dend-B3)

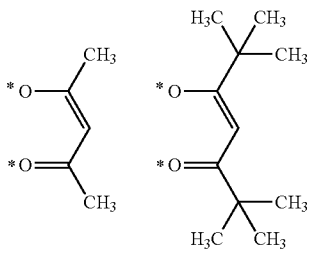

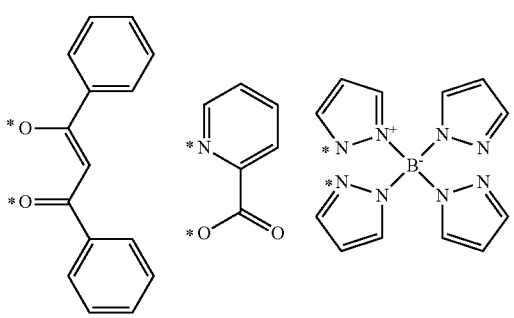

[in the formulae, * represents a bond to an iridium atom.]

The phosphorescent compound represented by the formulae Ir-1 is preferably a phosphorescent compound represented by the following formulae Ir-11 to Ir-13. The phosphorescent compound represented by the formulae Ir-2 is preferably a phosphorescent compound represented by the following formula Ir-21. The phosphorescent compound represented by the formula Ir-3 is preferably a phosphorescent compound represented by the following formulae Ir-31 to Ir-33.

[in the formulae (Dend-B1) to (Dend-B3), $R^{p1}$, $R^{p2}$ and $R^{p3}$ represent each independently an alkyl group, an alkoxy group, an aryl group, an aryloxy group, a monovalent aromatic heterocyclic group or a halogen atom. When there are a plurality of each of $R^{p1}$ and $R^{p2}$, these may each be mutually the same or different.

np1 represents an integer of 0 to 5, np2 represents an integer of 0 to 3, and np3 represents 0 or 1. When there are a plurality of each of np1 and np2, these may each be mutually the same or different.]

$R^{p1}$, $R^{p2}$ and $R^{p3}$ represent preferably an alkyl group, an aryl group or a monovalent aromatic heterocyclic group, more preferably an alkyl group.

np1 represents preferably 0 or 1, more preferably 1. np2 represents preferably 0 or 1, more preferably 0. np3 represents preferably 0.

The anionic bidentate ligand represented by -$A^{D1}$ - - - $A^{D2}$- includes, for example, ligands represented by the following formulae.

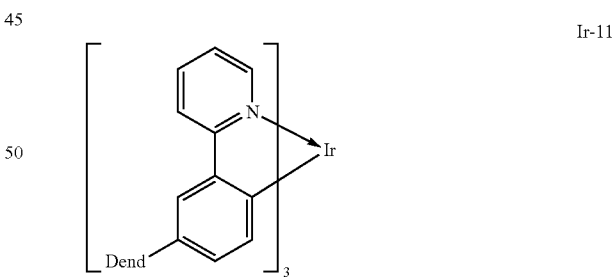

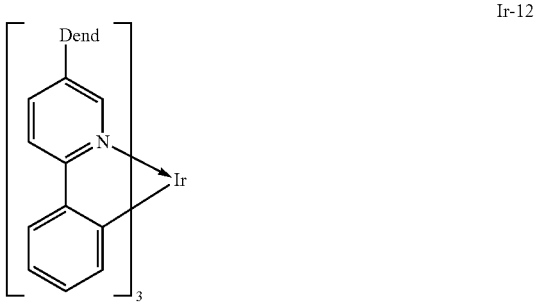

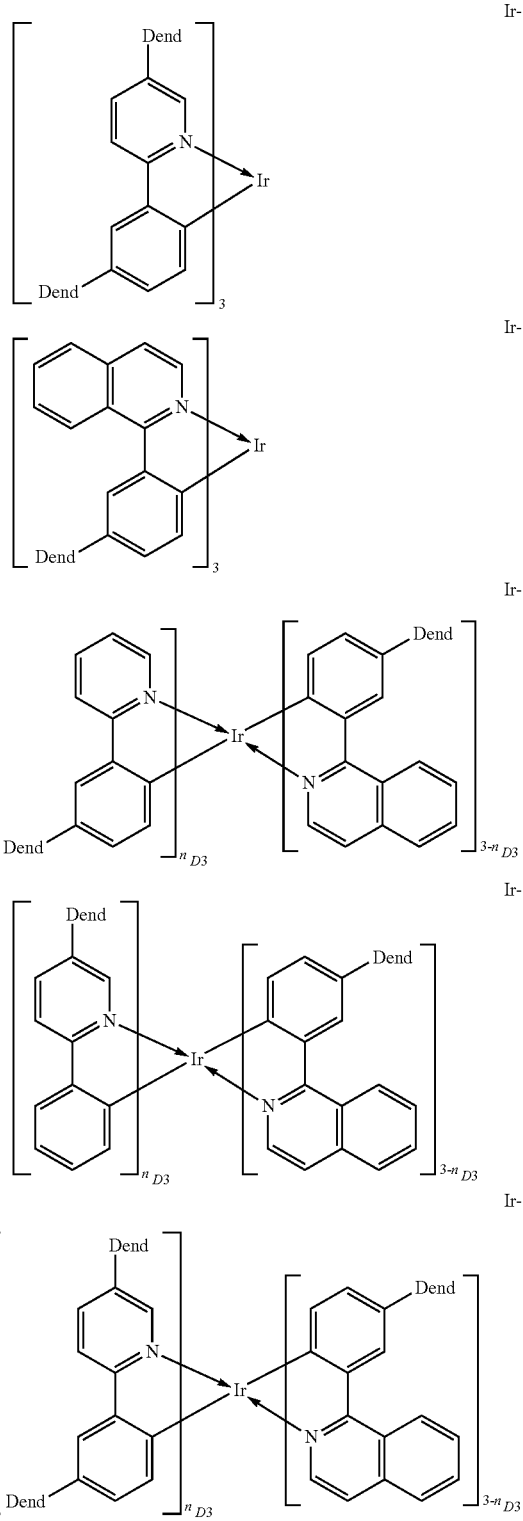

[in the formulae Ir-11 to Ir-31, Ir-21 and Ir-31 to Ir-33, Dend represents a group represented by the above-described formula (Dend-A) or (Dend-B). $n_{D3}$ represents the same meaning as described above.]

A composition comprising a phosphorescent compound represented by the formula (Ir-1), (Ir-2) or (Ir-3) and a polymer compound containing as a repeating unit a group represented by the following general formula (1B) is useful for production of a light emitting device excellent in luminance life.

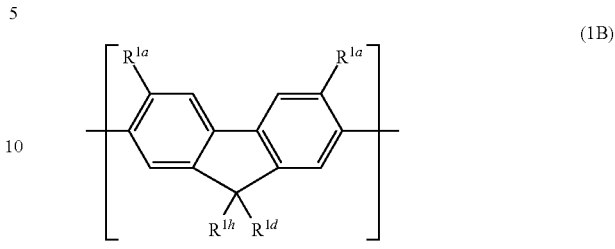

[in the formula (1B), $R^{1a}$ represents an alkyl group, an aryl group, a monovalent aromatic heterocyclic group or an aralkyl group, and these groups may have a substituent. A plurality of $R^{1a}$ may be the same or different.

$R^{1h}$ and $R^{1d}$ represent each independently an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom or a cyano group. $R^{1h}$ and $R^{1d}$ may be mutually linked to form a ring together with a carbon atom to which they are linked.]

Specific examples and preferable embodiments of the alkyl group, the aryl group, the monovalent aromatic heterocyclic group, the alkoxy group, the aryloxy group, the aralkyl group, the arylalkoxy group, the substituted amino group, the substituted carbonyl group, the substituted carboxyl group, the fluorine atom and the cyano group represented by $R^{1h}$ and $R^{1d}$ are the same as examples and preferable embodiments of the alkyl group, the aryl group, the monovalent aromatic heterocyclic group, the alkoxy group, the aryloxy group, the aralkyl group, the arylalkoxy group, the substituted amino group, the substituted carbonyl group, the substituted carboxyl group, the fluorine atom and the cyano group represented by $R^{1d}$ in the formula (1).

The polymer compound containing a group represented by the formula (1B) as a repeating unit contains, in more suitable embodiments, a group represented by the formula (2) and/or a group represented by the formula (3) as a repeating unit. The polymer compound containing as a repeating unit a group represented by the formula (1B) may also contain the other group than the group represented by the formula (2) and the group represented by the formula (3) as a repeating unit. The groups represented by the formula (1B), the groups represented by the formula (2) and the groups represented by the formula (3) may each be used singly or may each be used in combination.

As the phosphorescent compound represented by the formula (MM), the following compounds are exemplified, and Ir-2a to Ir-6a, Ir-10a to Ir-13a, Ir-17a to Ir-24a, Ir-2b to Ir-6b, Ir-10b to Ir-13b, Ir-18b to Ir-29b, Ir-1c to Ir-14c and Ir-1d to Ir-19d are preferable, Ir-10a to Ir-13a, Ir-17a to Ir-24a, Ir-10b to Ir-13b, Ir-18b to Ir-29b, Ir-1c, Ir-5c, Ir-8c, Ir-10c to Ir-14c, Ir-1d to Ir-2d, Ir-6d to Ir-12d and Ir-15d to Ir-19d are more preferable, from the standpoint of luminance life. In the following examples, Rp described as a substituent which a Dendron portion have includes preferably an alkyl group and an alkoxy group, more preferably an alkyl group, and from the standpoint of easiness of synthesis and easiness of dissolution in an organic solvent when the resultant phosphorescent compound is used for manufacturing a light emitting device, alkyl groups such as a tert-butyl group, a hexyl group, an ethylhexyl group and the like are still more preferable.

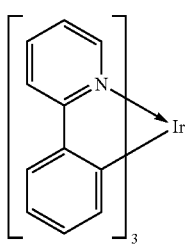 Ir-1a
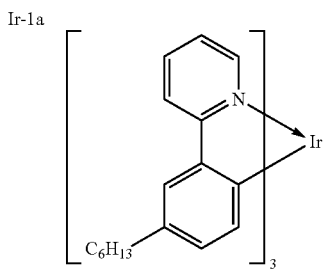 Ir-2a
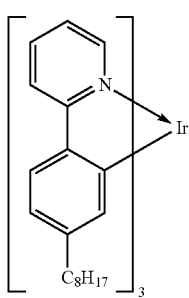 Ir-3a
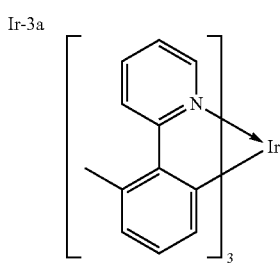 Ir-4a
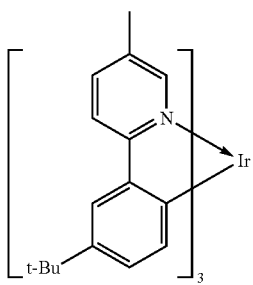 Ir-5a
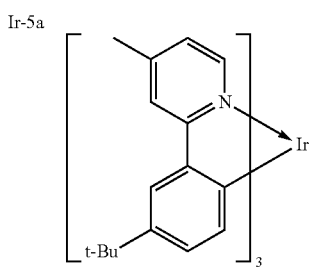 Ir-6a
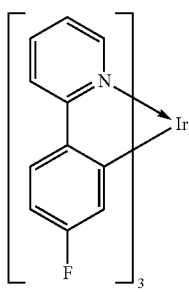 Ir-7a
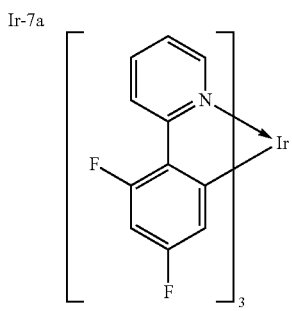 Ir-8a
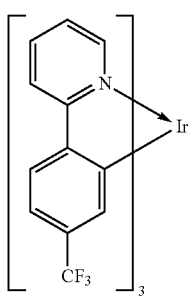 Ir-9a
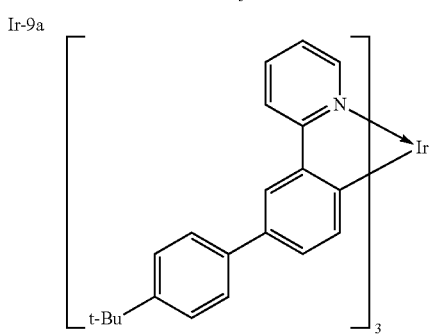 Ir-10a -continued
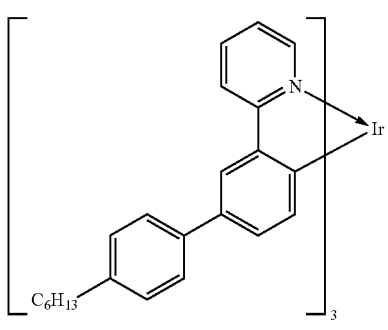
Ir-11a
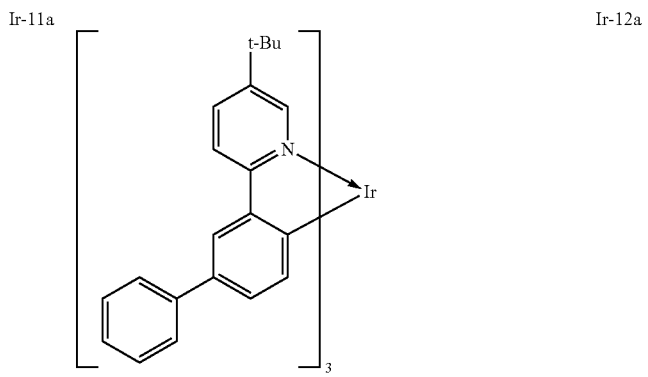
Ir-12a
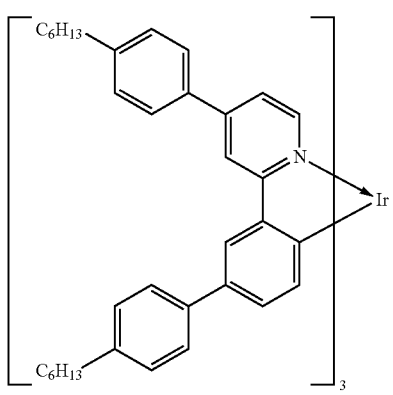
Ir-13a
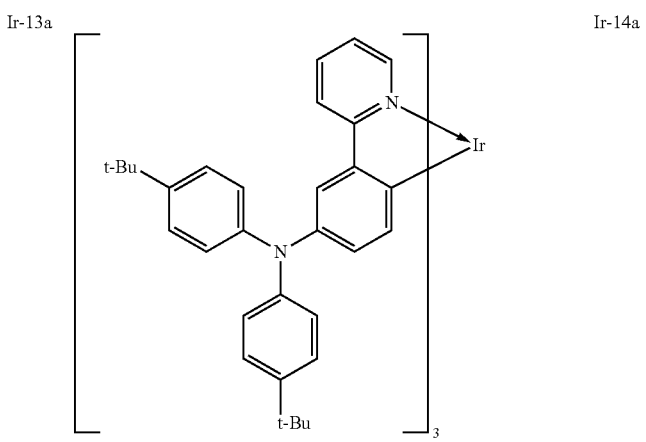
Ir-14a
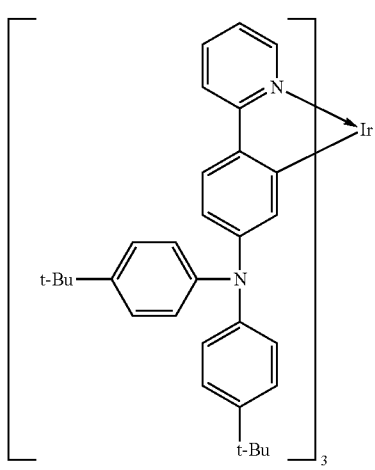
Ir-15a
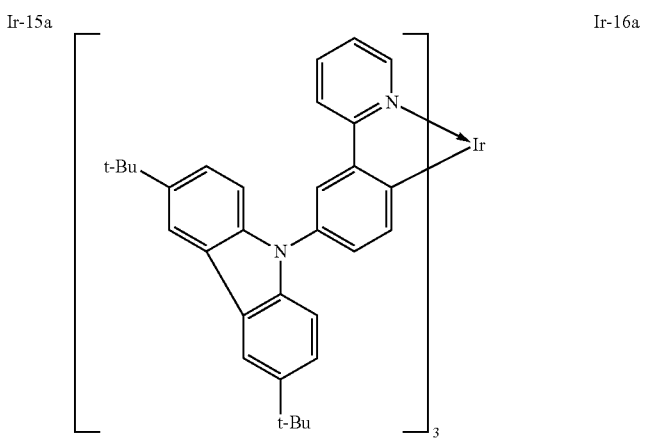
Ir-16a -continued
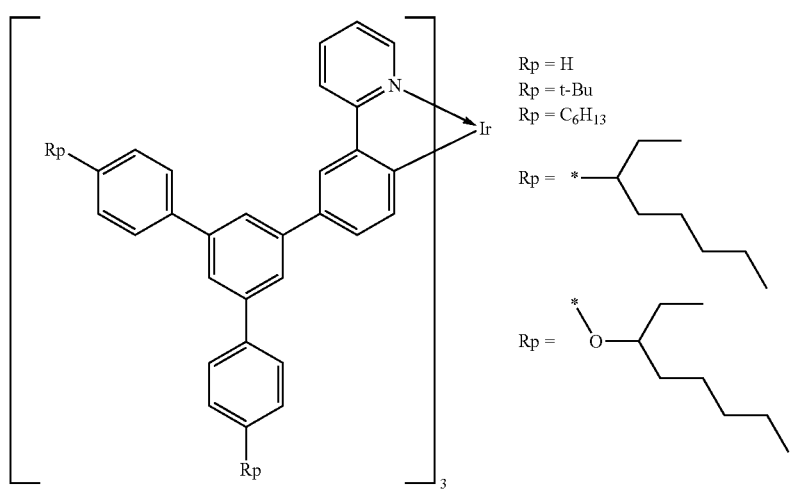
Ir-17a
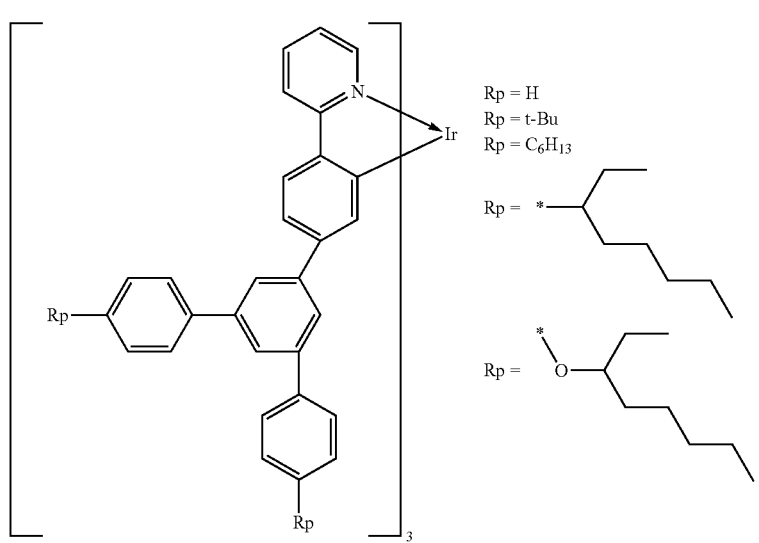
Ir-18a
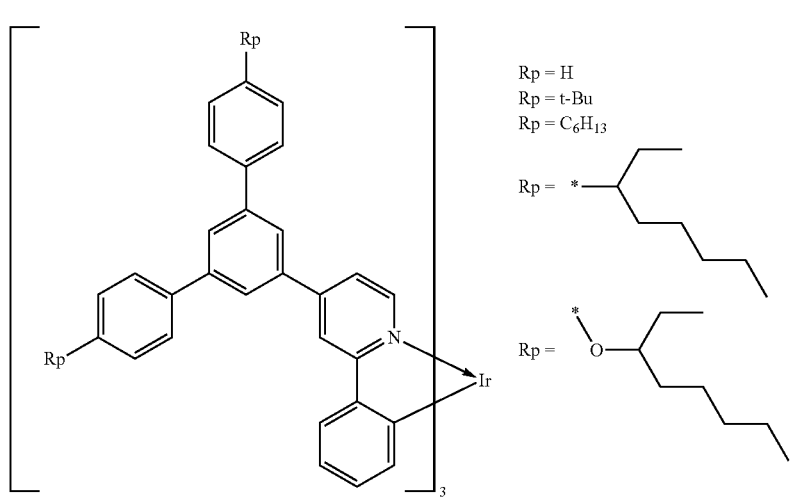
Ir-19a

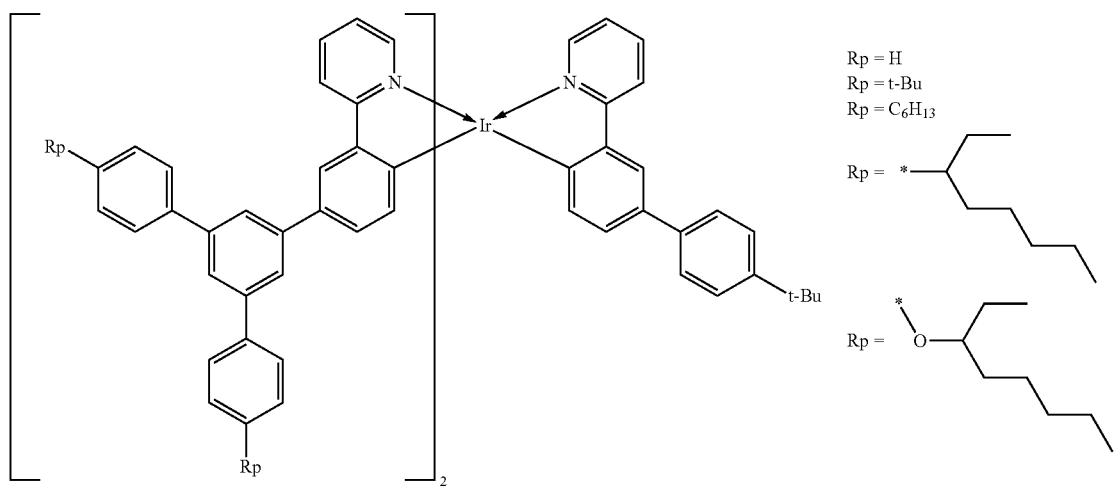
Ir-20a
Rp = H
Rp = t-Bu
Rp = C₆H₁₃
Rp = *−CH(C₂H₅)(C₅H₁₁)
Rp = *−O−CH(C₂H₅)(C₅H₁₁)
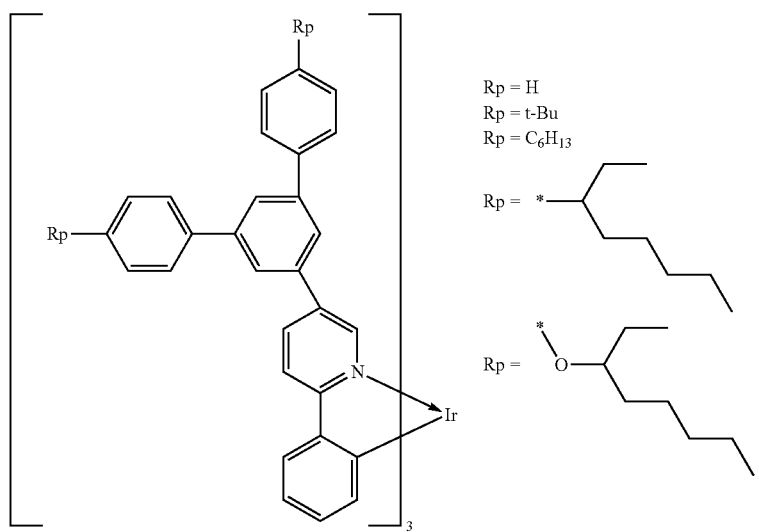
Ir-21a
Rp = H
Rp = t-Bu
Rp = C₆H₁₃
Rp = *−CH(C₂H₅)(C₅H₁₁)
Rp = *−O−CH(C₂H₅)(C₅H₁₁)
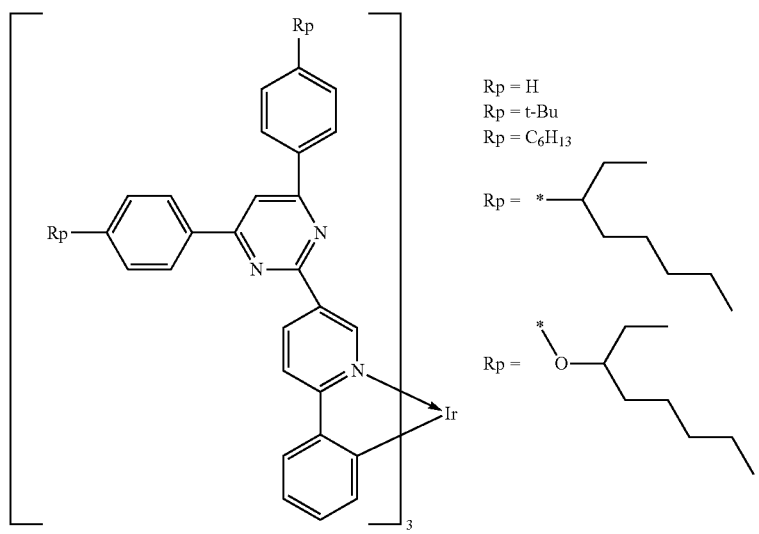
Ir-22a
Rp = H
Rp = t-Bu
Rp = C₆H₁₃
Rp = *−CH(C₂H₅)(C₅H₁₁)
Rp = *−O−CH(C₂H₅)(C₅H₁₁)

-continued
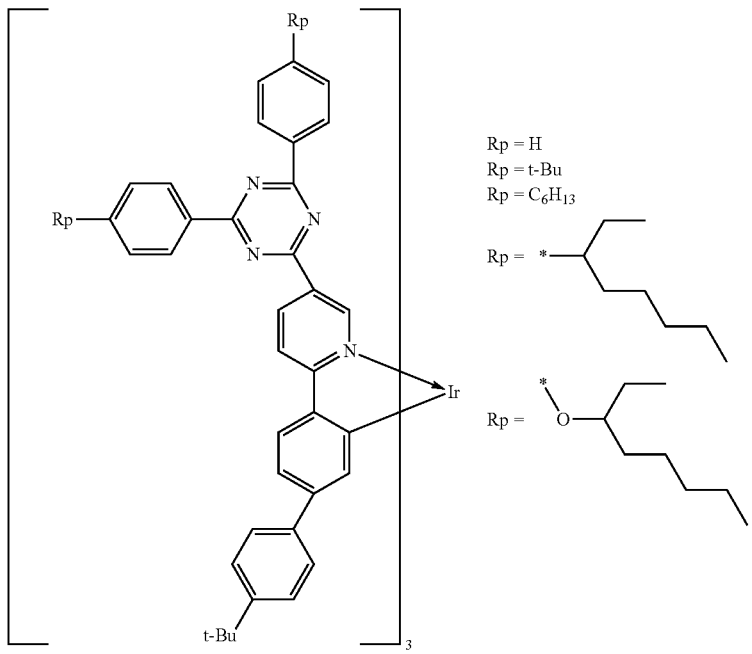
Ir-23a
Rp = H
Rp = t-Bu
Rp = C_6H_{13}
Rp = *—CH(C_2H_5)(C_5H_{11})
Rp = *—O—CH(C_2H_5)(C_5H_{11})
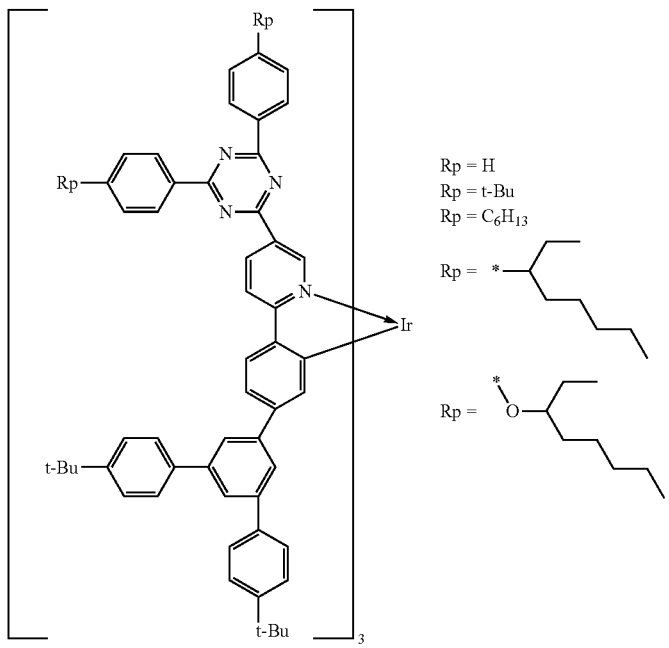
Ir-24a
Rp = H
Rp = t-Bu
Rp = C_6H_{13}
Rp = *—CH(C_2H_5)(C_5H_{11})
Rp = *—O—CH(C_2H_5)(C_5H_{11})
Ir-1b   Ir-2b -continued
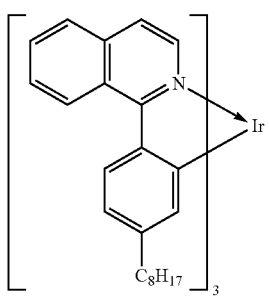
Ir-3b
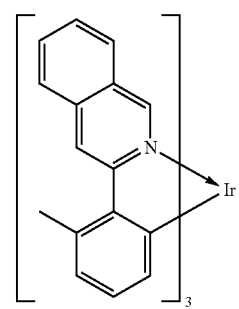
Ir-4b
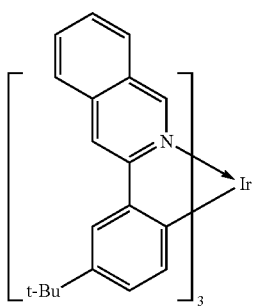
Ir-5b
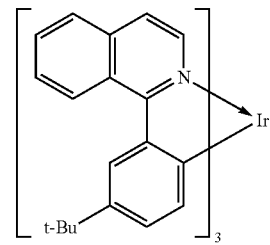
Ir-6b
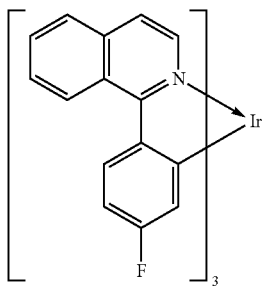
Ir-7b
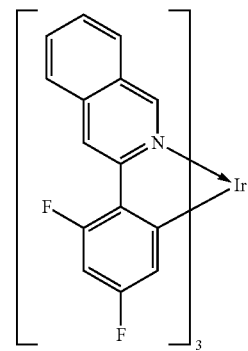
Ir-8b
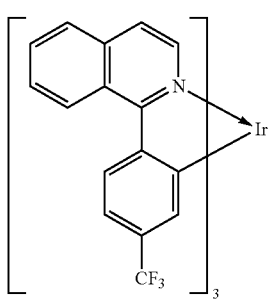
Ir-9b
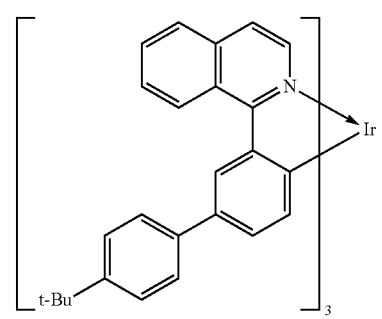
Ir-10b
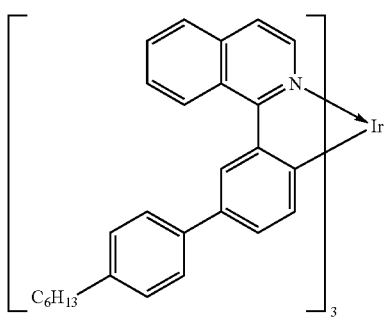
Ir-11b
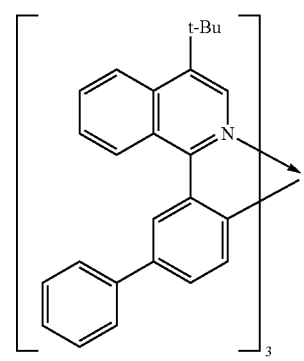
Ir-12b -continued
Ir-13b
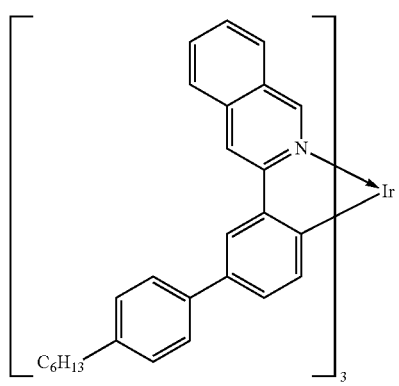
Ir-14b
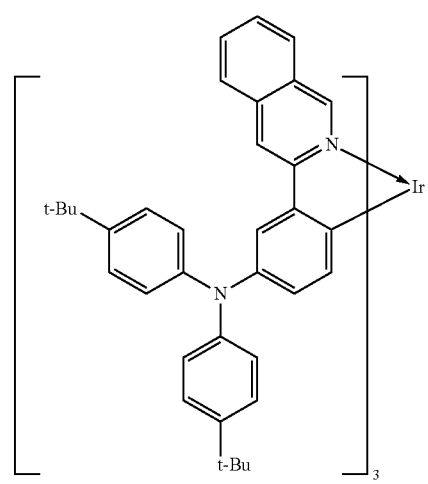
Ir-15b
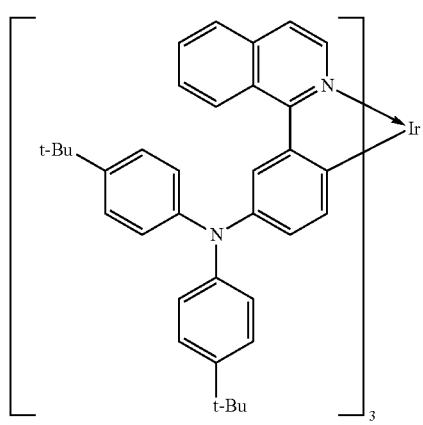
Ir-16b
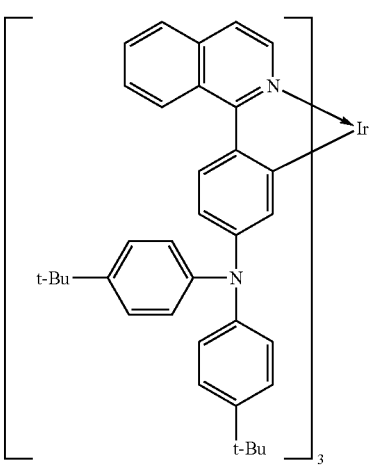
Ir-17b
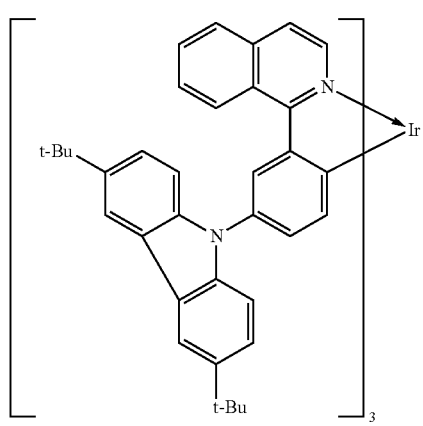

-continued
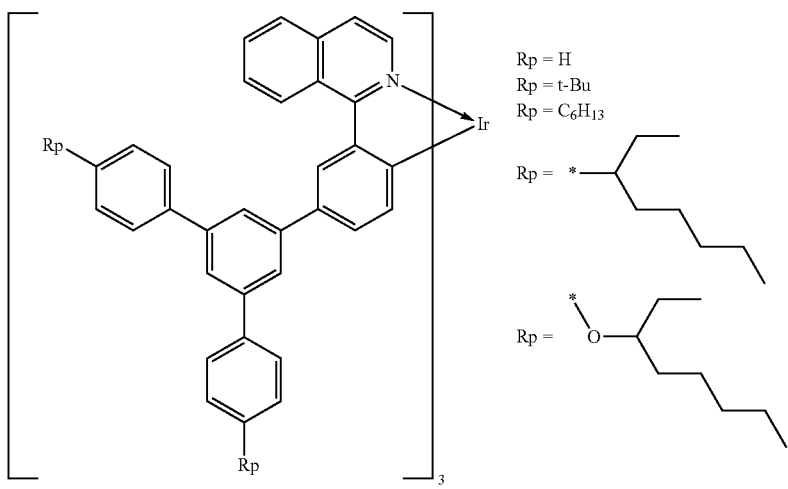
Ir-18b
Rp = H
Rp = t-Bu
Rp = C6H13
Rp = *—CH(C2H5)(C5H11)
Rp = *—O—CH(C2H5)(C5H11)
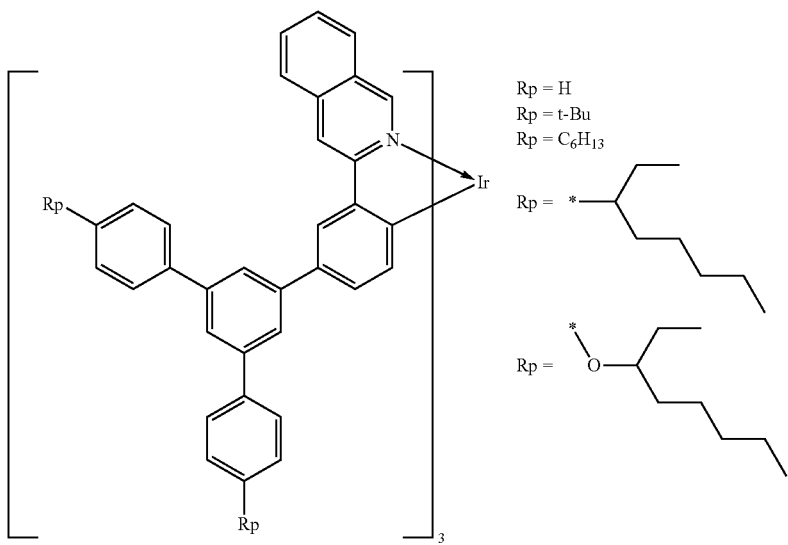
Ir-19b
Rp = H
Rp = t-Bu
Rp = C6H13
Rp = *—CH(C2H5)(C5H11)
Rp = *—O—CH(C2H5)(C5H11)
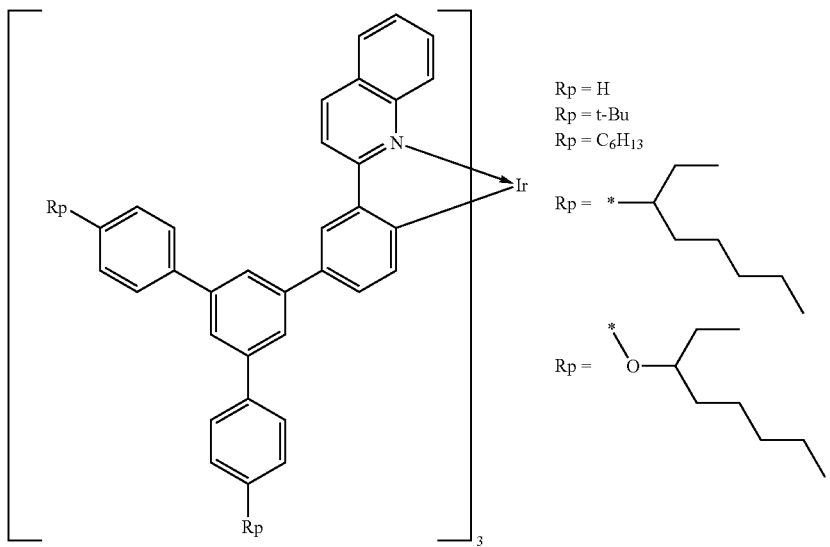
Ir-20b
Rp = H
Rp = t-Bu
Rp = C6H13
Rp = *—CH(C2H5)(C5H11)
Rp = *—O—CH(C2H5)(C5H11)

-continued
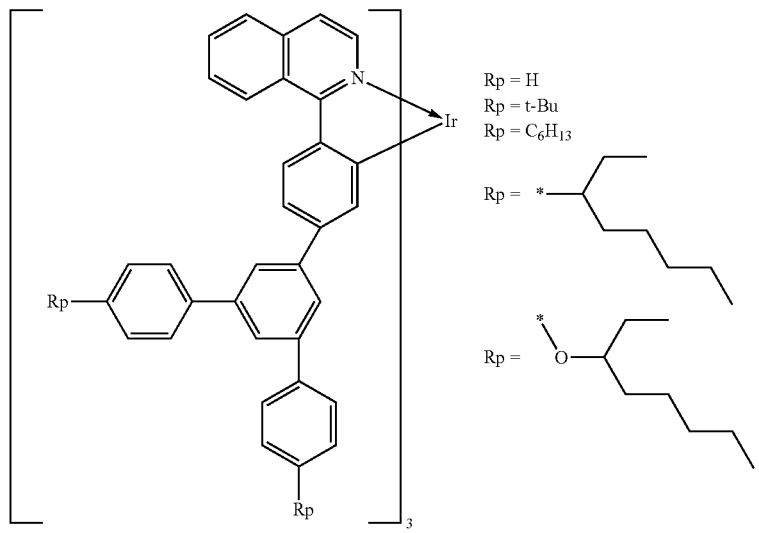
Ir-21b
Rp = H
Rp = t-Bu
Rp = C$_6$H$_{13}$
Rp = 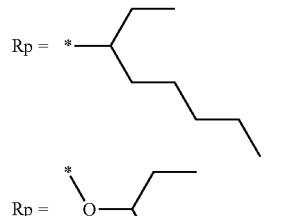
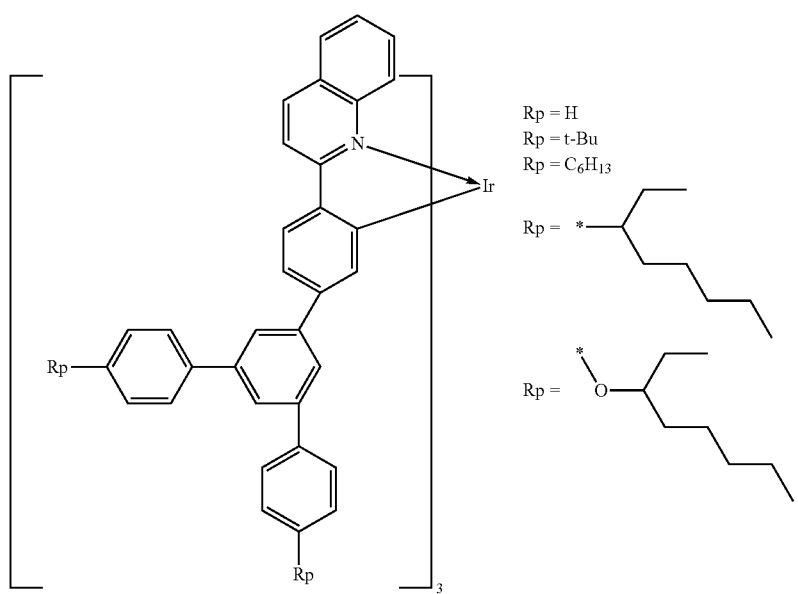
Ir-22b
Rp = H
Rp = t-Bu
Rp = C$_6$H$_{13}$
Rp = 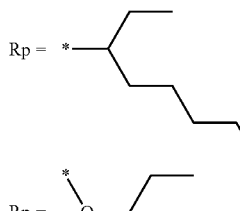
Rp = 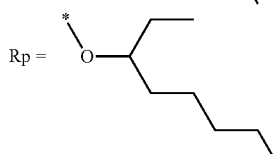

-continued
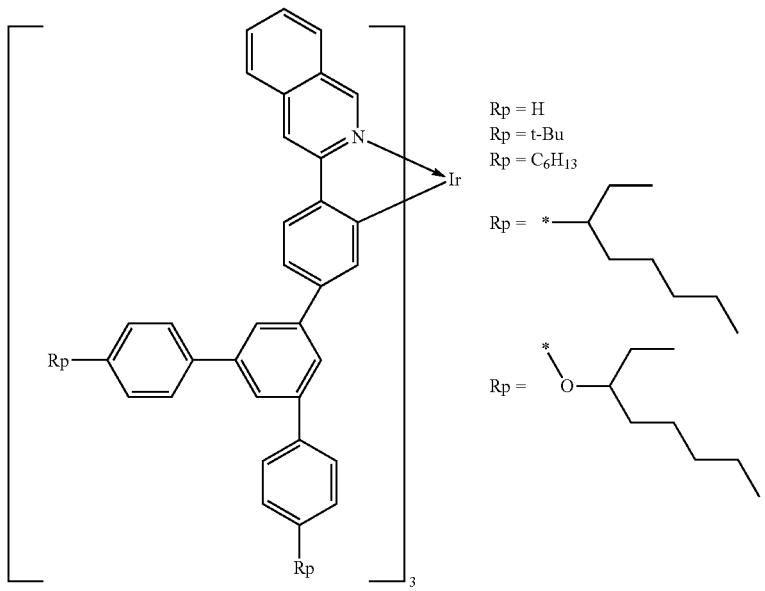
Ir-23b
Rp = H
Rp = t-Bu
Rp = C₆H₁₃
Rp = *CH(C₂H₅)(C₆H₁₃)
Rp = *O-CH(C₂H₅)(C₆H₁₃)
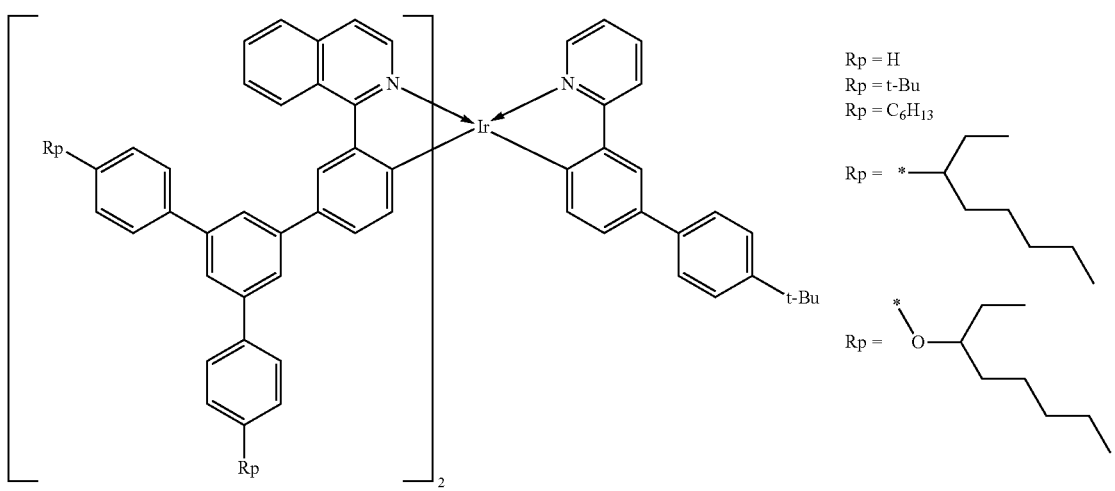
Ir-24b
Rp = H
Rp = t-Bu
Rp = C₆H₁₃
Rp = *CH(C₂H₅)(C₆H₁₃)
Rp = *O-CH(C₂H₅)(C₆H₁₃)
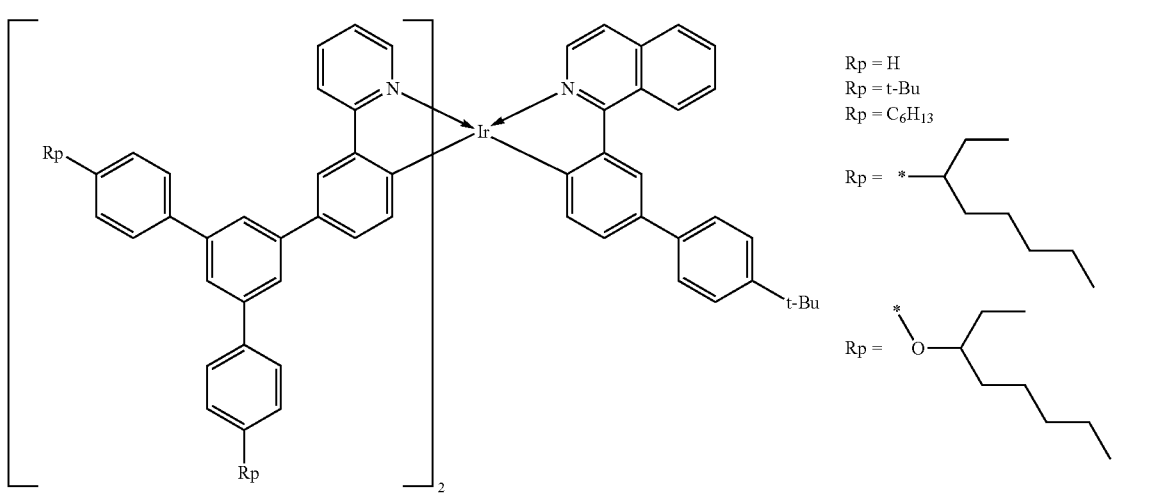
Ir-25b
Rp = H
Rp = t-Bu
Rp = C₆H₁₃
Rp = *CH(C₂H₅)(C₆H₁₃)
Rp = *O-CH(C₂H₅)(C₆H₁₃)

-continued
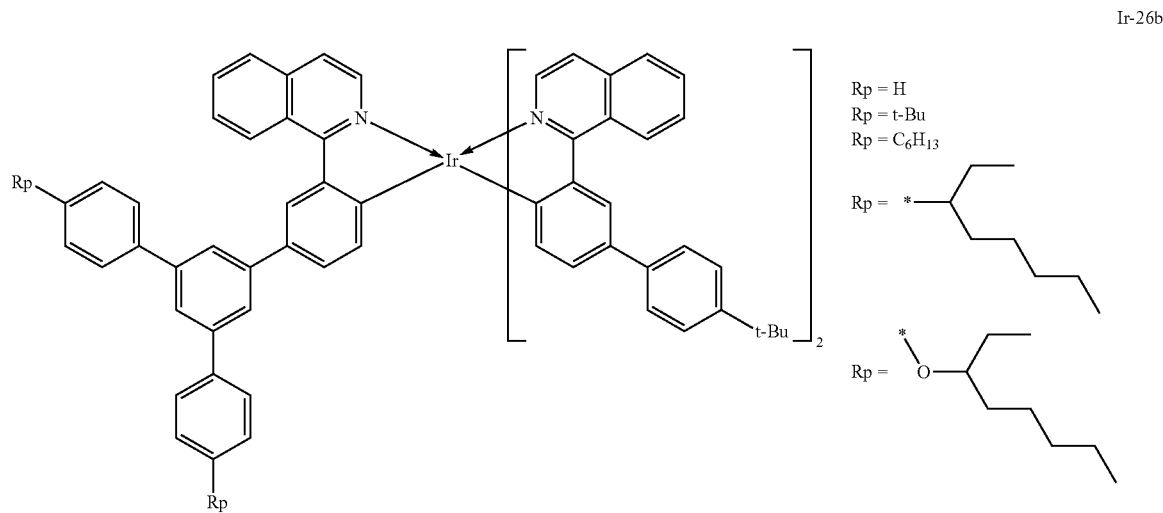
Ir-26b
Rp = H
Rp = t-Bu
Rp = C₆H₁₃
$Rp = $ *
$Rp = $ *O
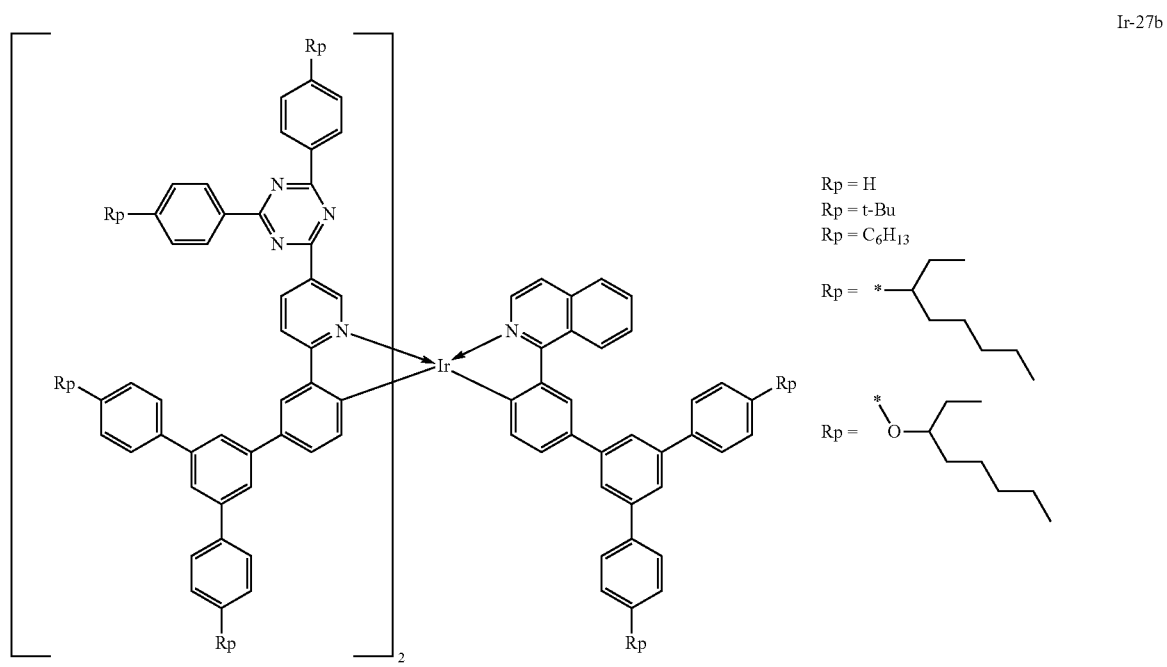
Ir-27b
Rp = H
Rp = t-Bu
Rp = C₆H₁₃
$Rp = $ *
$Rp = $ *O -continued
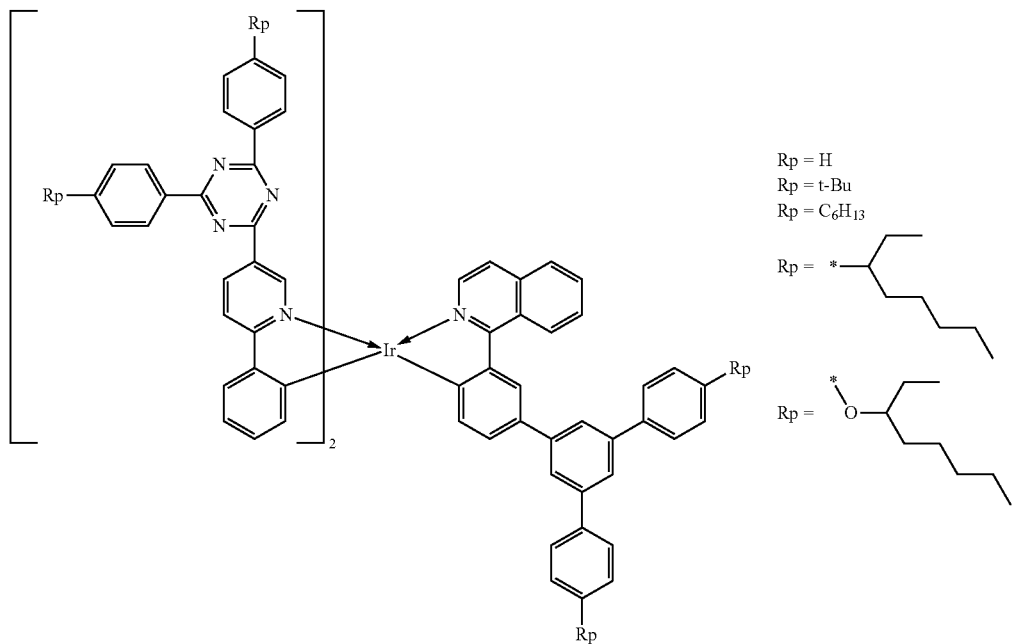
Ir-28b
Rp = H
Rp = t-Bu
Rp = C6H13
Rp = *⟨CH(C2H5)C5H11⟩
Rp = *O⟨CH(C2H5)C5H11⟩
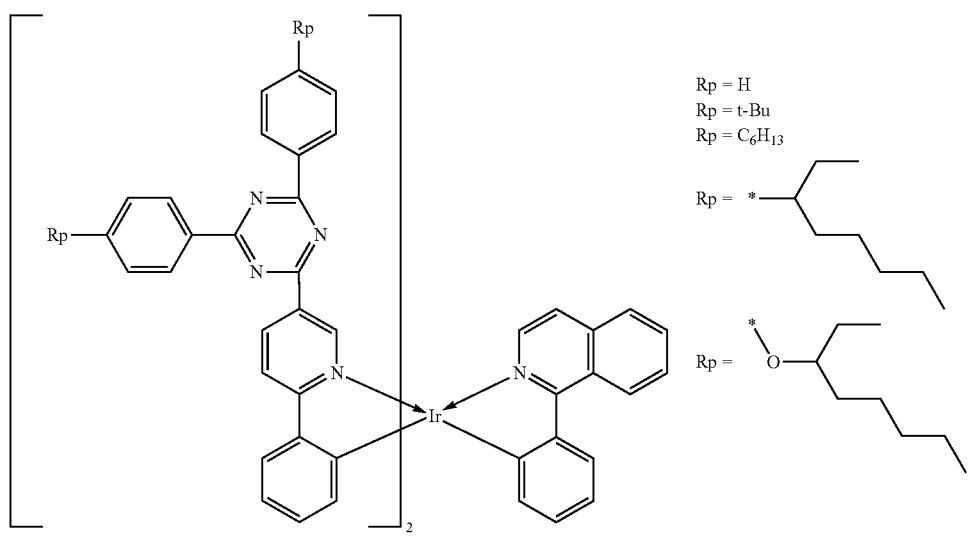
Ir-29b
Rp = H
Rp = t-Bu
Rp = C6H13
Rp = *⟨CH(C2H5)C5H11⟩
Rp = *O⟨CH(C2H5)C5H11⟩
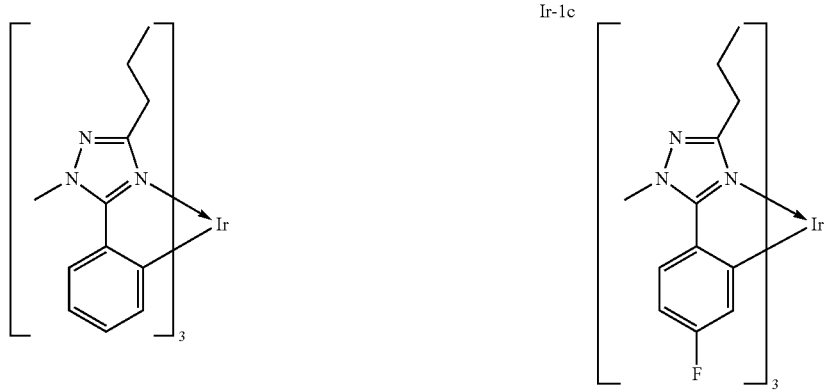
Ir-1c
Ir-2c -continued
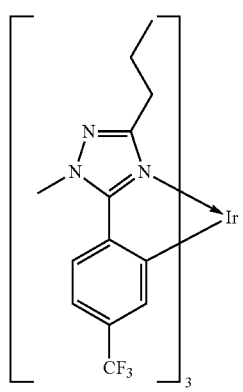
Ir-3c
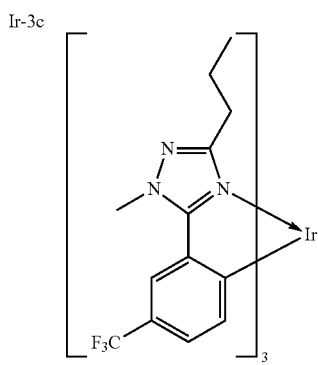
Ir-4c
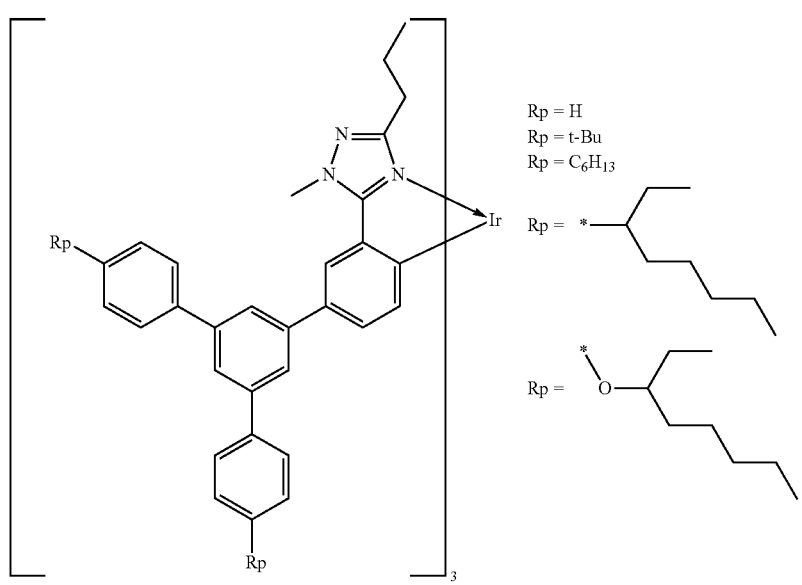
Rp = H
Rp = t-Bu
Rp = C₆H₁₃
Rp = 
Rp = 
Ir-5c
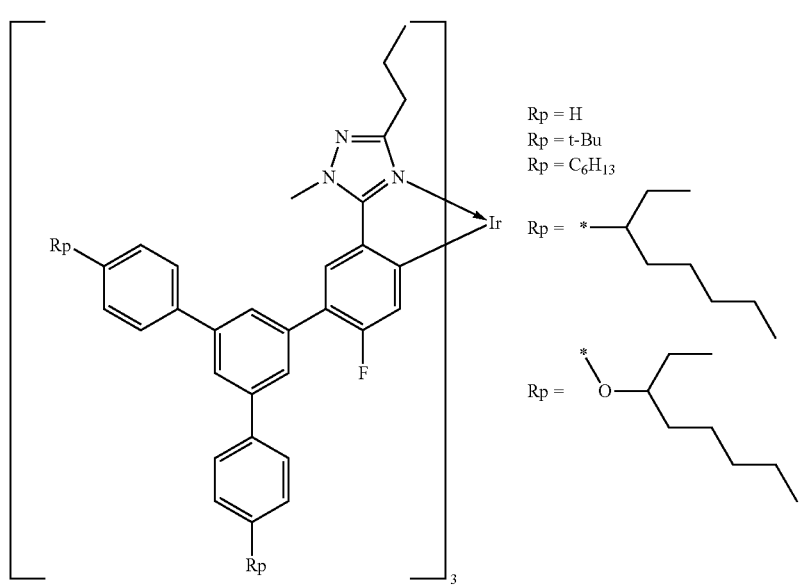
Rp = H
Rp = t-Bu
Rp = C₆H₁₃
Rp = 
Rp = 
Ir-6c

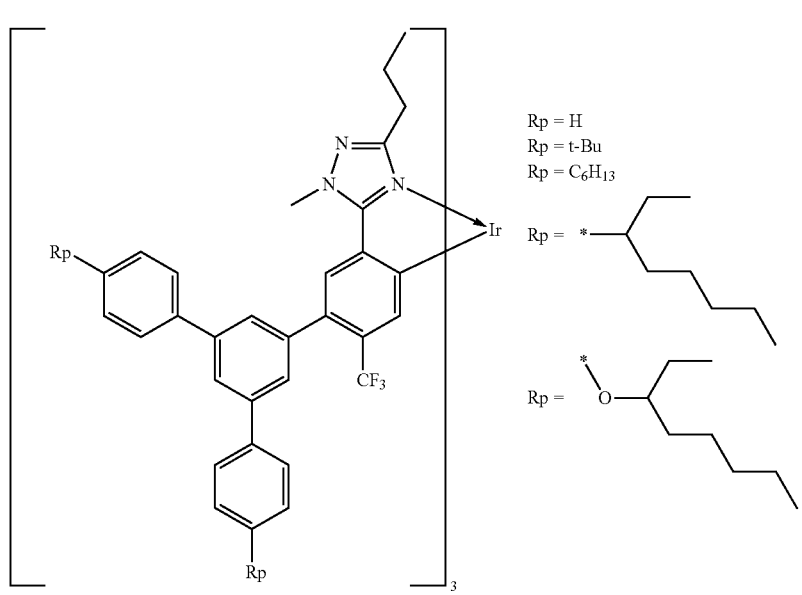
Ir-7c
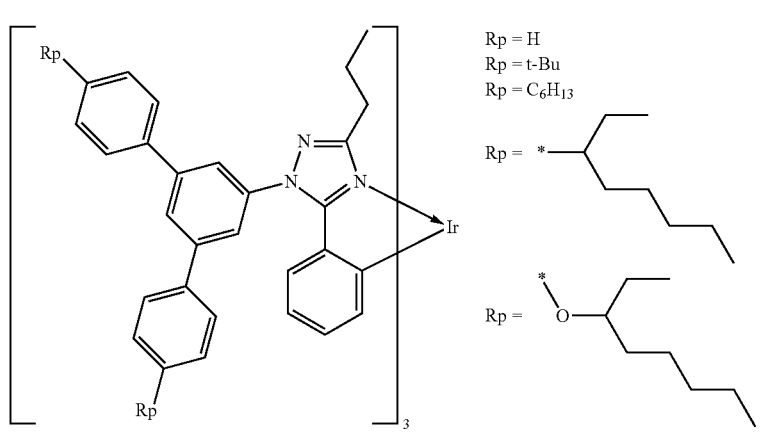
Ir-8c
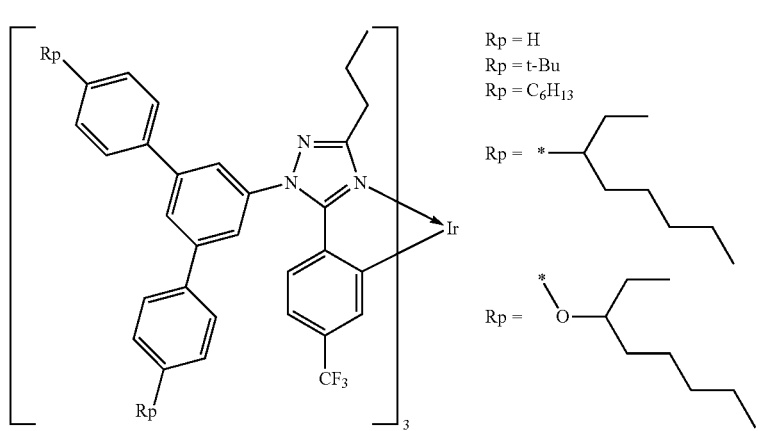
Ir-9c

-continued
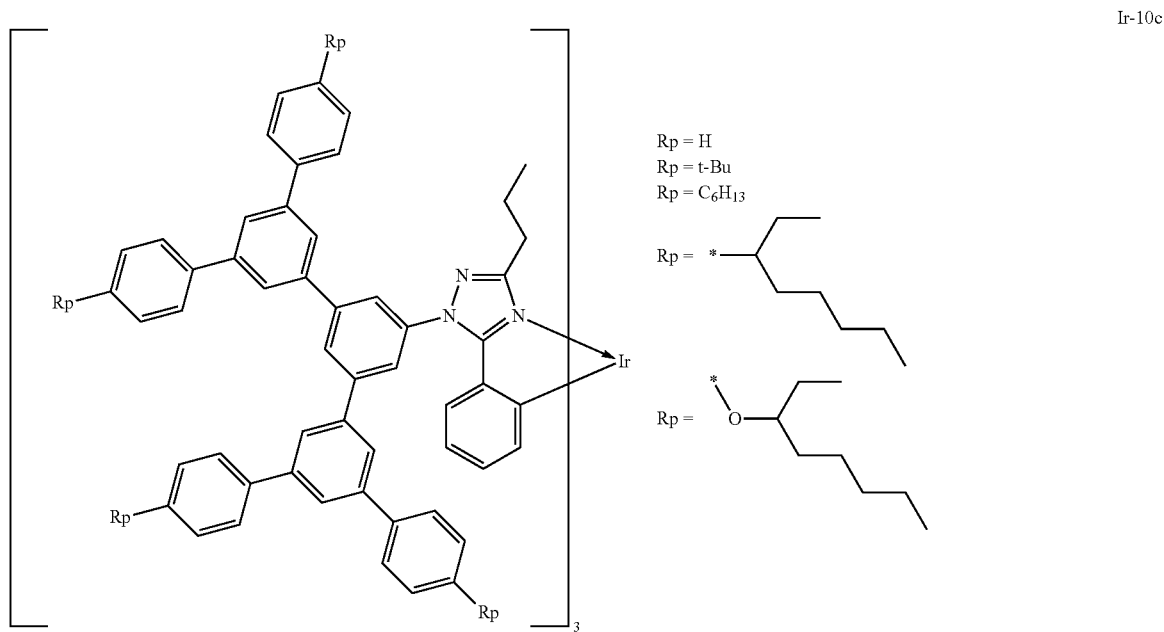
Ir-10c
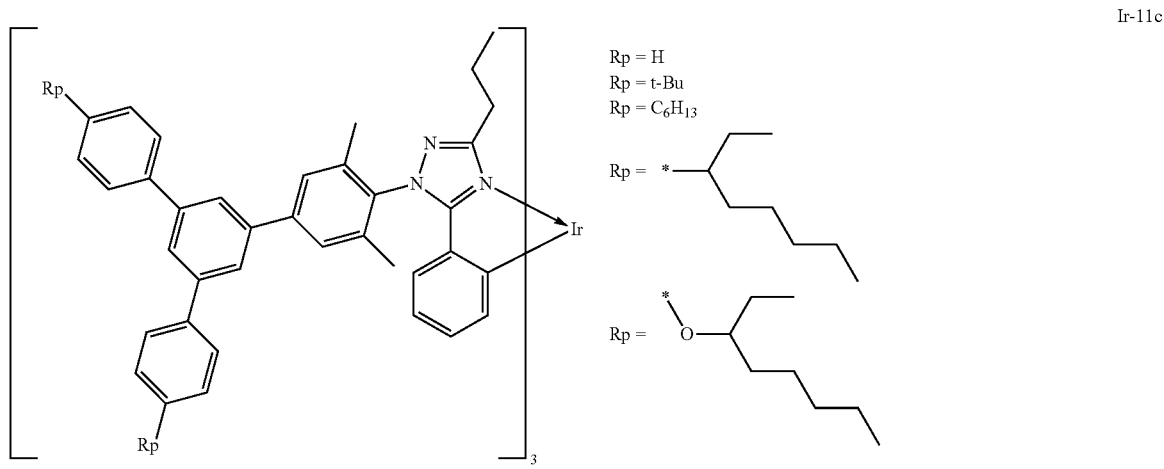
Ir-11c

-continued
Ir-12c
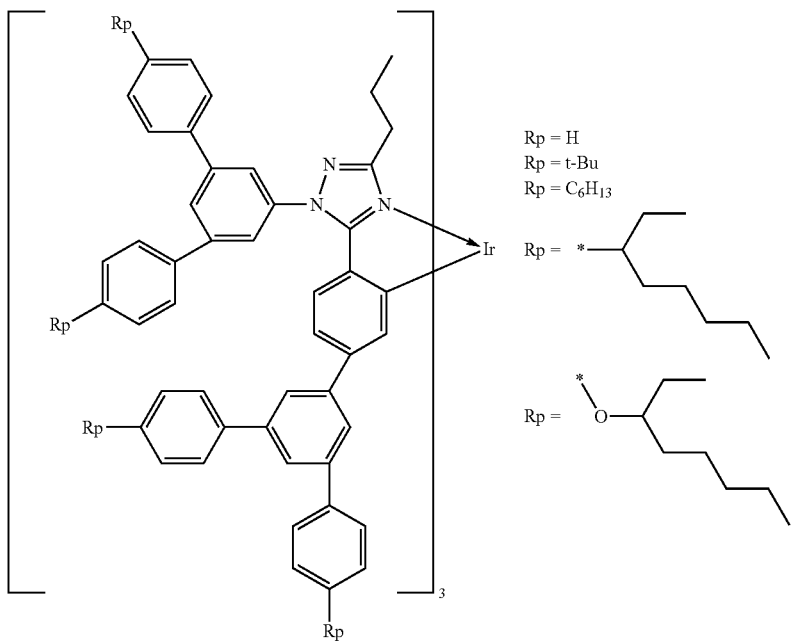
Rp = H
Rp = t-Bu
Rp = C6H13
Rp = *
Rp = *
Ir-13c
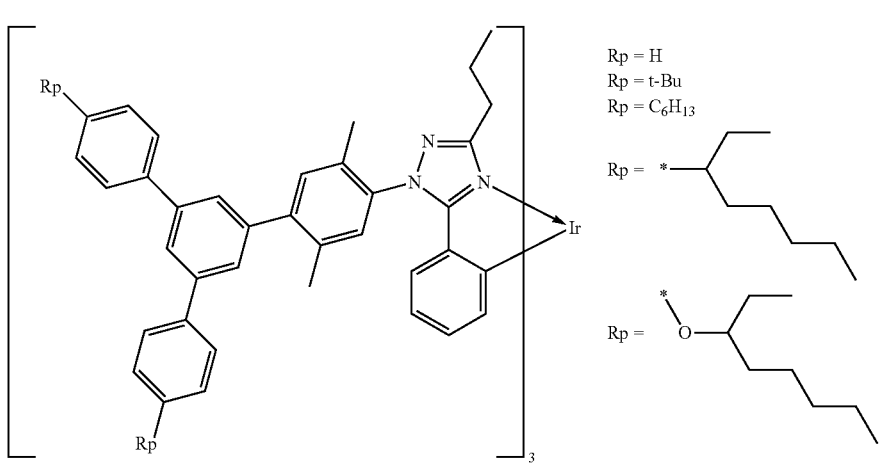
Rp = H
Rp = t-Bu
Rp = C6H13
Rp = *
Rp = *
Ir-14c
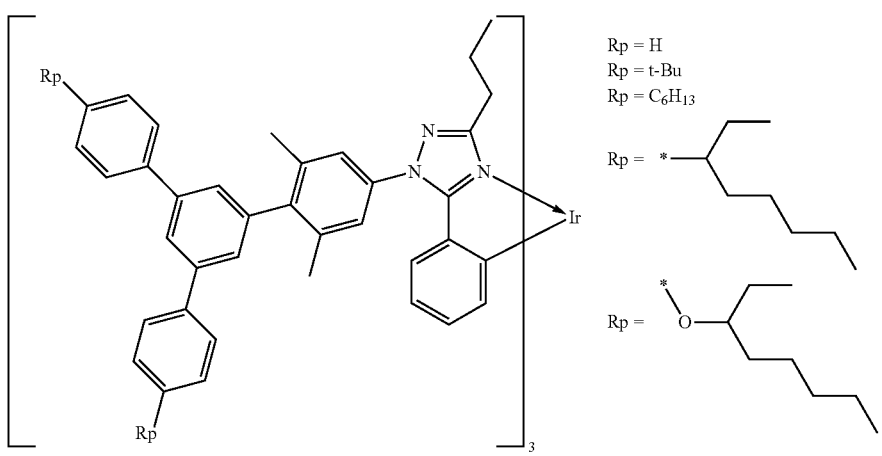
Rp = H
Rp = t-Bu
Rp = C6H13
Rp = *
Rp = *

-continued
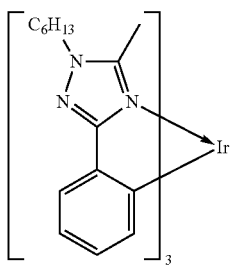
Ir-1d
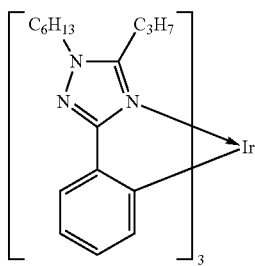
Ir-2d
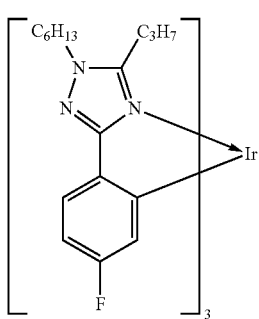
Ir-3d
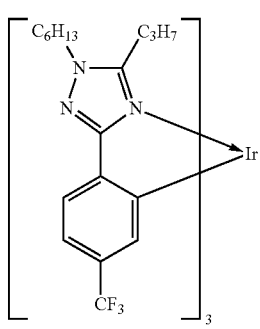
Ir-4d
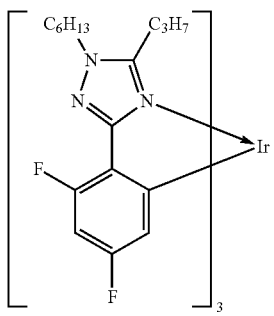
Ir-5d
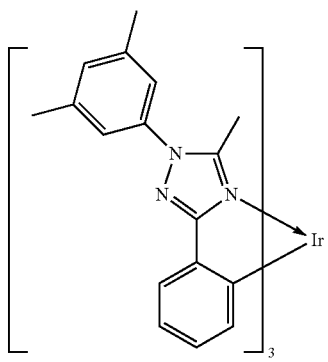
Ir-6d
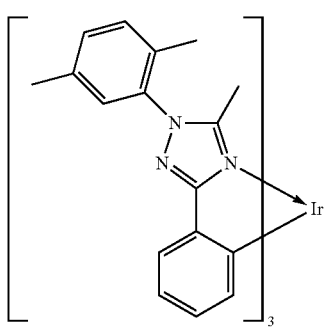
Ir-7d

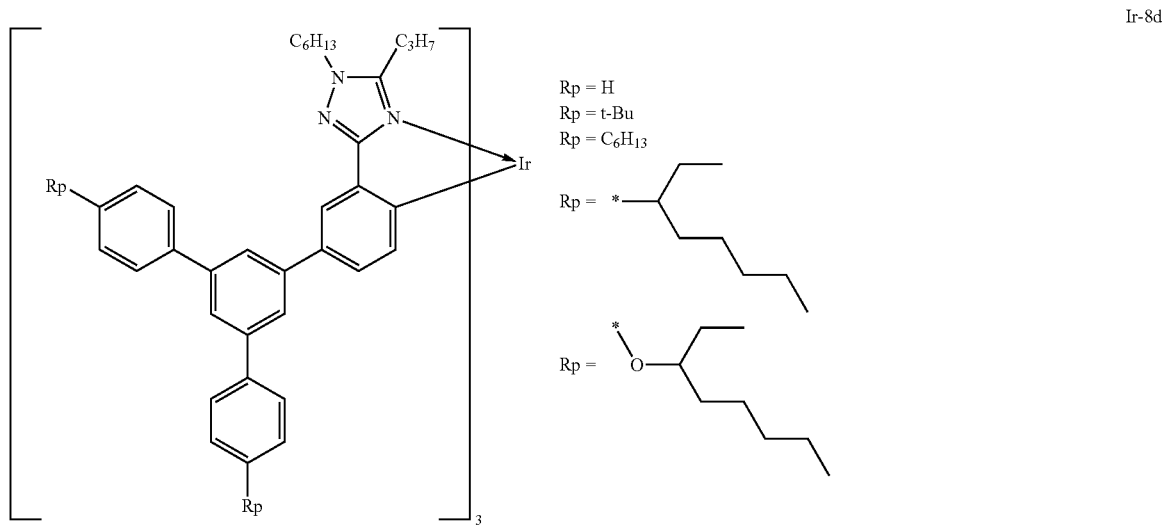
Ir-8d
Rp = H
Rp = t-Bu
Rp = C_6H_{13}
Rp = <image of chiral 2-ethylhexyl group>
Rp = <image of chiral 2-ethylhexyloxy group>
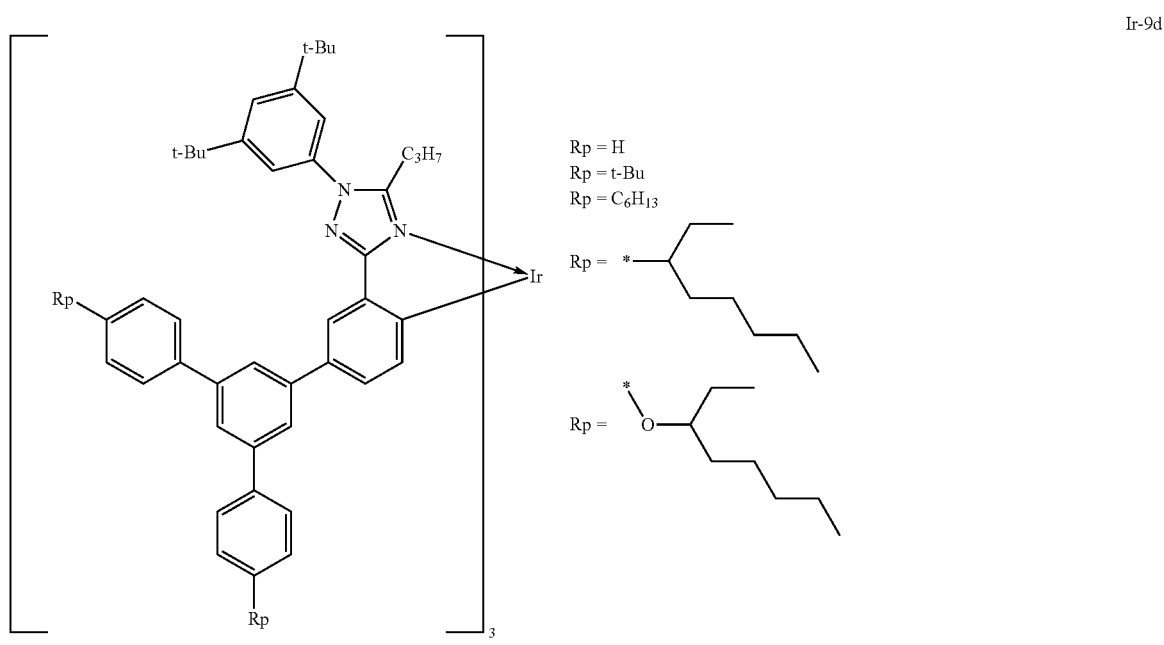
Ir-9d
Rp = H
Rp = t-Bu
Rp = C_6H_{13}
Rp = <image of chiral 2-ethylhexyl group>
Rp = <image of chiral 2-ethylhexyloxy group>

-continued
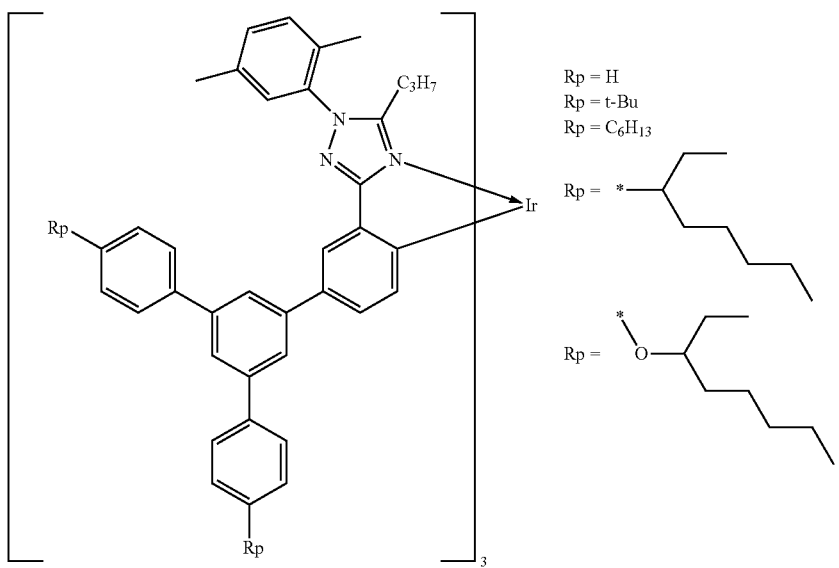
Ir-10d
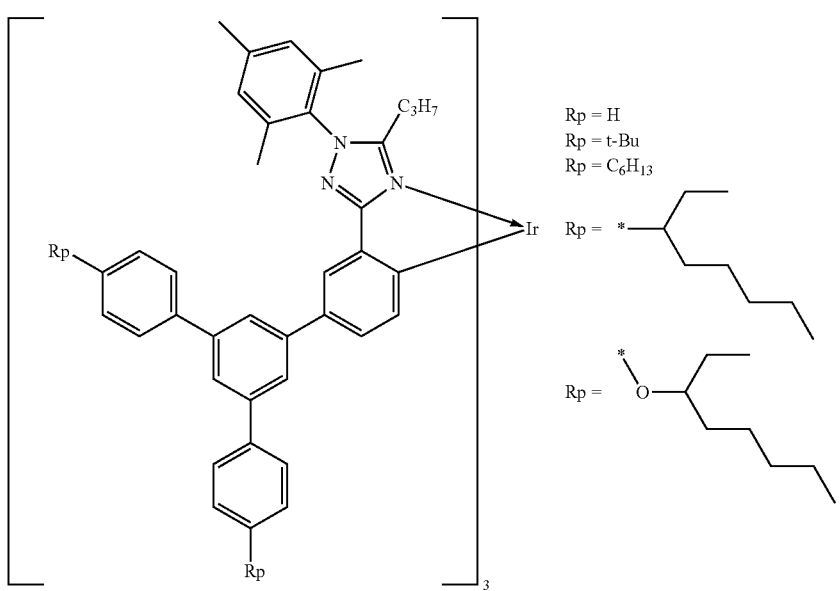
Ir-11d
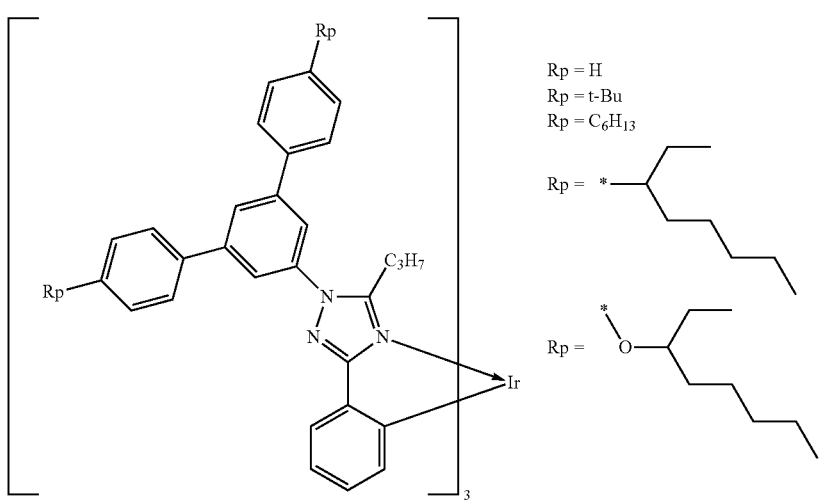
Ir-12d

-continued
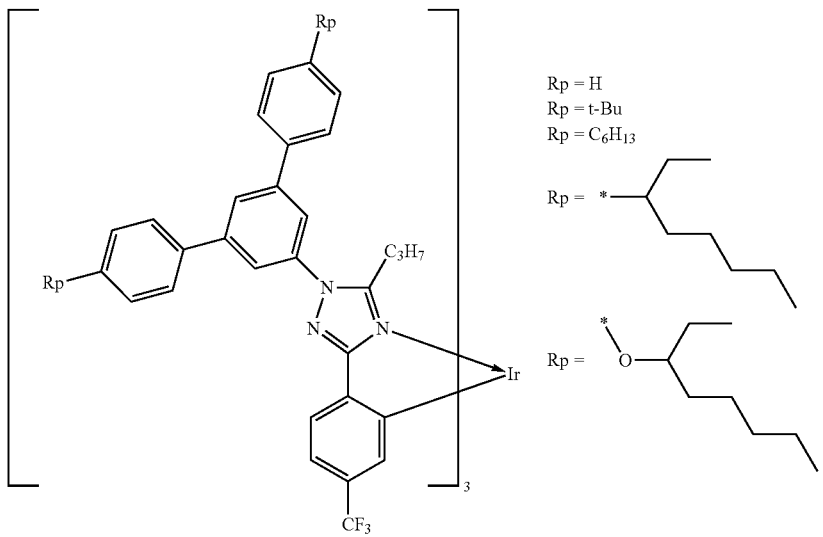
Ir-13d
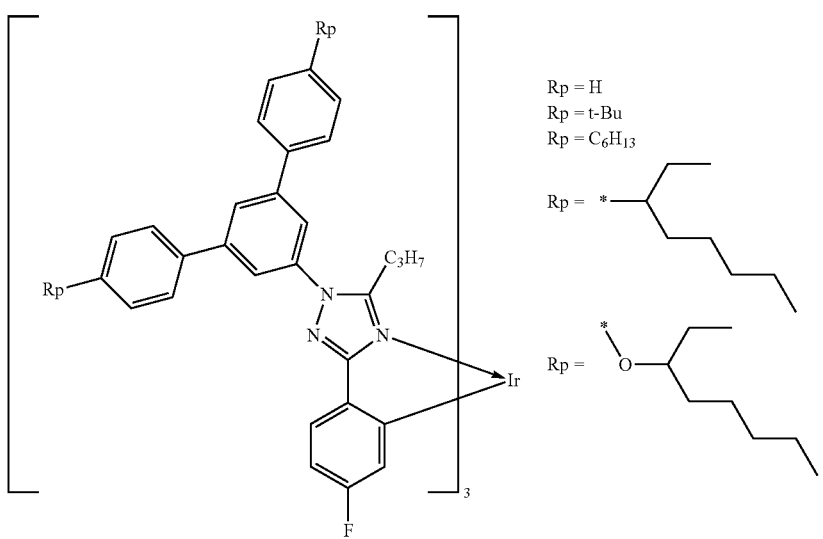
Ir-14d
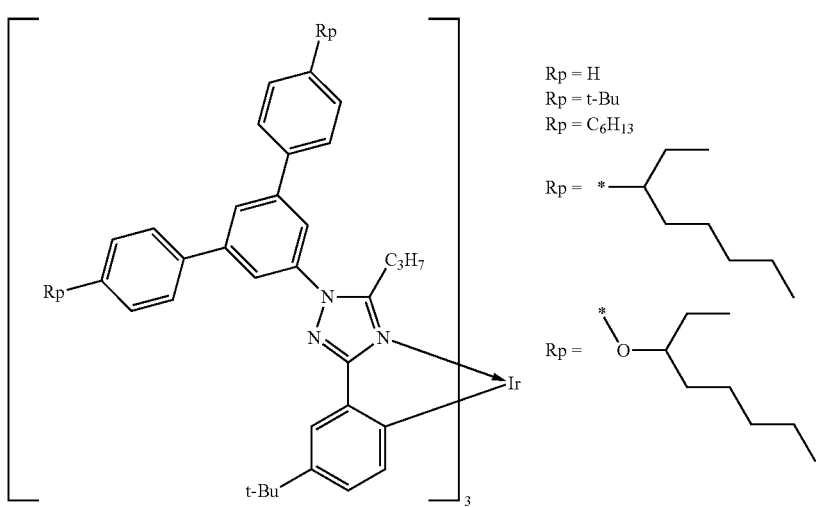
Ir-15d

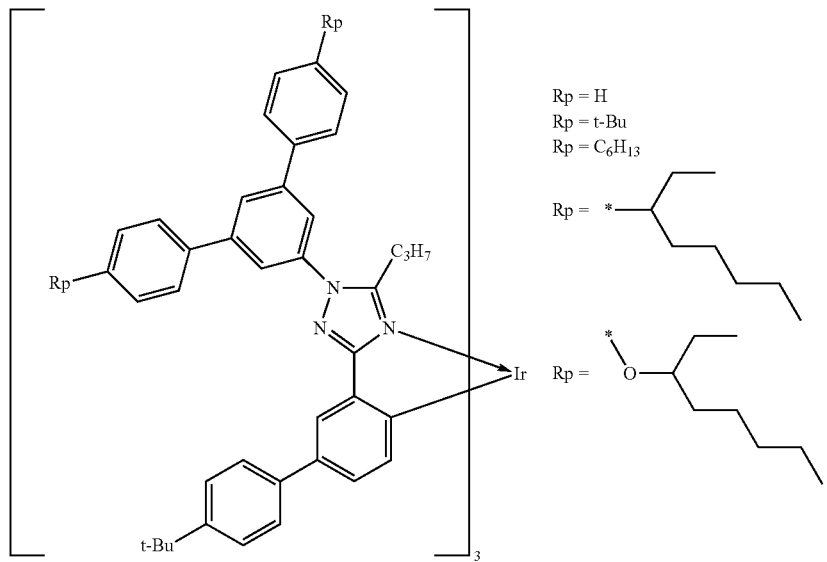
Ir-16d
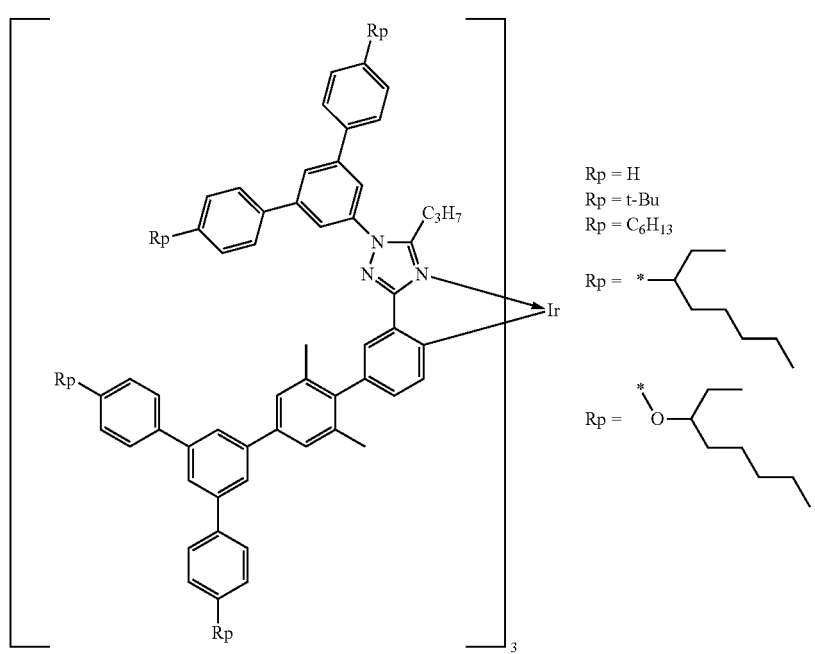
Ir-17d

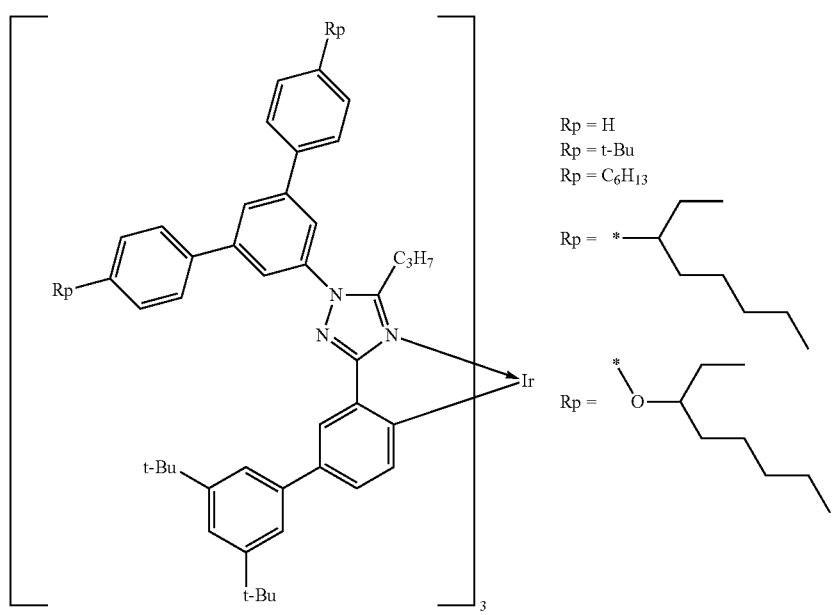

Ir-18d

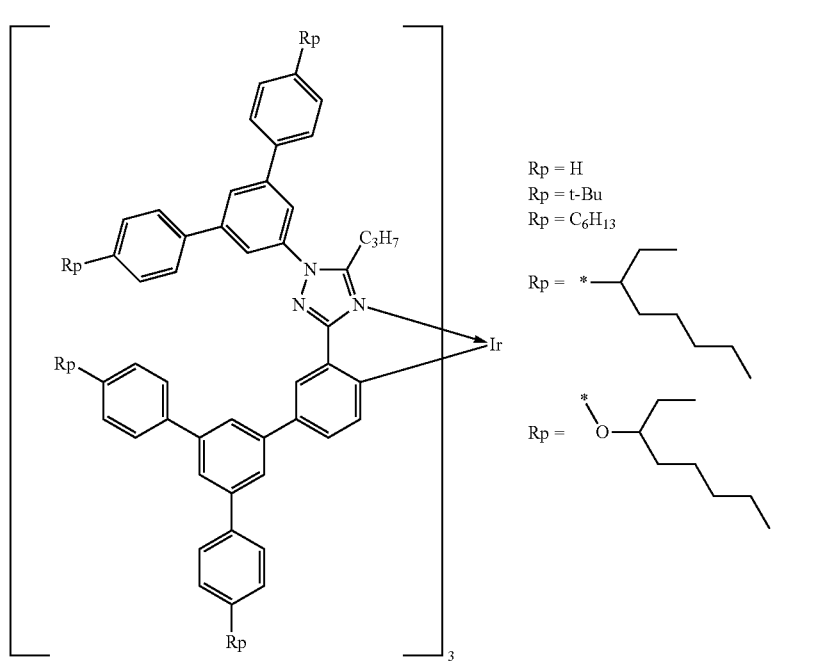

Ir-19d

The polymer compound of the present invention can provide more excellent light emission efficiency as compared with a composition using a conventional polymer compound particularly when a composition of the polymer compound with a phosphorescent compound showing light emission spectrum of short wavelength is prepared, and its effect is remarkable particularly when the peak at the shortest wavelength side of the light emission spectrum of the phosphorescent compound is 490 nm or less. Therefore, L in the formula (MM) is preferably a ligand shown below since a phosphorescent compound showing light emission spectrum of short wavelength can be obtained.

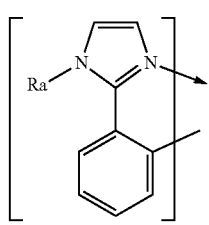

L-1e

L-2e
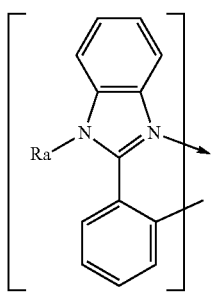
L-3e
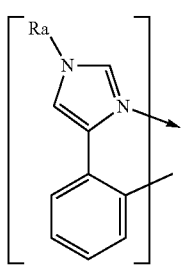
L-4e
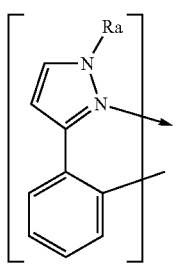
L-5e
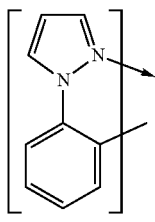
L-6e
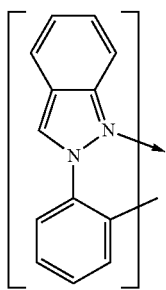
L-7e
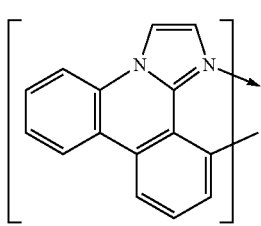
L-8e
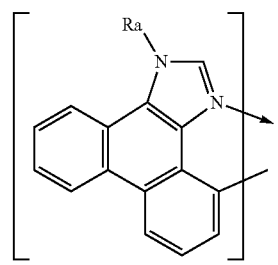
L-9e
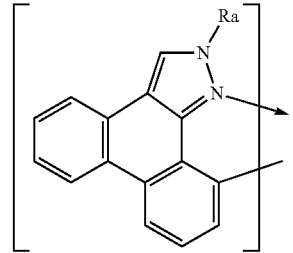
L-10e
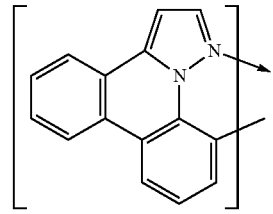
L-11e
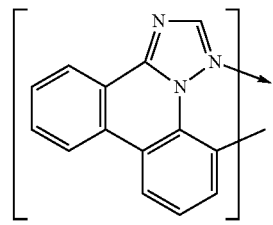
L-12e
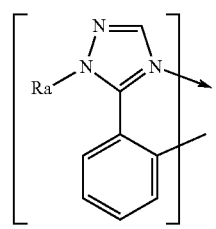
L-13e
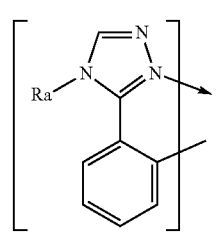

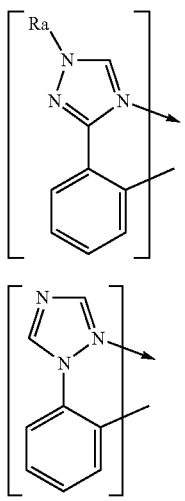

L-14e

L-15e (wherein, Ra represents the same meaning as described above.)

Any hydrogen atom in each ligand exemplified above may be substituted with an alkyl group, an aryl group, a monovalent aromatic heterocyclic group, an alkoxy group, an aryloxy group, an aralkyl group, an arylalkoxy group, a substituted amino group, a substituted carbonyl group, a substituted oxycarbonyl group, a fluorine atom or a cyano group. When there are a plurality of the substituents, these may be the same or different and may be mutually linked to form a ring structure together with an atom to which they are linked.

[Liquid Composition]

The polymer compound of the present invention may be dissolved or dispersed in a solvent (preferably, organic solvent) to prepare a liquid composition (solution or dispersion) of the present invention. Such a liquid composition is called also an ink or varnish. When the liquid composition of the present invention is used for forming an organic layer constituting a light emitting device, it is preferable that the liquid composition is a solution.

The liquid composition may contain at least one selected from the group consisting of a hole transporting material, an electron transporting material and a light emitting material in addition to the polymer compound of the present invention. To the liquid composition, other substances may be added providing the effect of the present invention is not prevented. The other substances include an antioxidant, a viscosity modifier, a surfactant and the like.

Here, the solvent is not particularly restricted providing it dissolves or disperses the polymer compound of the present invention, and includes the following organic solvents.

Aromatic hydrocarbon solvents: toluene, xylene (isomers or mixtures thereof), 1,2,3-trimethylbenzene, 1,2,4-trimethylbenzene, mesitylene (1,3,5-trimethylbenzene), ethylbenzene, propylbenzene, isopropylbenzene, butylbenzene, isobutylbenzene, 2-phenylbutane, tert-butylbenzene, pentylbenzene, neopentylbenzene, isoamylbenzene, hexylbenzene, cyclohexylbenzene, heptylbenzene, octylbenzene, 3-propyltoluene, 4-propyltoluene, 1-methyl-4-propylbenzene, 1,4-diethylbenzene, 1,4-dipropylbenzene, 1,4-di-tert-butylbenzene, indane, tetralin (1,2,3,4-tetrahydronaphthalene) and the like.

Aliphatic hydrocarbon solvents: n-pentane, n-hexane, cyclohexane, methylcyclohexane, n-heptane, n-octane, n-nonane, n-decane, decalin and the like.

Aromatic ether solvents: anisole, ethoxybenzene, propoxybenzene, butyloxybenzene, pentyloxybenzene, cyclopentyloxybenzene, hexyloxybenzene, cyclohexyloxybenzene, heptyloxybenzene, octyloxybenzene, 2-methylanisole, 3-methylanisole, 4-methylanisole, 4-ethylanisole, 4-propylanisole, 4-butylanisole, 4-pentylanisole, 4-hexylanisole, diphenyl ether, 4-methylphenoxybenzene, 4-ethylphenoxybenzene, 4-propylphenoxybenzene, 4-butylphenoxybenzene, 4-pentylphenoxybenzene, 4-hexylphenoxybenzene, 4-phenoxytoluene, 3-phenoxytoluene, 1,3-dimethoxybenzene, 2,6-dimethylanisole, 2,5-dimethylanisole, 2,3-dimethylanisole, 3,5-dimethylanisole and the like.

Aliphatic ether solvents: tetrahydrofuran, dioxane, dioxolane and the like.

Ketone solvents: acetone, methyl ethyl ketone, methyl isobutyl ketone, cyclohexanone, acetophenone and the like.

Ester solvents: ethyl acetate, butyl acetate, methyl benzoate, ethyl cellosolve acetate and the like.

Chlorine-based solvents: methylene chloride, chloroform, 1,2-dichloroethane, 1,1,2-trichloroethane, chlorobenzene, o-dichlorobenzene and the like.

Alcohol solvents: methanol, ethanol, propanol, isopropanol, cyclohexanol, phenol and the like.

Poly-hydric alcohols and derivatives thereof: ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexanediol and the like.

Aprotic polar solvents: dimethyl sulfoxide, N-methyl-2-pyrrolidone, N,N-dimethylformamide, N,N-dimethylacetamide and the like.

These organic solvents may be used singly or two or more of them may be used as a mixed solvent.

When a mixed solvent is used, it is preferable that two or three or more solvents selected from the above-described solvent groups are combined, and it may also be permissible that several solvents in the same solvent group exemplified above are combined or each one or more solvents from different solvent groups are combined. The composition ratio can be determined in view of the physical property of each solvent and the solubility of a polymer compound or the like.

When several solvents are selected from the same solvent group and combined, examples thereof include several solvents from the aromatic hydrocarbon solvent, several solvents from the aromatic ether solvent, and the like. When each one or more solvents are selected from different solvent groups and combined, examples thereof include the following combinations. An aromatic hydrocarbon solvent and an aliphatic hydrocarbon solvent, an aromatic hydrocarbon solvent and an aromatic ether solvent, an aromatic hydrocarbon solvent and an aliphatic ether solvent, an aromatic hydrocarbon solvent and an aprotic polar solvent, an aromatic ether solvent and an aprotic polar solvent, and the like.

Further, it is also possible to add water to a single solvent or a mixed solvent.

Of these organic solvents, a single solvent or mixed solvent containing one or more organic solvents having a structure containing a benzene ring, having a melting point of 0° C. or lower and having a boiling point of 100° C. or higher is preferable from the standpoint of viscosity, film formability and the like, and particularly, a single solvent or mixed solvent containing one or more solvents selected from the group consisting of aromatic hydrocarbon solvents and aromatic ether solvents is preferable.

The organic solvents may be used singly or two or more of them may be used as a mixed solvent, and from the standpoint of control of film formability, a mixed solvent is preferably used. The organic solvent may be purified by a method such as washing, distillation, contact with an adsorbent and the like before use, if necessary.

With the above-described liquid composition, an organic film containing the polymer compound of the present invention can be produced easily. Specifically, an organic film containing the polymer compound of the present invention is obtained by coating the above-described liquid composition on a substrate, and distilling off the organic solvent by heating, blast, pressure reduction and the like. In distillation off of an organic solvent, conditions can be varied depending on the organic solvent to be used, and examples thereof include an atmosphere temperature of about 50 to 150° C. (heating) or a pressure-reduced atmosphere of about $10^{-3}$ Pa.

For coating, coating methods such as a spin coat method, a casting method, a micro gravure coat method, a gravure coat method, a bar coat method, a roll coat method, a wire bar coat method, a dip coat method, a slit coat method, a capillary coat method, a spray coat method, a screen printing method, a flexo printing method, an offset printing method, an inkjet printing method, a nozzle coat method and the like can be used.

The suitable viscosity of the above-described liquid composition varies depending on a printing method, and it is preferably 0.5 to 1000 mPa·s, more preferably 0.5 to 500 mPa·s at 25° C. In the case of a method in which a liquid composition passes through a discharge device such as an inkjet printing method and the like, the viscosity at 25° C. is preferably 0.5 to 50 mPa·s, more preferably 0.5 to 20 mPa·s for preventing curved flying and clogging in discharging. Though the concentration of the polymer compound of the present invention in the liquid composition is not particularly restricted, it is preferably 0.01 to 10 wt %, more preferably 0.1 to 5 wt %.

[Organic Film]

The organic film of the present invention contains the polymer compound of the present invention, and examples thereof include organic films such as a luminous film, an electric conductive film, an organic semiconductor film or the like. These organic films may contain components constituting the composition of the present invention described above appropriately in combination depending on its application.

The organic film can be fabricated by a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet print method, a capillary coat method, a nozzle coat method and the like, using the polymer compound of the present invention as it is or in the form of the inventive composition or inventive liquid composition described above.

For example, when an organic film is formed using the solution described above, it is preferable to perform baking at a temperature of 100° C. or higher (for example, 130° C. to 160° C.), though varying depending on the glass transition temperature of the polymer compound of the present invention contained in the solution.

When the organic film is a luminous film, it has a light emission quantum yield of preferably 30% or more, more preferably 40% or more, further preferably 50% or more, particularly preferably 60% or more, from the standpoint of successfully obtaining the luminance and light emission voltage of a light emitting device.

When the organic film is an electric conductive film, it has a surface resistivity of preferably 1 KΩ/sq. or less, more preferably 100 Ω/sq. or less, further preferably 10 Ω/sq. or less. In the case of an electric conductive film, by doping with a Lewis acid, an ionic compound or the like, electric conductivity can be enhanced. "Ω/sq." is a unit showing surface resistivity.

Further, when the organic film is an organic semiconductor film, one larger parameter of electron mobility or hole mobility of the film is preferably $10^{-5}$ cm$^2$/V/s or more, more preferably $10^{-3}$ cm$^2$/V/s or more, further preferably $10^{-1}$ cm$^2$/V/s or more. For example, by forming this organic semiconductor film on a Si substrate carrying a gate electrode and an insulation film made of SiO$_2$ and the like formed thereon, and forming a source electrode and a drain electrode with Au and the like, an organic transistor can be fabricated.

[Light Emitting Device]

The light emitting device of the present invention has an anode and a cathode, and an organic layer containing the polymer compound of the present invention disposed between the anode and the cathode. The light emitting device may be composed of one organic layer or may be composed of two or more organic layers. When composed of two or more organic layers, at least one of them may advantageously contain the polymer compound of the present invention.

The organic layer containing the polymer compound of the present invention described above can function as a light emitting layer, a hole transporting layer or an electron block layer in a light emitting device. Therefore, in the light emitting device of the present invention, it is preferable that at least one of these layers is constituted of an organic layer containing the polymer compound of the present invention described above. Particularly, it is preferable that a light emitting layer is a light emitting device constituted of an organic layer containing the polymer compound of the present invention described above, in the light emitting device of the present invention. In addition to the anode, the cathode and the organic layer functioning as a light emitting layer (hereinafter, referred to simply as "light emitting layer"), the light emitting device may contain other layers between them. Each layer may be composed of one layer or composed of two or more layers. The materials and compounds constituting each layer may be used singly or two or more of them may be used in combination.

The layer to be disposed between an anode and a light emitting layer includes a hole injection layer, a hole transporting layer, an electron block layer and the like. When only one layer is disposed between an anode and a light emitting layer, it is a hole injection layer. When two or more layers are disposed between an anode and a light emitting layer, the layer next to an anode is a hole injection layer and other layers are hole transporting layers.

The hole injection layer is a layer having a function of improving hole injection efficiency from an anode. The hole transporting layer is a layer having a function of improving hole injection from a hole injection layer or a layer nearer to an anode. When these layers have a function of blocking transportation of electrons, these layers are called also an electron block layer. Whether the subject layer has a function of blocking transportation of electrons can be confirmed by fabricating a device allowing only electron current and measuring generation of a decrease in its current value.

The layer disposed between a cathode and a light emitting layer includes an electron injection layer, an electron transporting layer, a hole block layer and the like. When only one layer is disposed between a cathode and a light emitting layer, it is an electron injection layer. When two or more layers are disposed between a cathode and a light emitting layer, the layer next to a cathode is an electron injection layer and other layers are electron transporting layers.

The electron injection layer is a layer having a function of improving electron injection efficiency from a cathode. The electron transporting layer is a layer having a function of improving electron injection from an electron injection layer or a layer nearer to a cathode. When these layers have a function of blocking transportation of holes, these layers are called also a hole block layer. Whether the subject layer has a function of blocking transportation of holes can be confirmed by fabricating a device allowing only hole current and measuring generation of a decrease in its current value.

The structure of the light emitting device having a constitution having layers described above includes the following structures a) to d). "/" in the following structures means adjacent lamination of layers (the same shall apply hereinafter).
a) anode/light emitting layer/cathode
b) anode/hole transporting layer/light emitting layer/cathode
c) anode/light emitting layer/electron transporting layer/cathode
d) anode/hole transporting layer/light emitting layer/electron transporting layer/cathode Of hole transporting layers and electron transporting layers disposed adjacent to an electrode (cathode, anode), those having a function of improving charge (hole, electron) injection efficiency from an electrode and having an effect of lowering the driving voltage of a device are called a charge injection layer (hole injection layer, electron injection layer) in some cases.

Further, for improving close adherence with an electrode (cathode, anode) and improving charge injection from an electrode, a charge injection layer and an insulation layer may be disposed next to an electrode. In an interface of a charge transporting layer and a light emitting layer, a thin buffer layer may be further provided for improving close adherence in an interface between layers and preventing mixing of constituent materials. The order and number of layers to be laminated, and the thickness of each layer may be adjusted in view of light emission efficiency and device life.

The structure of the light emitting device in which a charge injection layer is further provided includes, for example, the following structures e) to p).
e) anode/charge injection layer/light emitting layer/cathode
f) anode/light emitting layer/charge injection layer/cathode
g) anode/charge injection layer/light emitting layer/charge injection layer/cathode
h) anode/charge injection layer/hole transporting layer/light emitting layer/cathode
i) anode/hole transporting layer/light emitting layer/charge injection layer/cathode
j) anode/charge injection layer/hole transporting layer/light emitting layer/charge injection layer/cathode
k) anode/charge injection layer/light emitting layer/charge transporting layer/cathode
l) anode/light emitting layer/electron transporting layer/charge injection layer/cathode
m) anode/charge injection layer/light emitting layer/electron transporting layer/charge injection layer/cathode
n) anode/charge injection layer/hole transporting layer/light emitting layer/charge transporting layer/cathode
o) anode/hole transporting layer/light emitting layer/electron transporting layer/charge injection layer/cathode
p) anode/charge injection layer/hole transporting layer/light emitting layer/electron transporting layer/charge injection layer/cathode The constitution of each layer in the light emitting device having structures a) to p) described above is, for example, as described below.

(Anode)

The anode is usually transparent or semi-transparent and constituted of film of a metal oxide, a metal sulfide or a metal having high electric conductivity, and particularly, the anode is preferably constituted of a material of high transmission. As the material of the anode, use is made of films fabricated using electric conductive inorganic compounds composed of indium oxide, zinc oxide, tin oxide, and composite thereof: indium•tin•oxide (ITO), indium•zinc•oxide and the like; NESA and the like, gold, platinum, silver, copper and the like. Of them, ITO, indium•zinc•oxide and tin oxide are preferable. For fabrication of the anode, a vacuum vapor-deposition method, methods such as a sputtering method, an ion plating method, a plating method and the like can be used. As the anode, organic transparent electric conductive films made of polyaniline and its derivatives, polythiophene and its derivatives, and the like may be used.

The thickness of the anode can be selected in view of light transmission and electric conductivity. For example, it is preferably 10 nm to 10 μm, more preferably 20 nm to 1 μm, further preferably 40 nm to 500 nm.

(Hole Injection Layer)

The material used in the hole injection layer includes phenyl amine compounds, starburst type amine compounds, phthalocyanine compounds, oxides such as vanadium oxide, molybdenum oxide, ruthenium oxide, aluminum oxide and the like, amorphous carbon, electric conductive polymers such as polyaniline and derivatives thereof, polythiophene and derivatives thereof, and the like.

When the hole injection layer is an electric conductive polymer or the polymer compound of the present embodiment described above, the hole injection layer may be doped with anions such as a polystyrenesulfonic ion, an alkylbenzenesulfonic ion, a camphor sulfonic ion and the like, if necessary, for improving the electric conductivity thereof.

(Hole Transporting Layer)

The material used in the hole transporting layer includes compounds exemplified as the hole transporting material. When the material used in the hole transporting layer is a low molecular weight compound, the low molecular weight compound is preferably dispersed in a polymer binder in use. When the polymer compound of the present embodiment described above is used in the hole transporting layer, it is preferable that the polymer compound has a group represented by the above-described formula (4) as a repeating unit.

Among them, preferable as the hole transporting material to be used in the hole transporting layer are polyvinylcarbazole and derivatives thereof, polysilane and derivatives thereof, polysiloxane derivatives having an aromatic amine in its side chain or main chain, and polyarylamine and derivatives thereof, and in addition, the polymer compound of the present embodiment.

As the method of formation of the hole transporting layer, film formation using a mixed solution with a polymer binder is used when the material used in the hole transporting layer is a low molecular weight compound, and film formation using a solution containing a polymer compound is used when the material is a high molecular weight compound.

The solvent used for film formation using a solution may advantageously be one which dissolves materials used in the hole transporting layer. The solvent includes chlorine-based solvents such as chloroform, methylene chloride, dichloroethane and the like, ether solvents such as tetrahydrofuran and the like, aromatic hydrocarbon solvents such as toluene, xylene and the like, ketone solvents such as acetone, methyl ethyl ketone and the like, ester solvents such as ethyl acetate, butyl acetate, ethylcellosolve acetate and the like.

For film formation using a solution, coating methods using a solution such as a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet print method and the like can be used.

As the polymer binder to be combined with a low molecular weight compound, those not extremely disturbing charge transportation are preferable, and those showing no strong absorption against visible light are suitable. The polymer binder as described above includes polycarbonate, polyacrylate, polymethyl acrylate, polymethyl methacrylate, polystyrene, polyvinyl chloride, polysiloxane and the like.

The thickness of the hole transporting layer can be selected in view of driving voltage and light emission efficiency. Though the thickness causing no easy generation of pin holes is necessary, when the thickness is too large, the driving voltage of a light emitting device increases in some cases. The thickness of the hole transporting layer is preferably 1 nm to 1 μm, more preferably 2 nm to 500 nm, further preferably 5 nm to 200 nm.

(Light Emitting Layer)

The light emitting layer is formed of an organic compound emitting fluorescence or phosphorescence (may be any of low molecular weight compound or high molecular weight compound), and a dopant aiding this if necessary. In the light emitting layer in the light emitting device of the present embodiment, the polymer compound of the present embodiment described above and a phosphorescent compound are preferably contained. When the light emitting material is a low molecular weight compound, it is preferably dispersed in a polymer binder in use.

To the light emitting layer, a dopant may be added for improving light emission efficiency and changing light emission wavelength. The dopant includes anthracene derivatives, perylene derivatives, coumarin derivatives, rubrene derivatives, quinacridone derivatives, squalium derivatives, porphyrin derivatives, styryl dyes, tetracene derivatives, pyrazolone derivatives, decacyclene, phenoxazone and the like.

The thickness of the light emitting layer can be selected in view of driving voltage and light emission efficiency, and, for example, it is preferably 2 to 200 nm.

For forming the light emitting layer, there can be used a method in which a solution containing a light emitting material is coated on or above a substrate, a vacuum vapor deposition method, a transfer method and the like. In the case of performing film formation using a solution, the same solvents as exemplified in film formation using a solution of a hole transporting layer can be used. For coating a solution containing a light emitting material on or above a substrate, there can be used printing methods such as a spin coat method, a dip coat method, an inkjet printing method, a flexo printing method, a gravure printing method, a slit coat method and the like. When the light emitting material is a low molecular weight compound showing a sublimation property, film formation can be conducted also by a vacuum vapor deposition method. Use can be made also of a method of forming a light emitting layer at a desired position, by laser transfer or thermal transfer.

(Electron Transporting Layer)

As the material to be used in the electron transporting layer, there are mentioned the polymer compound of the present embodiment described above, the electron transporting material described above and the like. When the polymer compound of the present embodiment described above is used in the electron transporting layer, it is preferable that the polymer compound of the present embodiment contains as a repeating unit at least one group selected from the group consisting of a group represented by the above-described formula (2B), a group represented by the above-described formula (3A) and a group represented by the above-described formula (3B).

Of them, preferable as the electron transporting material used in the electron transporting layer are the polymer compound of the present embodiment described above, oxadiazole derivatives, benzoquinone and derivatives thereof, anthraquinone and derivatives thereof, metal complexes of 8-hydroxyquinoline and derivatives thereof, polyquinoline and derivatives thereof, polyquinoxaline and derivatives thereof, and polyfluorene and derivatives thereof.

For forming the electron transporting layer, a vacuum vapor deposition method using a powder and a method of film formation in the form of a solution or in melted state are used when the material used in the electron transporting layer is a low molecular weight compound. In contrast, a method of film formation in the form of a solution or in melted state is used when the material used in the electron transporting layer is a high molecular weight compound. In film formation in the form of a solution or in melted state, a polymer binder may also be used together. Film formation using a solution can be conducted in the same manner as for formation of a hole transporting layer using a solution as described above.

The thickness of the electron transporting layer can be adjusted in view of driving voltage and light emission efficiency. Though the thickness causing no easy generation of pin holes is necessary, when the thickness is too large, the driving voltage of a light emitting device increases in some cases. The thickness of the electron transporting layer is preferably 1 nm to 1 μm, more preferably 2 nm to 500 nm, further preferably 5 nm to 200 nm.

(Electron Injection Layer)

The constitution of the electron injection layer can be appropriately selected according to the kind of a light emitting layer. Examples thereof include an electron injection layer having a single layer structure composed of a Ca layer, and an electron injection layer having a lamination structure composed of a Ca layer and a layer formed of one or two or more materials selected from the group consisting of metals belonging to group I and group II of the periodic table of elements and having a work function of 1.5 to 3.0 eV excluding Ca, and oxides, halides and carbonates of the metals. As the metals belonging to group I of the periodic table of elements and having a work function of 1.5 to 3.0 eV and oxides, halides and carbonates thereof, listed are lithium, lithium fluoride, sodium oxide, lithium oxide, lithium carbonate and the like. As the metals belonging to group II of the periodic table of elements and having a work function of 1.5 to 3.0 eV excluding Ca, and oxides, halides and carbonates thereof, listed are strontium, magnesium oxide, magnesium fluoride, strontium fluoride, barium fluoride, strontium oxide, magnesium carbonate and the like.

The electron injection layer can be formed by a vapor deposition method, a sputtering method, a printing method and the like. The thickness of the electron injection layer is preferably 1 nm to 1 μm.

(Cathode)

As the material of the cathode, materials having a small work function and providing easy injection of electrons into a light emitting layer are preferable. For example, use is made of metals such as lithium, sodium, potassium, rubidium, cesium, beryllium, magnesium, calcium, strontium, barium, aluminum, scandium, vanadium, zinc, yttrium, indium, cerium, samarium, europium, terbium, ytterbium and the like, alloys composed of two or more of these metals, or alloys composed of at least one of them and at least one of gold, silver, platinum, copper, manganese, titanium, cobalt, nickel, tungsten and tin, and, graphite or graphite intercalation compounds, and the like. The alloy includes a magnesium-silver alloy, a magnesium-indium alloy, a magnesium-aluminum alloy, an indium-silver alloy, a lithium-aluminum alloy, a lithium-magnesium alloy, a lithium-indium alloy, a calcium-aluminum alloy, and the like.

When the cathode has a laminated structure consisting of two or more layers, preferable is a laminated structure composed of a metal, a metal oxide, a metal fluoride or an alloy thereof and of a metal such as aluminum, silver, chromium and the like.

The cathode can be formed by, for example, a vacuum vapor deposition method, a sputtering method, a lamination method of thermally press-binding a metal film, and the like. The thickness of the cathode can be selected in view of electric conductivity and durability. For example, it is preferably 10 nm to 10 μm, more preferably 20 nm to 1 μm, further preferably 50 nm to 500 nm.

(Protective Layer)

After fabrication of the cathode, a protective layer for protecting a light emitting device may be further formed on its top. Particularly, for use of a light emitting device stably for a long period of time, it is preferable to install a protective layer and/or a protective cover, for protecting the light emitting device from outside.

As the constituent material of the protective layer, high molecular weight compounds, metal oxides, metal fluorides, metal borides and the like can be used. As the protective cover, a metal plate, a glass plate, and a plastic plate having a surface which has been subjected to a low water permeation treatment, and the like can be used. As the protective method of a light emitting device using a protective cover, a method in which the protective cover is pasted to a device substrate with a thermosetting resin or a photo-curing resin to attain sealing is used. When a space is kept using a spacer, blemishing of a device can be prevented easily. If an inert gas such as nitrogen, argon and the like is filled in this space, oxidation of a cathode can be prevented. Further, by placing a drying agent such as barium oxide and the like in this space, it becomes easy to suppress moisture adsorbed in a production process or a small amount of water invaded through a hardened resin from imparting a damage to the device. It is preferable to adopt at least one strategy among these methods, in a light emitting device.

The light emitting device of the suitable embodiment explained above can be used as a planar light source, a display (segment displays, dot matrix display), back light of a liquid crystal display, or the like.

For example, for obtaining light emission in the form of plane using a light emitting device, a planar anode and a planar cathode may advantageously be placed so as to overlap. For obtaining light emission in the form of pattern, there are a method in which a mask having a window in the form of pattern is placed on the surface of the planar light emitting device, a method in which an organic layer in non-light emitting parts is formed with extremely large thickness to give substantially no light emission, and a method in which either an anode or a cathode, or both electrodes are formed in the form of pattern. By forming a pattern by any of these methods, and placing several electrodes so that on/off is independently possible, a display of segment type is obtained which can display digits, letters, simple marks and the like.

Further, for providing a dot matrix device, it may be advantageous that both an anode and a cathode are formed in the form of stripe, and placed so as to cross. By using a method in which several polymer compounds showing different emission colors are painted separately or a method in which a color filter or a fluorescence conversion filter is used, partial color display and multi-color display are made possible. In the case of a dot matrix device, passive driving is possible, and active driving may be carried out by combining with TFT and the like.

The planar light emitting device described above is of self emitting and thin type, and can be suitably used as a planar light source for back light of a liquid crystal display, or as a planar light source for illumination, and the like. These display devices can be used as a display of a computer, a television, a portable terminal, a cellular telephone, a car navigation, a view finder of a video camera, and the like. Further, if a flexible substrate is used, it can also be used as a curved light source or display.

EXAMPLES

The present invention will be illustrated further in detail by examples below, but the present invention is not limited to the following examples.

[Measurement Method]

In the examples below, measurement of number-average molecular weight and weight-average molecular weight, high performance liquid chromatography (HPLC), measurement of NMR, measurement of LC/MS, measurement of glass transition temperature and measurement of triplet energy were carried out as described below.

(Measurement of Number-Average Molecular Weight and Weight-Average Molecular Weight)

Polystyrene-equivalent number-average molecular weight (Mn) and polystyrene-equivalent weight-average molecular weight (Mw) were determined by GPC (manufactured by Shimadzu. Corp., trade name: LC-10Avp). In this operation, the polymer compound to be measured was dissolved in tetrahydrofuran so as to give a concentration of about 0.05 wt % and the solution was injected in an amount of 10 μL into GPC. Tetrahydrofuran was used as the mobile phase of GPC and allowed to flow at a flow rate of 2.0 ml/min. PLgel MIXED-B (manufactured by Polymer Laboratories Ltd.) was used as the column. As the detector, a UV-VIS detector (manufactured by Shimadzu. Corp., trade name: SPD-10Avp) was used.

(High Performance Liquid Chromatography (HPLC))

The value of HPLC area percentage was used as an index of the purity of a compound. This value is a value at 254 nm by high performance liquid chromatography (HPLC, manufactured by Shimadzu Corp., trade name: LC-20A), unless otherwise stated. In this procedure, the compound to be measured was dissolved in tetrahydrofuran or chloroform so as to give a concentration of 0.01 to 0.2 wt %, and the solution was injected in an amount of 1 to 10 μL into HPLC depending on the concentration. As the mobile phase of HPLC, acetonitrile and tetrahydrofuran were used and allowed to flow at a flow rate of 1 ml/min in gradient mode of acetonitrile/tetrahydrofuran=100/0 to 0/100 (volume ratio). As the column, Kaseisorb LC ODS 2000 (manufactured by Tokyo Chemical Industry Co., Ltd.) or an ODS column having the equivalent performance was used. As the detector, a photodiode array detector (manufactured by Shimadzu. Corp., trade name: SPD-M20A) was used.

(Measurement of NMR)

A measurement sample (5 to 20 mg) was dissolved in about 0.5 ml of an organic solvent, and measurement of NMR was performed using NMR (manufactured by Varian, Inc., trade name: MERCURY300).

(Measurement of LC/MS)

A measurement sample was dissolved in a suitable organic solvent (chloroform, tetrahydrofuran, ethyl acetate, toluene and the like) so as to give a concentration of 1 to 10 mg/mL, and LC/MS was measured by LC/MS (manufactured by Agilent Technologies, trade name: 1100 LCMSD) and the measured value was analyzed. As the mobile phase of LC-MS, ion exchanged water, acetonitrile, tetrahydrofuran or a mixed solution thereof was used, and, if necessary, acetic acid was added. As the column, L-column 2 ODS (3 μm) (manufactured by Chemicals Evaluation and Research Institute, Japan, internal diameter: 4.6 mm, length: 250 mm, particle diameter: 3 μm) was used.

(Measurement of Energy Level of Lowest Triplet Excited State ($T_1$))

The energy level of the lowest triplet excited state ($T_1$) of a polymer compound (hereinafter, described as "TH") was determined by measuring the phosphorescence spectrum of the polymer compound at 77K. Specifically, a toluene solution of the polymer compound (concentration: $8\times10^{-4}$ mass %) was used as the measurement sample. As the exciting light source, a xenon lamp was used, and the measurement sample was irradiated with exciting light (exciting wavelength: 300 nm) dispersed using a diffraction grating, and a multi-channel spectrometer PMA-12 manufactured by Hamamatsu Photonics Co., Ltd. was used as the detector and the phosphorescence spectrum of the polymer compound was measured. When the intensity of the maximum peak wavelength (wavelength of the largest intensity) in the phosphorescent spectrum of the polymer compound was 1.0, the value obtained by converting the wavelength at the shortest side showing an intensity of 0.1 into energy was calculated as TH.

The energy level of the lowest triplet excited state ($T_1$) of a phosphorescent compound (hereinafter, described as "TM") was determined by measuring the phosphorescence spectrum of the phosphorescent compound at room temperature. Specifically, a toluene solution of the phosphorescent compound (concentration: $8\times10^{-4}$ mass %) was used as the measurement sample. As the exciting light source, a xenon lamp was used, and the measurement sample was irradiated with exciting light (exciting wavelength: 300 nm) dispersed using a diffraction grating, and a multi-channel spectrometer PMA-12 anufactured by Hamamatsu Photonics Co., Ltd. was used as the detector and the phosphorescence spectrum of the phosphorescent compound was measured. When the intensity of the maximum peak wavelength (wavelength of the largest intensity) in the phosphorescent spectrum of the phosphorescent compound was 1.0, the value obtained by converting the wavelength at the shortest side showing an intensity of 0.1 into energy was calculated as TM.

[Synthesis of Raw Material Monomer]

Compounds MM1, MM2, MM3, MM4, MM5, CM1, CM2 and CC1 to CC12 shown below were synthesized by a known method or a synthesis method described later, and subjected to a purification operation such as recrystallization, silica gel column chromatography, sublimation and the like, and those showing a purity of 99.5% or more in terms of the HPLC area percentage value were used as raw material monomers in synthesis of a polymer compound or as raw material compounds in synthesis of a raw material monomer.

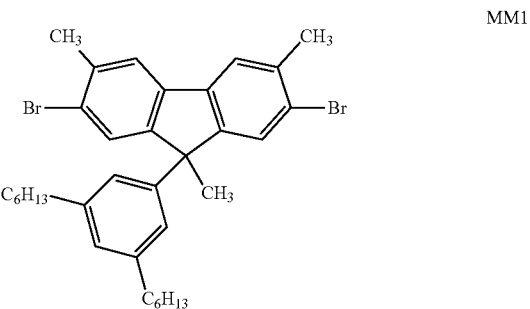

MM1

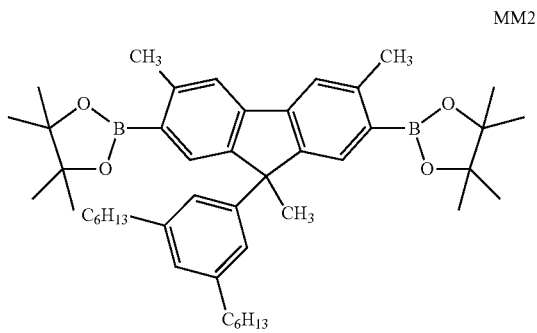

MM2

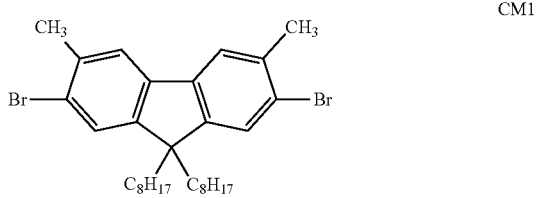

CM1

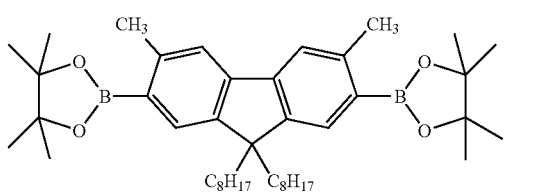

CM2

MM3
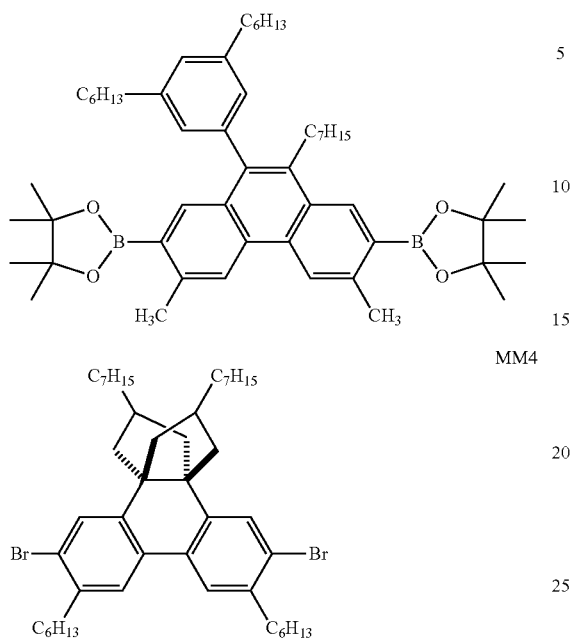
MM4
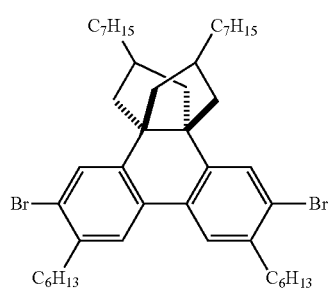
MM5
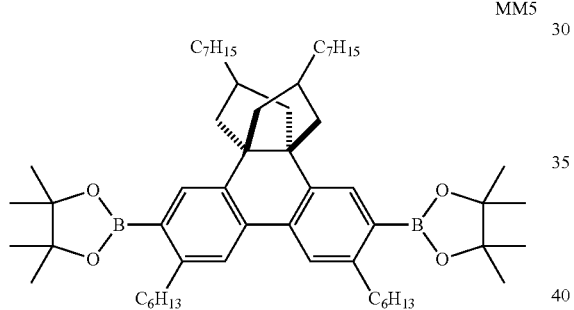
CC1
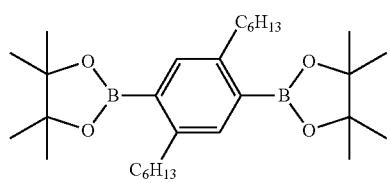
CC2
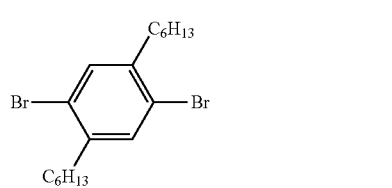
CC3
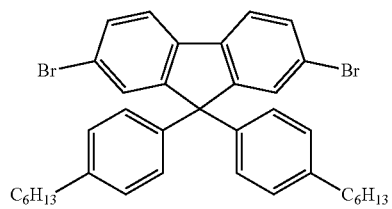
CC4
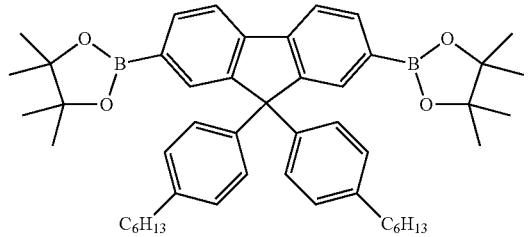
CC5
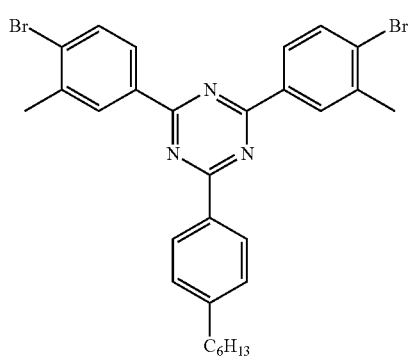
CC7
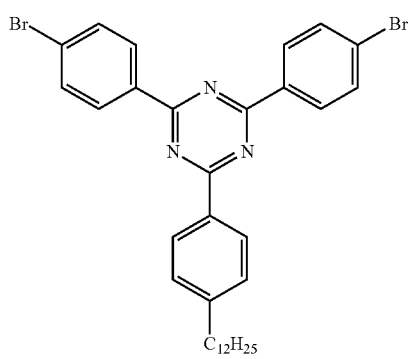
CC6
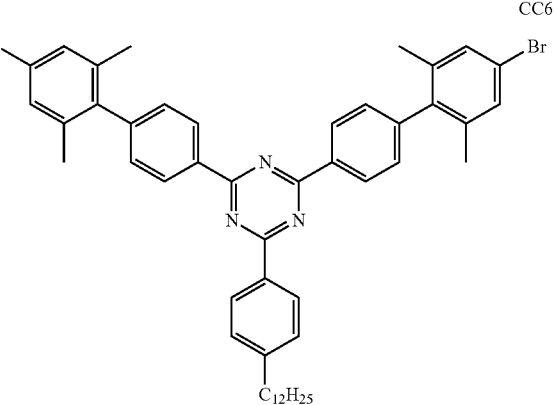
CC8
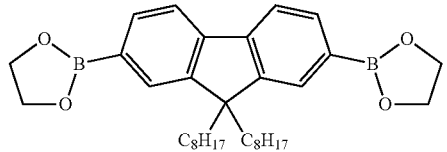

-continued

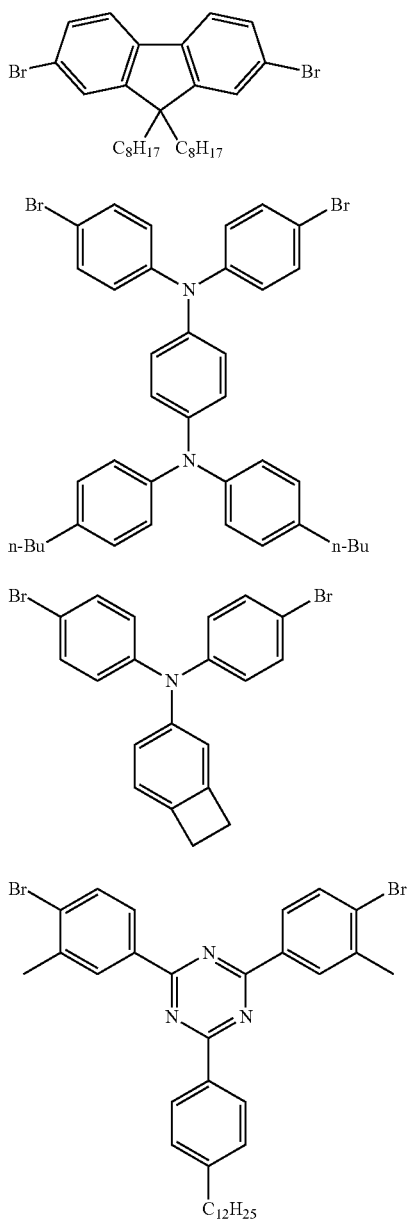

Example M1

Synthesis of Compound MM1

A compound MM1 was synthesized according to the following first to fourth steps.

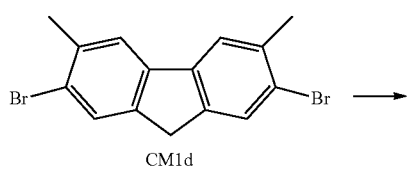

-continued

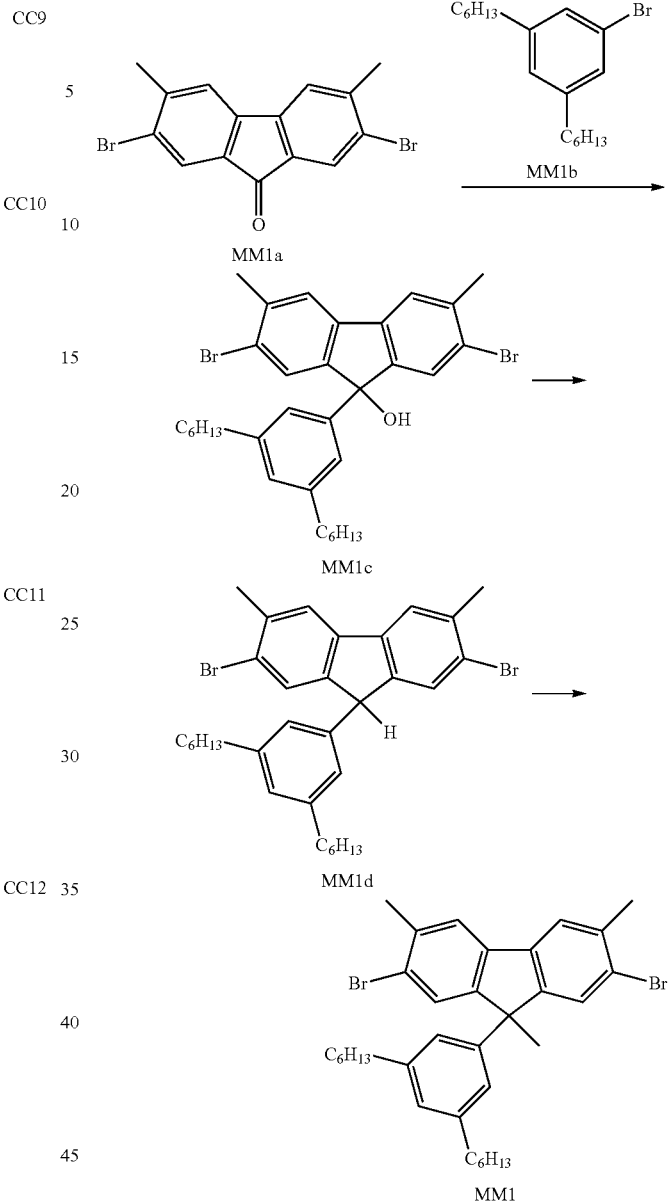

(First Step)

In a reaction vessel, pyridine (34.70 ml) was added to a compound CM1d (12.22 g, 34.70 mmol), then, benzyltrimethyl ammonium hydroxide (40% pyridine solution) (0.87 ml, preparation thereof is described later) was added at room temperature, and the mixture was heated at 40° C. in an oil bath and stirred for 16 hours while ventilating atmospheric air into the reaction vessel. Thereafter, benzyltrimethyl ammonium hydroxide (40% pyridine solution) (0.87 ml, preparation thereof is described later) was added again, and the mixture was heated in an oil bath at 60° C. and stirred for 8 hours, to obtain a reaction solution. To the resultant reaction solution were added ion exchanged water and acetic acid, to make acidic condition, then, the mixture was stirred at room temperature for 1 hour, and the deposited yellow solid was isolated by filtration and washed with water. The resultant solid was dried, then, dispersed in a mixed solvent composed of tetrahydrofuran and methanol (tetrahydrofuran/methanol=4/30 (v/v)), and the dispersion was stirred for 1.5 hours while heating in an oil bath at 80° C., and cooled down to room temperature, then, the deposited solid was isolated by filtration and dried under reduced pressure, to obtain the targeted compound MM1a (11.87 g) as a yellow solid. The yield was 93.5%. The resultant compound MM1a indicated a HPLC area percentage value (UV 254 nm) of 96.7%.

$^1$H-NMR (300 MHz, CDCl$_3$): δ (ppm)=7.77 (s, 2H), 7.36 (s, 2H), 2.47 (s, 6H).

LC/MS (APPI (posi)): 364[M]$^+$ (Preparation of Benzyltrimethyl Ammonium Hydroxide (40% Pyridine Solution))

Pyridine (50 ml) was added to benzyltrimethyl ammonium hydroxide (40% methanol solution) (referred to as "TRITON B" in some cases, manufactured by Kanto Chemical Co., Inc., 50 ml), then, the mixture was concentrated to 25 ml or less by an evaporator, and pyridine was again added for dilution to 50 ml. The solution obtained by this operation is called "benzyltrimethyl ammonium hydroxide (40% pyridine solution)".

(Second Step)

An atmosphere in the reaction vessel was changed to an argon gas atmosphere, then, a solution prepared by dissolving 3,5-di-n-hexyl-1-bromobenzene (compound MM1b, 13.82 g, 42.5 mmol) in tetrahydrofuran (dehydrated product, 324 ml) was cooled using a cool bath of −78° C. while stirring. Thereafter, a hexane solution of n-butyllithium (1.63 mol/L, 25.7 ml) was slowly dropped so that the temperature of the resultant solution was kept at −75° C. or lower, and the mixture was further stirred for 1 hour. Thereafter, a compound MM1a (11.87 g, 32.4 mmol) was added little by little so that the temperature of the resultant solution was kept at −75° C. or lower, and further, the mixture was stirred for 2 hours, then, methanol (about 20 ml) was dropped slowly, then, the cool bath was removed, and the temperature was raised slowly up to room temperature. The solvent of the resultant reaction solution was distilled off by concentration under reduce pressure, then, hexane was added, and the mixture was washed with ion exchanged water, to obtain an oil layer. The resultant oil layer was dried over anhydrous sodium sulfate, insoluble components were separated by filtration, then, the solvent was distilled off by concentration under reduced pressure, and further, the residue was purified by recrystallization (hexane), isolated by filtration and dried under reduced pressure, to obtain the targeted compound MM1c (9.12 g) as a white solid. The yield was 45%. The resultant compound MM1c indicated a HPLC area percentage value (UV254 nm) of 97.9%.

LC/MS (ESI (posi)): 610[M]$^+$ (Third Step)

A gas in a reaction vessel was changed to an argon gas atmosphere, then, a compound MM1c (9.12 g, 14.89 mmol), triethylsilane (4.53 ml, 59.6 mmol) and hexane (39 ml) were mixed, and trifluoroacetic acid (4.5 ml, 59.6=01) was dropped while heating at 70° C. in oil bath, then, and the mixture was further stirred for 3 hours with heating, to obtain a reaction solution. The resultant reaction solution was cooled down to room temperature, then, a 10 wt % potassium phosphate aqueous solution was added, and further, the organic layer was washed with saturated saline, dried over anhydrous sodium sulfate, insoluble components were separated by filtration, then, the solvent was distilled off by concentration under reduced pressure and drying under reduced pressure, to obtain an oily substance (8.9 g) containing a compound M1d. The resultant oily substance was used in the next step without performing further purification.

LC/MS (ESI (posi)): 594[M]$^+$ (Fourth Step)

A gas in a reaction vessel was changed to an argon gas atmosphere, then, N,N-dimethylformamide (74 ml) was added to an oily substance (8.9 g) containing a compound MM5d, to obtain a uniform solution. The resultant solution was bubbled with argon for 15 minutes, then, the mixture was cooled to 5° C. or lower using an ice bath. Potassium hydroxide (2.76 g, 49.1 mmol) was dissolved in ion exchanged water (2.4 ml), then, a potassium hydroxide aqueous solution bubbled with argon was prepared separately, and added to the solution obtained above. Thereafter, methyl iodide (6.34 g, 44.7 mmol) was dropped, and the mixture was stirred at 0 to 5° C. for 4 hours. The ice bath was removed, then, ion exchanged water was added, and further, the mixture was extracted with hexane, to obtain an oil layer. The resultant oil layer was dried over anhydrous sodium sulfate, insoluble components were separated by filtration, the solvent was distilled off, then, the residue was purified by medium pressure silica gel column chromatography (developing solvent: hexane). Fractions containing the targeted material MM1 were combined, concentrated, then, purified by recrystallization (a mixed solvent of hexane and isopropanol), and the resultant crystal was isolated by filtration and dried under reduced pressure, to obtain the targeted compound MM1 (7.10 g) as a white solid. The yield was 77%. The resultant compound MM1c had a HPLC area percentage value (UV 254 nm) of 99.9% or more.

$^1$H-NMR (300 MHz, CDCl$_3$): δ (ppm)=7.57 (s, 2H), 7.35 (s, 2H), 6.83 (s, 1H), 6.71 (s, 2H), 2.50-2.44 (m, 10H), 1.79 (s, 3H), 1.54-1.45 (m, 4H), 1.34-1.17 (m, 12H), 0.84 (t, 6H).

LC/MS (ESI (posi)): 608[M]+

Example M2

Synthesis of Compound MM2

A compound MM2 was synthesized according to the following step.

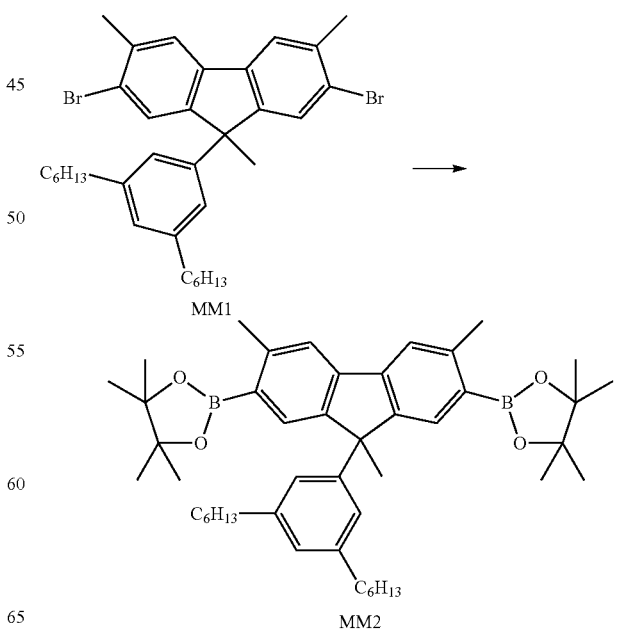

A gas in a reaction vessel was changed to an argon gas atmosphere, then, a mixture of bis(pinacol)diboron (9.10 g, 35.9 mmol), potassium acetate (7.04 g, 71.7 mmol), 1,4-dioxane (36 ml) and a dichloromethane complex of [1,1'-bis(diphenylphosphino)ferrocene]dichloropalladium(II) (Pd(dppf)Cl$_2$·CH$_2$Cl$_2$, CAS number: 95464-05-4, manufactured by Sigma-Aldrich Co. LCC, 0.293 g, 0.36 mmol) was stirred with heating in oil bath at 115° C., and a solution prepared by dissolving the compound MM1 (7.13 g, 11.9 mmol) synthesized separately by the above-described method in 1,4-dioxane (36 ml) was dropped over a period of 2 hours while stirring, then, the mixture was stirred for about 18 hours at the same temperature, to obtain a reaction solution. The resultant reaction solution was cooled down to room temperature, then, diluted by adding toluene, then, allowed to pass through a Celite and silica gel pad, to remove insoluble components and polar components. The resultant solution was dried over anhydrous sodium sulfate, insoluble materials were separated by filtration, then, the solvent was distilled off by concentration under reduced pressure, then, toluene was added to obtain a uniform solution. To the resultant solution was added activated carbon, and the mixture was stirred for 30 minutes while heating in an oil bath of 70° C., and cooled down to room temperature, then, insoluble materials were removed by filtration through Celite, the resultant solution was concentrated, then, purified by recrystallization (developing solvent: a mixed solvent of toluene and acetonitrile), the resultant crystal was isolated by filtration and dried under reduced pressure, to obtain the targeted compound MM2 (6.94 g) as a white solid. The yield was 82%. The resultant compound MM2 indicated a HPLC area percentage value (UV254 nm) of 99.9% or more.

$^1$H-NMR (300 MHz, CDCl$_3$): δ (ppm)=7.64 (s, 2H), 7.55 (s, 2H), 6.81 (s, 2H), 6.77 (s, 1H), 2.62 (s, 6H), 2.48-2.42 (m, 4H), 1.85 (s, 3H), 1.55-1.45 (m, 4H), 1.31 (s, 24H), 1.31-1.17 (m, 12H), 0.83 (t, 6H).

LC/MS (ESI (posi)): 704[M]%

Example M3

Synthesis of Compound MM3

A compound MM3 was synthesized according to the following first to fourth steps.

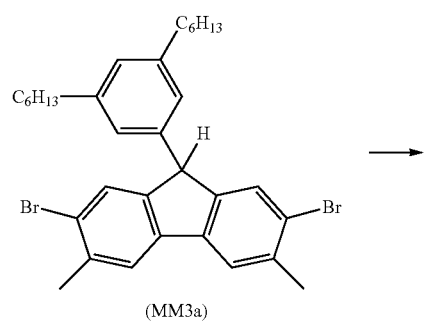

(MM3a)

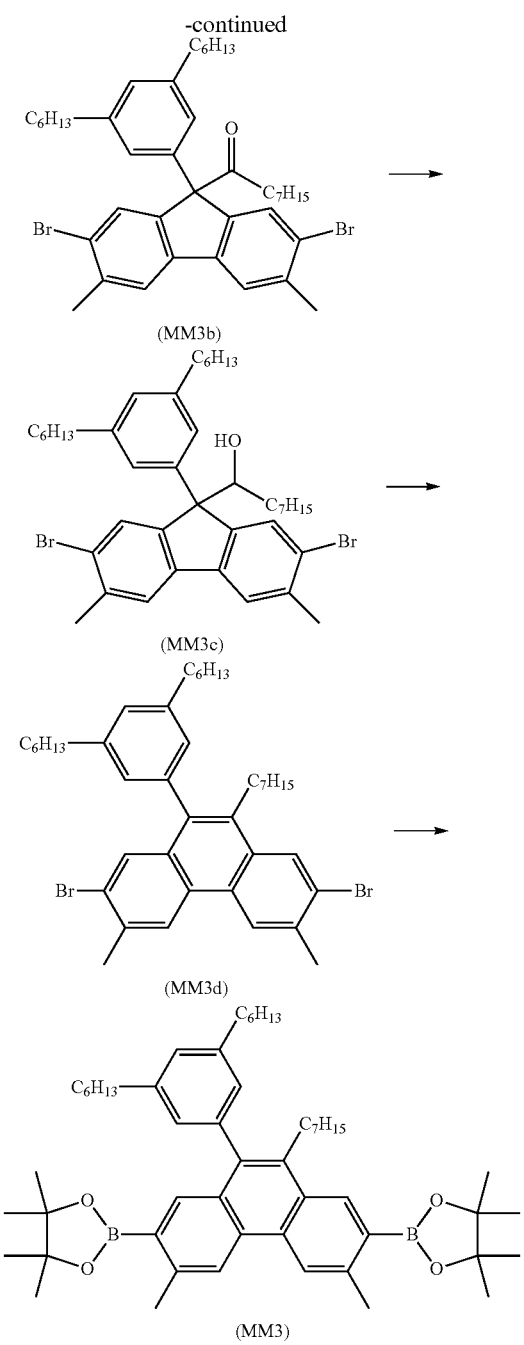

(MM3b)

(MM3c)

(MM3d)

(MM3)

(First Step)

An atmosphere in a reaction vessel was changed to an argon gas atmosphere, then, to a compound (MM3a) (85 g, 108 mmol) was added tetrahydrofuran (dehydrated product, 1290 ml) to dissolve the compound, and the solution was cooled using an ice bath. Under condition of a temperature in the reaction vessel kept at 6° C. or lower, tert-butoxypotassium (24 g, 216 mmol) was added bit by bit while stirring. Thereafter, under condition of a temperature in the reaction vessel kept at 6° C. or lower, the mixture was stirred for 1 hour. Thereafter, n-octanoyl chloride (25 g, 216 mmol) was dropped over a period of 30 minutes. Thereafter, under condition of a temperature in the reaction vessel kept at 6° C. or lower, the mixture was stirred for 2 hours. Thereafter, an ammonium chloride aqueous solution was added to complete the reaction. To the resultant reaction solution were added toluene and ion exchanged water, the resultant organic layer was washed with ion exchanged water three times, then, dried over anhydrous magnesium sulfate. The resultant reaction solution was allowed to pass through a silica gel pad to separate insoluble materials by filtration, and the resultant solution was concentrated. Thereafter, the concentrated product was purified by silica gel column chromatography (developing solvent: hexane), to obtain the targeted compound (MM3b) (63 g, 104 mmol) as an oily substance. The resultant compound (MM3b) indicated a HPLC area percentage value (UV254 nm) of 90.0%.

LC/MS (ESI (posi)): 720[M]$^+$ (Second Step)

An atmosphere in a reaction vessel was changed to an argon gas atmosphere, then, to a compound (MM3b) (58 g, 72 mmol) was added cyclopentylmethyl ether (dehydrated product, 1 L) to dissolve the compound, and the solution was cooled using an ice bath. Under condition of a temperature in the reaction vessel kept at 6° C. or lower, lithium aluminum hydride (1 g, 36 mmol) was added bit by bit while stirring. Thereafter, under condition of a temperature in the reaction vessel kept at 6° C. or lower, the mixture was stirred for 2 hours. Thereafter, an ammonium chloride aqueous solution was added to complete the reaction. The resultant organic layer was washed with ion exchanged water twice, then, dried over anhydrous magnesium sulfate. The resultant reaction solution was filtrated, and concentrated. Thereafter, the concentrated product was purified by medium pressure silica gel column chromatography (developing solvent: a mixed solvent of hexane and chloroform). Fractions containing the targeted compound (MM3c) were combined, concentrated, then, purified by recrystallization (a mixed solvent of hexane and methanol), to obtain the targeted compound (MM3c) (34 g, 47 mmol) as a white solid. The resultant compound (MM3c) indicated a HPLC area percentage value (UV254 nm) of 99.3%.

LC/MS (ESI (posi)): 722 [M]$^+$ (Third Step)

An atmosphere in a reaction vessel equipped with a reflux condenser was changed to an argon gas atmosphere, then, to a compound (MM3c) (33 g, 46 mmol) was added toluene (dehydrated product, 330 ml). Diphosphorus pentaoxide (26 g, 182 mmol) was added while stirred at room temperature. Thereafter, the mixture was stirred for 2.5 hours while heating the reaction vessel in an oil bath set at 80° C., and cooled down to room temperature. The resultant reaction solution was poured into ice water, thereby decomposing excess diphosphorus pentaoxide, to complete the reaction. The resultant organic layer was washed with ion exchanged water three times, then, dried over anhydrous magnesium sulfate. The resultant reaction solution filtrated, and concentrated. The resultant oily substance was dissolved toluene, and the solution was allowed to pass through a silica gel pad, and the resultant toluene solution was concentrated. Thereafter, the concentrated product was purified by silica gel column chromatography (developing solvent: hexane), and fractions containing the targeted compound (MM3d) were combined, and concentrated, to obtain the targeted compound (MM3d) (26 g, 37 mmol) as an oily substance. The resultant compound (MM3d) indicated a HPLC area percentage value (UV 254 nm) of 99.7%.

LC/MS (ESI (posi)): 704 [M]$^+$ (Fourth Step)

An atmosphere in a reaction vessel was changed to an argon gas atmosphere, then, potassium acetate (0.8 g, 8.5 mmol), bispinacolatodiboron (1.1 g, 1.4 mmol) and dioxane (dehydrated product, 5 ml) were added. While stirring at room temperature, 1,1'-bis (diphenylphosphino) ferrocene-palladium (II) dichloride-dichloromethane complex (0.04 g, 0.4 mmol) was added. Thereafter, a compound (MM3d) (1 g, 1.4 mmol) dissolved in dioxane (dehydrated product, 5 ml) was dropped over a period of 30 minutes while heating the reaction vessel in an oil bath set at 115° C., and the mixture was stirred further for 14 hours. Thereafter, the mixture was cooled down to room temperature to complete the reaction. To the resultant reaction solution were added toluene and ion exchanged water, and the resultant organic layer was washed with ion exchanged water three times, then, dried over anhydrous magnesium sulfate. The resultant reaction solution was filtrated, the concentrated. The resultant oily substance was dissolved in toluene, then, activated carbon was added and the mixture was stirred for 30 minutes. Thereafter, the mixture was allowed to pass through a Celite and silica gel pad, and the resultant toluene solution was concentrated. Thereafter, purification by medium pressure silica gel column chromatography (developing solvent: a mixed solvent of hexane and chloroform) was repeated, and fractions containing the targeted compound (MM3) were combined and concentrated, to obtain the targeted compound (MM3) (0.4 g, 0.6 mmol) as an oily substance. The resultant compound (MM3) indicated a HPLC area percentage value (UV254 nm) of 99.3%.

$^1$H-NMR (300 MHz, CDCl3): δ (ppm)=8.57 (s, 1H), 8.51 (s, 1H), 8.45 (s, 1H), 7.77 (s, 1H), 7.03 (s, 1H), 6.91 (d, 2H), 2.86 (t, 2H), 2.80 (s, 3H), 2.73 (s, 3H), 2.64 (t, 4H), 1.64 (m, 6H), 0.87 to 1.40 (m, 63H).

LC/MS (ESI (posi)): 786[M]$^+$

Example M4

Synthesis of Compound MM4

A compound MM4 was synthesized according to the following first to fifth steps.

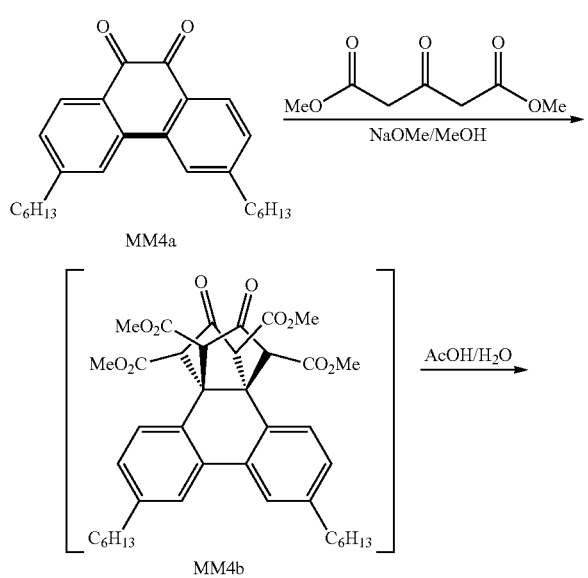

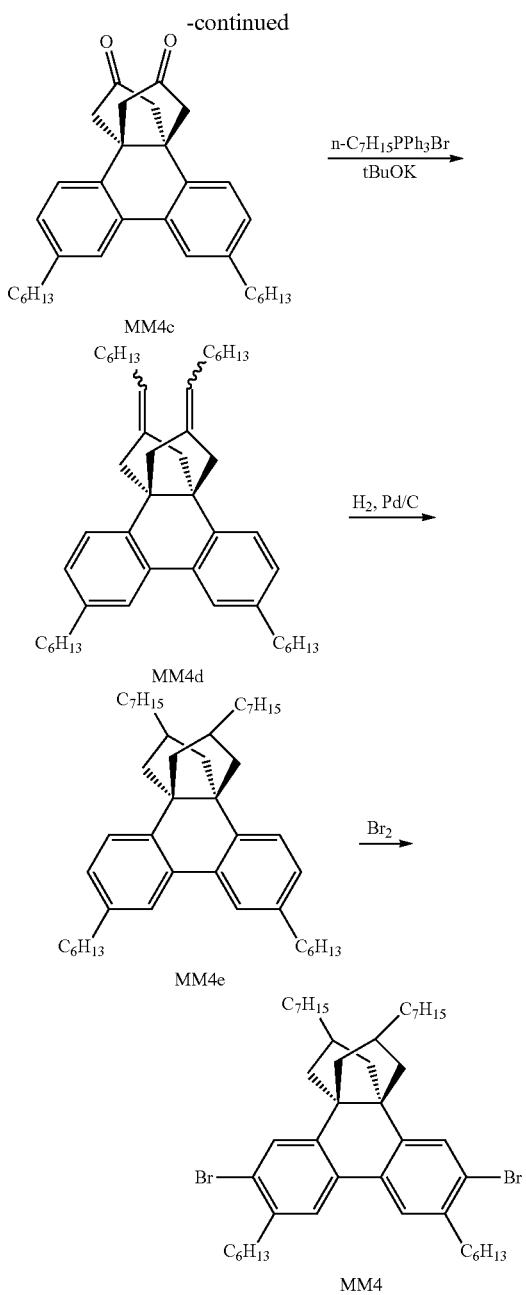

[in the formula, the wavy line means that a compound attached with this wavy line is a geometric isomer mixture.]

(First Step)

Into a reaction vessel equipped with a stirrer were added a compound MM4a (35.31 g) and methanol (1100 ml), then, an atmosphere in the reaction vessel was changed to an argon gas atmosphere. Thereafter, dimethyl 1,3-acetonedicarboxylate (34.65 g) was added to this bit by bit, then, sodium methoxide (5 mol/L methanol solution) (67.62 g) was dropped bit by bit. Thereafter, the mixture was thermally insulated at room temperature for 2 hours, and the temperature was raised up to 60° C. Thereafter, the mixture was stirred for 6 hours while thermally insulating at 60° C. The resultant reaction solution was cooled down to room temperature, and 35% hydrochloric acid (37.41 g) was added. Thereafter, water and toluene were added, and the mixture was stirred at room temperature. Thereafter, the aqueous layer was separated, and the resultant organic layer was washed with a saturated sodium chloride aqueous solution. To the resultant organic layer was added sodium sulfate, and the mixture was filtrated and concentrated, to obtain the targeted compound MM4b (60.1 g) as an oily substance. The resultant compound MM4b indicated a HPLC area percentage value (UV254 nm) of 42%.

(Second Step)

Into a reaction vessel equipped with a stirrer were added a compound MM4b (60.10 g), acetic acid (450 ml) and ion exchanged water (60 ml), and an atmosphere in the reaction vessel was changed to an argon gas atmosphere. Thereafter, the temperature was raised up to 100° C., and the mixture was stirred for 5 hours while thermally insulating at 100° C. The resultant reaction solution was cooled down to room temperature, then, water and toluene were added, the aqueous layer was separated, and the resultant organic layer was washed with a saturated sodium chloride aqueous solution. To the resultant organic layer was added sodium sulfate, and the mixture was filtrated and concentrated, to obtain a coarse product of the targeted compound MM4b. The resultant coarse product was purified by silica gel column chromatography (developing solvent: a mixed solvent of hexane and ethyl acetate), to obtain the targeted compound MM4c (19.5 g) as a white solid. The resultant compound MM4c indicated a HPLC area percentage value (UV254 nm) of 94.9%.

LC/MS (APCI, positive): $[M+H]^+$ 457

(Third Step)

Into a reaction vessel equipped with a stirrer was added heptyltriphenylphosphonium bromide (82.29 g), and an atmosphere in the reaction vessel was changed to an argon gas atmosphere. Thereafter, toluene (520 ml) was added, and the mixture was cooled to 5° C. or lower. Thereafter, potassium tert-butoxide (20.92 g) was added, the temperature was raised up to room temperature, then, the mixture was stirred for 3 hours while thermally insulating at room temperature. To the resultant red slurry was added a compound MM4c (18.0 g), and the mixture was stirred for 6.5 hours while thermally insulating at room temperature. To the resultant reaction solution was added acetic acid (7.2 g), and the mixture was stirred for 15 minutes, then, water and hexane were added, and the mixture was stirred at room temperature, then, the aqueous layer was separated, and the resultant organic layer was washed with a saturated sodium chloride aqueous solution. To the resultant organic layer was added sodium sulfate, and the mixture was filtrated and concentrated, to obtain a coarse product of the targeted compound MM4d. The resultant coarse product was purified by silica gel column chromatography (developing solvent: hexane), to the resultant hexane solution was added activated carbon, and the mixture was stirred for 1 hour while thermally insulating at 50° C. Thereafter, the mixture was cooled down to room temperature, and filtrated using a filtering apparatus pre-coated with Celite, the resultant residue was washed with hexane several times, and the resultant filtrates were combined and concentrated, to obtain the targeted compound MM4d (18.8 g) as a colorless transparent liquid. The resultant compound MM4d indicated a HPLC area percentage value (UV254 nm) of 98.2%.

LC/MS (APCI, positive): $[M+H]^+$ 621

(Fourth Step)

Into a reaction vessel equipped with a stirrer were added a compound MM4d (18.6 g), ethyl acetate (165 ml) and ethanol (150 ml), and an atmosphere in the reaction vessel was changed to a nitrogen gas atmosphere. Thereafter, 5 wt % Pd/C (about 50 wt % hydrous product) (3.7 g) was added, then, an atmosphere in the reaction vessel was changed to a hydrogen gas atmosphere. Thereafter, the mixture was stirred for 49 hours while thermally insulating at 50° C., and cooled down to room temperature. Thereafter, the mixture was filtrated using a filtering apparatus pre-coated with Celite, the resultant residue was washed with ethyl acetate several times, the resultant filtrates were combined and concentrated, to obtain the targeted coarse product. The resultant coarse product was purified by silica gel column chromatography (developing solvent: hexane), to the resultant hexane solution was added activated carbon, and the mixture was stirred for 1 hour while thermally insulating at 50° C. Thereafter, the mixture was cooled down to room temperature, and filtrated using a filtering apparatus pre-coated with Celite, the resultant residue was washed with hexane several times, and the resultant filtrates were combined and concentrated, to obtain the targeted compound MM4e (17.6 g) as a colorless transparent solution. The resultant compound MM4e indicated a HPLC area percentage value (UV254 nm) of 99.0%.

LC/MS (APCI, Positive): [M+H]$^+$625

(Fifth Step)

Into a reaction vessel equipped with a stirrer was added a compound MM4e (17.0 g), and an atmosphere in the reaction vessel was changed to an argon gas atmosphere. Thereafter, chloroform (230 ml) and trifluoroacetic acid (22 ml) were added, and the mixture was cooled to 5° C. or lower. Thereafter, the whole body of the reaction vessel was light-shielded, a mixture of bromine (8.9 g) and chloroform (45 ml) was dropped over a period of 15 minutes, then, the mixture was stirred for 3 hours while thermally insulating at 5° C. or lower. To the resultant reaction solution was added a 10 wt % sodium sulfite aqueous solution, then, the temperature was raised up to room temperature. The aqueous layer was separated from the resultant reaction solution, and the resultant organic layer was washed with water, a 5 wt % sodium hydrogen carbonate aqueous solution and water in this order. The resultant organic layer was dried over magnesium sulfate, and filtrated and concentrated, to obtain a coarse product of the targeted compound MM4. The resultant coarse product was purified by silica gel column chromatography (developing solvent: hexane), to the resultant hexane solution was added activated carbon, and the mixture was stirred for 1 hour while thermally insulating at 50° C. Thereafter, the mixture was cooled down to room temperature, and filtrated using a filtering apparatus pre-coated with Celite, the resultant residue was washed with hexane several times, and the resultant filtrates were combined and concentrated. This operation was further repeated twice, to obtain the targeted compound MM4 (19.3 g) as a colorless transparent solution. The resultant compound MM4 indicated a HPLC area percentage value (UV254 nm) of 99.7%.

LC-MS (APCI, positive): [M+H]$^+$781

$^1$H-NMR (CDCl$_3$, 300 MHz) δ (ppm): 0.91 (12H, m), 1.18 to 1.43 (36H, m), 1.56 to 1.77 (8H, m), 2.15 to 2.33 (4H, m), 2.70 to 2.75 (4H, m), 7.39 to 7.53 (2H, m), 7.61 to 7.66 (2H, m).

Example M5

Synthesis of Compound MM5

A compound MM5 was synthesized according to the following step.

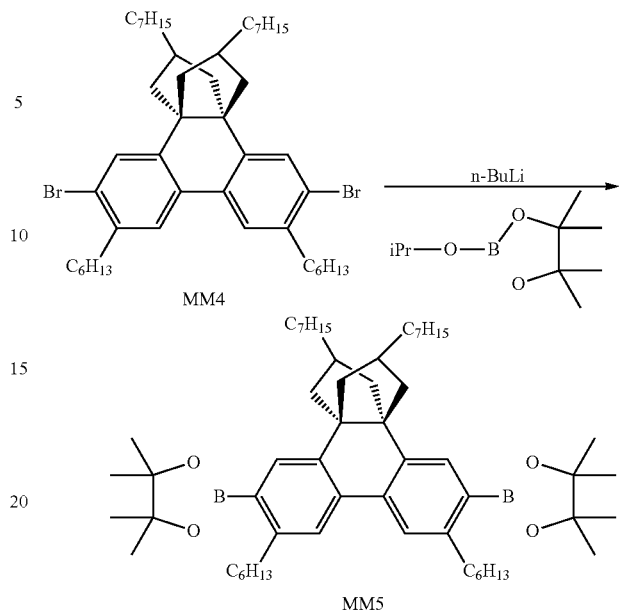

Into a reaction vessel equipped with a stirrer was added dehydrated tetrahydrofuran (210 ml), and it was cooled down to −70° C. or lower. Thereafter, n-butyllithium (1.6M hexane solution) (70 ml) was dropped over a period of 30 minutes or more, and the mixture was stirred for 30 minutes while thermally insulating at −70° C. or lower. Thereafter, a compound MM4 (18.2 g) and dehydrated tetrahydrofuran (210 ml) were dropped over a period of 30 minutes or more, and the mixture was stirred for 1 hour while thermally insulating at −70° C. or lower.

Thereafter, 2-isopropoxy-4,4,5,5-tetramethyl-1,3,2-dioxaborolane (32 ml) was dropped over a period of 10 minutes or more. Thereafter, the temperature was raised up to room temperature, and the mixture was stirred for 4 hours while thermally insulating. Thereafter, toluene was added to dilute the resultant reaction solution, then, water was added and the mixture was stirred at room temperature. Thereafter, the aqueous layer was separated, and the resultant organic layer was washed with a saturated sodium chloride aqueous solution. To the resultant organic layer was added sodium sulfate, and the mixture was filtrated and concentrated, to obtain a coarse product of the targeted compound MM5. The resultant coarse product was purified by silica gel column chromatography (developing solvent: a mixed solvent of hexane and ethyl acetate). Thereafter, recrystallization was performed using a mixed solvent of toluene and acetonitrile, to obtain a compound MM5 (14.6 g) as a white solid. The resultant compound MM5 indicated a HPLC area percentage value (UV254 nm) of 99.8%.

LC/MS (APCI, positive): [M+H]$^+$877

$^1$H-NMR (CD$_2$Cl$_2$, 300 MHz) δ (ppm): 0.94 (12H, m), 1.27 to 1.44 (60H, m), 1.64 to 1.74 (8H, m), 2.25 to 2.45 (4H, m), 2.94 (4H, m), 7.67 to 7.82 (4H, m).

Synthesis Example CM1

Synthesis of Compound CM1

A compound CM1 was synthesized according to the following first to fourth steps.

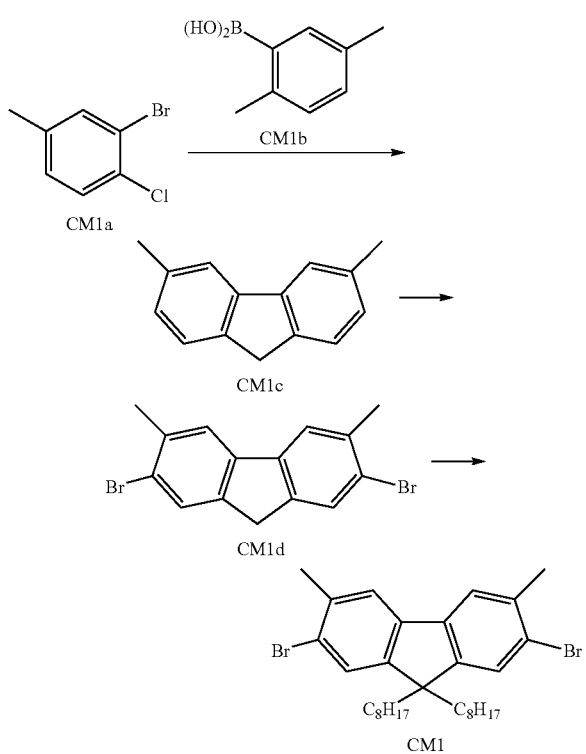

(First step)

A gas in a reaction vessel equipped with a reflux condenser was changed to an argon gas atmosphere, then, a mixture of 3-bromo-4-chlorotoluene (compound CM1a, 30.82 g, 150 mmol), 2,5-dimethylphenylboronic acid (compound CM1b, 24.75 g, 165 mmol), anhydrous potassium carbonate (124.39 g, 900 mmol), palladium(II) acetate (0.67 g, 6 m mol), tricyclohexylphosphine (1.68 g, 12 mmol), dimethylacetamide (dehydrated product, 600 ml) and pivalic acid (15.32 g, 150 mmol) was stirred for 10 hours while heating in an oil bath set at 150° C. Thereafter, the mixture was diluted with toluene (500 ml), then, and washed with ion exchanged water and liquid-separated three times. Thereafter, to the resultant oil layer was added activated white earth (manufactured by Wako Pure Chemical Industries, Ltd., 60 g) and the mixture was stirred for 2 hours, then, an operation of removing insoluble components by passing through a Celite and silica gel pad was repeated twice. The solvent was removed from the resultant solution by concentration under reduced pressure, then, the residue was purified by recrystallization (developing solvent: a mixed solvent of chloroform and ethanol), and the deposited crystal was isolated by filtration and dried under reduced pressure, to obtain the targeted compound CM1c (35.5 g) as a pale yellow to white solid. The yield was 51%. The resultant compound CM1c indicated a HPLC area percentage value of 99.3% (UV254 nm).

(Second Step)

A gas in a reaction vessel was changed to an argon gas atmosphere, then, to a compound CM1c (14.58 g, 75 mmol) were added trifluoroacetic acid (11.15 ml, 150 mmol) and chloroform (dehydrated product, 400 ml) and a uniform mixture was prepared, and the mixture was cooled to 5° C. or lower using an ice bath. Bromine (8.46 ml, 165 mmol) was slowly added while keeping the temperature of the resultant mixture at 5° C. or lower, then, the ice bath was removed, and the mixture was stirred at room temperature for 4 hours, to obtain a reaction solution. To the resultant reaction solution was added a saturated aqueous solution of sodium dithionite, excess bromine was decomposed, then, the mixture was concentrated under reduced pressure to remove the solvent, thereby obtaining a solid. To the resultant solid was added tetrahydrofuran (1 L), the mixture was stirred at 70° C. for 1 hour, then, cooled down to room temperature, water was added, the deposited inorganic salt was dissolved, then, concentrated under reduced pressure again to remove tetrahydrofuran, thereby obtaining a solid-liquid mixture. The deposited solid was isolated by filtration, toluene was added to this to dissolve the solid, then, the resultant toluene solution was concentrate by passing through a silica gel short column, to obtain a solid. An operation of purifying the resultant solid by recrystallization using a mixed solvent of toluene and isopropanol was repeated, to obtain the targeted compound CM1d (22.3 g). The yield was 84%. The resultant compound CM1d indicated a HPLC area percentage value (UV254 nm) of 99.9% or more.

$^1$H-NMR (300 MHz, CDCl$_3$): δ (ppm)=7.67 (s, 2H), 7.58 (s, 2H), 3.79 (s, 2H), 2.48 (s, 6H).

(Third Step)

A gas in a reaction vessel was changed to an argon gas atmosphere, then, a compound CM1d (5.00 g, 14.2 mmol), potassium hydroxide (3.51 g, 62.5 mmol), potassium iodide (236 mg, 1.4 mmol), dimethyl sulfoxide (dehydrated product, 60 ml) and tetrahydrofuran (dehydrated product, 80 ml) were mixed, then, 1-bromooctane (12.20 g, 62.5 mmol) was added at room temperature over a period of 10 minutes, then, the mixture was stirred for 3.5 hours while heating in an oil bath at 70° C., to obtain a reaction solution. The resultant reaction solution was cooled down to room temperature, then, toluene and ion exchanged water were added, the resultant oil layer was washed with ion exchanged water three times, then, dried over anhydrous sodium sulfate. Insoluble components were separated by filtration by passing through a silica gel pad, the resultant solution was concentrated, then, purified by medium pressure silica gel column chromatography (developing solvent: hexane), and fractions containing the targeted compound were combined and concentrated, then, purified by recrystallization (a mixed solvent of chloroform and ethanol), to obtain the targeted compound CM1 (7.13 g) as a white solid. The yield was 87.1%. The resultant compound CM1 indicated a HPLC area percentage value (UV254 nm) of 99.9% or more.

$^1$H-NMR (300 MHz, CDCl$_3$): δ (ppm)=7.50 (s, 2H), 7.44 (s, 2H), 2.47 (s, 6H), 1.89-1.84 (m, 4H), 1.23-1.04 (m, 20H), 0.83 (t, 6H), 0.66-0.55 (m, 4H).

Synthesis Example CM2

Synthesis of Compound CM2

A compound MM4 was synthesized according to the following step.

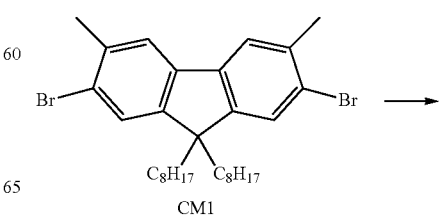

-continued

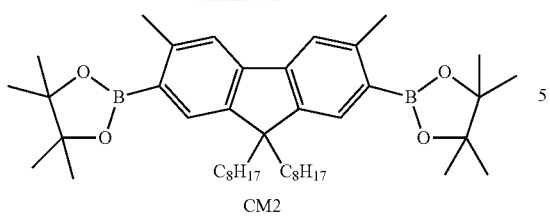

CM2

A gas in a reaction vessel was changed to an argon gas atmosphere, then, a mixture of a compound CM1 (2.34 g, 4.07 mmol), bis(pinacol)diboron (3.10 g, 12.21 mmol), a dichloromethane complex of [1,1'-bis(diphenylphosphino)ferrocene]dichloropalladium(II) (Pd(dppf)Cl$_2$.CH$_2$Cl$_2$, CAS number: 95464-05-4, manufactured by Sigma-Aldrich Co. LLC, 0.100 g, 0.12 mmol), 1,1'-bis(diphenylphosphino)ferrocene (referred to as "dppf" in some cases, 0.068 g, 0.12 mmol), potassium acetate (2.39 g, 24.4 mmol) and 1,4-dioxane (dehydrated product, 33 ml) was stirred for about 18 hours while heating in an oil bath at 110° C., then, insoluble components were removed by passing through a Celite and silica gel pad. The resultant solution was dried over anhydrous sodium sulfate, insoluble components were separated by filtration, then, the solvent was distilled off, to obtain a solid. The resultant solid was dissolved in toluene, activated carbon was added to the solution, the mixture was stirred for 1 hour while heating in an oil bath at 70° C., then, insoluble components were removed by filtrating through Celite, then, the solvent was distilled off, to obtain a solid. The resultant solid was purified by medium pressure silica gel column chromatography (developing solvent: hexane), and further, purified by recrystallization (a mixed solvent of chloroform and acetonitrile), isolated by filtration and dried under reduced pressure, to obtain the targeted compound CM2 (1.00 g). The yield was 37%. The resultant compound CM2 indicated a HPLC area percentage value (UV254 nm) of 99.7%.

$^1$H-NMR (300 MHz, CDCl$_3$): δ (ppm)=7.66 (s, 2H), 7.49 (s, 2H), 2.61 (s, 6H), 1.96-1.91 (m, 4H), 1.37 (s, 24H), 1.19-1.02 (m, 20H), 0.81 (t, 6H), 0.68-0.52 (m, 4H).

LC/MS (ESI (posi)): 670 [M]'

Synthesis Example CC5

Synthesis of Compound CC5

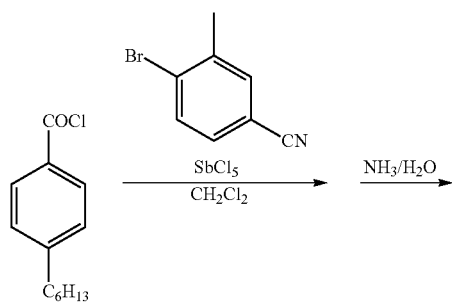

-continued

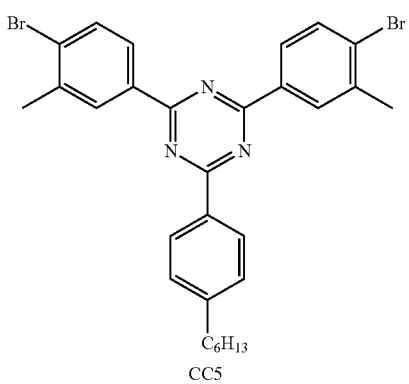

CC5

An atmosphere in a reaction vessel was changed to an argon gas atmosphere, then, 4-hexylbenzoyl chloride (11.24 g, 50 mmol), dichloromethane (90 ml) and molecular sieves 3A (manufactured by Wako Pure Chemical Industries, Ltd., 10 g) were added, and cooled down to 0° C., then, antimony pentachloride (14.7 g, 49 mmol) was dropped over a period of 10 minutes. Thereafter, the mixture was stirred at 0° C. for 20 minutes, then, 4-bromo-3-methylbenzonitrile (19.6 g, 100 mmol) dissolved in dichloromethane (60 ml) was dropped over a period of 1 hour. Thereafter, the mixture was stirred at room temperature for 30 minutes, then, stirred for 2 hours under reflux with heating. The mixture was allowed to stand still at room temperature overnight, then, a 25% ammonia aqueous solution (22 g) was dropped under condition keeping −10° C. After completion of dropping, the mixture was stirred at room temperature for 5 hours, then, chloroform (500 ml) was added, and the mixture was stirred for 1 hour under reflux with heating, then, a solid was removed by hot filtration, the resultant filtrate was washed with ion exchanged water (200 ml) three times, washed with 15 wt % saline (200 ml) once, and the resultant organic layer was dried over anhydrous sodium sulfate, the solid was separated by filtration, then, the resultant filtrate was concentrated under reduced pressure, to obtain an orange oily substance. The resultant oily substance was purified by conducting recrystallization (a mixed solvent of chloroform and methanol), recrystallization (a mixed solvent of toluene and ethanol), medium pressure silica gel column chromatography (developing solvent: a mixed solvent of hexane and chloroform) twice and recrystallization (a mixed solvent of chloroform and hexane) in series, and the resultant solid was dried under reduced pressure, to obtain the targeted compound CC5 (3.97 g) as a white solid. The resultant compound indicated a HPLC area percentage value of 99.6% or more.

$^1$H-NMR (300 MHz, THF-d$_8$): δ (ppm)=8.63 (d, 4H), 8.43 (d, 2H), 7.73 (d, 2H), 7.40 (d, 2H), 2.76 (t, 2H), 2.54 (s, 6H), 1.73 (m, 2H), 1.43 (m, 6H), 0.93 (t, 3H).

$^{13}$C-NMR (75 MHz, THF-d$_8$): δ (ppm)=173.7, 172.8, 150.3, 140.2, 137.6, 135.5, 134.6, 132.9, 131.7, 131.0, 130.6, 129.8, 37.9, 33.8, 33.3, 31.1, 24.7, 24.3, 15.6.

Synthesis Example CC6

Synthesis of Compound CC6

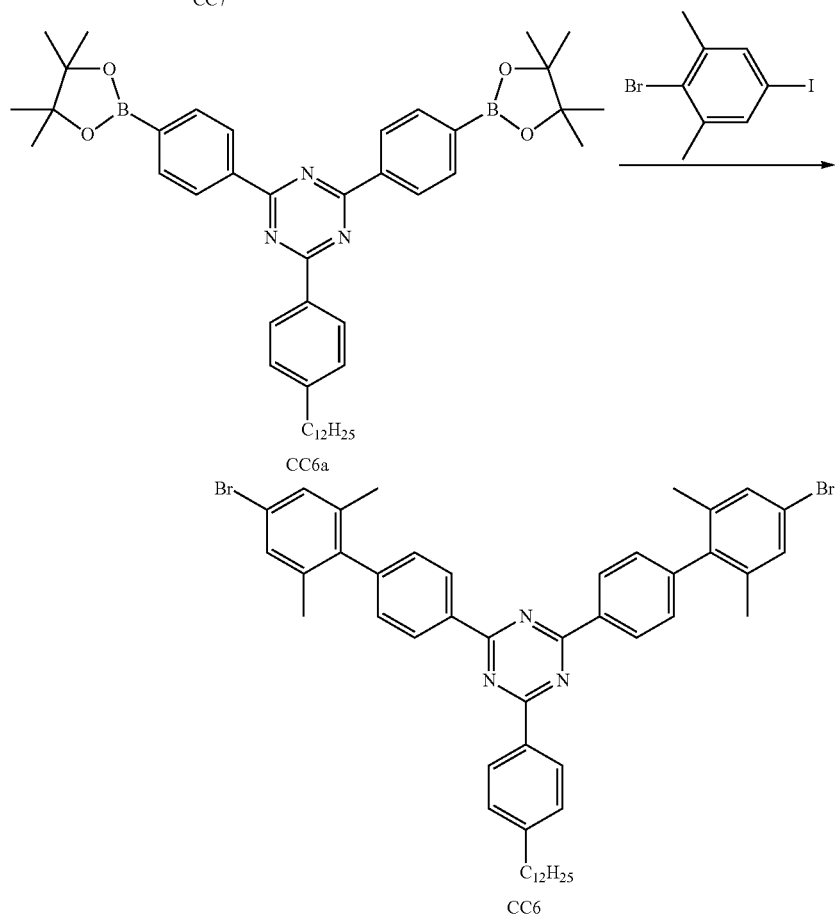

(First Step)

A gas in a reaction vessel was changed to an argon gas atmosphere, then, a mixture of a compound CC7 (41.77 g, 120 mmol), bis(pinacol)diboron (91.9 g, 362 mmol), a dichloromethane complex of [1,1'-bis(diphenylphosphino)ferrocene]dichloropalladium(II) (1:1) (Pd(dppf)Cl$_2$.CH$_2$Cl$_2$, CAS number: 95464-05-4, manufactured by Sigma-Aldrich Co. LLC, 5.096 g, 6.24 mmol), potassium acetate (70.67 g, 720 mmol) and 1,4-dioxane (commercially available dehydrated product, 500 ml) was stirred for about 8 hours while heating in an oil bath at 80° C., then, diluted with toluene (500 ml) and the solution was allowed to pass through a Celite and silica gel pad to remove insoluble components, then, the solvent was distilled off, to obtain a solid. To the resultant solid was added methanol (750 ml), and the mixture was stirred well, then, the solid was isolated by filtration, and dried under reduced pressure, to obtain a solid (57 g). The resultant solid was dissolved in hexane, activated carbon was added, and the mixture was stirred for 1 hour while heating in an oil bath at 60° C., then, insoluble components were removed by filtration through Celite, then, the solvent was distilled off, to obtain a shite solid. To the resultant solid was added methanol (750 ml), and the mixture was stirred for 1 hour while heating at 50° C., then, cooled down to room temperature, and the deposited solid was isolated by filtration, and dried under reduced pressure, to obtain a compound CC6a (40.59 g). The yield was 76%. The resultant compound CC6a indicated a HPLC area percentage value (UV254 nm) of 99.9% or more.

$^1$H-NMR (300 MHz, CDCl$_3$): δ (ppm)=8.75 (d, 2H), 8.68 (d, 2H), 8.06 (d, 2H), 7.39 (d, 2H), 2.73 (t, 2H), 1.71-1.60 (m, 2H), 1.50-1.20 (m, 46H), 0.88 (t, 3H).

TLC/MS (dART, posi): [M+H]$^+$=730.49

(Second Step)

A gas in a reaction vessel was changed to an argon gas atmosphere, then, a mixture of a compound CC6a (25.54 g, 35 mmol), 5-iodo-2-bromo-m-xylene (32.65 g, 105 mmol), toluene (210 ml), tert-butanol (140 ml), tetrahydrofuran (105 ml), ion exchanged water (70 ml), a 20 wt % tetraethyl ammonium hydroxide aqueous solution (103.1 g, 140 mmol) and tetrakis(triphenylphosphine)palladium(0) (2.45 g, 2.12 mmol) was stirred for 40 hours while heating in an oil bath set at 40° C., then, cooled down to room temperature, toluene (140 ml) and ion exchanged water (140 ml) were added, and the organic layer was obtained by liquid-separation. The resultant organic layer was washed with 5 wt % saline, then, dried over anhydrous magnesium sulfate, the resultant solid was removed by filtration, then, the solvent was distilled off by concentration under reduced pressure, to obtain a brown oily substance (37 g). The resultant brown oily substance was diluted with toluene and the solution was allowed to pass through a silica gel short column, the solvent was distilled off by concentration under reduced pressure, to obtain a yellow oily substance. The resultant yellow oily substance was purified by medium pressure silica gel column chromatography (hexane), fractions containing the targeted compound were concentrated under reduced pressure, then, purified by recrystallization (a mixed solvent of toluene and methanol), and the resultant solid was dried under reduced pressure, to obtain a compound CC6 (6.15 g). The yield was 21%. The resultant compound CC6 indicated a HPLC area percentage value of 99.9% or more.

H-NMR (300 MHz, CD$_2$Cl$_2$): δ (ppm)=8.86 (d, J=8.3 Hz, 4H), 8.72 (d, J=8.3 Hz, 2H), 7.43 (d, J=8.3 Hz, 2H), 7.37 (d, J=8.3 Hz, 4H),7.32 (s, 4H), 2.75 (t, J=7.7 Hz, 2H), 2.07 (s, 12H), 1.75-1.66 (mult, 2H), 1.42-1.22 (mult, 18H), 0.88 (t, J=6.6 Hz, 3H).

TLC/MS (dART, posi): [M+H]$^+$=842.27

Production of Polymer Compound

Example P1

Synthesis of Polymer Compound P1

A gas in a reaction vessel was changed to a nitrogen gas atmosphere, then, a mixture of a compound MM1 (1.3388 g), a compound MM2 (1.1600 g) and toluene(39 ml) was heated at about 80° C., then, bis[tris(2-methoxyphenyl)phosphine]palladium dichloride (1.65 mg) and a20 wt % tetraethyl ammonium hydroxide aqueous solution (6.7 g) were added, and the mixture was stirred for about 7.5 hours under reflux of an argon gas.

Thereafter, phenylboronic acid (46.8 mg), bis[tris(2-methoxyphenyl)phosphine]palladium dichloride (1.67 mg) and a 20 wt % tetraethyl ammonium hydroxide aqueous solution (6.7 g) were added, and the mixture was further stirred for about 15.5 hours under reflux of an argon gas. Thereafter, a solution prepared by dissolving sodium N,N-diethyldithiocarbamate trihydrate (0.54 g) in ion exchanged water (11 ml) was added, and the mixture was stirred for about 2.5 hours while heating at 85° C.

The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound (1.554 g, polymer compound P1). The polymer compound P1 had a polystyrene-equivalent number-average molecular weight (Mn) and a polystyrene-equivalent weight-average molecular weight (Mw) of Mn=4.7×10$^4$ and Mw=1.3×10$^5$, respectively. The polymer compound P1 had a TH of 2.67 eV.

The polymer compound P1 is estimated to be a polymer compound composed of the following repeating unit, based on the charging ratios of raw material monomers.

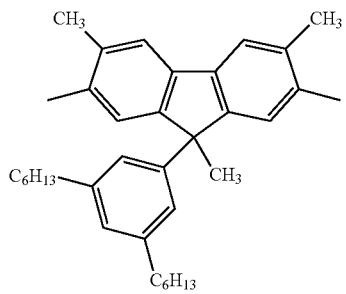

Example P2

A gas in a reaction vessel was changed to a nitrogen gas atmosphere, then, a mixture of a compound CC1 (1.2767 g), a compound MM1 (1.0948 g), a compound CC7 (0.4884 g) and toluene (38 ml) was heated at about 80° C., then, dichlorobis(tris(2-methoxyphenyl)phosphine)palladium (2.23 mg) and a 20 wt % tetraethyl ammonium hydroxide aqueous solution (9.0 g) were added, and the mixture was stirred for about 6.5 hours under reflux of an argon gas.

Thereafter, 2-isopropylphenylboronic acid (84.9 mg), dichlorobis(tris(2-methoxyphenyl)phosphine)palladium (2.33 mg) and a 20 wt % tetraethyl ammonium hydroxide aqueous solution (9.0 g) were added, and the mixture was further stirred for about 16.5 hours under reflux of an argon gas.

Thereafter, a solution prepared by dissolving sodium N,N-diethyldithiocarbamate trihydrate (0.72 g) in ion exchanged water (14 ml) was added, and the mixture was stirred for 2 hours while heating at 85° C.

The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound (1.686 g, polymer compound P2). The polymer compound P2 had a polystyrene-equivalent number-average molecular weight (Mn) and a polystyrene-equivalent weight-average molecular weight (Mw) of $Mn=6.5\times10^4$ and $Mw=1.9\times10^5$, respectively. The polymer compound P2 had a TH of 2.74 eV.

The polymer compound P2 is estimated to be a polymer compound having the following repeating units and mole fractions and in which a repeating unit of (PA) and a repeating unit selected from (PB) are alternately polymerized, based on the charging ratios of raw material monomers.

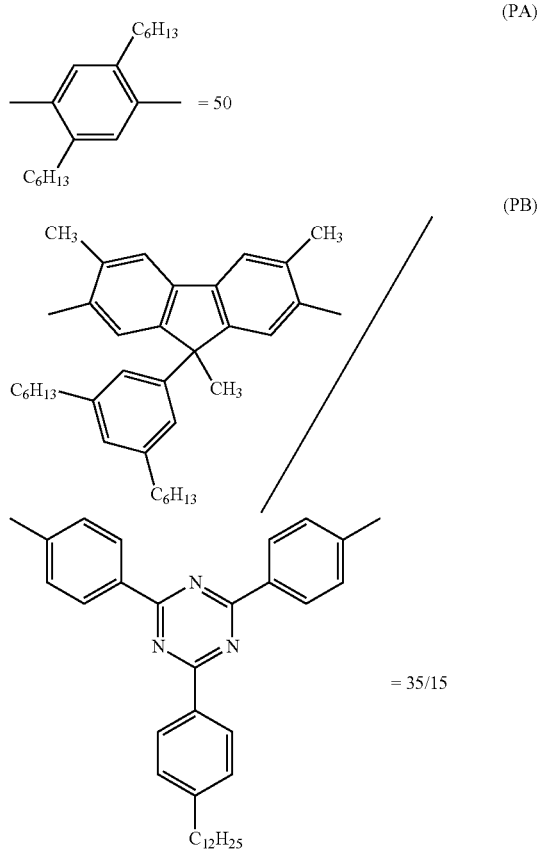

Example P3

Synthesis of Polymer Compound P3

A gas in a reaction vessel was changed to a nitrogen gas atmosphere, then, a mixture of a compound CC1 (1.1788 g), a compound MM1 (0.5776 g), a compound CC5 (0.8223 g) and toluene (33 ml) was heated at about 80° C., then, dichlorobis(tris(2-methoxyphenyl)phosphine)palladium (2.12 mg) and a 20 wt % tetraethyl ammonium hydroxide aqueous solution (8.4 g) were added, and the mixture was stirred for about 10 hours under reflux of an argon gas.

Thereafter, 2-isopropylphenylboronic acid (78.4 mg), dichlorobis(tris(2-methoxyphenyl)phosphine)palladium (2.07 mg) and a 20 wt % tetraethyl ammonium hydroxide aqueous solution (8.4 g) were added, and the mixture was further stirred for about 14 hours under reflux of an argon gas.

Thereafter, a solution prepared by dissolving sodium N,N-diethyldithiocarbamate trihydrate (0.67 g) in ion exchanged water (13 ml) was added, and the mixture was stirred for 4.5 hours while heating at 85° C.

The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound (1.471 g, polymer compound P3). The polymer compound P3 had a polystyrene-equivalent number-average molecular weight (Mn) and a polystyrene-equivalent weight-average molecular weight (Mw) of $Mn=4.4\times10^4$ and $Mw=1.6\times10^5$, respectively. The polymer compound P3 had a TH of 2.79 eV.

The polymer compound P3 is estimated to be a polymer compound having the following repeating units and mole fractions and in which a repeating unit of (PA) and a repeating unit selected from (PB) are alternately polymerized, based on the charging ratios of raw material monomers.

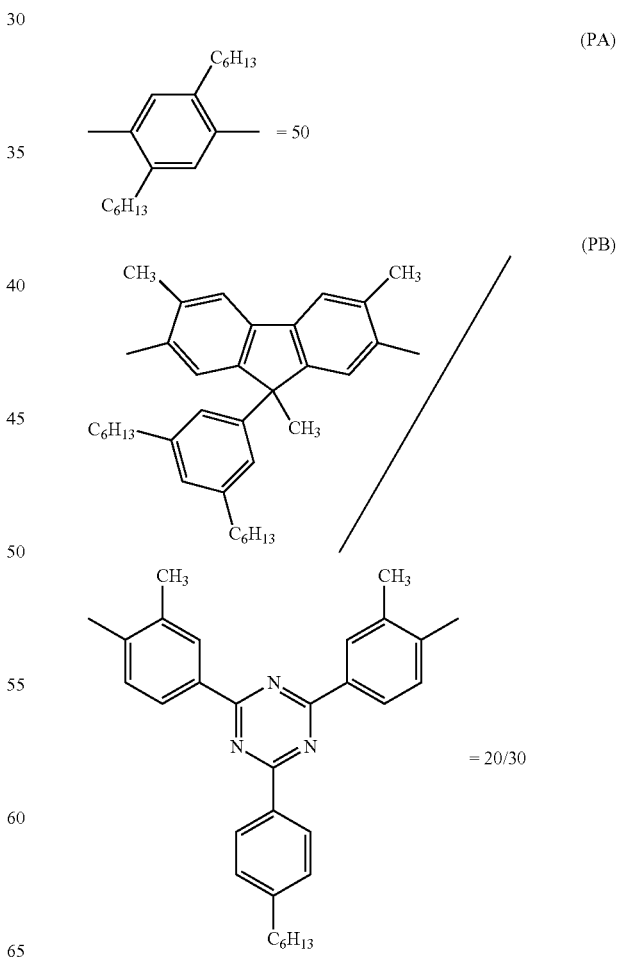

Example P4

Synthesis of Polymer Compound P4

A gas in a reaction vessel was changed to a nitrogen gas atmosphere, then, a mixture of a compound CC1 (1.1213 g), a compound MM1 (0.8791 g), a compound CC6 (0.6834 g) and toluene (38 ml) was heated at about 80° C., then, dichlorobis(tris(2-methoxyphenyl)phosphine)palladium (1.97 mg) and a 20 wt % tetraethyl ammonium hydroxide aqueous solution (8.0 g) were added, and the mixture was stirred for about 11 hours under reflux of an argon gas.

Thereafter, phenylboronic acid (55.4 mg), dichlorobis(tris (2-methoxyphenyl)phosphine)palladium (2.03 mg) and a 20 wt % tetraethyl ammonium hydroxide aqueous solution (8.0 g) were added, and the mixture was further stirred for about 12 hours under reflux of an argon gas.

Thereafter, a solution prepared by dissolving sodium N,N-diethyldithiocarbamate trihydrate (0.63 g) in ion exchanged water (13 ml) was added, and the mixture was stirred for 2 hours while heating at 85° C.

The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound (1.569 g, polymer compound P4). The polymer compound P4 had a polystyrene-equivalent number-average molecular weight (Mn) and a polystyrene-equivalent weight-average molecular weight (Mw) of Mn=$4.2 \times 10^4$ and Mw=$1.1 \times 10^5$, respectively. The polymer compound P4 had a TH of 2.78 eV.

The polymer compound P4 is estimated to be a polymer compound having the following repeating units and mole fractions and in which a repeating unit of (PA) and a repeating unit selected from (PB) are alternately polymerized, based on the charging ratios of raw material monomers.

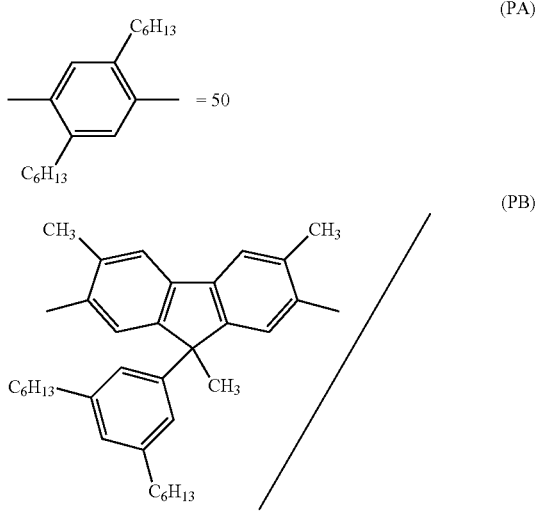

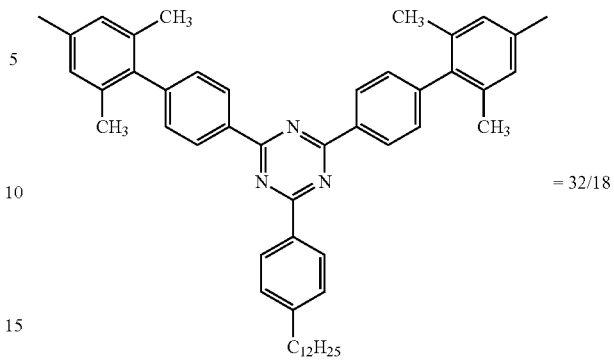

Example P5

Synthesis of Polymer Compound P5

A gas in a reaction vessel was changed to a nitrogen gas atmosphere, then, a mixture of a compound CC1 (1.0369 g), a compound CM1 (0.9595 g), a compound CC7 (0.2644 g) and toluene (31 ml) was heated at about 80° C., then, dichlorobis(tris(2-methoxyphenyl)phosphine)palladium (1.84 mg) and a 20 wt % tetraethyl ammonium hydroxide aqueous solution (11.1 g) were added, and the mixture was stirred for about 6.5 hours under reflux of an argon gas.

Thereafter, phenylboronic acid (51.2 mg), dichlorobis(tris (2-methoxyphenyl)phosphine)palladium (1.84 mg) and a 20 wt % tetraethyl ammonium hydroxide aqueous solution (11.1 g) were added, and the mixture was further stirred for about 17 hours under reflux of an argon gas.

Thereafter, a solution prepared by dissolving sodium N,N-diethyldithiocarbamate trihydrate (0.59 g) in ion exchanged water (12 ml) was added, and the mixture was stirred for 3.5 hours while heating at 85° C.

The resultant organic layer was washed with 3.6 wt % hydrochloric acid twice, with 2.5 wt % ammonia water twice and with ion exchanged water six times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound (1.303 g, polymer compound P5). The polymer compound P5 had a polystyrene-equivalent number-average molecular weight (Mn) and a polystyrene-equivalent weight-average molecular weight (Mw) of Mn=$5.8 \times 10^4$ and Mw=$1.6 \times 10^5$, respectively. The polymer compound P5 had a TH of 2.72 eV.

The polymer compound P5 is estimated to be a polymer compound having the following repeating units and mole fractions and in which a repeating unit of (PA) and a repeating unit selected from (PB) are alternately polymerized, based on the charging ratios of raw material monomers.

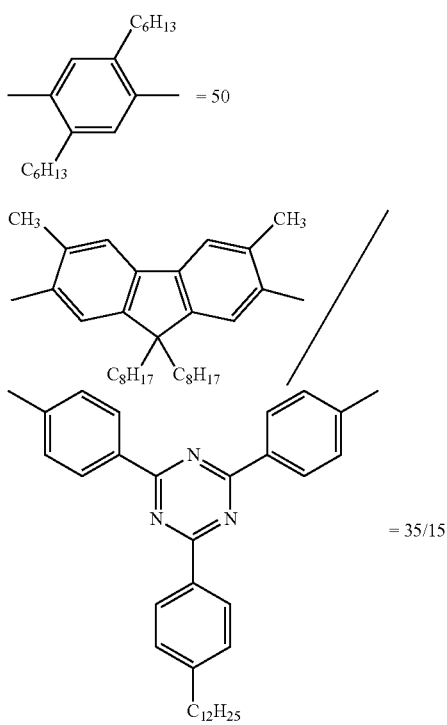

Synthesis Example CP1

Synthesis of Polymer Compound CP1

A gas in a reaction vessel was changed to a nitrogen gas atmosphere, then, a mixture of a compound CC1 (2.2425 g), a compound CC3 (2.3202 g), a compound CC7 (0.5719 g) and toluene (70 ml) was heated at about 80° C., then, bis[tris(2-methoxyphenyl)phosphine]palladium dichloride (3.97 mg) and a 20 wt % tetraethyl ammonium hydroxide aqueous solution (15.9 g) were added, and the mixture was stirred for about 6 hours under reflux of an argon gas.

Thereafter, phenylboronic acid (0.1109 g), bis[tris(2-methoxyphenyl)phosphine]palladium dichloride (4.00 mg) and a 20 wt % tetraethyl ammonium hydroxide aqueous solution (15.9 g) were added, and the mixture was further stirred for about 16.5 hours under reflux of an argon gas.

Thereafter, a solution prepared by dissolving sodium N,N-diethyldithiocarbamate trihydrate (1.27 g) in ion exchanged water (25 ml) was added, and the mixture was stirred for about 2 hours while heating at 85° C.

The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound CP1 (2.729 g). The polymer compound CP1 had a polystyrene-equivalent number-average molecular weight (Mn) and a polystyrene-equivalent weight-average molecular weight (Mw) of Mn=8.2×10$^4$ and Mw=2.1×10$^5$, respectively. The polymer compound CP1 had a TH of 2.65 eV.

The polymer compound CP1 is estimated to be a polymer compound having the following repeating units and mole fractions and in which a repeating unit of (PA) and a repeating unit selected from (PB) are alternately polymerized, based on the charging ratios of raw material monomers.

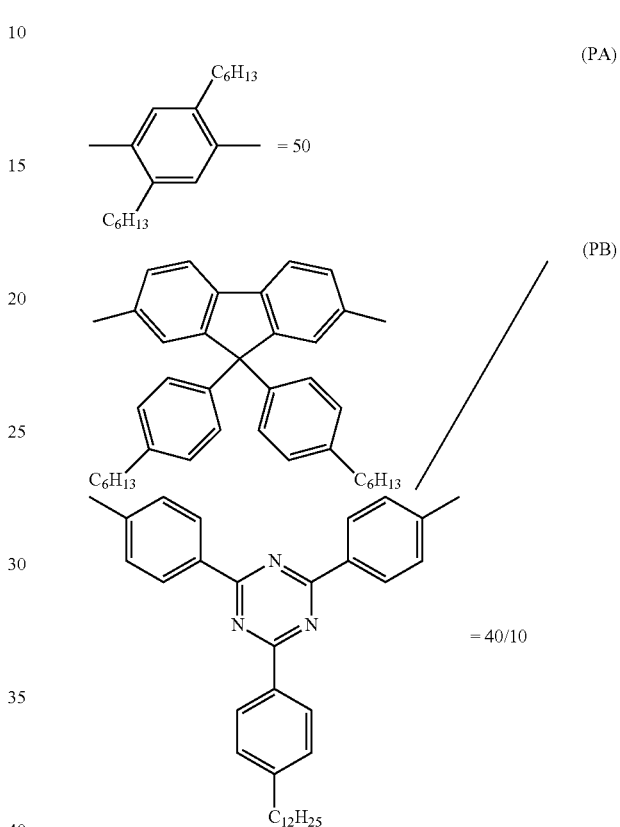

Synthesis Example CP2

Synthesis of Polymer Compound CP2

A gas in a reaction vessel was changed to a nitrogen gas atmosphere, then, a mixture of a compound CC1 (2.7651 g), a compound CC2 (1.7943 g), a compound CC12 (0.7363 g) and toluene (58 ml) was heated at about 80° C., then, palladium acetate (1.31 mg), tris(2-methoxyphenyl)phosphine (7.75 mg) and a 20 wt % tetraethyl ammonium hydroxide aqueous solution (19.6 g) were added, and the mixture was stirred for about 8.5 hours under reflux of an argon gas.

Thereafter, 2-isopropylphenylboronic acid (0.1366 g), palladium acetate (1.28 mg), tris(2-methoxyphenyl)phosphine (7.79 mg) and a 20 wt % tetraethyl ammonium hydroxide aqueous solution (19.6 g) were added, and the mixture was further stirred for about 15.5 hours under reflux of an argon gas.

Thereafter, a solution prepared by dissolving sodium N,N-diethyldithiocarbamate trihydrate (1.56 g) in ion exchanged water (31 ml) was added, and the mixture was stirred for about 2 hours while heating at 85° C.

The resultant organic layer was washed with 3.6 wt % hydrochloric acid twice, with 2.5 wt % ammonia water twice and with ion exchanged water four times, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound (2.732 g, polymer compound CP2). The polymer compound CP2 had a polystyrene-equivalent number-average molecular weight (Mn) and a polystyrene-equivalent weight-average molecular weight (Mw) of Mn=6.6×10$^4$ and Mw=2.9×10$^5$, respectively. The polymer compound CP2 had a TH of 2.95 eV.

The polymer compound CP2 is estimated to be a polymer compound having the following repeating units and mole fractions and in which a repeating unit of (PA) and a repeating unit selected from (PB) are alternately polymerized, based on the charging ratios of raw material monomers.

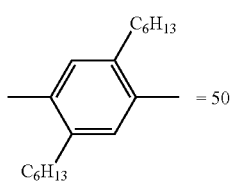

(PA)

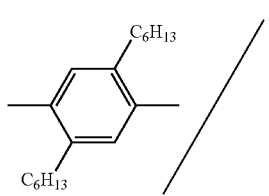

(PB)

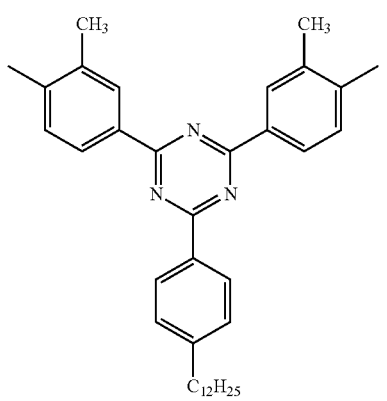

Synthesis Example IP1

Synthesis of Polymer Compound IP1

A gas in a reaction vessel was changed to a nitrogen gas atmosphere, then, a mixture of a compound CC8 (21.218 g), a compound CC9 (5.487 g), a compound CC10 (16.377 g), a compound CC11 (2.575 g), methyltrioctyl ammonium chloride (trade name: Aliquat (registered trademark) 336, manufactured by Sigma-Aldrich Co. LLC) (5.17 g) and toluene (400 ml) was heated at about 80° C., then, bistriphenylphosphinepalladium dichloride (56.2 mg) and a 17.5 wt % sodium carbonate aqueous solution (109 g) were added, and the mixture was stirred for about 6 hours under reflux of an argon gas.

Thereafter, phenylboronic acid (0.49 g) was added, and the mixture was further stirred for about 2 hours under reflux of an argon gas.

Thereafter, a solution prepared by dissolving sodium N,N-diethyldithiocarbamate trihydrate (24.3 g) in ion exchanged water (240 ml) was added, and the mixture was stirred for 2 hours while heating at 85° C.

The resultant organic layer was washed with ion exchanged water twice, with 3 wt % acetic acid twice and with ion exchanged water twice, in series. The resultant organic layer was dropped into methanol to cause generation of a precipitate, which was isolated by filtration, and dried, to obtain a solid. The resultant solid was dissolved in toluene, and the solution was allowed to pass through a silica gel column and an alumina column through which toluene had passed previously. The resultant solution was dropped into methanol to cause generation of a precipitate, which was isolated by filtration, and dried, to obtain a polymer compound (26.23 g, polymer compound IP1). The polymer compound IP1 had a polystyrene-equivalent number-average molecular weight (Mn) and a polystyrene-equivalent weight-average molecular weight (Mw) of Mn=7.8×10$^4$ and Mw=2.6×10$^5$, respectively.

The polymer compound IP1 is estimated to be a polymer compound having the following repeating units and mole fractions and in which a repeating unit of (PA) and a repeating unit selected from (PB) are alternately polymerized, based on the charging ratios of raw material monomers.

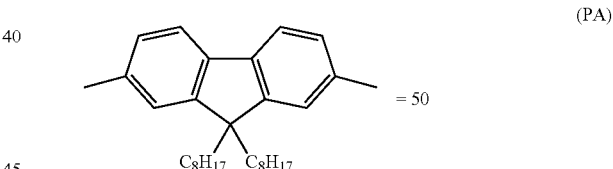

(PA)

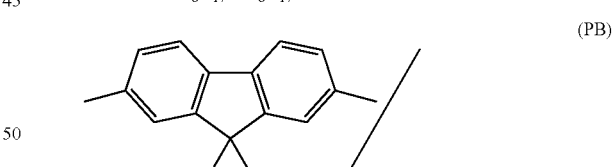

(PB)

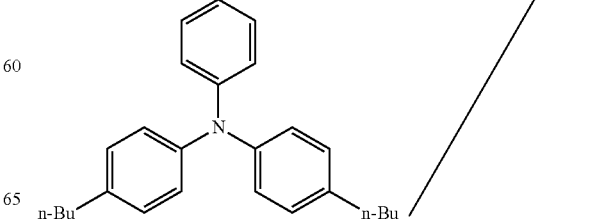

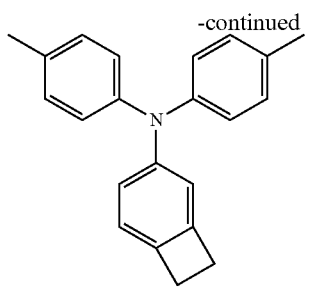

= 12.5/30/7.5

Preparation of Light Emitting Material

Synthesis Example EM1

Synthesis of Phosphorescent Compound EM1

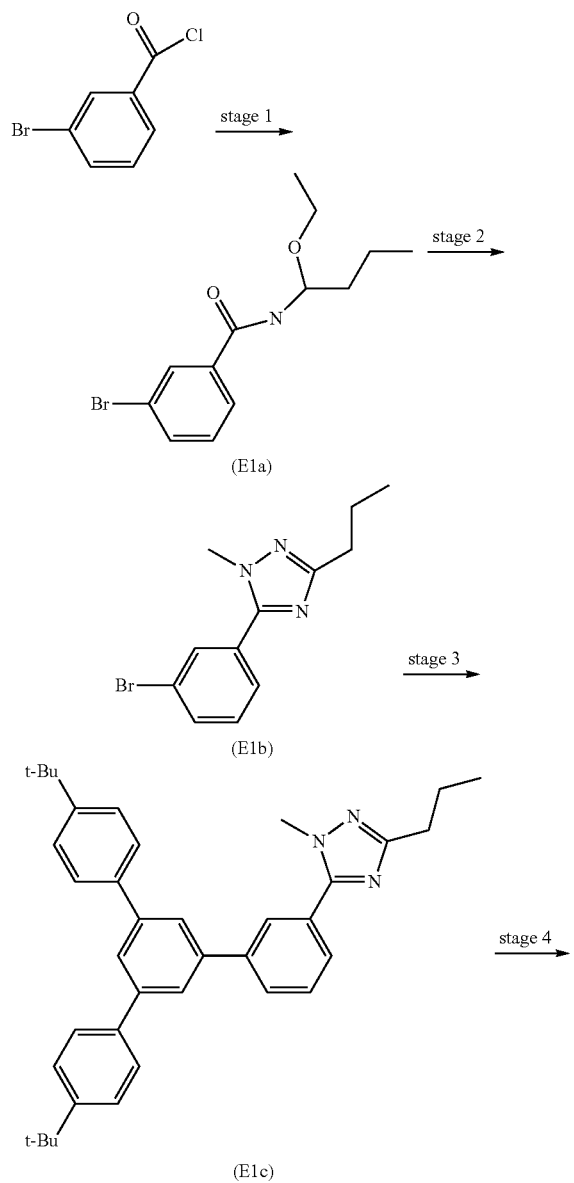

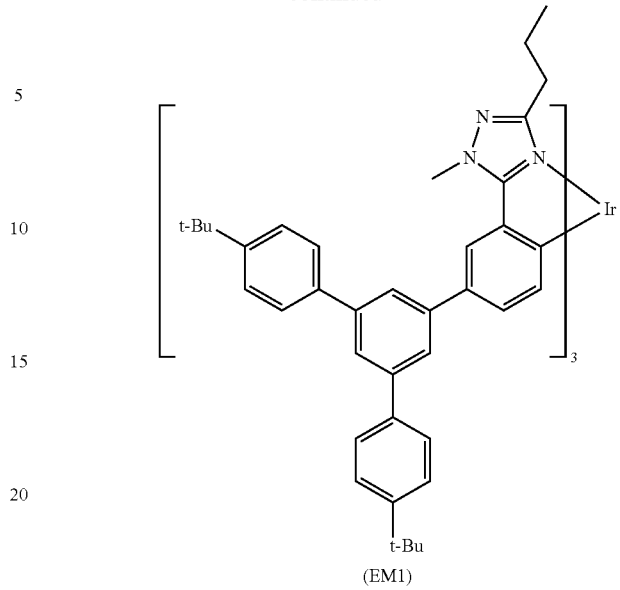

(EM1)

<Stage1>

In a reaction vessel, 6.92 g (31.5 mmol) of 3-bromobenzoyl chloride and 4.95 g (32.6 mmol) of ethyl butylimidate hydrochloride were weighed, and 150 ml of chloroform was added, then, a gas in the reaction vessel was changed to a nitrogen gas atmosphere. Thereafter, 20 ml of a chloroform solution containing 8.0 ml (60 mmol) of triethylamine was dropped, and the mixture was stirred at room temperature for 15 hours under a nitrogen gas atmosphere. The resultant solution was concentrated and suspended in dichloromethane, and the suspension was placed in a separating funnel and washed. The resultant oil layer was concentrated and dried, to obtain 9.47 g of a compound (E1a) as a colorless liquid. The results of $^1$H-NMR analysis are shown below.

$^1$H-NMR (400 MHz/CDCl$_3$): δ (ppm)=8.14 (t, 1H), 7.93 (dd, 1H), 7.65-7.63 (m, 1H), 7.31 (t, 1H), 4.29 (Q,2H), 2.36 (t, 2H), 1.60 (td,2H), 1.37 (t, 3H), 0.88 (t, 3H).

<Stage2>

In a reaction vessel, 9.0 g (30 mmol) of a compound (E1a) was dissolved in 100 ml of chloroform, then, a gas in the reaction vessel was changed to a nitrogen gas atmosphere. Thereafter, 15 ml of a chloroform solution containing 1.52 g (33 mmol) of methylhydrazine and 0.6 ml of water was dropped, and the mixture was stirred at room temperature for 7 hours under a nitrogen gas atmosphere. Into the resultant reaction solution, 100 ml of water was poured, and the solution was placed in a separating funnel and washed. The resultant oil layer was recovered and concentrated, and allowed to pass through a silica gel column. The product was separated and purified using a mixed solvent of dichloromethane and ethyl acetate, to obtain 5.8 g (21 mmol) of a compound (E1b) as a pale yellow liquid with a yield of 69%. The results of $^1$H-NMR analysis are shown below.

$^1$H-NMR (400 MHz/CDCl$_3$): δ (ppm)=7.85 (d, 1H), 7.60 (m, 2H), 7.37 (dd, 1H), 3.93 (s, 3H), 2.72 (t, 2H), 1.81 (m, 2H), 1.01 (t, 3H).

<Stage3>

In a reaction vessel, 1.3 g (4.6 mmol) of a compound (E1b), 2200 mg (4.7 mmol) of 3,5-di(4-tertiary-butylphenyl) phenylboronic acid pinacol ester and 1250 mg (11.6 mol) of sodium carbonate were weighed, and 5 ml of ethanol, 10 ml of water and 10 ml of toluene were added, then, a gas in the reaction vessel was changed to a nitrogen gas atmosphere. Thereafter, 260 mg (0.23 mmol) of tetrakistriphenylphosphinopalladium(0) was added, and the mixture was placed again under a nitrogen gas atmosphere. The resultant reaction mixture was heated at 80° C. for 15 hours. After left to cool, water and toluene were poured and washing was performed. The resultant oil layer was recovered, then, concentrated, to obtain a coarse product. The resultant coarse product was allowed to pass through a silica gel column and separated and purified with a mixed solvent of dichloromethane and ethyl acetate. A compound (E1c) (2.18 g, 4.0 mmol) was obtained as a white powder with a yield of 88%. The results of $^1$H-NMR analysis are shown below.

$^1$H-NMR (400 MHz/(CD$_3$)$_2$CO): δ (ppm)=8.19 (t, 1H), 7.98 (dt, 1H), 7.93 (d, 2H), 7.91 (t, 1H), 7.80 (t, 1H), 7.77 (dt, 4H), 7.66 (t, 1H), 7.54 (dt, 4H), 4.01 (s, 3H), 2.63 (t, 2H), 1.76 (td, 2H), 1.36 (s, 18H), 0.98 (t, 3H).

<Stage4>

In a reaction vessel, 226 mg (0.64 mmol) of iridium chloride and 760 mg (1.4 mmol) of a compound (E1c) were weighed, and 2 ml of water and 6 ml of 2-butoxyethanol were added, then, a gas in a reaction vessel was changed to a nitrogen gas atmosphere, and the mixture was refluxed with heating for 17 hours. After left to cool, water and dichloromethane were poured, and the resultant oil layer was washed. The resultant oil layer was concentrated and dried, to obtain 840 mg of a compound as a brownish-yellow amber-colored solid. In a reaction vessel, 840 mg of the resultant brownish-yellow amber-colored solid and 1300 mg (2.4 mmol) of a compound (E1c) were weighed, a gas in the reaction vessel was changed to an argon gas atmosphere, then, 165 mg (0.64 mmol) of silver trifluorosulfonate was added. Thereafter, 1.25 ml of diethylene glycol dimethyl ester was added, and the mixture was refluxed with heating for 15 hours. After left to cool, dichloromethane was poured, and the resultant suspension was filtrated under suction. The resultant filtrate was placed in a separating funnel and washed, and the resultant oil layer was recovered, then, concentrated, to obtain a coarse product. The resultant coarse product was allowed to pass through a silica gel column and separated and purified with a mixed solvent of dichloromethane and ethyl acetate. The resultant yellow solid was recrystallized using a mixed solvent of dichloromethane and methanol, then, recrystallized using a mixed solvent of dichloromethane and hexane. A phosphorescent compound (EM1) [fac-tris(1-methyl-3-propyl-5-(5-(3,5-di(4-tertiary-butylph enyl)phenyl)phenyl)-1H-[1,2,4]-triazolato-N,C2')iridium(III)] (850 mg, 0.48 mmol) was obtained as a yellow powder with a yield of 73%. The results of $^1$H-NMR analysis are shown below. The phosphorescent compound EM1 had a TM of 2.77 eV.

$^1$H-NMR (400 MHz/CDCl$_3$): δ (ppm)=7.82 (d, 3H), 7.75 (d, 6H), 7.72 (d, 3H), 7.62 (d, 12H), 7.48 (d, 12H), 7.20 (dd, 3H), 6.87 (d, 3H), 4.27 (s, 9H), 2.26 (ddd, 3H), 1.96 (ddd, 3H), 1.37 (s, 54H), 1.05 (m, 6H), 0.73 (t, 9H).

Synthesis Example EM2

Synthesis of Phosphorescent Compound EM2

A phosphorescent compound EM2 was synthesized according to a synthesis method described in WO 2002/066552. The phosphorescent compound EM2 had a TM of 2.52 eV.

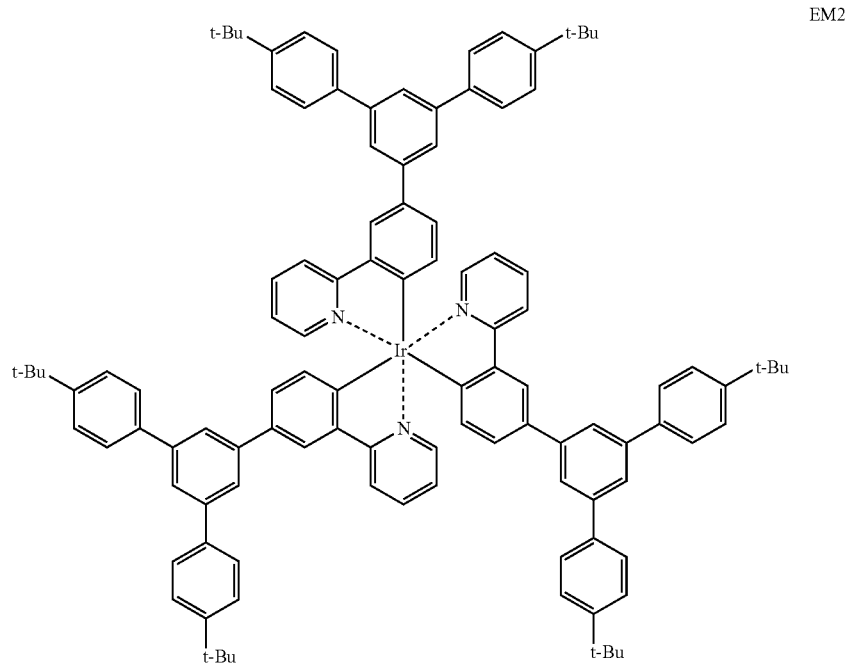

EM2

Example D1

Fabrication and Evaluation of Light Emitting Device D1

On a glass substrate carrying thereon an ITO film with a thickness of 45 nm formed by a sputtering method, a polythiophene-sulfonic acid type hole injecting agent AQ-1200 (Manufactured by Plextronics. Inc.) was spin-coated to form a film with a thickness of 35 nm, which was dried on a hot plate at 170° C. for 15 minutes. Next, a polymer compound IP1 was dissolved at a concentration of 0.6 wt % in xylene. The resultant xylene solution was used and spin-coated at a rotating rate of 1600 rpm to form a film of the polymer compound IP1 with a thickness of 20 nm on the above-described film, then, the film was dried at 180° C. for 60 minutes under a nitrogen gas atmosphere in which the oxygen concentration and the moisture concentration were 10 ppm or less (by weight). Next, the polymer compound P2 and the phosphorescent compound EM1 were dissolved each at a concentration of 2.0 wt % in xylene, and the solutions were mixed so that the weight ratio of polymer compound P2:phosphorescent compound EM1=60:40, to fabricate a composition D1. The resultant composition D1 was spin-coated at a rotating rate of 1860 rpm to form a film with a thickness of about 75 nm on the film of the above-described polymer compound IP1, then, the film was dried at 130° C. for 10 minutes under a nitrogen gas atmosphere in which the oxygen concentration and the moisture concentration were 10 ppm or less (by weight), to obtain a light emitting layer. Next, the pressure was reduced to $1.0 \times 10^{-4}$ Pa or less, then, sodium fluoride was vapor-deposited with a thickness of about 3 nm, as a cathode, on the film of the composition D1 and aluminum was vapor-deposited with a thickness of about 80 nm on the sodium fluoride layer. After vapor deposition, sealing was attained using a glass substrate, to fabricate a light emitting device D1. When voltage was applied to the resultant light emitting device D1, EL light emission showing an emission spectrum peak at 475 nm was obtained from this device, and blue light emission of CIE chromaticity coordinate (0.154, 0.319) was observed. The maximum current efficiency was 7.20 cd/A, the driving voltage in light emission at 1000 cd/m$^2$ was 7.53 V. The results are shown in Table 2.

The light emitting device D1 obtained above was driven at constant current after setting the current value so that the initial luminance was 400 cd/m$^2$, and the time change of luminance was measured. As a result, luminance was attenuated to 60% of the initial luminance after 11.2 hours. The results are shown in Table 2.

Example D2

Fabrication and Evaluation of Light Emitting Device D2

A light emitting device D2 was fabricated in the same manner as in Example D1 excepting that a solution of a polymer compound P3 dissolved at a concentration of 2.0 wt % in a xylene solvent and a solution of a phosphorescent compound EM1 dissolved at a concentration of 2.0 wt % in a xylene solution were mixed to prepare a composition D2 so that the weight ratio thereof was polymer compound P3:phosphorescent compound EM1=60:40 and the rotating rate of spin coating using the composition was changed from 1860 rpm to 1500 rpm, in Example D1. When voltage was applied to the resultant light emitting device D2, EL light emission showing an emission spectrum peak at 475 nm was obtained from this device, and blue light emission of CIE chromaticity coordinate (0.152, 0.321) was observed. The maximum current efficiency was 11.63 cd/A, and the driving voltage in light emission at 1000 cd/m$^2$ was 6.88. The results are shown in Table 2.

The light emitting device D2 obtained above was driven at constant current after setting the current value so that the initial luminance was 400 cd/m$^2$, and the time change of luminance was measured. As a result, luminance was attenuated to 60% of the initial luminance after 17.9 hours. The results are shown in Table 2.

Example D3

A light emitting device D3 was fabricated in the same manner as in Example D1 excepting that a solution of a polymer compound P4 dissolved at a concentration of 2.0 wt % in a xylene solvent and a solution of a phosphorescent compound EM1 dissolved at a concentration of 2.0 wt % in a xylene solution were mixed to prepare a composition D3 so that the weight ratio thereof was polymer compound P4:phosphorescent compound EM1=60:40 and the rotating rate of spin coating using the composition was changed from 1860 rpm to 1350 rpm, in Example D1. When voltage was applied to the resultant light emitting device D3, EL light emission showing an emission spectrum peak at 475 nm was obtained from this device, and blue light emission of CIE chromaticity coordinate (0.154, 0.330) was observed. The maximum current efficiency was 12.63 cd/A, and the driving voltage in light emission at 1000 cd/m$^2$ was 6.92 V. The results are shown in Table 2.

The light emitting device D3 obtained above was driven at constant current after setting the current value so that the initial luminance was 400 cd/m$^2$, and the time change of luminance was measured. As a result, luminance was attenuated to 60% of the initial luminance after 37.7 hours. The results are shown in Table 2.

Comparative Example CD1

A light emitting device CD1 was fabricated in the same manner as in Example D1 excepting that a solution of a polymer compound CP1 dissolved at a concentration of 2.0 wt % in a xylene solvent and a solution of a phosphorescent compound EM1 dissolved at a concentration of 2.0 wt % in a xylene solution were mixed to prepare a composition CD1 so that the weight ratio thereof was polymer compound CP1:phosphorescent compound EM1=60:40 and this composition was used, in Example D1. When voltage was applied to the resultant light emitting device CD1, EL light emission showing an emission spectrum peak at 475 nm was obtained from this device, and blue light emission of CIE chromaticity coordinate (0.169, 0.329) was observed. The maximum current efficiency was 1.98 cd/A, and the driving voltage in light emission at 1000 cd/m$^2$ was 10.51 V. The results are shown in Table 2.

The light emitting device CD1 obtained above was driven at constant current after setting the current value so that the initial luminance was 400 cd/m$^2$, and the time change of luminance was measured. As a result, luminance was attenuated to 60% of the initial luminance after 6.0 hours. The results are shown in Table 2.

Example D4

Fabrication and Evaluation of Light Emitting Device D4

A light emitting device D4 was fabricated in the same manner as in Example D1 excepting that a solution of a polymer compound P1 dissolved at a concentration of 2.0 wt % in a xylene solvent and a solution of a phosphorescent compound EM2 dissolved at a concentration of 2.0 wt % in a xylene solution were mixed to prepare a composition D4 so that the weight ratio thereof was polymer compound P1:phosphorescent compound EM2=60:40 and the rotating rate of spin coating using the composition was changed from 1860 rpm to 1750 rpm, in Example D1. When voltage was applied to the resultant light emitting device D4, EL light emission showing an emission spectrum peak at 520 nm was obtained from this device, and green light emission of CIE chromaticity coordinate (0.301, 0.640) was observed. The maximum current efficiency was 33.65 cd/A, and the driving voltage in light emission at 1000 cd/m$^2$ was 8.09 V. The results are shown in Table 3.

The light emitting device D4 obtained above was driven at constant current after setting the current value so that the initial luminance was 12000 cd/m$^2$, and the time change of luminance was measured. As a result, luminance was attenuated to 60% of the initial luminance after 19.6 hours. The results are shown in Table 3.

Example D5

Fabrication and Evaluation of Light Emitting Device D5

A light emitting device D5 was fabricated in the same manner as in Example D1 excepting that a solution of a polymer compound P2 dissolved at a concentration of 2.0 wt % in a xylene solvent and a solution of a phosphorescent compound EM2 dissolved at a concentration of 2.0 wt % in a xylene solution were mixed to prepare a composition D5 so that the weight ratio thereof was polymer compound P2:phosphorescent compound EM2=60:40 and the rotating rate of spin coating using the composition was changed from 1860 rpm to 1900 rpm, in Example D1. When voltage was applied to the resultant light emitting device D5, EL light emission showing an emission spectrum peak at 520 nm was obtained from this device, and green light emission of CIE chromaticity coordinate (0.301, 0.636) was observed. The maximum current efficiency was 37.01 cd/A, and the driving voltage in light emission at 1000 cd/m$^2$ was 6.68 V. The results are shown in Table 3.

The light emitting device D5 obtained above was driven at constant current after setting the current value so that the initial luminance was 12000 cd/m$^2$, and the time change of luminance was measured. As a result, luminance was attenuated to 60% of the initial luminance after 10.1 hours. The results are shown in Table 3.

Example D6

Fabrication and Evaluation of Light Emitting Device D6

A light emitting device D6 was fabricated in the same manner as in Example D1 excepting that a solution of a polymer compound P3 dissolved at a concentration of 2.0 wt % in a xylene solvent and a solution of a phosphorescent compound EM2 dissolved at a concentration of 2.0 wt % in a xylene solution were mixed to prepare a composition D6 so that the weight ratio thereof was polymer compound P3:phosphorescent compound EM2=60:40 and the rotating rate of spin coating using the composition was changed from 1860 rpm to 1610 rpm, in Example D1. When voltage was applied to the resultant light emitting device D6, EL light emission showing an emission spectrum peak at 520 nm was obtained from this device, and green light emission of CIE chromaticity coordinate (0.307, 0.637) was observed. The maximum current efficiency was 24.38 cd/A, and the driving voltage in light emission at 1000 cd/m$^2$ was 6.83 V. The results are shown in Table 3.

The light emitting device D6 obtained above was driven at constant current after setting the current value so that the initial luminance was 12000 cd/m$^2$, and the time change of luminance was measured. As a result, luminance was attenuated to 60% of the initial luminance after 7.4 hours. The results are shown in Table 3.

Example D7

Fabrication and Evaluation of Light Emitting Device D7

A light emitting device D7 was fabricated in the same manner as in Example D1 excepting that a solution of a polymer compound P4 dissolved at a concentration of 2.0 wt % in a xylene solvent and a solution of a phosphorescent compound EM2 dissolved at a concentration of 2.0 wt % in a xylene solution were mixed to prepare a composition D7 so that the weight ratio thereof was polymer compound P4:phosphorescent compound EM2=60:40 and the rotating rate of spin coating using the composition was changed from 1860 rpm to 1550 rpm, in Example D1. When voltage was applied to the resultant light emitting device D7, EL light emission showing an emission spectrum peak at 520 nm was obtained from this device, and green light emission of CIE chromaticity coordinate (0.299, 0.640) was observed. The maximum current efficiency was 29.13 cd/A, and the driving voltage in light emission at 1000 cd/m$^2$ was 7.31 V. The results are shown in Table 3.

The light emitting device D7 obtained above was driven at constant current after setting the current value so that the initial luminance was 12000 cd/m$^2$, and the time change of luminance was measured. As a result, luminance was attenuated to 60% of the initial luminance after 18.4 hours. The results are shown in Table 3.

Example D8

Fabrication and Evaluation of Light Emitting Device D8

A light emitting device D8 was fabricated in the same manner as in Example D1 excepting that a solution of a polymer compound P5 dissolved at a concentration of 2.0 wt % in a xylene solvent and a solution of a phosphorescent compound EM2 dissolved at a concentration of 2.0 wt % in a xylene solution were mixed to prepare a composition D8 so that the weight ratio thereof was polymer compound P5:phosphorescent compound EM2=60:40 and the rotating rate of spin coating using the composition was changed from 1860 rpm to 1850 rpm, in Example D1. When voltage was applied to the resultant light emitting device D8, EL light emission showing an emission spectrum peak at 520 nm was obtained from this device, and green light emission of CIE chromaticity coordinate (0.309, 0.636) was observed. The maximum current efficiency was 47.80 cd/A, and the driving voltage in light emission at 1000 cd/m$^2$ was 8.60 V. The results are shown in Table 3.

The light emitting device D8 obtained above was driven at constant current after setting the current value so that the initial luminance was 12000 cd/m$^2$, and the time change of luminance was measured. As a result, luminance was attenuated to 60% of the initial luminance after 3.44 hours. The results are shown in Table 3.

Comparative Example CD2

Fabrication and Evaluation of Light Emitting Device CD2

A light emitting device CD2 was fabricated in the same manner as in Example D1 excepting that a solution of a polymer compound CP2 dissolved at a concentration of 2.0 wt % in a xylene solvent and a solution of a phosphorescent compound EM2 dissolved at a concentration of 2.0 wt % in a xylene solution were mixed to prepare a composition CD2 so that the weight ratio thereof was polymer compound CP2:phosphorescent compound EM2=60:40 and the rotating rate of spin coating using the composition was changed from 1860 rpm to 2900 rpm, in Example D1. When voltage was applied to the resultant light emitting device CD2, EL light emission showing an emission spectrum peak at 520 nm was obtained from this device, and green light emission of CIE chromaticity coordinate (0.309, 0.636) was observed. The maximum current efficiency was 51.96 cd/A, and the driving voltage in light emission at 1000 cd/m² was 10.53 V. The results are shown in Table 3.

The light emitting device CD2 obtained above was driven at constant current after setting the current value so that the initial luminance was 12000 cd/m², and the time change of luminance was measured. As a result, luminance was attenuated to 60% of the initial luminance after 0.1 hour. The results are shown in Table 3.

TABLE 2

| | Polymer compound | Formula (1) | Formula (2) | Formula (3) | LT60 [hrs] |
|---|---|---|---|---|---|
| Example D1 | P2 | MM1 | CC1 | CC7 | 11.2 |
| Example D2 | P3 | MM1 | CC1 CC5 | | 17.9 |
| Example D3 | P4 | MM1 | CC1 | CC6 | 37.7 |
| Comparative Example CD1 | CP1 | | CC1 | CC3 CC7 | 6.0 |

(in the table, LT60 represents time until luminance reduces to 60% with respect to the initial luminance when a light emitting device is driven at constant current.)

TABLE 3

| | Polymer compound | Formula (1) | Formula (2) | Formula (3) | LT60 [hrs] |
|---|---|---|---|---|---|
| Example D4 | P1 | MM1 MM2 | | | 19.58 |
| Example D5 | P2 | MM1 | CC1 | CC7 | 10.13 |
| Example D6 | P3 | MM1 | CC1 CC5 | | 7.38 |
| Example D7 | P4 | MM1 | CC1 | CC6 | 18.41 |
| Example D8 | P5 | CM1 | CC1 | CC7 | 3.44 |
| Comparative Example CD2 | CP2 | | CC1 CC2 | | 0.08 |

(in the table, LT60 represents the same meaning as described above.)

INDUSTRIAL APPLICABILITY

The present invention is a polymer compound as a host material for a phosphorescent compound, which is useful for production of a light emitting device excellent in luminance life.

The invention claimed is:

1. A polymer compound comprising a group represented by the following general formula (1) as a repeating unit:

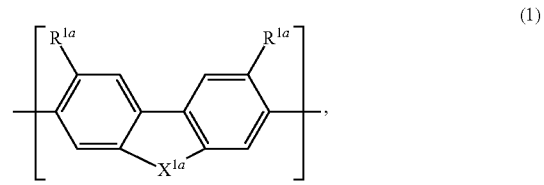

in the formula (1), $R^{1a}$ represents an alkyl group, an aryl group, a monovalent aromatic heterocyclic group or an aralkyl group, and each of these groups is optionally substituted with a substituent, a plurality of $R^{1a}$ can be the same or different, $X^{1a}$ represents a group selected from the group consisting of the following formulae (1a) to (1c):

in the formulae (1a) to (1c), $R^{1c}$ represents an aryl group or a monovalent aromatic heterocyclic group, and each of these groups is optionally substituted with a substituent, $R^{1d}$ to $R^{1f}$ represent each independently an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom or a cyano group, in the formula (1b), $R^{1d}$ and $R^{1e}$ can be mutually linked to form a ring together with a carbon atom to which they are linked, and in the formula (1c), $R^{1d}$ and $R^{1e}$ can be mutually linked to form a ring together with a carbon atom to which they are linked, $R^{1f}$ and $R^{1g}$ can be mutually linked to form a ring together with a carbon atom to which they are linked, $R^{1d}$ and $R^{1f}$ can be mutually linked to form a ring together with a carbon atom to which they are linked, and $R^{1e}$ and $R^{1g}$ can be mutually linked to form a ring together with a carbon atom to which they are linked.

2. The polymer compound according to claim 1, wherein the group represented by said general formula (1) is a group represented by the following general formula (1A):

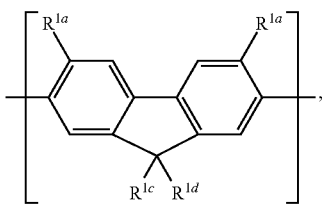

in the formula (1A), $R^{1a}$, $R^{1c}$ and $R^{1d}$ represent the same meaning as described above.

3. The polymer compound according to claim 1, wherein the group represented by said $R^{1c}$ is an aryl group.

4. The polymer compound according to claim 1, further comprising as a repeating unit at least one group selected from the group consisting of groups represented by the following general formulae (2) and (3):

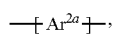

in the formula (2),
Ar$^{2a}$ represents an arylene group, a divalent aromatic heterocyclic group, or a divalent group obtained by mutually linking 2 to 10 groups selected from the group consisting of an arylene group and a divalent aromatic heterocyclic group, and each of these groups is optionally substituted with a substituent,
wherein in the group represented by the formula (2), at least one of carbon atoms adjacent to a carbon atom forming a bond to the other repeating unit has an alkyl group, an aryl group, a monovalent aromatic heterocyclic group or an aralkyl group as a substituent, the group represented by the formula (2) is different from the group represented by the formula (1):

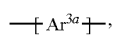

in the formula (3),
Ar$^{3a}$ represents an arylene group, a divalent aromatic heterocyclic group, or a divalent group obtained by mutually linking 2 to 10 groups selected from the group consisting of an arylene group and a divalent aromatic heterocyclic group, and each of these groups is optionally substituted with a substituent,
wherein the group represented by the formula (3) is different from the group represented by formula (1) and the group represented by formula (2).

5. The polymer compound according to claim 4, wherein the group represented by general formula (2) is a group represented by the following general formula (2A):

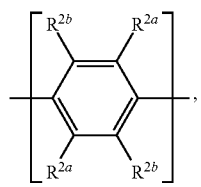

in the formula (2A),
$R^{2a}$ represents an alkyl group, an aryl group, a monovalent aromatic heterocyclic group or an aralkyl group, and each of these groups is optionally substituted with a substituent, and a plurality of $R^{2a}$ can be the same or different,
$R^{2b}$ represents a hydrogen atom, an alkyl group, an aryl group, a monovalent aromatic heterocyclic group or an aralkyl group, and each of these groups is optionally substituted with a substituent, and a plurality of $R^{2b}$ can be the same or different.

6. The polymer compound according to claim 4, wherein the group represented by general formula (2) is a group represented by the following general formula (2B):

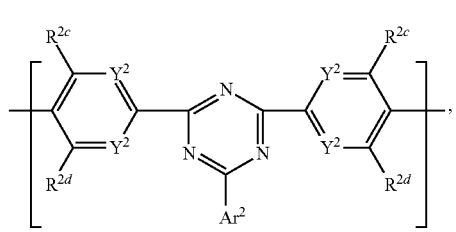

in the formula (2B),
$Y^2$ represents a carbon atom or a nitrogen atom, and the carbon atom is optionally substituted with an alkyl group, an aryl group, a monovalent aromatic heterocyclic group or an aralkyl group, and a plurality of $Y^2$ can be the same or different,
$R^{2c}$ represents an alkyl group, an aryl group, a monovalent aromatic heterocyclic group or an aralkyl group, and each of these groups is optionally substituted with a substituent, and a plurality of $R^{2c}$ can be the same or different,
$R^{2d}$ represents a hydrogen atom, an alkyl group, an aryl group, a monovalent aromatic heterocyclic group or an aralkyl group, and each of these groups is optionally substituted with a substituent, and a plurality of $R^{2d}$ can be the same or different,
Ar$^2$ represents an aryl group or a monovalent aromatic heterocyclic group, and each of these groups is optionally substituted with a substituent.

7. The polymer compound according to claim 4, wherein the group represented by general formula (3) is a group represented by the following general formula (3A):

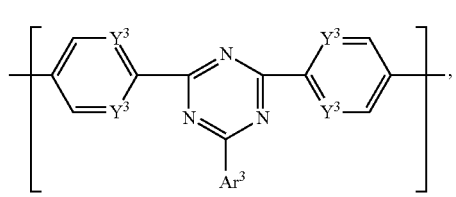

in the formula (3A),
$Y^3$ represents a carbon atom or a nitrogen atom, and the carbon atom is optionally substituted with an alkyl group, an aryl group, a monovalent aromatic heterocyclic group or an aralkyl group, and a plurality of $Y^3$ can be the same or different,
Ar$^3$ represents an aryl group or a monovalent aromatic heterocyclic group, and each of these groups is optionally substituted with a substituent.

8. The polymer compound according to claim 4, wherein the group represented by general formula (3) is a group represented by the following general formula (3B):

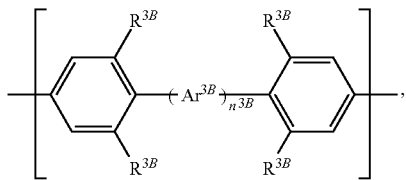

in the formula (3B),
$n^{3B}$ represents an integer of 1 to 3,
$Ar^{3B}$ represents an arylene group or a divalent aromatic heterocyclic group, and each of these groups is optionally substituted with a substituent, and when there is a plurality of $Ar^{3B}$, these can be the same or different,
$R^{3B}$ represents an alkyl group, an aryl group, a monovalent aromatic heterocyclic group or an aralkyl group, and each of these groups is optionally substituted with a substituent, and a plurality of $R^{3B}$ can be the same or different.

9. The polymer compound according to claim 4, wherein the content of the groups represented by formula (3) is 0.1 mol % or more and 50 mol % or less with respect to the total content of repeating units contained in the polymer compound and the groups represented by formula (3) are not mutually substantially adjacent.

10. A composition comprising the polymer compound according to claim 1 and at least one material selected from the group consisting of a hole transporting material, an electron transporting material and a light emitting material.

11. The composition according to claim 10, wherein said light emitting material is a phosphorescent compound.

12. A composition comprising a polymer compound containing a group represented by the following general formula (1B) as a repeating unit, and a phosphorescent compound represented by the following general formula (Ir-1), (Ir-2) or (Ir-3):

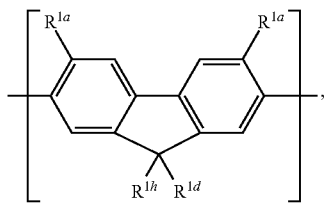

in the formula (1B), $R^{1a}$ represents an alkyl group, an aryl group, a monovalent aromatic heterocyclic group or an aralkyl group, and each of these groups is optionally substituted with a substituent, and a plurality of $R^{1a}$ can be the same or different,
$R^{1h}$ and $R^{1d}$ represent each independently an alkyl group, an aryl group, a monovalent aromatic heterocyclic group, an alkoxy group, an aryloxy group, an aralkyl group, an arylalkoxy group, a substituted amino group, a substituted carbonyl group, a substituted carboxyl group, a fluorine atom or a cyano group, and $R^{1h}$ and $R^{1d}$ can be mutually linked to form a ring together with a carbon atom to which they are linked:

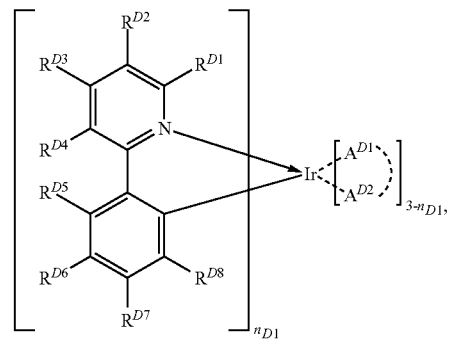

in the formula (Ir-1),
$R^{D1}$, $R^{D2}$, $R^{D3}$, $R^{D4}$, $R^{D5}$, $R^{D6}$, $R^{D7}$ and $R^{D8}$ represent each independently a hydrogen atom, an alkyl group, an alkoxy group, an aryl group, an aryloxy group, a monovalent aromatic heterocyclic group or a halogen atom, and each of these groups is optionally substituted with a substituent, wherein at least one of $R^{D1}$, $R^{D2}$, $R^{D3}$, $R^{D4}$, $R^{D5}$, $R^{D6}$, $R^{D7}$ and $R^{D8}$ is a group represented by the following formula (Dend-A) or (Dend-B),
-$A^{D1}$---$A^{D2}$- represents an anionic bidentate ligand, and $A^{D1}$ and $A^{D2}$ each independently represent a carbon atom, an oxygen atom or a nitrogen atom linking to an iridium atom,
$n_{D1}$ represents 1, 2 or 3:

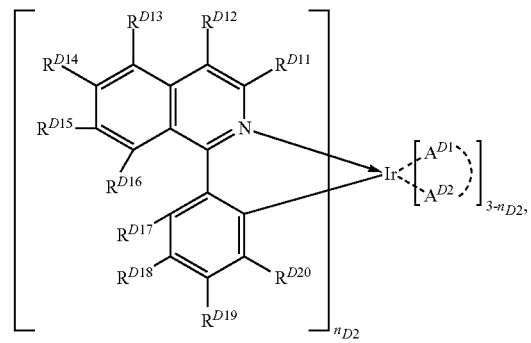

in the formula (Ir-2),
$R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ each independently represent a hydrogen atom, an alkyl group, an alkoxy group, an aryl group, an aryloxy group, a monovalent aromatic heterocyclic group or a halogen atom, and each of these groups is optionally substituted with a substituent, wherein at least one of $R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ is a group represented by the following formula (Dend-A) or (Dend-B),
-$A^{D1}$---$A^{D2}$- represents an anionic bidentate ligand, and $A^{D1}$ and $A^{D2}$ each independently represent a carbon atom, an oxygen atom or a nitrogen atom linking to an iridium atom,
$n_{D2}$ represents 1, 2 or 3:

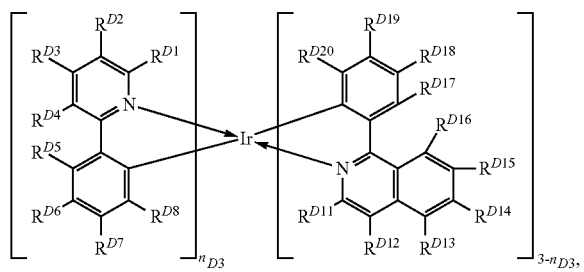

(Ir-3)

in the formula (Ir-3), $R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$, $R^{D15}$, $R^{D16}$, $R^{D17}$, $R^{D18}$, $R^{D19}$ and $R^{D20}$ each independently represent a hydrogen atom, an alkyl group, an alkoxy group, an aryl group, an aryloxy group, a monovalent aromatic heterocyclic group or a halogen atom, and each of these groups is optionally substituted with a substituent, wherein at least one of $R^{D1}$, $R^{D2}$, $R^{D3}$, $R^{D4}$, $R^{D5}$, $R^{D6}$, $R^{D7}$, $R^{D8}$, $R^{D11}$, $R^{D12}$, $R^{D13}$, $R^{D14}$ $R^{D15}$, $R^{D16}$, $R^{D17}$, $R^{D18}$, $R^{D19}$ and $R^{D20}$ is a group represented by the following formula (Dend-A) or (Dend-B), $-A^{D1}$ - - - $A^{D2}$- represents an anionic bidentate ligand, and $A^{D1}$ and $A^{D2}$ each independently represent a carbon atom, an oxygen atom or a nitrogen atom linking to an iridium atom, $n_{D3}$ represents 1 or 2:

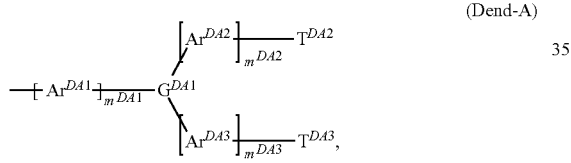

(Dend-A)

in the formula (Dend-A), $G^{DA1}$ represents a nitrogen atom, a trivalent aromatic hydrocarbon group or a trivalent aromatic heterocyclic group, $Ar^{DA1}$, $Ar^{DA2}$ and $Ar^{DA3}$ each independently represent an arylene group or a divalent aromatic heterocyclic group, $T^{DA2}$ and $T^{DA3}$ each independently represent an aryl group or a monovalent aromatic heterocyclic group, $m^{DA1}$, $m^{DA2}$ and $m^{DA3}$ each independently represent an integer of 0 or more:

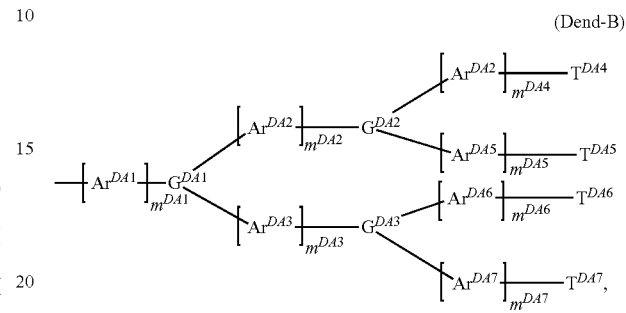

(Dend-B)

in the formula (Dend-B), $G^{DA1}$, $G^{DA2}$ and $G^{DA3}$ each independently represent a nitrogen atom, a trivalent aromatic hydrocarbon group or a trivalent aromatic heterocyclic group, $Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent aromatic heterocyclic group, $T^{DA4}$, $T^{DA5}$, $T^{DA6}$ and $T^{DA7}$ each independently represent an aryl group or a monovalent aromatic heterocyclic group, and $m^{DA1}$, $m^{DA2}$, $m^{DA3}$, $m^{DA4}$, $m^{DA5}$, $m^{DA6}$ and $m^{DA7}$ each independently represent an integer of 0 or more.

13. A liquid composition comprising the polymer compound according to claim 1 and a solvent.

14. An organic film comprising the polymer compound according to claim 1.

15. A light emitting device having an anode and a cathode and an organic layer disposed between the anode and the cathode, wherein the organic layer contains the polymer compound according to claim 1.

* * * * *